(12) United States Patent
Prétôt et al.

(10) Patent No.: US 8,492,749 B2
(45) Date of Patent: Jul. 23, 2013

(54) ELECTROLUMINESCENT METAL COMPLEXES WITH NUCLEOPHILIC CARBENE LIGANDS

(75) Inventors: Roger Prétôt, Basel (CH); Paul Adriaan Van Der Schaaf, Hagenthal-le-Haut (FR); Jemima Schmidt, Maulburg (DE); Beat Schmidhalter, Bubendorf (CH); Thomas Schäfer, Liestal (CH); Bernd Lamatsch, Riehen (CH)

(73) Assignee: BASF SE, Ludwigshafen (DE)

( * ) Notice: Subject to any disclaimer, the term of this patent is extended or adjusted under 35 U.S.C. 154(b) by 1115 days.

(21) Appl. No.: 11/793,513

(22) PCT Filed: Dec. 14, 2005

(86) PCT No.: PCT/EP2005/056767
§ 371 (c)(1),
(2), (4) Date: Jan. 28, 2011

(87) PCT Pub. No.: WO2006/067074
PCT Pub. Date: Jun. 29, 2006

(65) Prior Publication Data
US 2011/0114922 A1    May 19, 2011

(30) Foreign Application Priority Data
Dec. 23, 2004  (EP) ..................................... 04106916

(51) Int. Cl.
*H01L 35/24* (2006.01)
(52) U.S. Cl.
USPC ..................................... 257/40; 257/E51.001
(58) Field of Classification Search
USPC ........................................... 257/40, E51.001
See application file for complete search history.

(56) References Cited

U.S. PATENT DOCUMENTS

| | | | | |
|---|---|---|---|---|
| 6,160,267 | A | 12/2000 | Kunugi et al. | 257/40 |
| 6,338,977 | B1 | 1/2002 | Kunugi et al. | 438/49 |
| 2001/0019782 | A1 | 9/2001 | Igarashi et al. | 428/690 |
| 2002/0063516 | A1 | 5/2002 | Tsuboyama et al. | 313/504 |
| 2002/0182441 | A1 | 12/2002 | Lamansky et al. | 428/690 |
| 2005/0260441 | A1 | 11/2005 | Thompson et al. | 428/690 |
| 2006/0025564 | A1 | 2/2006 | Craig et al. | 528/422 |
| 2006/0258043 | A1 | 11/2006 | Bold et al. | 438/99 |
| 2007/0043314 | A1 | 2/2007 | Rogers et al. | 528/314 |
| 2007/0282076 | A1 | 12/2007 | Bold et al. | 525/370 |
| 2008/0018221 | A1 | 1/2008 | Egen et al. | 313/483 |

FOREIGN PATENT DOCUMENTS

| | | |
|---|---|---|
| EP | 1 191 612 | 3/2002 |
| JP | 2007-084635 | 4/2007 |
| WO | 2005/019373 | 3/2005 |
| WO | 2005113704 | 12/2005 |
| WO | 2006056418 A2 | 6/2006 |
| WO | 2007/018067 | 2/2007 |
| WO | 2007/058255 | 5/2007 |

OTHER PUBLICATIONS

Danopoulos et al., J. Chem. Soc. Dalton Trans., No. 16, (2002), pp. 3090-3091.
Hiraki et al., Journal of Organometallic Chemistry, vol. 216 (1981) pp. 413-419.
Hitchcock et al., Journal of Organometallic Chemistry vol. 239, (1982) pp. C26-C30.
Weskamp et al., Journal of Organometallic Chemistry, vol. 582 (1999) pp. 362-365.
V. Yam et al., J. Chem. Soc. Dalton Trans. (2001) pp. 1911-1919.
S. Lai et al., Angew. Chem. Int. Ed. (1998) vol. 37, No. 1/2 pp. 182-184.
S. Lai et al., Journal of Organometallic Chemistry 617-618 (2001) pp. 133-140.
S. Gründemann et al., J. Am. Chem. Soc., vol. 124, (2002) pp. 10473-10481.
W. Xue et al., Organometallics (1998), vol. 17 pp. 1622-1630.
A. Chianese et al., Organometallics (2003), vol. 22, pp. 1663-1667.
English language abstract of WO 2006/056418 Jun. 1, 2006.
Hiraki et al., Journal of Organometallic Chemistry, vol. 201, pp. 469-475 (1980).
Hiraki et al., Bull. Chem. Soc. Japan, vol. 53, pp. 1976-1981 (1980).
Patent Abstracts of Japan Pub. No. 2007-084635.

*Primary Examiner* — Anthony Ho
(74) *Attorney, Agent, or Firm* — Tyler A. Stevenson

(57) ABSTRACT

This invention relates to electroluminescent metal complexes of the formula (I), wherein the ring A, formula (II), represents an optionally substituted aryl group which can optionally contain heteroatoms, the ring B, formula (III), represents an optionally substituted nitrogen containing aryl group, which can optionally contain further heteroatoms, or the ring A may be taken with the ring B binding to the ring A to form a ring; the group C, formula (IV), represents an acyclic carbene, or a cyclic carbene (ring C), which can optionally contain heteroatoms, the ring D, formula (V), represents an optionally substituted aryl group which can optionally contain heteroatoms, n1 is an integer of 1 to 3, m1 is an integer of 0, 1, or 2, m2 is an integer 0, or 1, $M^1$ is a metal with an atomic weight of greater than 40, $L^3$ is a monodentate ligand, or a bidentate ligand, Y is —C(=O)—, or —C($X^1$)$_2$—, wherein $X^1$ is hydrogen, or $C_{1-4}$alkyl, especially hydrogen, and y is 0, or 1, especially 0; a process for their preparation, electronic devices comprising the metal complexes and their use in electronic devices, especially organic light emitting diodes (OLEDs), as oxygen sensitive indicators, as phosphorescent indicators in bioassays, and as catalysts.

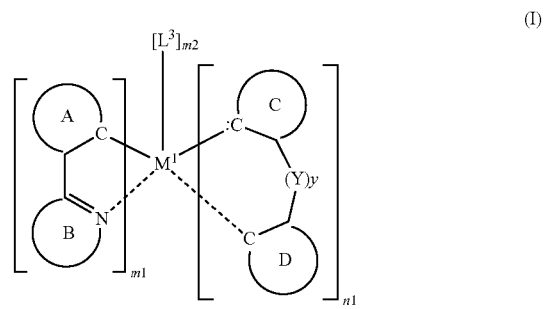

(I)

18 Claims, No Drawings

ELECTROLUMINESCENT METAL COMPLEXES WITH NUCLEOPHILIC CARBENE LIGANDS

This invention relates to electroluminescent metal complexes with nucleophilic carbene ligands, a process for their preparation, electronic devices comprising the metal complexes and their use in electronic devices, especially organic light emitting diodes (OLEDs), as oxygen sensitive indicators, as phosphorescent indicators in bioassays, and as catalysts.

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers. It is well known to use organic electroluminescent compounds as the active component in light-emitting diodes. Simple organic molecules such as anthracene, thiadiazole derivatives, and coumarin derivatives are known to show electroluminescence. Semiconductive conjugated polymers have also been used as electroluminescent components, as has been disclosed in, for example, in U.S. Pat. Nos. 5,247,190, 5,408,109 and EP-A-443 861. Complexes of 8-hydroxyquinolate with trivalent metal ions, particularly aluminum, have been extensively used as electroluminescent components, as has been disclosed in, for example, U.S. Pat. No. 5,552,678. Burrows and Thompson have reported that fac-tris(2-phenylpyridine) iridium can be used as the active component in organic light-emitting devices. (Appl. Phys. Lett. 1999, 75, 4.) The performance is maximized when the iridium compound is present in a host conductive material. Thompson has further reported devices in which the active layer is poly(N-vinyl carbazole) doped with fac-tris[2-(4',5'-difluorophenyl)pyridine-C'$_2$,N] iridium(III). (Polymer Preprints 2000, 41(1), 770.)

P. B. Hitchcock et al., J. Organometallic Chemistry 239 (1982) C26-C30, describe the preparation of the Ir complexes of the formula

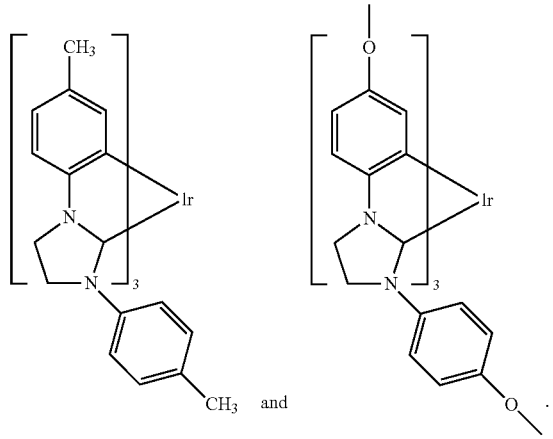

Hiraki et al., J. Organomet. Chem. 1981, 413 bis 419 describe the preparation and the characterization of the following carbene complexes:

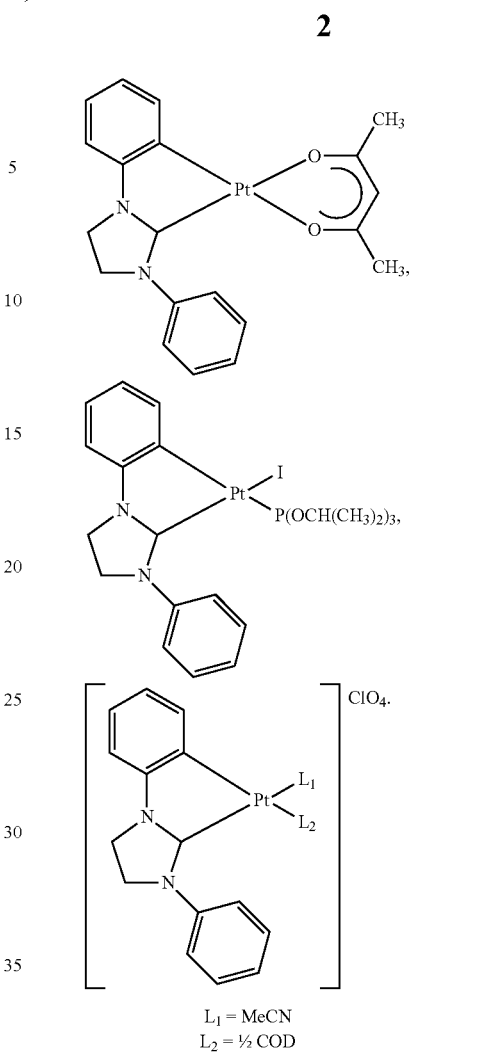

Danapoulos et al., J. Chem. Soc., Dalton Trans. (2002) 3090 bis 3091 describe the preparation of the following carbene complex:

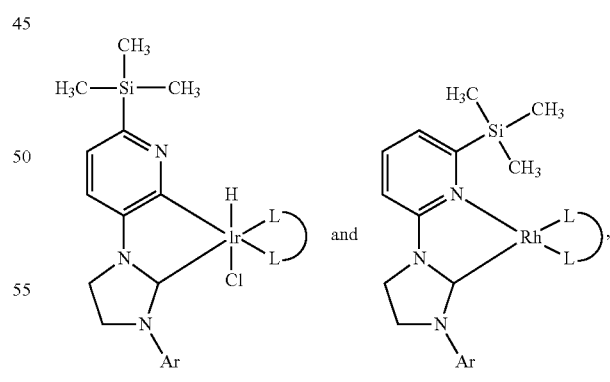

wherein L-L=$\eta^4$-1,5-cyclooctadiene; Ar=2,6-diisopropylphenyl.

There is, however, a continuing need for electroluminescent compounds with excellent light emitting characteristics and durability.

Accordingly the present invention is directed to compounds (metal complexes) of the formula

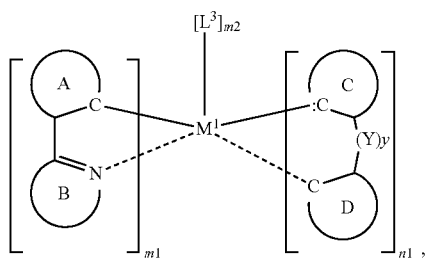

wherein
the ring A,

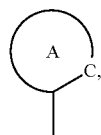

represents an optionally substituted aryl group which can optionally contain heteroatoms,
the ring B,

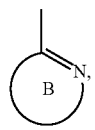

represents an optionally substituted nitrogen containing aryl group, which can optionally contain further heteroatoms, or the ring A may be taken with the ring B binding to the ring A to form a ring;
the group C,

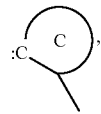

represents an acyclic carbene, or a cyclic carbene (ring C), which can optionally contain heteroatoms,
the ring D,

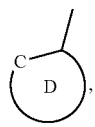

represents an optionally substituted aryl group which can optionally contain heteroatoms,
n1 is an integer of 1 to 3,
m1 is an integer of 0, 1, or 2,
m2 is an integer 0, or 1,
$M^1$ is a metal with an atomic weight of greater than 40,
$L^3$ is a monodentate ligand, or a bidentate ligand,
Y is —C(=O)—, or —C($X^1$)$_2$-, wherein $X^1$ is hydrogen, or $C_{1-4}$alkyl, especially hydrogen, and
y is 0, or 1, especially 0; with the proviso that the following compounds

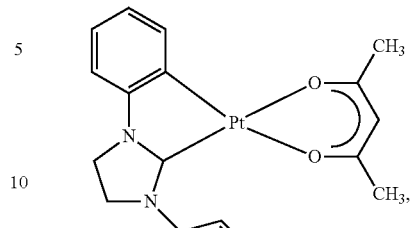

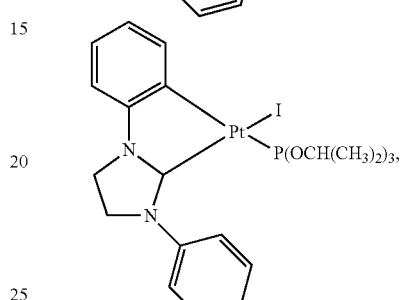

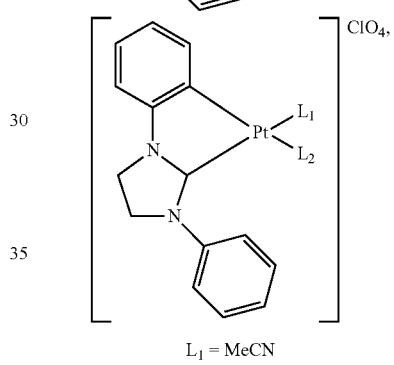

$L_1$ = MeCN
$L_2$ = ½ COD

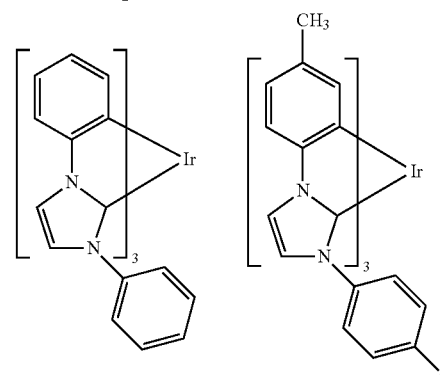

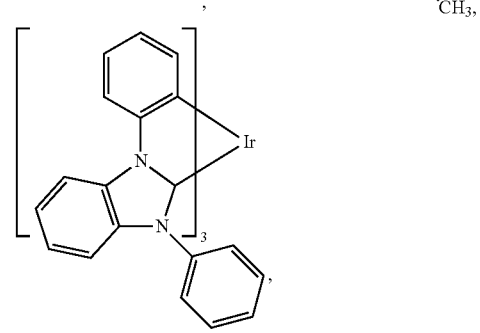

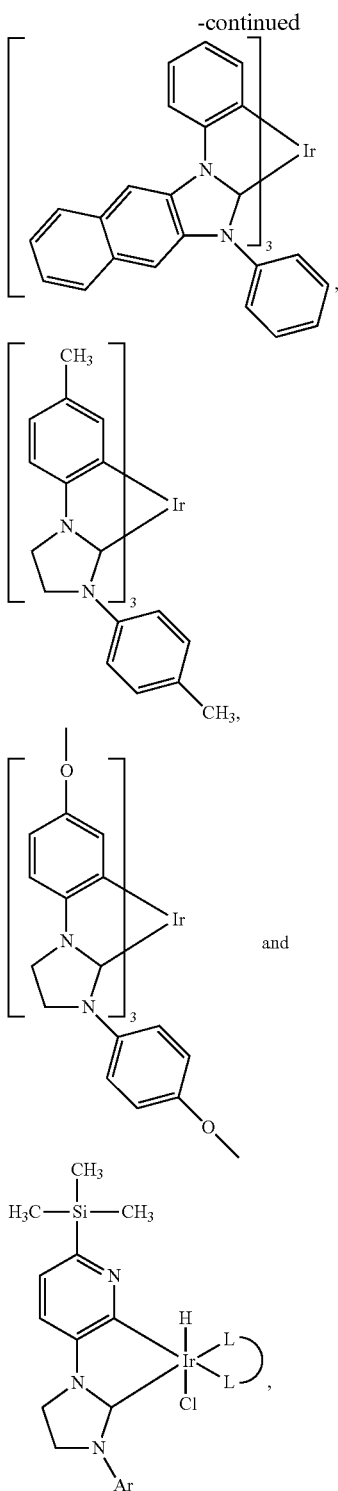

wherein L-L=η⁴-1,5-cyclooctadiene; Ar=2,6-diisopropylphenyl, are excluded; a process for their preparation, electronic devices comprising the metal complexes and their use in electronic devices, especially organic light emitting diodes (OLEDs), as oxygen sensitive indicators, as phosphorescent indicators in bioassays, and as catalysts.

The metal complexes of the present invention are characterized in that at least one ligand is derived from a nucleophilic carbene.

The metal is generally a metal $M^1$ with an atomic weight of greater than 40, Preferably the metal $M^1$ is selected from Tl, Pb, Bi, In, Sn, Sb, Te, especially Mo, Cr, Mn, Ta, V, Cu, Fe, Ru, Ni, Co, Ir, Pt, Pd, Rh, Re, Os, Ag and Au. More preferably the metal is selected from Ir and Ru as well as Ag, Au, Pt and Pd, wherein Ir and Pt are most preferred.

"Nucleophilic carbene ligand" in the context of the present invention means typical σ-donor ligands that can substitute classical 2e⁻ donor ligands. They can be cyclic or acyclic. They can have no or several different heteroatoms or several heteroatoms of the same kind. Possible carbenes are, for example, diarylcarbenes, cyclic diaminocarbenes, imidazol-2-ylidenes, imidazolidin-2-ylidene, 1,2,4-triazol-3-ylidenes, 1,3-thiazol-2-ylidenes, acyclic diaminocarbenes, acyclic aminooxycarbenes, acyclic aminothiocarbenes, cyclic diborylcarbenes, acyclic diborylcarbenes, phosphinosilyl-carbenes, phosphinophosphonio-carbenes, sulfenyl-trifluormethylcarbenes, sulfenylpentafluorothiocarbenes etc.

The term "ligand" is intended to mean a molecule, ion, or atom that is attached to the coordination sphere of a metallic ion. The term "complex", when used as a noun, is intended to mean a compound having at least one metallic ion and at least one ligand. The term "group" is intended to mean a part of a compound, such a substituent in an organic compound or a ligand in a complex. The term "facial" is intended to mean one isomer of a complex, $Ma_3b_3$, having octahedral geometry, in which the three "a" groups are all adjacent, i.e. at the corners of one triangular face of the octahedron. The term "meridional" is intended to mean one isomer of a complex, $Ma_3b_3$, having octahedral geometry, in which the three "a" groups occupy three positions such that two are trans to each other, i.e. the three "a" groups sit in three coplanar positions, forming an arc across the coordination sphere that can be thought of as a meridion. The phrase "adjacent to," when used to refer to layers in a device, does not necessarily mean that one layer is immediately next to another layer. The term "photoactive" refers to any material that exhibits electroluminescence and/or photosensitivity.

If $M^1$ is Co, or Fe, especially Ir, or Rh, n1 is preferably 3, more preferably 1.

If $M^1$ is Ni, Rh, or Ru, especially Pd, or Pt, n1 is preferably 2, more preferably 1.

In an embodiment of the present invention compounds of formula I are preferred, wherein $M^1$ is Co, or Fe, especially Ir, or Rh, m2 is 0, n1 is 1 and m1 is 2.

In another embodiment of the present invention compounds of formula I are preferred, wherein $M^1$ is Ni, Rh, or Ru, especially Pd, or Pt, m2 is 0, n1 is 1 and m1 is 1.

If the group

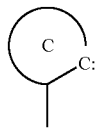

represents an acyclic nucleophilic carbene it is preferably a group of the following formula

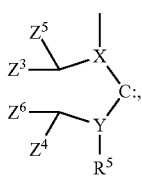

wherein X=Y=N, B, or P;

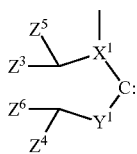

wherein $X^1$ is N, or P and $Y^1$ is S, or O; $>SiX^2X^3$, or $>CZ^5Z^3$, wherein $X^2$ and $X^3$ are independently of each other $C_1$-$C_4$alkyl and $R^5$, $Z^3$, $Z^4$, $Z^5$ and $Z^6$ are as defined below.

y is 0, or 1, especially 0. The ring D,

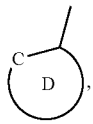

is preferably a group of formula

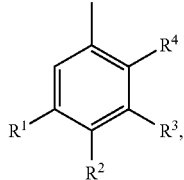

wherein $R^1$ to $R^4$ are substitutents and can be taken together to form a ring.

Examples that specify the possibilities for the group designated above are as follows:

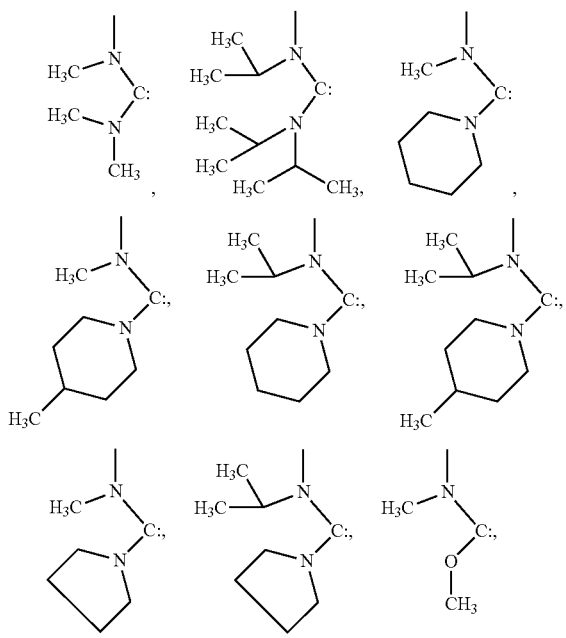

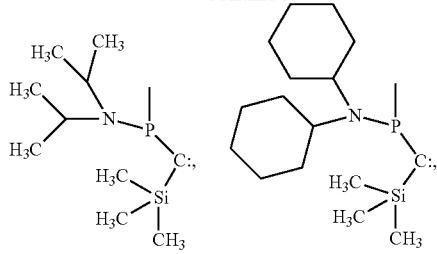

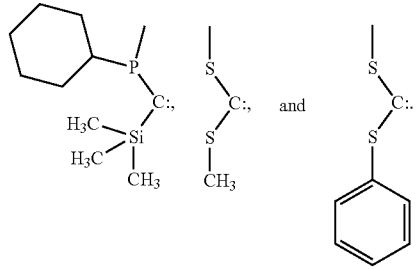

Cyclic carbenes,

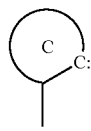

(ring C), are preferred against acyclic carbenes. Examples of a ring C are as follows:

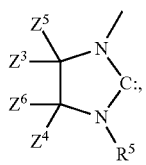 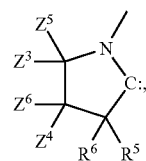 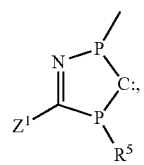

especially

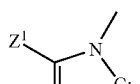 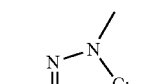 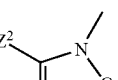

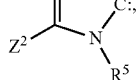 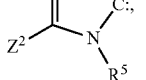 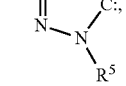

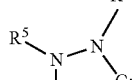 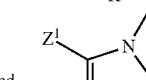 

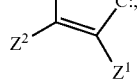 and 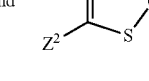

wherein
$R^5$ is a substitutent, such as hydrogen, $C_1$-$C_{24}$alkyl, $C_2$-$C_{24}$alkenyl, $C_2$-$C_{24}$alkynyl, $C_2$-$C_{24}$alkoxycarbonyl, $C_1$-$C_{24}$carboxylate, $C_1$-$C_{24}$alkoxy, $C_2$-$C_{24}$alkenyloxy, $C_2$-$C_{24}$alkynyloxy, or aryloxy, which can optionally be substituted with $C_1$-$C_8$alkyl, halogen, $C_1$-$C_8$alkoxy, or with a phenyl group, which can be substituted with halogen, $C_1$-$C_8$alkyl, or $C_1$-$C_8$alkoxy, especially aryl, which can optionally be substituted; and $R^6$, $Z^1$, $Z^2$, $Z^3$, $Z^4$, $Z^5$ and $Z^6$ are independently of each other selected from the group consisting of hydrogen, $C_1$-$C_{24}$alkyl, $C_1$-$C_{24}$halogenalkyl, especially $C_1$-$C_8$perfluoroalkyl, $C_2$-$C_{24}$alkenyl, $C_2$-$C_{24}$alkynyl, $C_2$-$C_{24}$alkoxycarbonyl, aryl, which can optionally be substituted, $C_1$-$C_{24}$carboxylate, $C_1$-$C_{24}$alkoxy, $C_2$-$C_{24}$alkenyloxy, $C_2$-$C_{24}$alkynyloxy, or aryloxy, wherein each of $Z^1$, $Z^2$, $Z^3$ and $Z^4$ optionally being substituted with $C_1$-$C_8$alkyl, halogen, $C_1$-$C_8$alkoxy, or with a phenyl group, which can optionally be substituted with halogen, $C_1$-$C_8$alkyl, or $C_1$-$C_8$alkoxy, or $Z^1$ and $Z^2$, if possible, form an aromatic or heteroaromatic ring, and/or $Z^3$, $Z^4$, $Z^5$ and $Z^6$, if possible, form an alkyl or heteroalkyl ring.

In one embodiment cyclic carbenes,

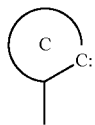

(ring C), are preferred, wherein ring C is represented by the following formula:

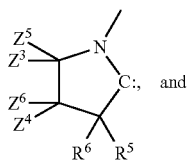 and 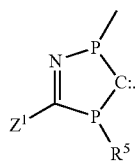

In another embodiment cyclic carbenes,

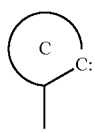

(ring C), are preferred, wherein ring C is represented by the following formula:

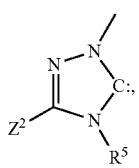 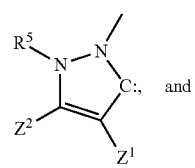 and 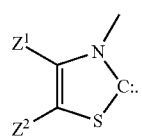

In said embodiment the ligand

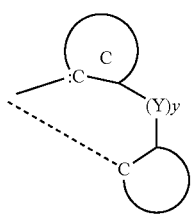

($L^1$) is preferably a group of formula

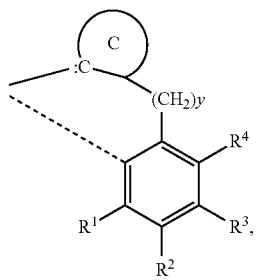

wherein $R^1$ to $R^4$ are substitutents and can be taken together to form a ring, y is 0, or 1, especially 0, the group C,

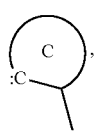

is a group (nucleophilic carbene) of the following formula

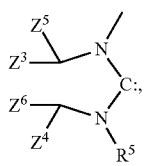

especially

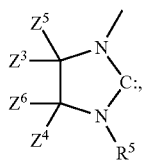

very especially

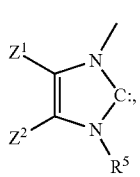 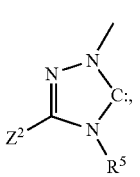 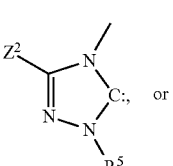 or

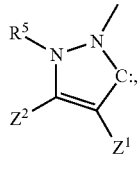 or 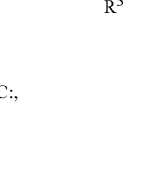

wherein $R^5$ is a substitutent, especially hydrogen, $C_1$-$C_{24}$alkyl, $C_2$-$C_{24}$alkenyl, $C_2$-$C_{24}$alkynyl, $C_2$-$C_{24}$alkoxycarbonyl, $C_1$-$C_{24}$carboxylate, $C_1$-$C_{24}$alkoxy, $C_2$-$C_{24}$alkenyloxy, $C_2$-$C_{24}$alkynyloxy, or aryloxy, which can optionally be substituted with $C_1$-$C_8$alkyl, halogen, $C_1$-$C_8$alkoxy, or with a phenyl group, which can be substituted with halogen, $C_1$-$C_8$alkyl, or $C_1$-$C_8$alkoxy, especially aryl, which can optionally be substituted; and $Z^1$, $Z^2$, $Z^3$, $Z^4$, $Z^5$ and $Z^6$ are independently of each other selected from the group consisting of hydrogen, $C_1$-$C_{24}$alkyl, $C_1$-$C_{24}$halogenalkyl, especially $C_1$-$C_8$perfluoroalkyl, $C_2$-$C_{24}$alkenyl, $C_2$-$C_{24}$alkynyl, $C_2$-$C_{24}$alkoxycarbonyl, aryl, which can optionally be substituted, $C_1$-$C_{24}$carboxylate, $C_1$-$C_{24}$alkoxy, $C_2$-$C_{24}$alkenyloxy, $C_2$-$C_{24}$alkynyloxy, or aryloxy, wherein each of $Z^1$, $Z^2$, $Z^3$ and $Z^4$ optionally being substituted with $C_1$-$C_8$alkyl, halogen, $C_1$-$C_8$alkoxy, or with a phenyl group, which can optionally be substituted with halogen, $C_1$-$C_8$alkyl, or $C_1$-$C_8$alkoxy, or $Z^1$ and $Z^2$, if possible, form an aromatic or heteroaromatic ring, and/or $Z^3$, $Z^4$, $Z^5$ and $Z^6$, if possible, form an alkyl or heteroalkyl ring.

$R^1$, $R^2$, $R^3$ and $R^4$ are independently of each other hydrogen, halogen, especially F, or Cl; nitro, cyano, $C_1$-$C_4$alkyl, $C_1$-$C_4$perfluoroalkyl, or $C_1$-$C_4$alkoxy, —S—$C_1$-$C_4$alkyl, —O—$C_1$-$C_4$perfluoroalkyl, —$SO_2X^{22}$, —$CO_2H$, —$CO_2X^{22}$, wherein $X^{22}$ is $C_1$-$C_4$alkyl; $C_6H_4CF_3$, cyclohexyl, optionally substituted $C_6$-$C_{10}$aryl, especially phenyl, optionally substituted —O—$CH_2$—$C_6$-$C_{10}$aryl, especially benzyloxy, or optionally substituted —O—$C_6$-$C_{10}$aryl, especially phenoxy.

$R^1$ is preferably hydrogen, halogen, especially F, or Cl; nitro, cyano, $C_1$-$C_4$alkyl, $C_1$-$C_4$perfluoroalkyl, or $C_1$-$C_4$alkoxy.

$R^2$ is preferably hydrogen, halogen, especially F, or Cl; nitro, cyano, $C_1$-$C_4$alkyl, $C_1$-$C_4$perfluoroalkyl, $C_1$-$C_4$alkoxy, —O—$C_1$-$C_4$perfluoroalkyl, —$SO_2X^{22}$, —$CO_2X^{22}$, wherein $X^{22}$ is $C_1$-$C_4$alkyl; $C_6H_4CF_3$, or optionally substituted —O—$C_6$-$C_{10}$aryl, especially phenoxy.

$R^3$ is preferably hydrogen, halogen, especially F, or Cl; nitro, cyano, $C_1$-$C_4$alkyl, $C_1$-$C_4$perfluoroalkyl, $C_1$-$C_4$alkoxy, —S—$C_1$-$C_4$alkyl, or —O—$C_1$-$C_4$perfluoroalkyl.

$R^4$ is preferably hydrogen, halogen, especially F, or Cl.

According to the present invention the metal complexes comprise at least a nucleophilic carbene ligand, i.e. it may comprise two or three (or more) nucleophilic carbene ligands ($L^1$).

Especially preferred examples of ring C are

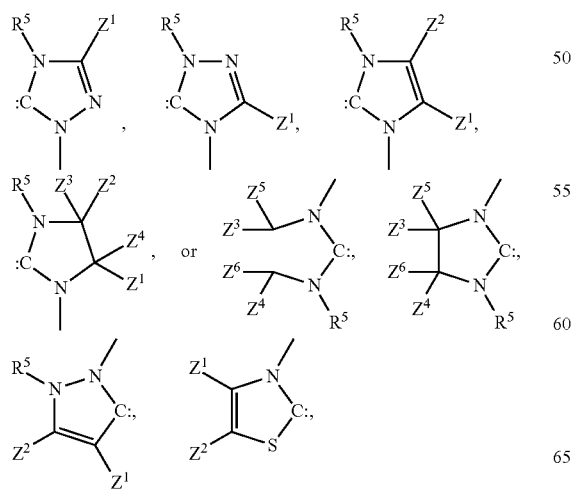

wherein $R^5$, $Z^1$, $Z^2$, $Z^3$, and $Z^4$ are as defined above. $R^5$ is preferably optionally substituted $C_6$-$C_{10}$aryl, especially phenyl. $Z^1$ is preferably $C_1$-$C_4$perfluoroalkyl, or optionally substituted $C_6$-$C_{10}$aryl, especially phenyl. In a preferred embodiment $R^5$ is optionally substituted $C_6$-$C_{10}$aryl, especially phenyl and $Z^1$ is $C_1$-$C_4$perfluoroalkyl.

An optionally substituted $C_6$-$C_{10}$aryl group is especially a phenyl group, which is substituted by one or more $C_1$-$C_4$alkyl groups, $C_1$-$C_4$perfluoroalkyl groups and/or fluorine atoms.

Examples of a group of formula

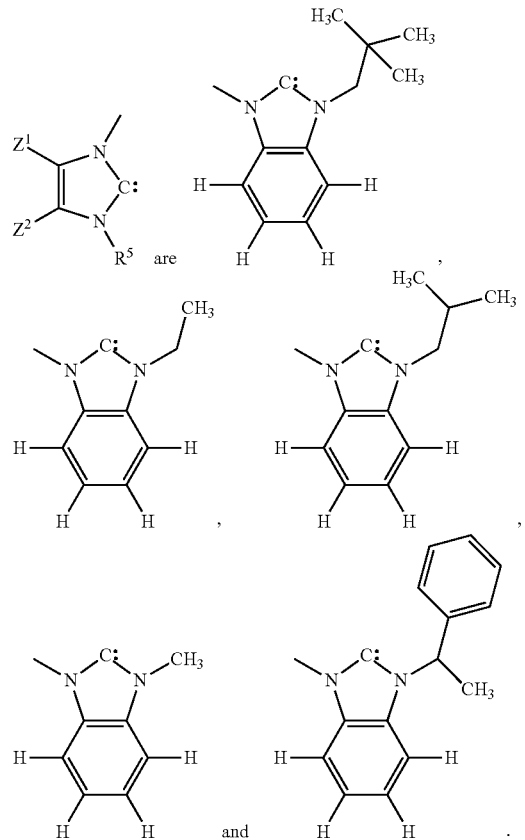

Examples of a group of formula $$\begin{array}{c} Z^1 \diagdown X \\ \diagup \diagdown C: \\ Z^2 \diagup N \diagup \\ \diagup \\ R^5 \end{array}$$

wherein X can be O, or S are

Especially preferred examples of ligands L¹ are

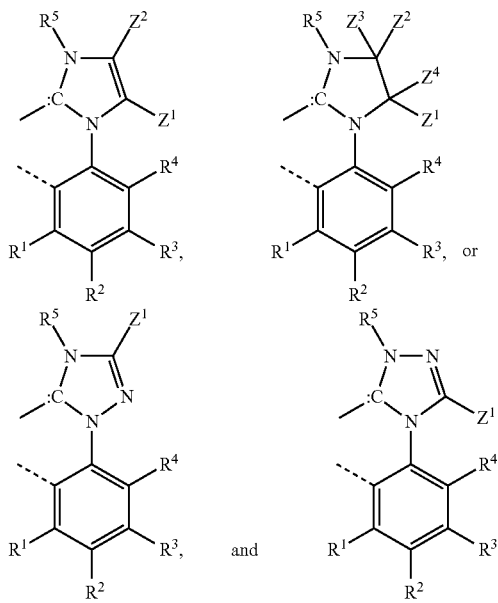

wherein
$R^1$ is hydrogen, halogen, especially F, or Cl; nitro, cyano, $C_1$-$C_4$alkyl, $C_1$-$C_4$perfluoroalkyl, or $C_1$-$C_4$alkoxy, $R^2$ is hydrogen, halogen, especially F, or Cl; nitro, cyano, $C_1$-$C_4$alkyl, $C_1$-$C_4$perfluoroalkyl, $C_1$-$C_4$alkoxy, —S—$C_1$-$C_4$alkyl, —O—$C_1$-$C_4$perfluoroalkyl, —$SO_2X^{22}$, —$CO_2X^{22}$, wherein $X^{22}$ is $C_1$-$C_4$alkyl; $C_6H_4CF_3$; or optionally substituted —O—$C_6$-$C_{10}$aryl, especially phenoxy, $R^3$ is hydrogen, halogen, especially F, or Cl; nitro, cyano, $C_1$-$C_4$alkyl, $C_1$-$C_4$perfluoroalkyl, $C_1$-$C_4$alkoxy, —S—$C_1$-$C_4$alkyl, or —O—$C_1$-$C_4$perfluoroalkyl, $R^4$ is hydrogen, halogen, especially F, or Cl;

$R^5$ is optionally substituted $C_6$-$C_{10}$aryl, $C_1$-$C_4$alkyl, $C_1$-$C_4$perfluoroalkyl, $C_1$-$C_4$alkoxy, or —O—$C_1$-$C_4$perfluoroalkyl, especially phenyl, and $Z^1$ is $C_1$-$C_4$perfluoroalkyl, or optionally substituted $C_6$-$C_{10}$aryl, especially phenyl.

In a further embodiment the present invention is directed to metal complexes comprising at least one ligand derived from a nucleophilic carbene ($L^1$) and at least one ligand of formula

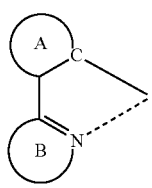

($L^2$).

The preferred ring B includes a phenyl group, a substituted phenyl group, a naphthyl group, a substituted naphthyl group, a furyl group, a substituted furyl group, a benzofuryl group, a substituted benzofuryl group, a thienyl group, a substituted thienyl group, a benzothienyl group, a substituted benzothienyl group, and the like. The substitutent on the substituted phenyl group, substituted naphthyl group, substituted furyl group, substituted benzofuryl group, substituted thienyl group, and substituted benzothienyl group include $C_1$-$C_{24}$alkyl groups, $C_2$-$C_{24}$alkenyl groups, $C_2$-$C_{24}$alkynyl groups, aryl groups, heteroaryl groups, $C_1$-$C_{24}$alkoxy groups, $C_1$-$C_{24}$alkylthio groups, a cyano group, $C_2$-$C_{24}$acyl groups, $C_1$-$C_{24}$alkyloxycarbonyl groups, a nitro group, halogen atoms, alkylenedioxy groups, and the like.

In said embodiment the ligand

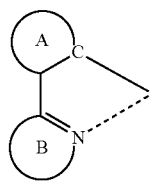

($L^2$) is preferably a group of formula

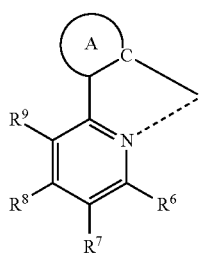

wherein $R^6$, $R^7$, $R^8$, and $R^9$ are independently of each other hydrogen, $C_1$-$C_{24}$alkyl, $C_2$-$C_{24}$alkenyl, $C_2$-$C_{24}$alkynyl, aryl, heteroaryl, $C_1$-$C_{24}$alkoxy, $C_1$-$C_{24}$alkylthio, cyano, acyl, alkyloxycarbonyl, a nitro group, or a halogen atom; or two substituents $R^6$, $R^7$, $R^8$, and $R^9$, which are adjacent to each other, together form a group

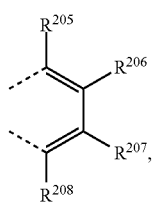

wherein $R^{205}$, $R^{206}$, $R^{207}$ and $R^{208}$ m are independently of each other H, or $C_1$-$C_8$alkyl, the ring A represents an optionally substituted aryl or heteroaryl group; or the ring A may be taken with the pyridyl group binding to the ring A to form a ring; the alkyl group, alkenyl group, alkynyl group, aryl group, heteroaryl group, alkoxy group, alkylthio group, acyl group, and alkyloxycarbonyl group represented by $R^6$, $R^7$, $R^8$, and $R^9$ may be substituted.

An example of a preferred class of ligands $L^2$ are compounds of the formula

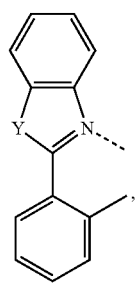

especially

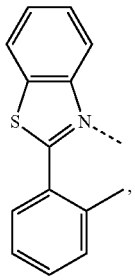

wherein Y is S, O, $NR^{200}$, wherein $R^{200}$ is hydrogen, cyano, $C_1$-$C_4$alkyl, $C_2$-$C_4$alkenyl, optionally substituted $C_6$-$C_1$ aryl, especially phenyl, —$(CH_2)_r$—Ar, wherein Ar is an optionally substituted $C_6$-$C_{10}$aryl, especially

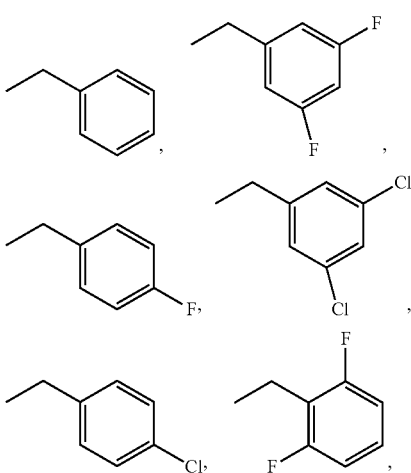

a group —$(CH_2)_{r'}X^{20}$, wherein r' is an integer of 1 to 5, $X^{20}$ is halogen, especially F, or Cl; hydroxy, cyano, —O—$C_1$-$C_4$alkyl, di($C_1$-$C_4$alkyl)amino, amino, or cyano; a group —$(CH_2)_rOC(O)(CH_2)r''CH_3$, wherein r is 1, or 2, and r'' is 0, or 1;

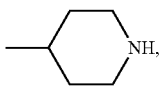

—NH-Ph, —C(O)CH$_3$, —CH$_2$—O—(CH$_2$)$_2$—Si(CH$_3$)$_3$, or

Another preferred class of ligands $L^2$ is described in European patent application 04102981.0, of which the following can advantageously be used according to the present invention:

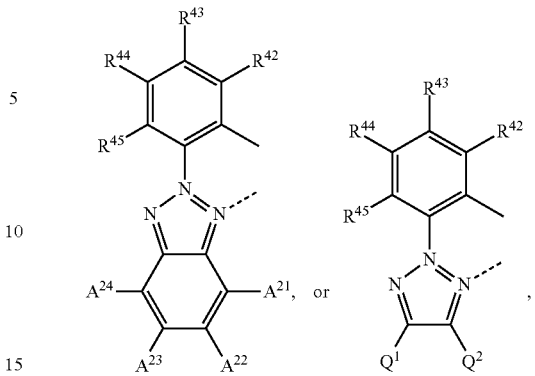

wherein
$Q^1$ and $Q^2$ are independently of each other hydrogen, $C_1$-$C_{24}$alkyl, or $C_6$-$C_{18}$aryl, $A^{21}$ is hydrogen,
$A^{22}$ is hydrogen, or $C_6$-$C_{10}$aryl,
$A^{23}$ is hydrogen, or $C_6$-$C_{10}$aryl,
$A^{24}$ is hydrogen, or
$A^{23}$ and $A^{24}$, or $A^{23}$ and $A^{24}$ together form a group

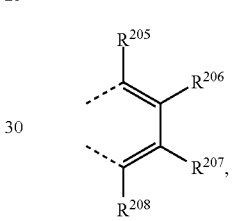

wherein $R^{205}$, $R^{206}$, $R^{207}$ and
$R^{208}$ are independently of each other H, or $C_1$-$C_8$alkyl,
$R^{42}$ is H, F, $C_1$-$C_4$alkyl, $C_1$-$C_8$alkoxy, or $C_1$-$C_4$perfluoroalkyl,
$R^{43}$ is H, F, $C_1$-$C_4$alkyl, $C_1$-$C_8$alkoxy, $C_1$-$C_4$perfluoroalkyl, or $C_6$-$C_{10}$aryl,
$R^{44}$ is H, F, $C_1$-$C_4$alkyl, $C_1$-$C_8$alkoxy, or $C_1$-$C_4$perfluoroalkyl, and
$R^{45}$ is H, F, $C_1$-$C_4$alkyl, $C_1$-$C_8$alkoxy, or $C_1$-$C_4$perfluoroalkyl.

Another preferred class of ligands $L^2$ is a compound of formula

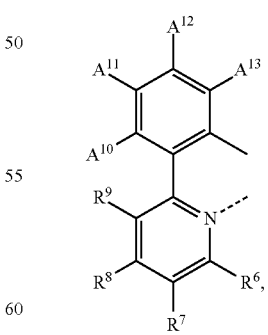

wherein $R^6$ is hydrogen, halogen, especially F, or Cl; nitro, $C_1$-$C_4$alkyl, $C_1$-$C_4$perfluoroalkyl, $C_1$-$C_4$alkoxy, or optionally substituted $C_6$-$C_{10}$aryl, especially phenyl,
$R^7$ is hydrogen, halogen, especially F, or Cl; $C_1$-$C_4$alkyl, $C_1$-$C_4$perfluoroalkyl, optionally substituted $C_6$-$C_{10}$aryl, especially phenyl, or optionally substituted $C_6$-$C_{10}$perfluoroaryl, especially $C_6F_5$, $R^8$ is hydrogen, $C_1$-$C_4$alkyl, $C_1$-$C_8$alkoxy, $C_1$-$C_4$perfluoroalkyl, optionally substituted $C_6$-$C_{10}$aryl, especially phenyl, or optionally substituted $C_6$-$C_{10}$perfluoroaryl, especially $C_6F_5$, $R^9$ is hydrogen, halogen, especially F, or Cl; nitro, cyano, $C_1$-$C_4$alkyl, $C_1$-$C_4$perfluoroalkyl, $C_1$-$C_4$alkoxy, or optionally substituted $C_6$-$C_{10}$aryl, especially phenyl, $A^{10}$ is hydrogen, halogen, especially F, or Cl; nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, especially tri(methyl)silanyl, optionally substituted $C_6$-$C_{10}$aryl, especially phenyl, or optionally substituted $C_6$-$C_{10}$perfluoroaryl, especially $C_6F_5$, $A^{11}$ is hydrogen, halogen, especially F, or Cl; nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, especially tri(methyl)silanyl, optionally substituted $C_6$-$C_{10}$aryl, especially phenyl, or optionally substituted $C_6$-$C_{10}$perfluoroaryl, especially $C_6F_5$, $A^{12}$ is hydrogen, halogen, especially F, or Cl; nitro, hydroxy, mercapto, amino, $C_1$-$C_4$alkyl, $C_2$-$C_4$alkenyl, $C_1$-$C_4$perfluoroalkyl, $C_1$-$C_4$alkoxy, —O—$C_1$-$C_4$perfluoroalkyl, —S—$C_1$-$C_4$alkyl, a group —$(CH_2)_rX^{20}$, wherein r is 1, or 2, $X^{20}$ is halogen, especially F, or Cl; hydroxy, cyano, —O—$C_1$-$C_4$alkyl, di($C_1$-$C_4$alkyl)amino, —$CO_2X^{21}$, wherein $X^{21}$ is H, or $C_1$-$C_4$alkyl; —CH=$CHCO_2X^{22}$, wherein $X^{22}$ is $C_1$-$C_4$alkyl; —CH(O), —$SO_2X^{23}$, —$SOX^{23}$, —$NC(O)X^{23}$, —$NSO_2X^{23}$, —$NHX^{23}$, —$N(X^{23})_2$, wherein $X^{23}$ is $C_1$-$C_4$alkyl; tri($C_1$-$C_4$alkyl)siloxanyl, optionally substituted —O—$C_6$-$C_{10}$aryl, especially phenoxy, cyclohexyl, optionally substituted $C_6$-$C_{10}$aryl, especially phenyl, or optionally substituted $C_6$-$C_{10}$perfluoroaryl, especially $C_6F_5$, and $A^{13}$ is hydrogen, nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, or optionally substituted $C_6$-$C_{10}$aryl.

Specific examples of $L^2$ are the following compounds (VI-1) to (VI-53):

(VI-1)

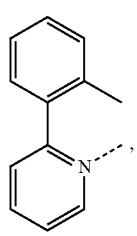

(VI-2)

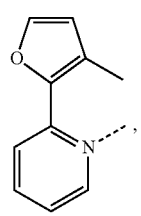

(VI-3)

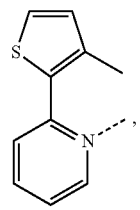

(VI-4)

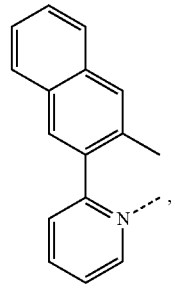

(VI-5)

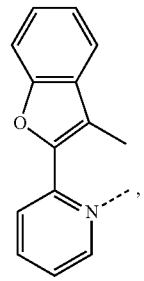

(VI-6)

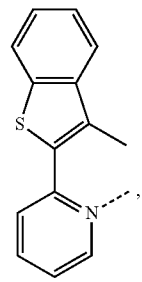

(VI-7)

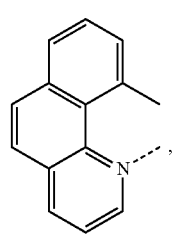

(VI-8)

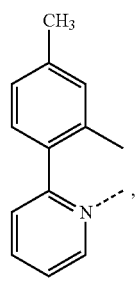

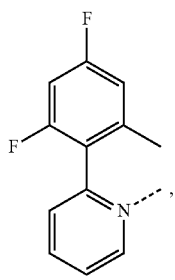
(VI-9)
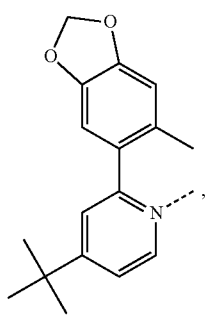
(VI-10)
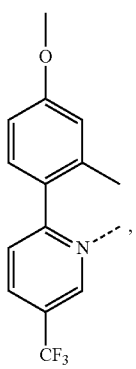
(VI-11)
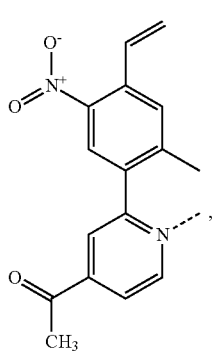
(VI-12)
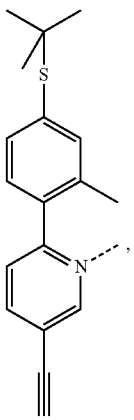
(VI-13)
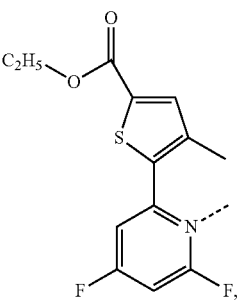
(VI-14)
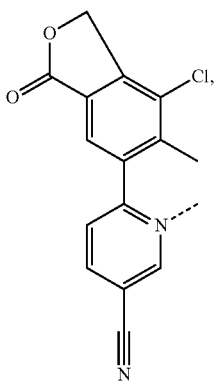
(VI-15)
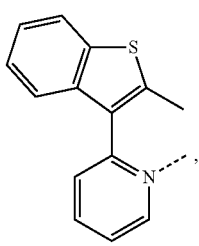
(VI-16)

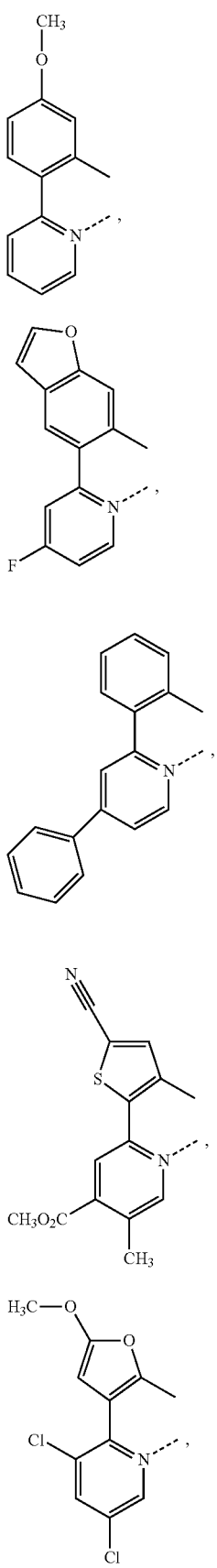
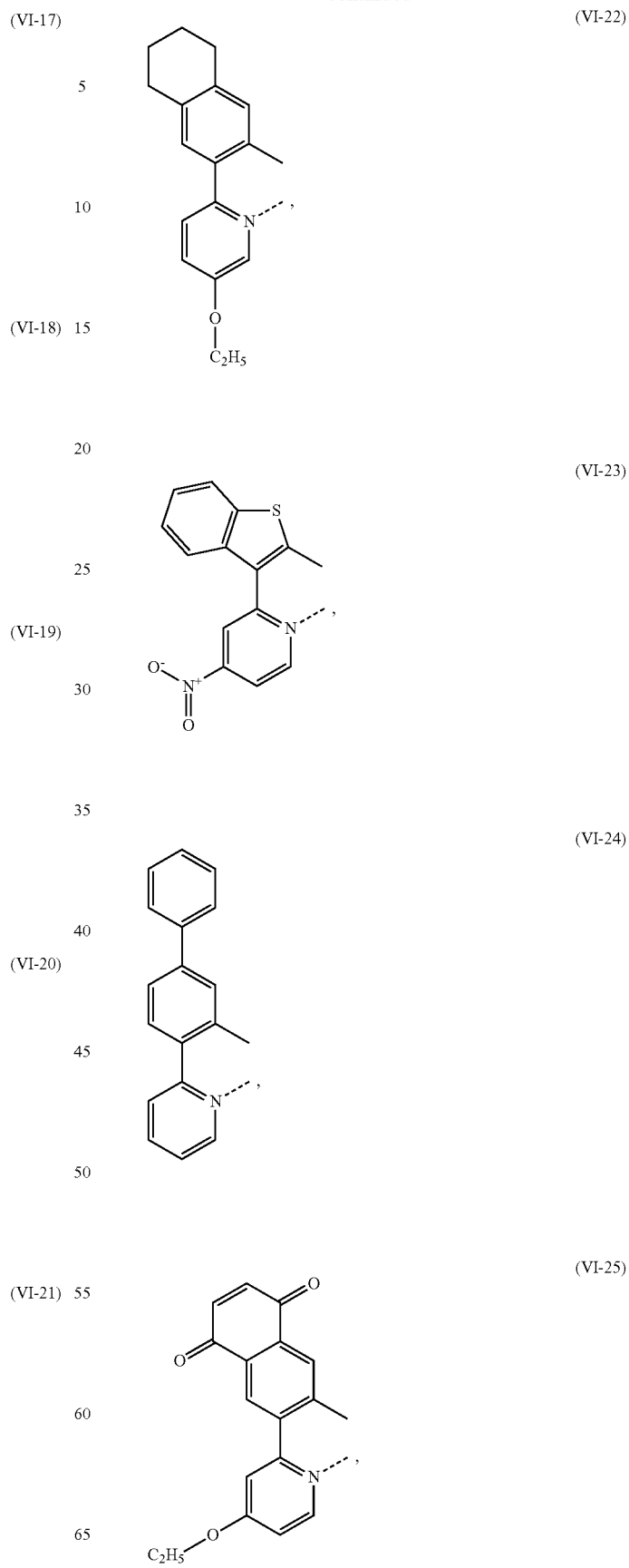

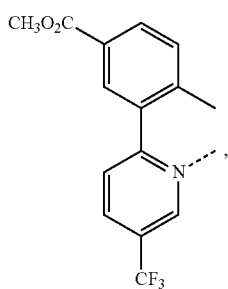 (VI-26)
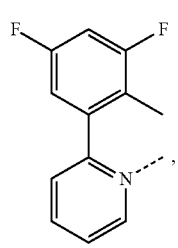 (VI-27)
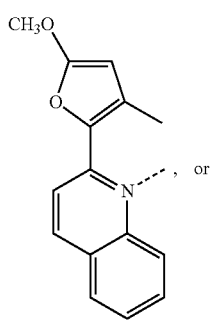 (VI-28)
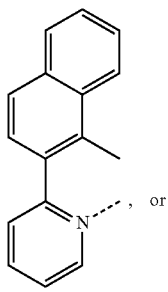 (VI-29)
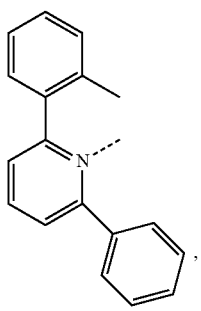 (VI-30)
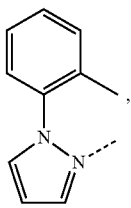 (VI-31)
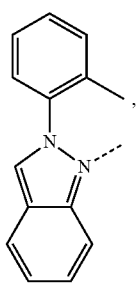 (VI-32)
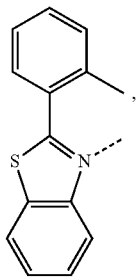 (VI-33)
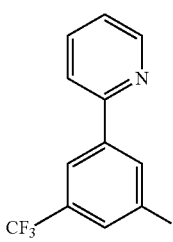 (VI-34)
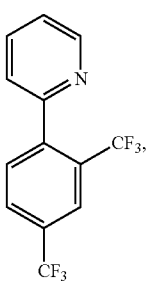 (VI-35)

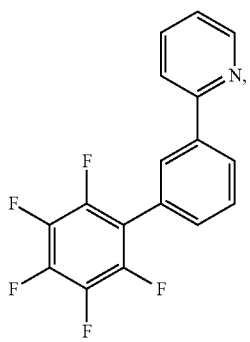 (VI-36)
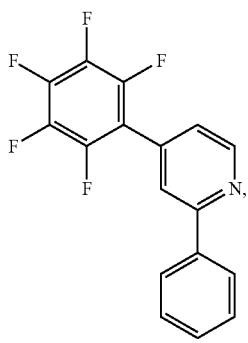 (VI-37)
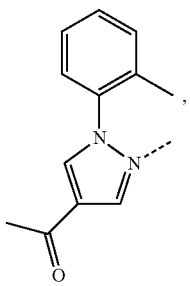 (VI-39)
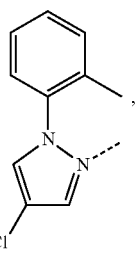 (VI-40)
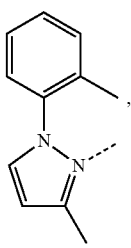 (VI-41)
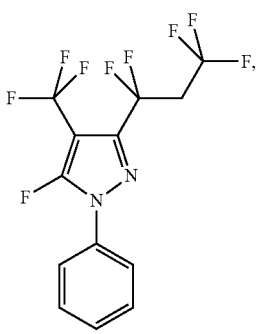 (VI-42)
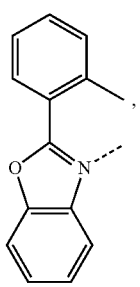 (VI-43)

-continued

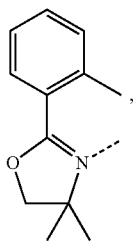
(VI-44)

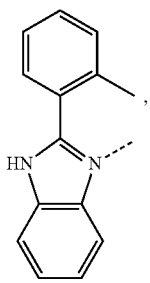
(VI-45)

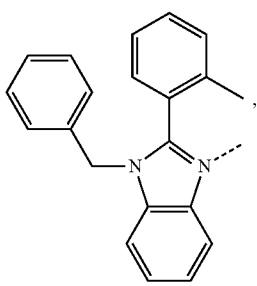
(VI-46)

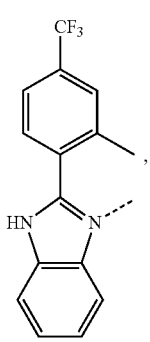
(VI-47)

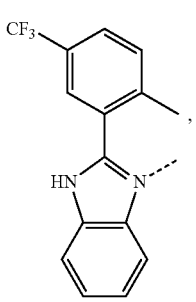
(VI-48)

-continued

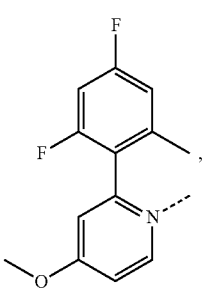
(VI-49)

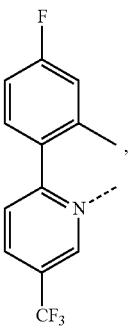
(VI-50)

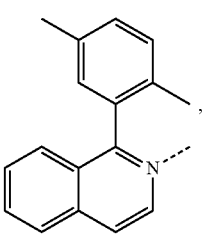
(VI-51)

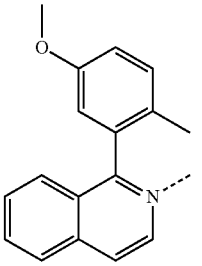
(VI-52)

and

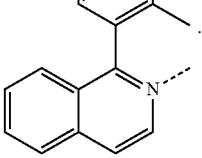
(VI-53)

Special emphasis among them is given to (VI-1) to (VI-47).

The ligand $L^3$ is preferably a (monoanionic) bidentate ligand. In general these ligands have N, O, P, or S as coordinating atoms and form 5- or 6- membered rings when coordinated to the iridium. Suitable coordinating groups include amino, imino, amido, alkoxide, carboxylate, phosphino, thiolate, and the like. Examples of suitable parent compounds for these ligands include β-dicarbonyls (β-enolate ligands), and their N and S analogs; amino carboxylic acids(aminocarboxylate ligands); pyridine carboxylic acids (iminocarboxylate ligands); salicylic acid derivatives (salicylate ligands); hydroxyquinolines (hydroxyquinolinate ligands) and their S analogs; and diarylphosphinoalkanols (diarylphosphinoalkoxide ligands).
Examples of bidentate ligands $L^3$ are
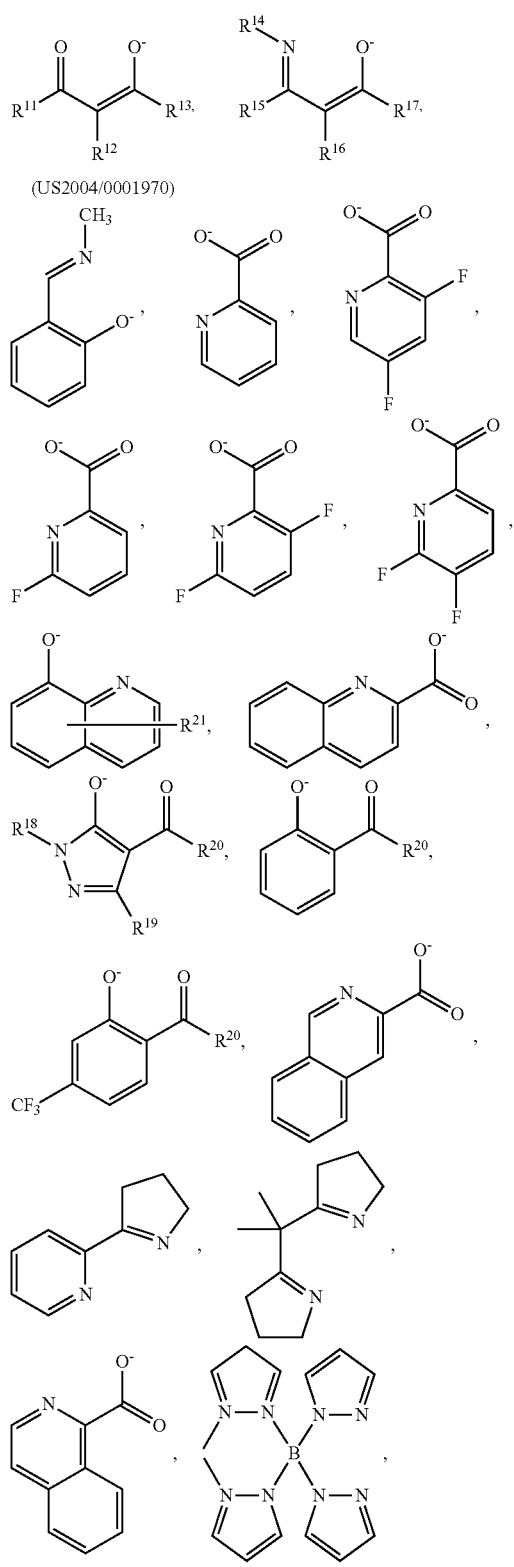
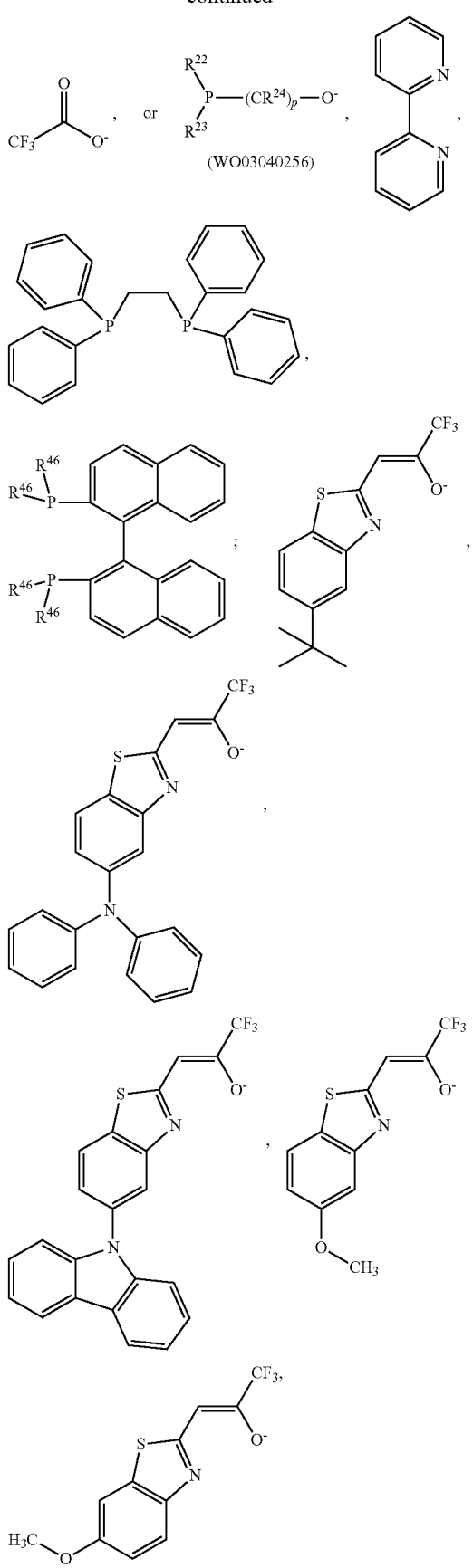

-continued

[chemical structures: bis(trifluoromethylsulfonyl)amide; bis(diphenylphosphoryl)amide; 3-(2-pyridyl)-5-phenyl-1,2,4-triazole; bis(diphenylphosphinothioyl)amide], or wherein R$^{11}$ and R$^{15}$ are independently of each other hydrogen, C$_1$-C$_8$alkyl, C$_6$-C$_{18}$aryl, C$_2$-C$_{10}$heteroaryl, or C$_1$-C$_8$perfluoroalkyl, R$^{12}$ and R$^{16}$ are independently of each other hydrogen, or C$_1$-C$_8$alkyl, and R$^{13}$ and R$^{17}$ are independently of each other hydrogen, C$_1$-C$_8$alkyl, C$_6$-C$_{18}$aryl, C$_2$-C$_{10}$heteroaryl, C$_1$-C$_8$perfluoroalkyl, or C$_1$-C$_8$alkoxy, and R$^{14}$ is C$_1$-C$_8$alkyl, C$_6$-C$_{10}$aryl, C$_7$-C$_{11}$aralkyl, or C$_1$-C$_8$alkoxy, R$^{18}$ is C$_6$-C$_{10}$aryl, R$^{19}$ is C$_1$-C$_8$alkyl, R$^{20}$ is C$_1$-C$_8$alkyl, or C$_6$-C$_{10}$aryl, R$^{21}$ is hydrogen, C$_1$-C$_8$alkyl, or C$_1$-C$_8$alkoxy, which may be partially or fully fluorinated, R$^{22}$ and R$^{23}$ are independently of each other C$_n$(H+F)$_{2n+1}$, or C$_6$(H+F)$_5$, R$^{24}$ can be the same or different at each occurrence and is selected from H, or C$_n$H+F)$_{2n+1}$, p is 2, or 3, and R$^{46}$ is C$_1$-C$_8$alkyl, C$_6$-C$_{18}$aryl, or C$_6$-C$_{18}$aryl, which is substituted by C$_1$-C$_8$alkyl.

Examples of suitable phosphino alkoxide ligands

[structure: R$^{22}$R$^{23}$P—(CR$^{24}$)$_p$—O$^-$]

(WO03040256) are listed below:
  3-(diphenylphosphino)-1-oxypropane [dppO]
  1,1-bis(trifluoromethyl)-2-(diphenylphosphino)-ethoxide [tfmdpeO].

Examples of particularly suitable compounds HL$^3$,

[structure with R$^{11}$, R$^{12}$, R$^{13}$]

from which the ligands L$^3$ are derived, include

[structures:]

(2,4-pentanedionate [acac]), (2,2,6,6-tetramethyl-3,5-heptanedionate [TMH]), (1,3-diphenyl-1,3-propanedionate [DI])

(4,4,4-trifluoro-1-(2-thienyl)-1,3-butanedionate [TTFA]), (7,7-dimethyl-1,1,1,2,2,3,3-heptafluoro-4,6-octanedionate [FOD]), (1,1,1,3,5,5,5-heptafluoro-2,4-pentanedionate [F7acac]), (1,1,1,5,5,5-hexafluoro-2,4-pentanedionate [F6acac]), -continued

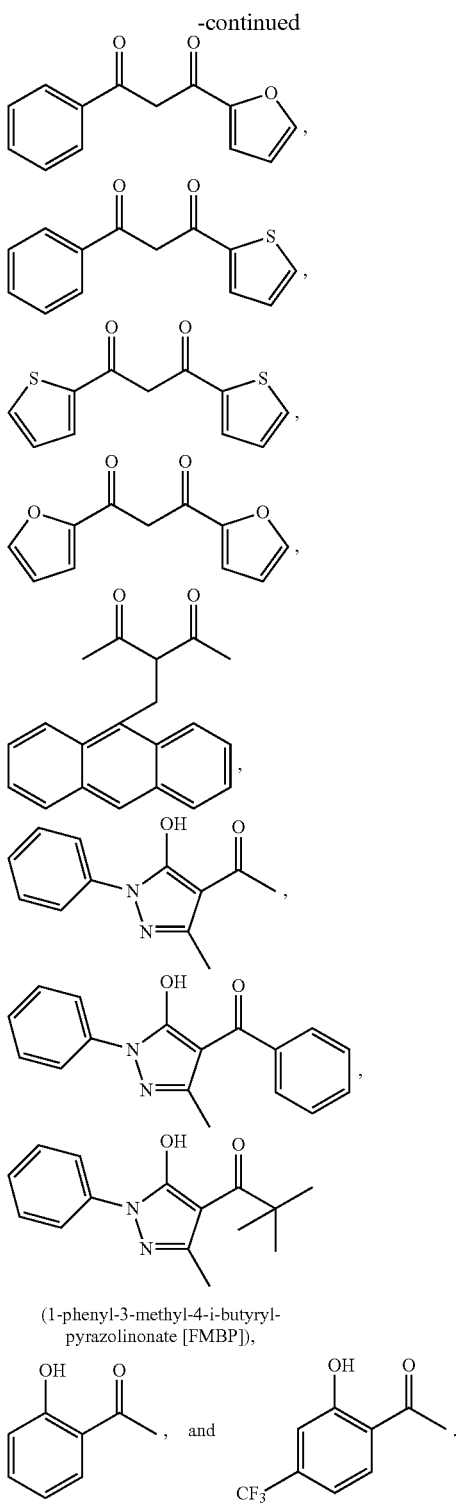

(1-phenyl-3-methyl-4-i-butyryl-pyrazolinonate [FMBP]),

The hydroxyquinoline parent compounds, $HL^3$, can be substituted with groups such as alkyl or alkoxy groups which may be partially or fully fluorinated.

8-hydroxyquinaldine, 7-N-propyl-8-hydroxyquinoline, 5,7-dimethyl-8-hydroxyquinoline, 2-phenyl-quinolin-8-ol, 8-hydroxy-3-methylquinoline, 4-acridinol, 5,7-dibromo-8-hydroxyquinoline, 5,7-dichloro-8-hydroxyquinoline, 5-chloro-8-hydroxy-7-iodoquinoline, 5-chloro-8-hydroxyquinoline, 5,7-diiodo-8-hydroxyquinoline, 7-bromo-5-chloro-8-hydroxyquinoline, 5-fluoro-8-hydroxyquinoline, 2,5,7-trichloro-quinolin-8-ol, 5-hydroxymethyl-quinolin-8-ol, quinoline-2,8-diol, 5-nitro-quinolin-8-ol, 6-nitro-quinolin-8-ol 5-amino-8-hydroxyquinoline dihydrochloride, 5-nitroso-quinolin-8-ol, 2-amino-quinolin-8-ol, 2-(butyl-quinolin-2-yl-amino)-quinolin-8-ol, 7-piperidin-1-ylmethyl-quinolin-8-ol, 5-chloro-7-morpholin-4-ylmethyl-quinolin-8-ol, 8-hydroxy-5-nitro-quinoline-2-carbaldehyde, 8-hydroxy-quinoline-5-carbaldehyde, 8-hydroxy-5,7-dimethyl-quinoline-2-carbaldehyde, 8-hydroxy-quinoline-2-carbaldehyde, 8-hydroxy-quinoline-2-carbonitrile, 2-hydrazino-5,7-dimethyl-quinolin-8-ol, 5-octyloxymethyl-quinolin-8-ol, 5-(chloromethyl)-8-quinolinol hydrochloride, 2-[(E)-2-(5-bromo-thiophen-2-yl)-vinyl]-quinolin-8-ol, 2-[(E)-2-(2-bromo-phenyl)-vinyl]-quinolin-8-ol, and 2-[(E)-2-(2-amino-phenyl)-vinyl]-quinolin-8-ol.

In general, these compounds are commercially available. Examples of especially suitable hydroxyquinolate ligands, $L^3$, include:
8-hydroxyquinolinate [8hq]
2-methyl-8-hydroxyquinolinate [Me-8hq]
10-hydroxybenzoquinolinate [10-hbq].

In a preferred embodiment of the present invention the metal complex of formula I is a compound of formula

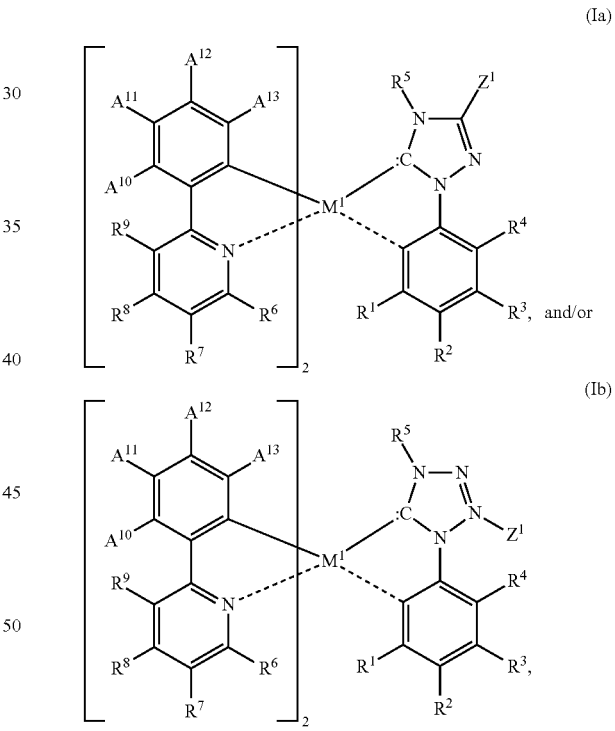

wherein
$M^1$ is Co, or Fe, especially Ir, or Rh,
$R^1$, $R^2$, $R^3$ and $R^4$ are hydrogen, or halogen, especially F, or Cl;
$R^5$ is optionally substituted $C_6$-$C_{10}$aryl, $C_1$-$C_4$alkyl, $C_1$-$C_4$perfluoroalkyl, $C_1$-$C_4$alkoxy, or —O—$C_1$-$C_4$perfluoroalkyl, especially phenyl,
$R^6$ is hydrogen, halogen, especially F, or Cl; nitro, $C_1$-$C_4$alkyl, $C_1$-$C_4$perfluoroalkyl, $C_1$-$C_4$alkoxy, or optionally substituted $C_6$-$C_{10}$aryl, especially phenyl,
$R^7$ is hydrogen, halogen, especially F, or Cl; $C_1$-$C_4$alkyl, $C_1$-$C_4$perfluoroalkyl, optionally substituted $C_6$-$C_{10}$aryl, especially phenyl, or optionally substituted $C_6$-$C_{10}$perfluoroaryl, especially $C_6F_5$, $R^8$ is hydrogen, $C_1$-$C_4$alkyl, $C_1$-$C_8$alkoxy, $C_1$-$C_4$perfluoroalkyl, optionally substituted $C_6$-$C_{10}$aryl, especially phenyl, or optionally substituted $C_6$-$C_{10}$perfluoroaryl, especially $C_6F_5$, $R^9$ is hydrogen, halogen, especially F, or Cl; nitro, cyano, $C_1$-$C_4$alkyl, $C_1$-$C_4$perfluoroalkyl, $C_1$-$C_4$alkoxy, or optionally substituted $C_6$-$C_{10}$aryl, especially phenyl, $A^{10}$ is hydrogen, halogen, especially F, or Cl; nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, especially tri(methyl)silanyl, optionally substituted $C_6$-$C_{10}$aryl, especially phenyl, or optionally substituted $C_6$-$C_{10}$perfluoroaryl, especially $C_6F_5$, $A^{11}$ is hydrogen, halogen, especially F, or Cl; nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, especially tri(methyl)silanyl, optionally substituted $C_6$-$C_{10}$aryl, especially phenyl, or optionally substituted $C_6$-$C_{10}$perfluoroaryl, especially $C_6F_5$, $A^{12}$ is hydrogen, halogen, especially F, or Cl; nitro, hydroxy, mercapto, amino, $C_1$-$C_4$alkyl, $C_2$-$C_4$alkenyl, $C_1$-$C_4$perfluoroalkyl, $C_1$-$C_4$alkoxy, —O—$C_1$-$C_4$perfluoroalkyl, —S—$C_1$-$C_4$alkyl, a group —$(CH_2)_rX^{20}$, wherein r is 1, or 2, $X^{20}$ is halogen, especially F, or Cl; hydroxy, cyano, —O—$C_1$-$C_4$alkyl, di($C_1$-$C_4$alkyl)amino, —$CO_2X^{21}$, wherein $X^{21}$ is H, or $C_1$-$C_4$alkyl; —CH=$CHCO_2X^{22}$, wherein $X^{22}$ is $C_1$-$C_4$alkyl; —CH(O), —$SO_2X^{23}$, —$SOX^{23}$, —$NC(O)X^{23}$, —$NSO_2X^{23}$, —$NHX^{23}$, —$N(X^{23})_2$, wherein $X^{23}$ is $C_1$-$C_4$alkyl; tri($C_1$-$C_4$alkyl)siloxanyl, optionally substituted —O—$C_6$-$C_{10}$aryl, especially phenoxy, cyclohexyl, optionally substituted $C_6$-$C_{10}$aryl, especially phenyl, or optionally substituted $C_6$-$C_{10}$perfluoroaryl, especially $C_6F_5$, $A^{13}$ is hydrogen, nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, or optionally substituted $C_6$-$C_{10}$aryl, especially phenyl, and $Z^1$ is $C_1$-$C_4$perfluoroalkyl, or optionally substituted $C_6$-$C_{10}$aryl, especially phenyl.

Examples of specific compounds are compounds A-1 to A-320 and A'-1 to A'-320 (see claim 7). Special emphasis among them is given to compounds A-1 to A-58 and A-60 to A-79, especially A-1, A-2, A-4 to A-7, A-10, A-12, A-17, A-18, A-23 to A-26, A-32, A-36, A-39, A-40, A-42, A-43, A-45, A-47 to A-50, A-53 to A-55, A-71, A-72, A-77, A-79. Compounds of special industrial importance among them are the compounds of type A as well as A', corresponding to the above formulae (Ia) and (Ib) wherein $M^1$ is Ir, of the numbers 1-7, 9, 12, 17-18, 24, 32, 34, 36, 38-40, 42-43, 45, 47, 49-50, 53-54, 71-74, 76-77, 80-83, 85-117, 119, 122, 127-128, 134, 142, 144, 146, 148-150, 152-153, 155, 157, 159-160, 163-164, 181-184, 186-187, 190-193, 195-217, 219, 222, 227-228, 234, 242, 244, 246, 248-250, 252-253, 255, 257, 259-260, 263-263, 281-284, 286-287, 290-293, 295-320.

Examples for more preferred embodiments include compounds of the above formula (Ib) or especially (Ia) wherein $R^1$, $R^2$, $R^3$, $R^4$, $R^6$ and $A^{13}$ each are hydrogen;

$R^5$ is optionally substituted $C_6$-$C_{10}$aryl such as phenyl;

$Z^1$ is $CF_3$ or phenyl or substituted phenyl;

$R^7$ is hydrogen, F or $CF_3$;

one of $R^8$ and $R^9$, especially $R^8$, is hydrogen, $C_1$-$C_4$alkyl, $C_1$-$C_8$alkoxy, and the other is hydrogen; or $R^8$ and $R^9$, together with the carbon atoms they are bonding to, form an annellated aromatic, optionally substituted, carbocyclic 6-membered ring, an example for $R^8$ and $R^9$ together thus being the divalent moiety —CH=CH—CH=CH—;

and $A^{10}$, $A^{11}$ and $A^{12}$ independently are selected from hydrogen, F, $CF_3$, CN, such as the compounds:

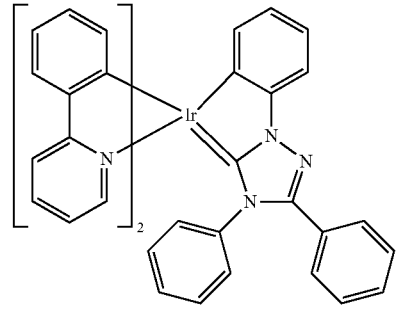

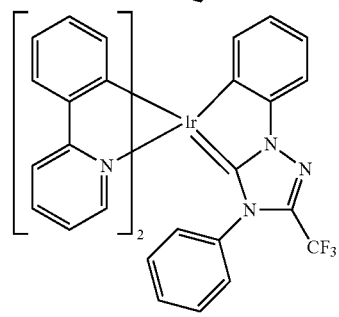

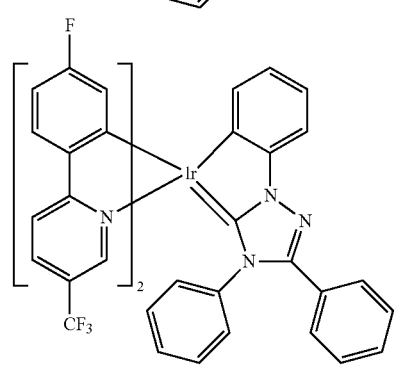

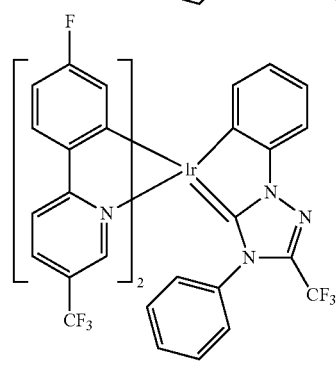

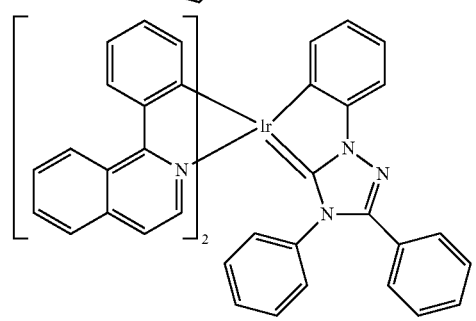

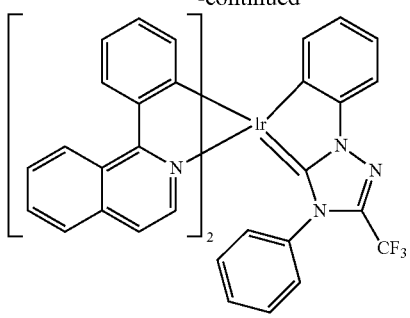

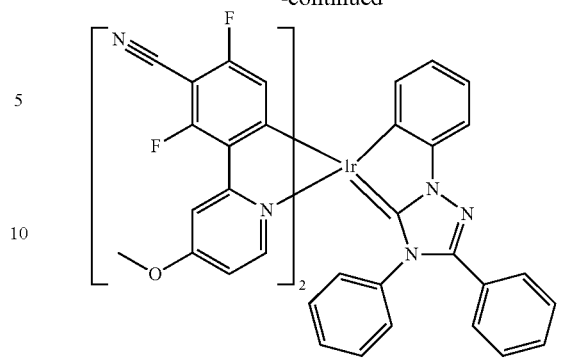

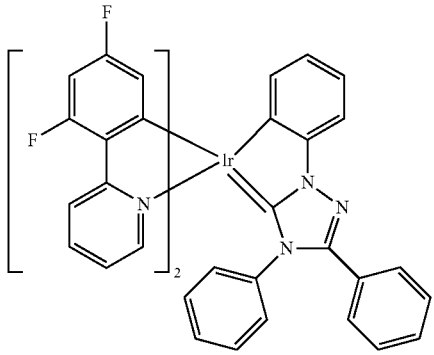

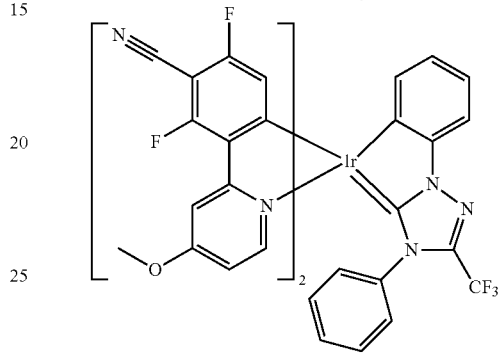

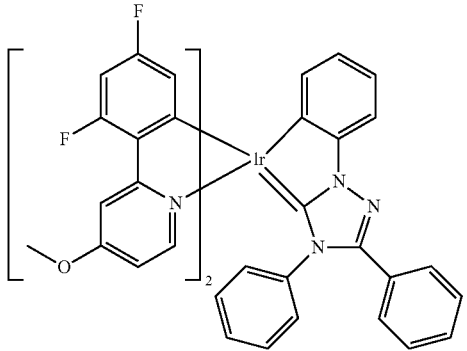

In a preferred embodiment of the present invention the metal complex of formula I is a compound of formula

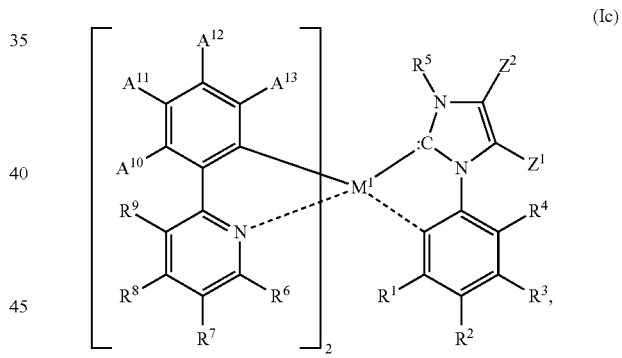

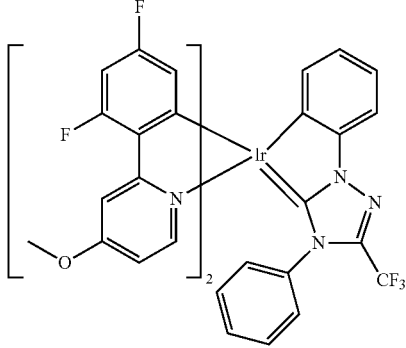

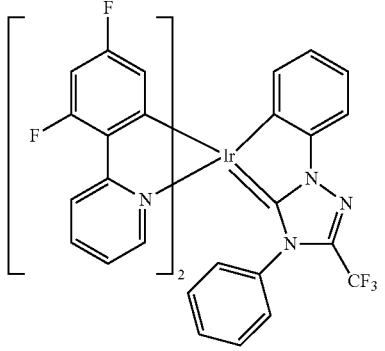

wherein $M^1$ is Co, or Fe, especially Ir, or Rh, $R^1, R^2, R^3$ and $R^4$ are hydrogen, or halogen, especially F, or Cl;

$R^5$ is optionally substituted $C_6$-$C_{10}$aryl, $C_1$-$C_4$alkyl, $C_1$-$C_4$perfluoroalkyl, $C_1$-$C_4$alkoxy, or —O—$C_1$-$C_4$perfluoroalkyl, especially phenyl, $R^6$ is hydrogen, halogen, especially F, or Cl; nitro, $C_1$-$C_4$alkyl, $C_1$-$C_4$perfluoroalkyl, $C_1$-$C_4$alkoxy, or optionally substituted $C_6$-$C_{10}$aryl, especially phenyl, $R^7$ is hydrogen, halogen, especially F, or Cl; $C_1$-$C_4$alkyl, $C_1$-$C_4$perfluoroalkyl, optionally substituted $C_6$-$C_{10}$aryl, especially phenyl, or optionally substituted $C_6$-$C_{10}$perfluoroaryl, especially $C_6F_5$, $R^8$ is hydrogen, $C_1$-$C_4$alkyl, $C_1$-$C_8$alkoxy, $C_1$-$C_4$perfluoroalkyl, optionally substituted $C_6$-$C_{10}$aryl, especially phenyl, or optionally substituted $C_6$-$C_{10}$perfluoroaryl, especially $C_6F_5$, $R^9$ is hydrogen, halogen, especially F, or Cl; nitro, cyano, $C_1$-$C_4$alkyl, $C_1$-$C_4$perfluoroalkyl, $C_1$-$C_4$alkoxy, or optionally substituted $C_6$-$C_{10}$aryl, especially phenyl, $A^{10}$ is hydrogen, halogen, especially F, or Cl; nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, especially tri(methyl)silanyl, optionally substituted $C_6$-$C_{10}$aryl, especially phenyl, or optionally substituted $C_6$-$C_{10}$perfluoroaryl, especially $C_6F_5$, $A^{11}$ is hydrogen, halogen, especially F, or Cl; nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, especially tri(methyl)silanyl, optionally substituted $C_6$-$C_{10}$aryl, especially phenyl, or optionally substituted $C_6$-$C_{10}$perfluoroaryl, especially $C_6F_5$, $A^{12}$ is hydrogen, halogen, especially F, or Cl; nitro, hydroxy, mercapto, amino, $C_1$-$C_4$alkyl, $C_2$-$C_4$alkenyl, $C_1$-$C_4$perfluoroalkyl, $C_1$-$C_4$alkoxy, —O—$C_1$-$C_4$perfluoroalkyl, —S—$C_1$-$C_4$alkyl, a group —$(CH_2)_rX^{20}$, wherein r is 1, or 2, $X^{20}$ is halogen, especially F, or Cl; hydroxy, cyano, —O—$C_1$-$C_4$alkyl, di($C_1$-$C_4$alkyl)amino, —$CO_2X^{21}$, wherein $X^{21}$ is H, or $C_1$-$C_4$alkyl; —CH=$CHCO_2X^{22}$, wherein $X^{22}$ is $C_1$-$C_4$alkyl; —CH(O), —$SO_2X^{23}$, —$SOX^{23}$, —$NC(O)X^{23}$, —$NSO_2X^{23}$, —$NHX^{23}$, —$N(X^{23})_2$, wherein $X^{23}$ is $C_1$-$C_4$alkyl; tri($C_1$-$C_4$alkyl)siloxanyl, optionally substituted —O—$C_6$-$C_{10}$aryl, especially phenoxy, cyclohexyl, optionally substituted $C_6$-$C_{10}$aryl, especially phenyl, or optionally substituted $C_6$-$C_{10}$perfluoroaryl, especially $C_6F_5$, $A^{13}$ is hydrogen, nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, or optionally substituted $C_6$-$C_{10}$aryl, especially phenyl, and $Z^1$ and $Z^2$ are independently of each other $C_1$-$C_4$perfluoroalkyl, or optionally substituted $C_6$-$C_{10}$aryl, especially hydrogen.

Examples of specific compounds are compounds B-1 to B-110 or B'-1 to B'-79 (see claim 7). Special emphasis among them is given to compounds B'-1 to B'-79, especially B'-1, B'-2, B'-4 to B'-7, B'-10, B'-12, B'-17, B'-18, B'-24 to B'-26, B'-32, B'-34, B'-36, B'-39, B'-40, B'-42, B'-43, B'-45, B'-47 to B'-50, B'-53 to B'-55, B'-71, B'-72, B'-76, B'-78. Compounds of special industrial importance are the compounds of type B, corresponding to the above formula (Ic) wherein $M^1$ is Ir, of the numbers 1-7, 9, 12, 17-18, 24, 32, 34, 36, 38-40, 42-43, 45, 47, 49-50, 53-54, 71-74, 76-77, 80-83, and 85-110.

In a preferred embodiment of the present invention the metal complex of formula I is a compound of formula (Id)

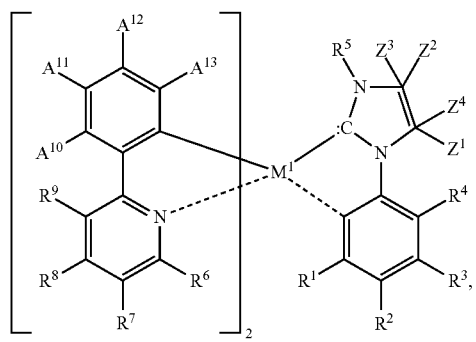

wherein $M^1$ is Co, or Fe, especially Ir, or Rh, $R^1$, $R^2$, $R^3$ and $R^4$ are hydrogen, or halogen, especially F, or Cl;

$R^5$ is optionally substituted $C_6$-$C_{10}$aryl, $C_1$-$C_4$alkyl, $C_1$-$C_4$perfluoroalkyl, $C_1$-$C_4$alkoxy, or —O—$C_1$-$C_4$perfluoroalkyl, especially phenyl, $R^6$ is hydrogen, halogen, especially F, or Cl; nitro, $C_1$-$C_4$alkyl, $C_1$-$C_4$perfluoroalkyl, $C_1$-$C_4$alkoxy, or optionally substituted $C_6$-$C_{10}$aryl, especially phenyl, $R^7$ is hydrogen, halogen, especially F, or Cl; $C_1$-$C_4$alkyl, $C_1$-$C_4$perfluoroalkyl, optionally substituted $C_6$-$C_{10}$aryl, especially phenyl, or optionally substituted $C_6$-$C_{10}$perfluoroaryl, especially $C_6F_5$, $R^8$ is hydrogen, $C_1$-$C_4$alkyl, $C_1$-$C_8$alkoxy, $C_1$-$C_4$perfluoroalkyl, optionally substituted $C_6$-$C_{10}$aryl, especially phenyl, or optionally substituted $C_6$-$C_{10}$perfluoroaryl, especially $C_6F_5$, $R^9$ is hydrogen, halogen, especially F, or Cl; nitro, cyano, $C_1$-$C_4$alkyl, $C_1$-$C_4$perfluoroalkyl, $C_1$-$C_4$alkoxy, or optionally substituted $C_6$-$C_{10}$aryl, especially phenyl, $A^{10}$ is hydrogen, halogen, especially F, or Cl; nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, especially tri(methyl)silanyl, optionally substituted $C_6$-$C_{10}$aryl, especially phenyl, or optionally substituted $C_6$-$C_{10}$perfluoroaryl, especially $C_6F_5$, $A^{11}$ is hydrogen, halogen, especially F, or Cl; nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, especially tri(methyl)silanyl, optionally substituted $C_6$-$C_{10}$aryl, especially phenyl, or optionally substituted $C_6$-$C_{10}$perfluoroaryl, especially $C_6F_5$, $A^{12}$ is hydrogen, halogen, especially F, or Cl; nitro, hydroxy, mercapto, amino, $C_1$-$C_4$alkyl, $C_2$-$C_4$alkenyl, $C_1$-$C_4$perfluoroalkyl, $C_1$-$C_4$alkoxy, —O—$C_1$-$C_4$perfluoroalkyl, —S—$C_1$-$C_4$alkyl, a group —$(CH_2)_rX^{20}$, wherein r is 1, or 2, $X^{20}$ is halogen, especially F, or Cl; hydroxy, cyano, —O—$C_1$-$C_4$alkyl, di($C_1$-$C_4$alkyl)amino, —$CO_2X^{21}$, wherein $X^{21}$ is H, or $C_1$-$C_4$alkyl; —CH=$CHCO_2X^{22}$, wherein $X^{22}$ is $C_1$-$C_4$alkyl; —CH(O), —$SO_2X^{23}$, —$SOX^{23}$, —$NC(O)X^{23}$, —$NSO_2X^{23}$, —$NHX^{23}$, —$N(X^{23})_2$, wherein $X^{23}$ is $C_1$-$C_4$alkyl; tri($C_1$-$C_4$alkyl)siloxanyl, optionally substituted —O—$C_6$-$C_{10}$aryl, especially phenoxy, cyclohexyl, optionally substituted $C_6$-$C_{10}$aryl, especially phenyl, or optionally substituted $C_6$-$C_{10}$perfluoroaryl, especially $C_6F_5$, $A^{13}$ is hydrogen, nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, or optionally substituted $C_6$-$C_{10}$aryl, especially phenyl, and $Z^1$, $Z^2$, $Z^3$, $Z^4$, $Z^5$ and are independently of each other selected from the group consisting of hydrogen, $C_1$-$C_{24}$alkyl, $C_1$-$C_{24}$halogenalkyl, $C_1$-$C_8$perfluoroalkyl, $C_2$-$C_{24}$alkenyl, $C_2$-$C_{24}$alkynyl, $C_2$-$C_{24}$alkoxycarbonyl, aryl, which can optionally be substituted, $C_1$-$C_{24}$carboxylate, $C_1$-$C_{24}$alkoxy, $C_2$-$C_{24}$alkenyloxy, $C_2$-$C_{24}$alkynyloxy, or aryloxy, wherein each of $Z^1$, $Z^2$, $Z^3$ and $Z^4$ optionally being substituted with $C_1$-$C_8$alkyl, halogen, $C_1$-$C_8$alkoxy, or with a phenyl group, which can optionally be substituted with halogen, $C_1$-$C_8$alkyl, or $C_1$-$C_8$alkoxy, or $Z^1$ and $Z^2$, if possible, form an aromatic or heteroaromatic ring, and/or $Z^3$, $Z^4$, $Z^5$ and $Z^6$, if possible, form an alkyl or heteroalkyl ring.

Examples of specific compounds are compounds C-1 to C-110 (see claim 7). Compounds of special industrial importance are those compounds C, corresponding to the above formula (Id) wherein $M^1$ is Ir, of the numbers 1-7, 9, 12, 17-18, 24, 32, 34, 36, 38-40, 42-43, 45, 47, 49-50, 53-54, 71-74, 76-77, 80-83, and 85-110.

In a preferred embodiment of the present invention the metal complex of formula I is a compound of formula

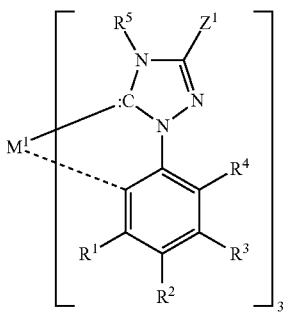

(Ie)

wherein $M^1$ is Co, or Fe, especially Ir, or Rh, $R^1$ is hydrogen, halogen, especially F, or Cl; nitro, cyano, $C_1$-$C_4$alkyl, $C_1$-$C_4$perfluoroalkyl, or $C_1$-$C_4$alkoxy, $R^2$ is hydrogen, halogen, especially F, or Cl; nitro, cyano, $C_1$-$C_4$alkyl, $C_1$-$C_4$perfluoroalkyl, $C_1$-$C_4$alkoxy, —S—$C_1$-$C_4$alkyl, —O—$C_1$-$C_4$perfluoroalkyl, —$SO_2X^{22}$, —$CO_2X^{22}$, wherein $X^{22}$ is $C_1$-$C_4$alkyl; $C_6H_4CF_3$, or optionally substituted —O—$C_6$-$C_{10}$aryl, especially phenoxy, $R^3$ is hydrogen, halogen, especially F, or Cl; nitro, cyano, $C_1$-$C_4$alkyl, $C_1$-$C_4$perfluoroalkyl, $C_1$-$C_4$alkoxy, —S—$C_1$-$C_4$alkyl, or —O—$C_1$-$C_4$perfluoroalkyl, $R^4$ is hydrogen, halogen, especially F, or Cl;

$R^5$ is optionally substituted $C_6$-$C_{10}$aryl, $C_1$-$C_4$alkyl, $C_1$-$C_4$perfluoroalkyl, $C_1$-$C_4$alkoxy, or —O—$C_1$-$C_4$perfluoroalkyl, especially phenyl, and $Z^1$ is $C_1$-$C_4$perfluoroalkyl, or optionally substituted $C_6$-$C_{10}$aryl, especially phenyl.

Examples of specific compounds are compounds D-1 to D-90 (see claim 7); special emphasis among them is given to compounds D-1 to D-30, especially D-2 to D-4, D-6, D-8, D-9, D-11, D-22 to D-28, D-30. Of special industrial importance are those compounds D, corresponding to the above formula (Ie) wherein $M^1$ is Ir, of the numbers 1-4, 6, 8-9, 11, 22-24, 26-28, 31-34, 36, 38-39, 41, 52-54, 56-58, 61-64, 66, 68-69, 71, 82-84, 86-88.

In a preferred embodiment of the present invention the metal complex of formula I is a compound of formula

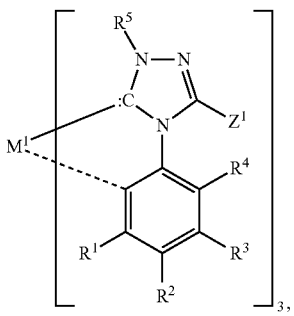

(If)

wherein $M^1$ is Co, or Fe, especially Ir, or Rh, $R^1$ is hydrogen, halogen, especially F, or Cl; nitro, cyano, $C_1$-$C_4$alkyl, $C_1$-$C_4$perfluoroalkyl, or $C_1$-$C_4$alkoxy, $R^2$ is hydrogen, halogen, especially F, or Cl; nitro, cyano, $C_1$-$C_4$alkyl, $C_1$-$C_4$perfluoroalkyl, $C_1$-$C_4$alkoxy, —S—$C_1$-$C_4$alkyl, —O—$C_1$-$C_4$perfluoroalkyl, —$SO_2X^{22}$, —$CO_2X^{22}$, wherein $X^{22}$ is $C_1$-$C_4$alkyl; $C_6H_4CF_3$, or optionally substituted —O—$C_8$-$C_{10}$aryl, especially phenoxy, $R^3$ is hydrogen, halogen, especially F, or Cl; nitro, cyano, $C_1$-$C_4$alkyl, $C_1$-$C_4$perfluoroalkyl, $C_1$-$C_4$alkoxy, —S—$C_1$-$C_4$alkyl, or —O—$C_1$-$C_4$perfluoroalkyl, $R^4$ is hydrogen, halogen, especially F, or Cl;

$R^5$ is optionally substituted $C_8$-$C_{10}$aryl, $C_1$-$C_4$alkyl, $C_1$-$C_4$perfluoroalkyl, $C_1$-$C_4$alkoxy, or —O—$C_1$-$C_4$perfluoroalkyl, especially phenyl, and $Z^1$ is $C_1$-$C_4$perfluoroalkyl, or optionally substituted $C_8$-$C_{10}$aryl, especially phenyl.

Examples of specific compounds are compounds E-1 to E-90 (see claim 7); special emphasis among them is given to compounds E-1 to E-30, especially E-2 to E-4, E-6, E-8, E-9, E-11, E-22 to E-29. Of special industrial importance are those compounds E, corresponding to the above formula (If) wherein $M^1$ is Ir, of the numbers 1-4, 6, 8-9, 11, 22-24, 26-28, 31-34, 36, 38-39, 41, 52-54, 56-58, 61-64, 66, 68-69, 71, 82-84, 86-88.

In a preferred embodiment of the present invention the metal complex of formula I is a compound of formula

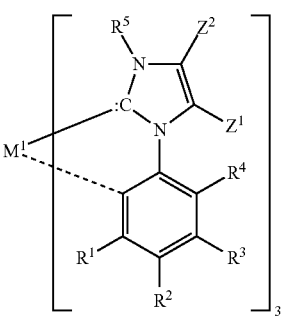

(Ig)

wherein $M^1$ is Co, or Fe, especially Ir, or Rh, $R^1$ is hydrogen, halogen, especially F, or Cl; nitro, cyano, $C_1$-$C_4$alkyl, $C_1$-$C_4$perfluoroalkyl, or $C_1$-$C_4$alkoxy, $R^2$ is hydrogen, halogen, especially F, or Cl; nitro, cyano, $C_1$-$C_4$alkyl, $C_1$-$C_4$perfluoroalkyl, $C_1$-$C_4$alkoxy, —S—$C_1$-$C_4$alkyl, —O—$C_1$-$C_4$perfluoroalkyl, —$SO_2X^{22}$, —$CO_2X^{22}$, wherein $X^{22}$ is $C_1$-$C_4$alkyl; $C_6H_4CF_3$, or optionally substituted —O—$C_8$-$C_{10}$aryl, especially phenoxy, $R^3$ is hydrogen, halogen, especially F, or Cl; nitro, cyano, $C_1$-$C_4$alkyl, $C_1$-$C_4$perfluoroalkyl, $C_1$-$C_4$alkoxy, —S—$C_1$-$C_4$alkyl, or —O—$C_1$-$C_4$perfluoroalkyl, $R^4$ is hydrogen, halogen, especially F, or Cl;

$R^5$ is optionally substituted $C_8$-$C_{10}$aryl, $C_1$-$C_4$alkyl, $C_1$-$C_4$perfluoroalkyl, $C_1$-$C_4$alkoxy, or —O—$C_1$-$C_4$perfluoroalkyl, especially phenyl, and $Z^1$ and $Z^2$ are independently of each other selected from the group consisting of hydrogen, $C_1$-$C_{24}$alkyl, $C_1$-$C_{24}$halogenalkyl, $C_1$-$C_8$perfluoroalkyl, $C_2$-$C_{24}$alkenyl, $C_2$-$C_{24}$alkynyl, $C_2$-$C_{24}$alkoxycarbonyl, aryl, aryl which can be substituted, $C_1$-$C_{24}$carboxylate, $C_1$-$C_{24}$alkoxy, $C_2$-$C_{24}$alkenyloxy, $C_2$-$C_{24}$alkynyloxy, or aryloxy, wherein each of $Z^1$ and $Z^2$ optionally being substituted with $C_1$-$C_8$alkyl, halogen, $C_1$-$C_8$alkoxy, or with a phenyl group, which can optionally be substituted with halogen, $C_1$-$C_8$alkyl, or $C_1$-$C_8$alkoxy, or $Z^1$ and $Z^2$, if possible, form an aromatic or heteroaromatic ring. $Z^1$ is preferably $C_1$-$C_4$perfluoroalkyl, or optionally substituted $C_6$-$C_{10}$aryl, especially phenyl.

Examples of specific compounds are compounds F-1 to F-30 (see claim 7). Of special industrial importance are those compounds F, corresponding to the above formula (Ig) wherein $M^1$ is Ir, of the numbers 1-4, 6, 8-9, 11, 22-24, 26-28.

In a preferred embodiment of the present invention the metal complex of formula I is a compound of formula

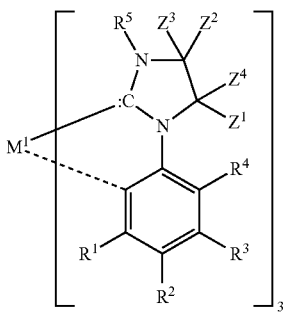
(Ih)

wherein $M^1$ is Co, or Fe, especially Ir, or Rh, $R^1$ is hydrogen, halogen, especially F, or Cl; nitro, cyano, $C_1$-$C_4$alkyl, $C_1$-$C_4$perfluoroalkyl, or $C_1$-$C_4$alkoxy, $R^2$ is hydrogen, halogen, especially F, or Cl; nitro, cyano, $C_1$-$C_4$alkyl, $C_1$-$C_4$perfluoroalkyl, $C_1$-$C_4$alkoxy, —S—$C_1$-$C_4$alkyl, —O—$C_1$-$C_4$perfluoroalkyl, —SO$_2$X$^{22}$, —CO$_2$X$^{22}$, wherein $X^{22}$ is $C_1$-$C_4$alkyl; $C_6H_4CF_3$, or optionally substituted —O—$C_6$-$C_{10}$aryl, especially phenoxy, $R^3$ is hydrogen, halogen, especially F, or Cl; nitro, cyano, $C_1$-$C_4$alkyl, $C_1$-$C_4$perfluoroalkyl, $C_1$-$C_4$alkoxy, —S—$C_1$-$C_4$alkyl, or —O—$C_1$-$C_4$perfluoroalkyl, $R^4$ is hydrogen, halogen, especially F, or Cl;

$R^5$ is optionally substituted $C_6$-$C_{10}$aryl, $C_1$-$C_4$alkyl, $C_1$-$C_4$perfluoroalkyl, $C_1$-$C_4$alkoxy, or —O—$C_1$-$C_4$perfluoroalkyl, especially phenyl, and $Z^1$, $Z^2$, $Z^3$, $Z^4$, and $Z^5$ are independently of each other selected from the group consisting of hydrogen, $C_1$-$C_{24}$alkyl, $C_1$-$C_{24}$halogenalkyl, $C_1$-$C_8$perfluoroalkyl, $C_2$-$C_{24}$alkenyl, $C_2$-$C_{24}$alkynyl, $C_2$-$C_{24}$alkoxycarbonyl, aryl, which can optionally be substituted, $C_1$-$C_{24}$carboxylate, $C_1$-$C_{24}$alkoxy, $C_2$-$C_{24}$alkenyloxy, $C_2$-$C_{24}$alkynyloxy, or aryloxy, wherein each of $Z^1$, $Z^2$, $Z^3$ and $Z^4$ optionally being substituted with $C_1$-$C_8$alkyl, halogen, $C_1$-$C_8$alkoxy, or with a phenyl group, which can optionally be substituted with halogen, $C_1$-$C_8$alkyl, or $C_1$-$C_8$alkoxy, or $Z^1$ and $Z^2$, if possible, form an aromatic or heteroaromatic ring, and/or $Z^3$, $Z^4$, $Z^5$ and $Z^6$, if possible, form an alkyl or heteroalkyl ring. $Z^1$ is preferably $C_1$-$C_4$perfluoroalkyl, or optionally substituted $C_6$-$C_{10}$aryl, especially phenyl.

Examples of specific compounds are compounds G-1 to G-30 (see claim 7).

In a preferred embodiment of the present invention the metal complex of formula I is a compound of formula

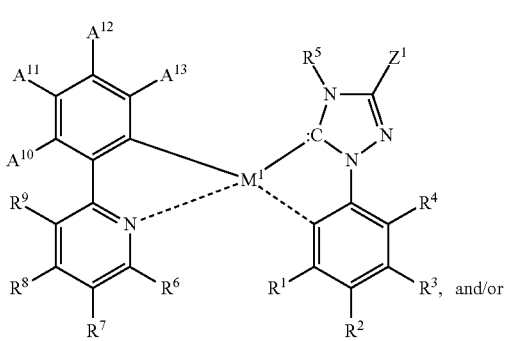
(Ii)

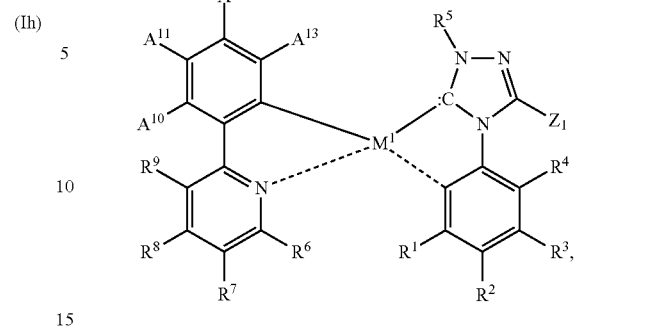
(Ij)

wherein
$M^1$ is Ni, Rh, or Ru, especially Pd, or Pt,
$R^1$, $R^2$, $R^3$ and $R^4$ are hydrogen, or halogen, especially F, or Cl;
$R^5$ is optionally substituted $C_6$-$C_{10}$aryl, $C_1$-$C_4$alkyl, $C_1$-$C_4$perfluoroalkyl, $C_1$-$C_4$alkoxy, or —O—$C_1$-$C_4$perfluoroalkyl, especially phenyl,
$R^6$ is hydrogen, halogen, especially F, or Cl; nitro, $C_1$-$C_4$alkyl, $C_1$-$C_4$perfluoroalkyl, $C_1$-$C_4$alkoxy, or optionally substituted $C_6$-$C_{10}$aryl, especially phenyl,
$R^7$ is hydrogen, halogen, especially F, or Cl; $C_1$-$C_4$alkyl, $C_1$-$C_4$perfluoroalkyl, optionally substituted $C_6$-$C_{10}$aryl, especially phenyl, or optionally substituted $C_6$-$C_{10}$perfluoroaryl, especially $C_6F_5$,
$R^8$ is hydrogen, $C_1$-$C_4$alkyl, $C_1$-$C_8$alkoxy, $C_1$-$C_4$perfluoroalkyl, optionally substituted $C_6$-$C_{10}$aryl, especially phenyl, or optionally substituted $C_6$-$C_{10}$perfluoroaryl, especially $C_6F_5$,
$R^9$ is hydrogen, halogen, especially F, or Cl; nitro, cyano, $C_1$-$C_4$alkyl, $C_1$-$C_4$perfluoroalkyl, $C_1$-$C_4$alkoxy, or optionally substituted $C_6$-$C_{10}$aryl, especially phenyl,
$A^{10}$ is hydrogen, halogen, especially F, or Cl; nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, especially tri(methyl)silanyl, optionally substituted $C_6$-$C_{10}$aryl, especially phenyl, or optionally substituted $C_6$-$C_{10}$perfluoroaryl, especially $C_6F_5$,
$A^{11}$ is hydrogen, halogen, especially F, or Cl; nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, especially tri(methyl)silanyl, optionally substituted $C_6$-$C_{10}$aryl, especially phenyl, or optionally substituted $C_6$-$C_{10}$perfluoroaryl, especially $C_6F_5$,
$A^{12}$ is hydrogen, halogen, especially F, or Cl; nitro, hydroxy, mercapto, amino, $C_1$-$C_4$alkyl, $C_2$-$C_4$alkenyl, $C_1$-$C_4$perfluoroalkyl, $C_1$-$C_4$alkoxy, —O—$C_1$-$C_4$perfluoroalkyl, —S—$C_1$-$C_4$alkyl, a group —(CH$_2$)$_r$X$^{20}$, wherein r is 1, or 2, $X^{20}$ is halogen, especially F, or Cl; hydroxy, cyano, —O—$C_1$-$C_4$alkyl, di($C_1$-$C_4$alkyl)amino, —CO$_2$X$^{21}$, wherein $X^{21}$ is H, or $C_1$-$C_4$alkyl; —CH═CHCO$_2$X$^{22}$, wherein $X^{22}$ is $C_1$-$C_4$alkyl; —CH(O), —SO$_2$X$^{23}$, —SOX$^{23}$, —NC(O)X$^{23}$, —NSO$_2$X$^{23}$, —NHX$^{23}$, —N(X$^{23}$)$_2$, wherein $X^{23}$ is $C_1$-$C_4$alkyl; tri($C_1$-$C_4$alkyl)siloxanyl, optionally substituted —O—$C_6$-$C_{10}$aryl, especially phenoxy, cyclohexyl, optionally substituted $C_6$-$C_{10}$aryl, especially phenyl, or optionally substituted $C_6$-$C_{10}$perfluoroaryl, especially $C_6F_5$,
$A^{13}$ is hydrogen, nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, or optionally substituted $C_6$-$C_{10}$aryl, especially phenyl, and $Z^1$ is $C_1$-$C_4$perfluoroalkyl, or optionally substituted $C_6$-$C_{10}$aryl, especially phenyl.

Examples of specific compounds are compounds H-1 to H-320 and H'-1 to H'-330 (see claim 7); special emphasis among them is given to compounds H-1 to H-58, H-60 to H-79, H'-1 to H'-58, and H'-60 to H'-79; especially to H-1, H-2, H-4 to H-7, H-10, H-12, H-17, H-18, H-24 to H-26, H-32, H-34, H-36, H-39, H-40, H-42, H-43, H-45, H-47 to 50, H-53 to H-55, H-71, H-72, H-76, H-78, H'-1, H'-2, H'-4 to H'-7, H'-10, H'-12, H'-17, H'-18, H'-24 to H'-26, H'-32, H'-34, H'-36, H'-39, H'-40, H'-42, H'-43, H'-45, H'-47 to H'-50, H'-53 to H'-55, H'-71, H'-76, H'-78. Of special industrial importance are those compounds H, corresponding to the above formula (Ii) wherein $M^1$ is Pt, of the numbers 1-7, 9, 12, 17-18, 24, 32, 34, 36, 38-40, 42-43, 45, 47, 49-50, 53-54, 71-74, 76-77, 80-83, 85-117, 119, 127-128, 134, 142, 144, 146, 148-150, 152-153, 155, 157, 159-160, 163-164, 181-184, 186-187, 190-193, 195-219, 222, 227-228, 234, 242, 244, 246, 248-250, 252-253, 255, 257, 259-260, 263-264, 281-284, 286-287, 290-293, 295-320; or those compounds H', corresponding to the above formula (Ij) wherein $M^1$ is Pt, of the numbers 1-7, 9, 12, 17-18, 24, 32, 34, 36, 38-40, 42-43, 45, 47, 49-50, 53-54, 71-74, 76-77, 80-83, 85-117, 119, 127-128, 134, 142, 144, 146, 148-150, 152-153, 155, 157, 159-160, 163-164, 181-184, 186-187, 190-193, 195-227, 229, 232, 237-238, 244, 252, 254, 256, 258-260, 262-263, 265, 267, 269-270, 273-274, 291-294, 296-297, 300-303, 305-330.

In a preferred embodiment of the present invention the metal complex of formula I is a compound of formula

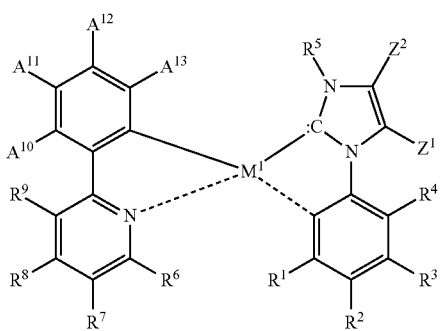

(Ik)

wherein $M^1$ is Ni, Rh, or Ru, especially Pd, or Pt, $R^1$, $R^2$, $R^3$ and $R^4$ are hydrogen, or halogen, especially F, or Cl;

$R^5$ is optionally substituted $C_6$-$C_{10}$aryl, $C_1$-$C_4$alkyl, $C_1$-$C_4$perfluoroalkyl, $C_1$-$C_4$alkoxy, or —O—$C_1$-$C_4$perfluoroalkyl, especially phenyl, $R^6$ is hydrogen, halogen, especially F, or Cl; nitro, $C_1$-$C_4$alkyl, $C_1$-$C_4$perfluoroalkyl, $C_1$-$C_4$alkoxy, or optionally substituted $C_6$-$C_{10}$aryl, especially phenyl, $R^7$ is hydrogen, halogen, especially F, or Cl; $C_1$-$C_4$alkyl, $C_1$-$C_4$perfluoroalkyl, optionally substituted $C_6$-$C_{10}$aryl, especially phenyl, or optionally substituted $C_6$-$C_{10}$perfluoroaryl, especially $C_6F_5$, $R^8$ is hydrogen, $C_1$-$C_4$alkyl, $C_1$-$C_8$alkoxy, $C_1$-$C_4$perfluoroalkyl, optionally substituted $C_6$-$C_{10}$aryl, especially phenyl, or optionally substituted $C_6$-$C_{10}$perfluoroaryl, especially $C_6F_5$, $R^9$ is hydrogen, halogen, especially F, or Cl; nitro, cyano, $C_1$-$C_4$alkyl, $C_1$-$C_4$perfluoroalkyl, $C_1$-$C_4$alkoxy, or optionally substituted $C_6$-$C_{10}$aryl, especially phenyl, $A^{10}$ is hydrogen, halogen, especially F, or Cl; nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, especially tri(methyl)silanyl, optionally substituted $C_6$-$C_{10}$aryl, especially phenyl, or optionally substituted $C_6$-$C_{10}$perfluoroaryl, especially $C_6F_5$, $A^{11}$ is hydrogen, halogen, especially F, or Cl; nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, especially tri(methyl)silanyl, optionally substituted $C_6$-$C_{10}$aryl, especially phenyl, or optionally substituted $C_6$-$C_{10}$perfluoroaryl, especially $C_6F_5$, $A^{12}$ is hydrogen, halogen, especially F, or Cl; nitro, hydroxy, mercapto, amino, $C_1$-$C_4$alkyl, $C_2$-$C_4$alkenyl, $C_1$-$C_4$perfluoroalkyl, $C_1$-$C_4$alkoxy, —O—$C_1$-$C_4$perfluoroalkyl, —S—$C_1$-$C_4$alkyl, a group —$(CH_2)_rX^{20}$, wherein r is 1, or 2, $X^{20}$ is halogen, especially F, or Cl; hydroxy, cyano, —O—$C_1$-$C_4$alkyl, di($C_1$-$C_4$alkyl)amino, —$CO_2X^{21}$, wherein $X^{21}$ is H, or $C_1$-$C_4$alkyl; —CH=CHCO$_2X^{22}$, wherein $X^{22}$ is $C_1$-$C_4$alkyl; —CH(O), —$SO_2X^{23}$, —$SOX^{23}$, —NC(O)$X^{23}$, —NSO$_2X^{23}$, NHX$^{23}$, —N($X^{23}$)$_2$, wherein $X^{23}$ is $C_1$-$C_4$alkyl; tri($C_1$-$C_4$alkyl)siloxanyl, optionally substituted —O—$C_6$-$C_{10}$aryl, especially phenoxy, cyclohexyl, optionally substituted $C_6$-$C_{10}$aryl, especially phenyl, or optionally substituted $C_6$-$C_{10}$perfluoroaryl, especially $C_6F_5$, $A^{13}$ is hydrogen, nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, or optionally substituted $C_6$-$C_{10}$aryl, especially phenyl, and $Z^1$ and $Z^2$ are independently of each other selected from the group consisting of hydrogen, $C_1$-$C_{24}$alkyl, $C_1$-$C_{24}$halogenalkyl, $C_1$-$C_8$perfluoroalkyl, $C_2$-$C_{24}$alkenyl, $C_2$-$C_{24}$alkynyl, $C_2$-$C_{24}$alkoxycarbonyl, aryl, aryl which can be substituted, $C_1$-$C_{24}$carboxylate, $C_1$-$C_{24}$alkoxy, $C_2$-$C_{24}$alkenyloxy, $C_2$-$C_{24}$alkynyloxy, or aryloxy. wherein each of $Z^1$ and $Z^2$ optionally being substituted with $C_1$-$C_8$alkyl, halogen, $C_1$-$C_8$alkoxy, or with a phenyl group, which can optionally be substituted with halogen, $C_1$-$C_8$alkyl, or $C_1$-$C_8$alkoxy, or $Z^1$ and $Z^2$, if possible, form an aromatic or heteroaromatic ring.

Examples of specific compounds are compounds I-1 to I-110 (see claim 7). Of special industrial importance are those compounds I, corresponding to the above formula (Ik) wherein $M^1$ is Pt, of the numbers 1-7, 9, 12, 17-18, 24, 32, 34, 36, 38-40, 42-43, 45, 47, 49-50, 53-54, 71-74, 76-77, 80-83, 85-110.

In a preferred embodiment of the present invention the metal complex of formula I is a compound of formula

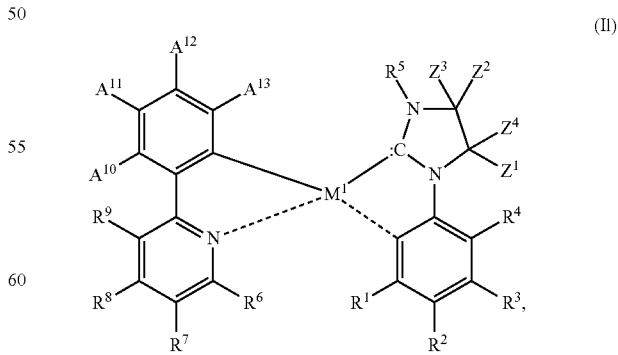

(Il)

wherein $M^1$ is Ni, Rh, or Ru, especially Pd, or Pt, $R^1$, $R^2$, $R^3$ and $R^4$ are hydrogen, or halogen, especially F, or Cl;

$R^5$ is optionally substituted $C_6$-$C_{10}$aryl, $C_1$-$C_4$alkyl, $C_1$-$C_4$perfluoroalkyl, $C_1$-$C_4$alkoxy, or —O—$C_1$-$C_4$perfluoroalkyl, especially phenyl, $R^6$ is hydrogen, halogen, especially F, or Cl; nitro, $C_1$-$C_4$alkyl, $C_1$-$C_4$perfluoroalkyl, $C_1$-$C_4$alkoxy, or optionally substituted $C_6$-$C_{10}$aryl, especially phenyl, $R^7$ is hydrogen, halogen, especially F, or Cl; $C_1$-$C_4$alkyl, $C_1$-$C_4$perfluoroalkyl, optionally substituted $C_6$-$C_{10}$aryl, especially phenyl, or optionally substituted $C_6$-$C_{10}$perfluoroaryl, especially $C_6F_5$, $R^8$ is hydrogen, $C_1$-$C_4$alkyl, $C_1$-$C_8$alkoxy, $C_1$-$C_4$perfluoroalkyl, optionally substituted $C_6$-$C_{10}$aryl, especially phenyl, or optionally substituted $C_6$-$C_{10}$perfluoroaryl, especially $C_6F_5$, $R^9$ is hydrogen, halogen, especially F, or Cl; nitro, cyano, $C_1$-$C_4$alkyl, $C_1$-$C_4$perfluoroalkyl, $C_1$-$C_4$alkoxy, or optionally substituted $C_6$-$C_{10}$aryl, especially phenyl, $A^{10}$ is hydrogen, halogen, especially F, or Cl; nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, especially tri(methyl)silanyl, optionally substituted $C_6$-$C_{10}$aryl, especially phenyl, or optionally substituted $C_6$-$C_{10}$perfluoroaryl, especially $C_6F_5$, $A^{11}$ is hydrogen, halogen, especially F, or Cl; nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, especially tri(methyl)silanyl, optionally substituted $C_6$-$C_{10}$aryl, especially phenyl, or optionally substituted $C_6$-$C_{10}$perfluoroaryl, especially $C_6F_5$, $A^{12}$ is hydrogen, halogen, especially F, or Cl; nitro, hydroxy, mercapto, amino, $C_1$-$C_4$alkyl, $C_2$-$C_4$alkenyl, $C_1$-$C_4$perfluoroalkyl, $C_1$-$C_4$alkoxy, —O—$C_1$-$C_4$perfluoroalkyl, —S—$C_1$-$C_4$alkyl, a group —$(CH_2)_rX^{20}$, wherein r is 1, or 2, $X^{20}$ is halogen, especially F, or Cl; hydroxy, cyano, —O—$C_1$-$C_4$alkyl, di($C_1$-$C_4$alkyl)amino, —$CO_2X^{21}$, wherein $X^{21}$ is H, or $C_1$-$C_4$alkyl; —CH=$CHCO_2X^{22}$, wherein $X^{22}$ is $C_1$-$C_4$alkyl; —CH(O), —$SO_2X^{23}$, —$SOX^{23}$, —$NC(O)X^{23}$, —$NSO_2X^{23}$, —$NHX^{23}$, —$N(X^{23})_2$, wherein $X^{23}$ is $C_1$-$C_4$alkyl; tri($C_1$-$C_4$alkyl)siloxanyl, optionally substituted —O—$C_6$-$C_{10}$aryl, especially phenoxy, cyclohexyl, optionally substituted $C_6$-$C_{10}$aryl, especially phenyl, or optionally substituted $C_6$-$C_{10}$perfluoroaryl, especially $C_6F_5$, $A^{13}$ is hydrogen, nitro, cyano, $C_1$-$C_4$alkyl, $C_2$-$C_4$alkenyl, $C_1$-$C_4$perfluoroalkyl, —O—$C_1$-$C_4$perfluoroalkyl, tri($C_1$-$C_4$alkyl)silanyl, or optionally substituted $C_6$-$C_{10}$aryl, especially phenyl, and $Z^1$, $Z^2$, $Z^3$, and $Z^4$ are independently of each other selected from the group consisting of hydrogen, $C_1$-$C_{24}$alkyl, $C_1$-$C_{24}$halogenalkyl, $C_1$-$C_8$perfluoroalkyl, $C_2$-$C_{24}$alkenyl, $C_2$-$C_{24}$alkynyl, $C_2$-$C_{24}$alkoxycarbonyl, aryl, aryl which can be substituted, $C_1$-$C_{24}$carboxylate, $C_1$-$C_{24}$alkoxy, $C_2$-$C_{24}$alkenyloxy, $C_2$-$C_{24}$alkynyloxy, or aryloxy, wherein each of $Z^1$, $Z^2$, $Z^3$ and $Z^4$ optionally being substituted with $C_1$-$C_8$alkyl, halogen, $C_1$-$C_8$alkoxy, or with a phenyl group, which can optionally be substituted with halogen, $C_1$-$C_8$alkyl, or $C_1$-$C_8$alkoxy, or $Z^1$ and $Z^2$, if possible, form an aromatic or heteroaromatic ring, and/or $Z^3$ and $Z^4$, if possible, form an alkyl or heteroalkyl ring.

Examples of specific compounds are compounds J-1 to J-110 (see claim 7). Of special industrial importance are those compounds J, corresponding to the above formula (II) wherein $M^1$ is Pt, of the numbers 1-7, 9, 12, 17-18, 24, 32, 34, 36, 38-40, 42-43, 45, 47, 49-50, 53-54, 71-74, 76-77, 80-83, 85-110.

In a preferred embodiment of the present invention the metal complex of formula I is a compound of formula

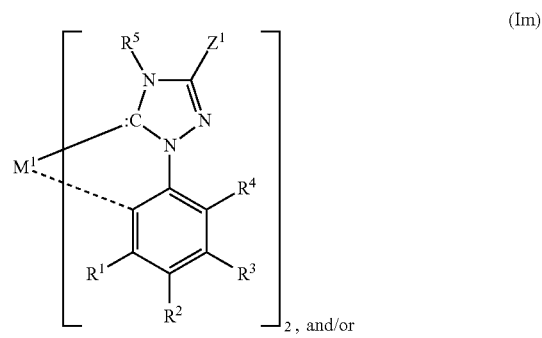

(Im)

, and/or

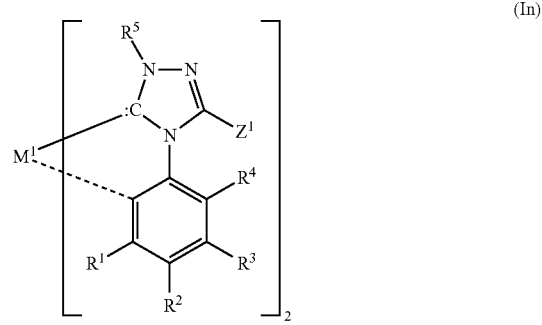

(In)

wherein $M^1$ Ni, Rh, or Ru, especially Pd, or Pt, $R^1$ is hydrogen, halogen, especially F, or Cl; nitro, cyano, $C_1$-$C_4$alkyl, $C_1$-$C_4$perfluoroalkyl, or $C_1$-$C_4$alkoxy, $R^2$ is hydrogen, halogen, especially F, or Cl; nitro, cyano, $C_1$-$C_4$alkyl, $C_1$-$C_4$perfluoroalkyl, $C_1$-$C_4$alkoxy, —S—$C_1$-$C_4$alkyl, —O—$C_1$-$C_4$perfluoroalkyl, —$SO_2X^{22}$, —$CO_2X^{22}$, wherein $X^{22}$ is $C_1$-$C_4$alkyl; $C_6H_4CF_3$, or optionally substituted —O—$C_6$-$C_{10}$aryl, especially phenoxy, $R^3$ is hydrogen, halogen, especially F, or Cl; nitro, cyano, $C_1$-$C_4$alkyl, $C_1$-$C_4$perfluoroalkyl, $C_1$-$C_4$alkoxy, —S—$C_1$-$C_4$alkyl, or —O—$C_1$-$C_4$perfluoroalkyl, $R^4$ is hydrogen, halogen, especially F, or Cl;

$R^5$ is optionally substituted $C_6$-$C_{10}$aryl, $C_1$-$C_4$alkyl, $C_1$-$C_4$perfluoroalkyl, $C_1$-$C_4$alkoxy, or —O—$C_1$-$C_4$perfluoroalkyl, especially phenyl, and $Z^1$ is $C_1$-$C_4$perfluoroalkyl, or optionally substituted $C_6$-$C_{10}$aryl, especially phenyl.

Examples of specific compounds are compounds K-1 to K-90 and K'-1 to K'-90 (see claim 7); special emphasis among them is given to compounds K-1 to K-30 and K'-1 to K'-30; especially to K-2 to K-4, K-6, K-8, K-9, K-11, K-15, K-22 to K-28, K'-2 to K'-4, K'-6, K'-8, K'-9, K'-11, K'-15, K'-22 to K'-28. Of special industrial importance are those compounds K and K', corresponding to the above formulae (Im) and (In) wherein $M^1$ is Pt, of the numbers 1-6, 8-9, 11, 23-25, 27-29, 31-36, 38-39, 41, 52-54, 56-58, 61-66, 68-69, 71, 82-84, 86-88.

In a preferred embodiment of the present invention the metal complex of formula I is a compound of formula

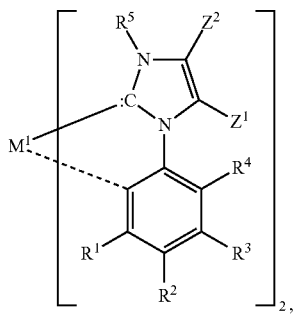

(Io)

wherein $M^1$ is Ni, Rh, or Ru, especially Pd, or Pt, $R^1$ is hydrogen, halogen, especially F, or Cl; nitro, cyano, $C_1$-$C_4$alkyl, $C_1$-$C_4$perfluoroalkyl, or $C_1$-$C_4$alkoxy, $R^2$ is hydrogen, halogen, especially F, or Cl; nitro, cyano, $C_1$-$C_4$alkyl, $C_1$-$C_4$perfluoroalkyl, $C_1$-$C_4$alkoxy, —S—$C_1$-$C_4$alkyl, —O—$C_1$-$C_4$perfluoroalkyl, —$SO_2X^{22}$, —$CO_2X^{22}$, wherein $X^{22}$ is $C_1$-$C_4$alkyl; $C_6H_4CF_3$, or optionally substituted —O—$C_6$-$C_{10}$aryl, especially phenoxy, $R^3$ is hydrogen, halogen, especially F, or Cl; nitro, cyano, $C_1$-$C_4$alkyl, $C_1$-$C_4$perfluoroalkyl, $C_1$-$C_4$alkoxy, —S—$C_1$-$C_4$alkyl, or —O—$C_1$-$C_4$perfluoroalkyl, $R^4$ is hydrogen, halogen, especially F, or Cl;

$R^5$ is optionally substituted $C_6$-$C_{10}$aryl, $C_1$-$C_4$alkyl, $C_1$-$C_4$perfluoroalkyl, $C_1$-$C_4$alkoxy, or —O—$C_1$-$C_4$perfluoroalkyl, especially phenyl, and $Z^1$ and $Z^2$ are independently of each other selected from the group consisting of hydrogen, $C_1$-$C_{24}$alkyl, $C_1$-$C_{24}$halogenalkyl, $C_1$-$C_8$perfluoroalkyl, $C_2$-$C_{24}$alkenyl, $C_2$-$C_{24}$alkynyl, $C_2$-$C_{24}$alkoxycarbonyl, aryl, aryl which can be substituted, $C_1$-$C_{24}$carboxylate, $C_1$-$C_{24}$alkoxy, $C_2$-$C_{24}$alkenyloxy, $C_2$-$C_{24}$alkynyloxy, or aryloxy, wherein each of $Z^1$ and $Z^2$ optionally being substituted with $C_1$-$C_8$alkyl, halogen, $C_1$-$C_8$alkoxy, or with a phenyl group, which can optionally be substituted with halogen, $C_1$-$C_8$alkyl, or $C_1$-$C_8$alkoxy, or $Z^1$ and $Z^2$, if possible, form an aromatic or heteroaromatic ring. $Z^1$ is preferably $C_1$-$C_4$perfluoroalkyl, or optionally substituted $C_6$-$C_{10}$aryl, especially phenyl.

Examples of specific compounds are compounds L-1 to L-30 (see claim 7). Of special industrial importance are those compounds L corresponding to the above formula (Io) wherein $M^1$ is Pt, of the numbers 1-6, 8-9, 11, 22-24, 26-28.

In a preferred embodiment of the present invention the metal complex of formula I is a compound of formula

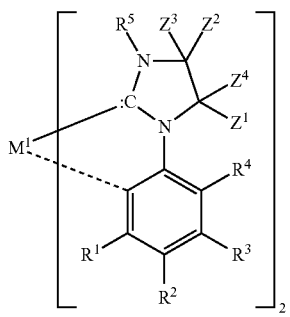

(Ip)

wherein $M^1$ is Ni, Rh, or Ru, especially Pd, or Pt, $R^1$ is hydrogen, halogen, especially F, or Cl; nitro, cyano, $C_1$-$C_4$alkyl, $C_1$-$C_4$perfluoroalkyl, or $C_1$-$C_4$alkoxy, $R^2$ is hydrogen, halogen, especially F, or Cl; nitro, cyano, $C_1$-$C_4$alkyl, $C_1$-$C_4$perfluoroalkyl, $C_1$-$C_4$alkoxy, —S—$C_1$-$C_4$alkyl, —O—$C_1$-$C_4$perfluoroalkyl, —$SO_2X^{22}$, —$CO_2X^{22}$, wherein $X^{22}$ is $C_1$-$C_4$alkyl; $C_6H_4CF_3$, or optionally substituted —O—$C_6$-$C_{10}$aryl, especially phenoxy, $R^3$ is hydrogen, halogen, especially F, or Cl; nitro, cyano, $C_1$-$C_4$alkyl, $C_1$-$C_4$perfluoroalkyl, $C_1$-$C_4$alkoxy, —S—$C_1$-$C_4$alkyl, or —O—$C_1$-$C_4$perfluoroalkyl, $R^4$ is hydrogen, halogen, especially F, or Cl;

$R^5$ is optionally substituted $C_6$-$C_{10}$aryl, $C_1$-$C_4$alkyl, $C_1$-$C_4$perfluoroalkyl, $C_1$-$C_4$alkoxy, or —O—$C_1$-$C_4$perfluoroalkyl, especially phenyl, and $Z^1$, $Z^2$, $Z^3$ and $Z^4$ are independently of each other selected from the group consisting of hydrogen, $C_1$-$C_{24}$alkyl, $C_1$-$C_{24}$halogenalkyl, $C_1$-$C_8$perfluoroalkyl, $C_2$-$C_{24}$alkenyl, $C_2$-$C_{24}$alkynyl, $C_2$-$C_{24}$alkoxycarbonyl, aryl, which can optionally be substituted, $C_1$-$C_{24}$carboxylate, $C_1$-$C_{24}$alkoxy, $C_2$-$C_{24}$alkenyloxy, $C_2$-$C_{24}$alkynyloxy, or aryloxy, wherein each of $Z^1$, $Z^2$, $Z^3$ and $Z^4$ optionally being substituted with $C_1$-$C_8$alkyl, halogen, $C_1$-$C_8$alkoxy, or with a phenyl group, which can optionally be substituted with halogen, $C_1$-$C_8$alkyl, or $C_1$-$C_8$alkoxy, or $Z^1$ and $Z^2$, if possible, form an aromatic or heteroaromatic ring, and/or $Z^3$, $Z^4$, $Z^5$ and $Z^6$, if possible, form an alkyl or heteroalkyl ring. $Z^1$ is preferably $C_1$-$C_4$perfluoroalkyl, or optionally substituted $C_6$-$C_{10}$aryl, especially phenyl.

Examples of specific compounds are compounds M-1 to M-30 (see claim 7). Of special industrial importance are those compounds L corresponding to the above formula (Ip) wherein $M^1$ is Pt, of the numbers 1-6, 8-9, 11, 22-24, 26-28.

Examples of further specific compounds are given below:

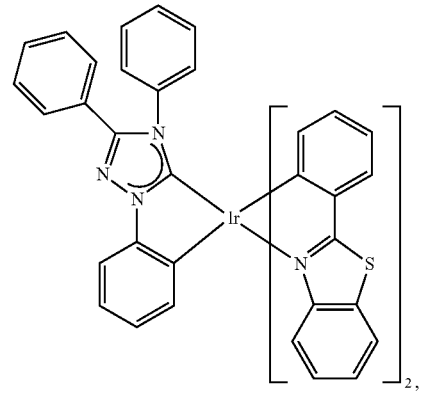

(N-1)

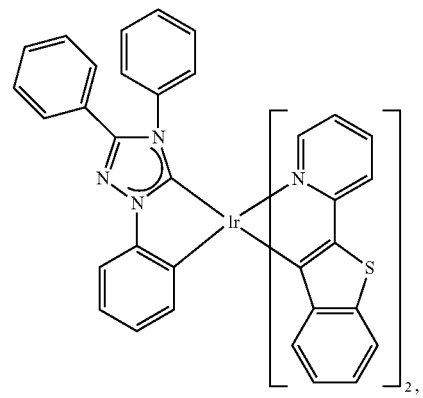

(N-2)

-continued

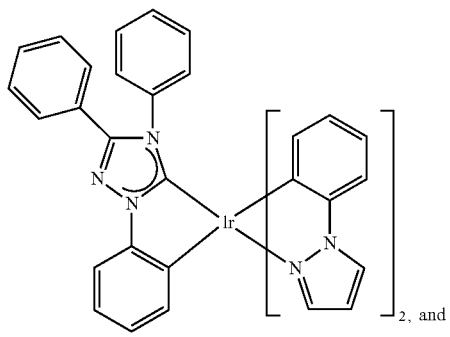

(N-3)

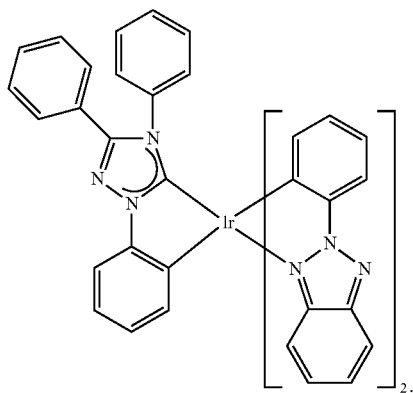

(N-4)

Halogen is fluorine, chlorine, bromine and iodine.

$C_1$-$C_{24}$alkyl, especially $C_1$-$C_8$alkyl, is a branched or unbranched radical such as for example methyl, ethyl, propyl, isopropyl, n-butyl, sec-butyl, isobutyl, tert-butyl, 2-ethylbutyl, n-pentyl, isopentyl, 1-methylpentyl, 1,3-dimethylbutyl, n-hexyl, 1-methylhexyl, n-heptyl, isoheptyl, 1,1,3,3-tetra methyl butyl, 1-methyl heptyl, 3-methyl heptyl, n-octyl, 2-ethyl hexyl, 1,1,3-trimethylhexyl, 1,1,3,3-tetramethylpentyl, nonyl, decyl, undecyl, 1-methylundecyl, dodecyl, 1,1,3,3,5,5-hexamethylhexyl, tridecyl, tetradecyl, pentadecyl, hexadecyl, heptadecyl, octadecyl, icosyl or docosyl.

$C_1$-$C_{24}$perfluoroalkyl, especially $C_1$-$C_4$perfluoroalkyl, is a branched or unbranched radical such as for example —$CF_3$, —$CF_2CF_3$, —$CF_2CF_2CF_3$, —$CF(CF_3)_2$, —$(CF_2)_3CF_3$, and —$C(CF_3)_3$.

$C_1$-$C_{24}$alkoxy radicals are straight-chain or branched alkoxy radicals, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy.

$C_2$-$C_{24}$alkenyl radicals are straight-chain or branched alkenyl radicals, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_{2-24}$alkynyl is straight-chain or branched and preferably $C_{2-8}$alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

$C_4$-$C_{18}$cycloalkyl, especially $C_6$-$C_{12}$cycloalkyl, is preferably $C_6$-$C_{12}$cycloalkyl or said cycloalkyl substituted by one to three $C_1$-$C_4$alkyl groups, such as, for example, cyclopentyl, methyl-cyclopentyl, dimethylcyclopentyl, cyclohexyl, methylcyclohexyl, di methylcyclohexyl, trimethyl-cyclohexyl, tert-butylcyclohexyl, cycloheptyl, cyclooctyl, cyclononyl, cyclodecyl, cyclododecyl, 1-adamantyl, or 2-adamantyl. Cyclohexyl, 1-adamantyl and cyclopentyl are most preferred.

Examples of $C_4$-$C_{18}$cycloalkyl, which is interrupted by S, O, or $NR^5$, are piperidyl, piperazinyl and morpholinyl.

Aryl is usually $C_6$-$C_{30}$aryl, preferably $C_6$-$C_{24}$aryl, which optionally can be substituted, such as, for example, phenyl, 4-methylphenyl, 4-methoxyphenyl, naphthyl, biphenylyl, 2-fluorenyl, phenanthryl, anthryl, tetracyl, pentacyl, hexacyl, terphenylyl or quadphenylyl; or phenyl substituted by one to three $C_1$-$C_4$alkyl groups, for example o-, m- or p-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2-methyl-6-ethylphenyl, 4-tert-butylphenyl, 2-ethylphenyl or 2,6-diethylphenyl. Important examples for $C_6$-$C_{10}$aryl are phenyl and naphthyl, especially phenyl.

$C_7$-$C_{24}$aralkyl radicals are preferably $C_7$-$C_{15}$aralkyl radicals, which may be substituted, such as, for example, benzyl, 2-benzyl-2-propyl, β-phenethyl, α-methyl benzyl, α,α-dimethylbenzyl, ω-phenyl-butyl, ω-phenyl-octyl, ω-phenyl-dodecyl; or phenyl-$C_1$-$C_4$alkyl substituted on the phenyl ring by one to three $C_1$-$C_4$alkyl groups, such as, for example, 2-methylbenzyl, 3-methylbenzyl, 4-methyl benzyl, 2,4-dimethylbenzyl, 2,6-dimethylbenzyl or 4-tert-butylbenzyl.or 3-methyl-5-(1',1',3',3'-tetramethyl-butyl)-benzyl.

Heteroaryl is typically $C_2$-$C_{26}$heteroaryl, i.e. a ring with five to seven ring atoms or a condensed rig system, wherein nitrogen, oxygen or sulfur are the possible hetero atoms, and is typically an unsaturated heterocyclic radical with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, perimidinyl, phenanthrolinyl, phenazinyl, isothiazolyl, phenothiazinyl, isoxazolyl, furazanyl or phenoxazinyl, which can be unsubstituted or substituted.

$C_6$-$C_{18}$cycloalkoxy is, for example, cyclopentyloxy, cyclohexyloxy, cycloheptyloxy or cyclooctyloxy, or said cycloalkoxy substituted by one to three $C_1$-$C_4$alkyl, for example, methylcyclopentyloxy, dimethylcyclopentyloxy, methylcyclohexyloxy, dimethylcyclohexyloxy, trimethylcyclohexyloxy, or tert-butylcyclohexyloxy.

$C_6$-$C_{24}$aryloxy is typically phenoxy or phenoxy substituted by one to three $C_1$-$C_4$alkyl groups, such as, for example o-, m- or p-methylphenoxy, 2,3-dimethylphenoxy, 2,4-dimethylphenoxy, 2,5-dimethylphenoxy, 2,6-dimethylphenoxy, 3,4-dimethylphenoxy, 3,5-dimethylphenoxy, 2-methyl-6-ethylphenoxy, 4-tert-butylphenoxy, 2-ethylphenoxy or 2,6-diethylphenoxy.

$C_6$-$C_{24}$aralkoxy is typically phenyl-$C_1$-$C_9$alkoxy, such as, for example, benzyloxy, α-methylbenzyloxy, α,α-dimethylbenzyloxy or 2-phenylethoxy.

$C_1$-$C_{24}$alkylthio radicals are straight-chain or branched alkylthio radicals, such as e.g. methylthio, ethylthio, propylthio, isopropylthio, n-butylthio, isobutylthio, pentylthio, isopentyl-thio, hexylthio, heptylthio, octylthio, decylthio, tetradecylthio, hexadecylthio or octadecylthio.

Examples of a ring formed by $Z^3$, $Z^4$, $Z^5$ and $Z^6$, respectively are cycloalkanes having from 3 to 7 carbon atoms or heterocycloalkanes having from 3 to 6 carbon atoms which can have one or more additional hetero atoms selected from nitrogen, oxygen and sulfur, for example, cyclopentane, cyclohexane, pyrrolidine, pyrimidine, or morpholine, which can optionally be substituted by one or more $C_1$-$C_8$alkyl groups.

Examples of a ring formed by $Z^1$ and $Z^2$ are aryl groups having from 6 to 10 carbon atoms which can have one or more additional hetero atoms selected from nitrogen, oxygen and sulfur, and which can optionally be substituted by, for example, one or more $C_1$-$C_8$alkyl groups, such as benzene.

An example, wherein ring A and ring B form an additional ring is

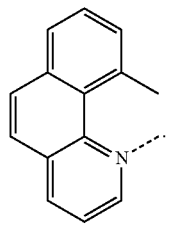

Possible substituents of the above-mentioned groups are $C_1$-$C_8$alkyl, a hydroxyl group, a mercapto group, $C_1$-$C_8$alkoxy, $C_1$-$C_8$alkylthio, halogen, halo-$C_1$-$C_8$alkyl, a cyano group, an aldehyde group, a ketone group, a carboxyl group, an ester group, a carbamoyl group, an amino group, a nitro group or a silyl group.

The term "haloalkyl" means groups given by partially or wholly substituting the above-mentioned alkyl group with halogen, such as trifluoromethyl etc. The "aldehyde group, ketone group, ester group, carbamoyl group and amino group" include those substituted by an $C_1$-$C_{24}$alkyl group, a $C_4$-$C_{18}$cycloalkyl group, an $C_6$-$C_{30}$aryl group, an $C_7$-$C_{24}$aralkyl group or a heterocyclic group, wherein the alkyl group, the cycloalkyl group, the aryl group, the aralkyl group and the heterocyclic group may be unsubstituted or substituted. The term "silyl group" means a group of formula —$SiR^{105}R^{106}R^{107}$, wherein $R^{105}$, $R^{106}$ and $R^{107}$ are independently of each other a $C_1$-$C_8$alkyl group, in particular a $C_1$-$C_4$alkyl group, a $C_6$-$C_{24}$aryl group or a $C_7$-$C_{12}$aralkylgroup, such as a trimethylsilyl group.

If a substituent occurs more than one time in a group, it can be different in each occurrence.

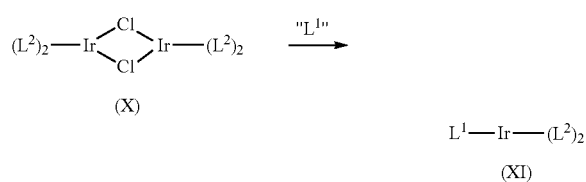

The synthesis of the tetrakis-(C^N)-μ-(dichloro)-diiridium (III) complexes can, for example, be done according to the procedure described in M. Nonoyama, *Bull. Chem. Soc. Jp.* 1974, 47, 767, or M. E. Thompson et al., *J. Am. Chem. Soc.,* 2001, 123, 4304. The (C^N) ligand ($L^2$) is stirred in the presence of iridium(III) chloride in a mixture of ethanol/water at 120° C. for 8 to 24 hours. After filtration a product is obtained which is used in the next step of the synthesis without further purification.

In case the carbene is created from 5-methoxy-1,3,4-triphenyl-1,2,4(5H)-triazoline, it is obtained by heating of 5-methoxy-1,3,4-triphenyl-1,2,4(5H)-triazoline at 80° C. for 8 to 24 hours. The iridium dimer of formula X is added to a solution of the carbene in toluene, whereby the iridium complex of formula XI is obtained. The iridium complex of formula XI can be purified by chromatography, or precipitation, for example, in hexane.

5-methoxy-1,3,4-triphenyl-1,2,4(5H)-triazoline is commercially available or can be prepared according to the procedure described in gemäss D. Ender et al., *Synthesis* 2003, 8, 1292.

The synthesis of the tris-cyclometalated Ir(III) complexes can be done according to the procedure by M. E. Thompson et al., *J. Am. Chem. Soc.,* 2003, 125, 7377, by heating the tetrakis-(C^N)-μ-(dichloro)-diiridium(III) complexes in the presence of appropriate cyclometalating ligand and a base, like potassium carbonate in glycerol or by the reaction of cyclometalating ligand in the presence if Ir(acac)$_3$ at elevated temperature as described by S. Kwon et al. in *Eur. J. Inorg. Chem.* 2004, 3415 or by R. J. Wattse et al. in *Inorg Chem.* 1991, 30, 1687. Alternatively the tris-cyclometalated Ir(III) complexes can be prepared as described by M. C. DeRosa et al. in *J. Am. Chem. Soc.,* 2004, 126, 7619, by the reaction of the tetrakis-(C^N)-μ-(dichloro)-diiridium(III) with silver triflate and subsequent treatment with the appropriate cyclometalating ligand.

Dichloride-bridged dimers of the general structure C^NPt (μ-Cl)$_2$PtC^N can be done according to the procedure described by M. E. Thompson et al. in *Inorg. Chem.,* 2002, 41 (12), 3055 by the reaction of potassium tetrachloroplatinate with a cyclometalating ligand precursor (HC^N) in 2-ethoxyethanol.

$$K_2PtCl_4 + HC^\wedge N \rightarrow C^\wedge NPt(\mu\text{-}Cl)_2PtC^\wedge N$$

The dimers can be dissociated in the presence of a base and appropriate cyclometalating ligands as described by M. E. Thompson et al., *Inorg. Chem.,* 2002, 41 (12), 3055.

The present invention is also directed to an electronic device comprising the metal complex and its fabrication process. The electronic device can comprise at least one organic active material positioned between two electrical contact layers, wherein at least one of the layers of the device includes the metallic complex compound. The electronic device can comprise an anode layer (a), a cathode layer (e), and an active layer (c). Adjacent to the anode layer (a) is an optional hole-injecting/transport layer (b), and adjacent to the cathode layer (e) is an optional electron-injection/transport layer (d). Layers (b) and (d) are examples of charge transport layers.

The active layer (c) can comprise at least approximately 1 weight percent of metal complex previously described.

In some embodiments, the active layer (c) may be substantially 100% of the metal complex because a host charge transporting material, such as Alq$_3$ is not needed. By "substantially 100%" it is meant that the metal complex is the only material in the layer, with the possible exception of impurities or adventitious by-products from the process to form the layer. Still, in some embodiments, the metal complex may be a dopant within a host material, which is typically used to aid charge transport within the active layer (c). The active layer (c), including any of the metal complexes, can be a small molecule active material.

The device may include a support or substrate (not shown) adjacent to the anode layer (a) or the cathode layer (e). Most frequently, the support is adjacent the anode layer (a). The support can be flexible or rigid, organic or inorganic. Generally, glass or flexible organic films are used as a support. The anode layer (a) is an electrode that is more efficient for injecting holes compared to the cathode layer (e). The anode can include materials containing a metal, mixed metal, alloy, metal oxide or mixed-metal oxide. Suitable metal elements within the anode layer (a) can include the Groups 4, 5, 6, and 8-11 transition metals. If the anode layer (a) is to be light transmitting, mixed-metal oxides of Groups 12, 13 and 14 metals, such as indium-tin-oxide, may be used. Some non-limiting, specific examples of materials for anode layer (a) include indium-tin-oxide ("ITO"), aluminum-tin-oxide, gold, silver, copper, nickel, and selenium.

The anode layer (a) may be formed by a chemical or physical vapor deposition process or spin-cast process. Chemical vapor deposition may be performed as a plasma-enhanced chemical vapor deposition ("PECVD") or metal organic chemical vapor deposition ("MOCVD").

Physical vapor deposition can include all forms of sputtering (e. g., ion beam sputtering), e-beam evaporation, and resistance evaporation.

Specific forms of physical vapor deposition include rf magnetron sputtering or inductively-coupled plasma physical vapor deposition("ICP-PVD"). These deposition techniques are well-known within the semiconductor fabrication arts.

A hole-transport layer (b) may be adjacent the anode. Both hole transporting small molecule compounds and polymers can be used.

Commonly used hole transporting molecules include: polyvinyl-carbazol, N,N'-diphenyl-N, N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl] 4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino) benzaldehydediphenyl hydrazone (DEH), triphenylamine (TPA), bis[4-(N,N-diethylamino)-2-methylphenyl](4-methylphenyl)methane (MPMP), 1-phenyl-3-[p-(diethylamino) styryl]-5-[p-(diethylamino)phenyl]pyrazoline (PPR or DEASP), 1,2-trans-bis (9H-carbazol-9-yl)cyclobutane (DCZB), N,N,N',N'-tetrakis (4-methylphenyl)-(1,1'-biphenyl)-4,4'-diamine (TTB), 4,4'-N,N-dicarbazole-biphenyl (CBP), N,N-dicarbazoyl-1,4-dimethene-benzene (DCB), porphyrinic compounds, and combinations thereof.

Commonly used hole transporting polymers are polyvinylcarbazole, (phenylmethyl) polysilane, poly(3,4-ethylendioxythiophene) (PEDOT), and polyaniline. Hole-transporting polymers can be obtained by doping hole-transporting molecules such as those mentioned above into polymers such as polystyrene and polycarbonate.

The hole-injection/transport layer (b) can be formed using any conventional means, including spin-coating, casting, and printing, such as gravure printing. The layer can also be applied by ink jet printing, thermal patterning, or chemical, or physical vapor deposition.

Usually, the anode layer (a) and the hole-injection/transport layer (b) are patterned during the same lithographic operation. The pattern may vary as desired. The layers can be formed in a pattern by, for example, positioning a patterned mask or resist on the first flexible composite barrier structure prior to applying the first electrical contact layer material. Alternatively, the layers can be applied as an overall layer (also called blanket deposit) and subsequently patterned using, for example, a patterned resist layer and wet-chemical or dry-etching techniques. Other processes for patterning that are well known in the art can also be used. When the electronic devices are located within an array, the anode layer (a) and hole injection/transport layer (b) typically are formed into substantially parallel strips having lengths that extend in substantially the same direction.

The active layer (c) may comprise the metal complexes described herein. The particular material chosen may depend on the specific application, potentials used during operation, or other factors. The active layer (c) may comprise a host material capable of transporting electrons and/or holes, doped with an emissive material that may trap electrons, holes, and/or excitons, such that excitons relax from the emissive material via a photoemissive mechanism. Active layer (c) may comprise a single material that combines transport and emissive properties. Whether the emissive material is a dopant or a major constituent, the active layer may comprise other materials, such as dopants that tune the emission of the emissive material. Active layer (c) may include a plurality of emissive materials capable of, in combination, emitting a desired spectrum of light. Examples of phosphorescent emissive materials include the metal complexes of the present invention. Examples of fluorescent emissive materials include DCM and DMQA. Examples of host materials include $Alq_3$, CBP and mCP. Examples of emissive and host materials are disclosed in U.S. Pat. No. 6,303,238, which is incorporated by reference in its entirety.

The active layer (c) can be applied from solutions by any conventional technique, including spin coating, casting, and printing. The active organic materials can be applied directly by vapor deposition processes, depending upon the nature of the materials.

Optional layer (d) can function both to facilitate electron injection/transport, and also serve as a buffer layer or confinement layer to prevent quenching reactions at layer interfaces. More specifically, layer (d) may promote electron mobility and reduce the likelihood of a quenching reaction if layers (c) and (e) would otherwise be in direct contact. Examples of materials for optional layer (d) include metalcheated oxinoid compounds (e. g., tris(8-hydroxyquinolato) aluminum ($Alq_3$) or the like); phenanthroline-based compounds (e. g., 2,9-dimethyl-4,7-diphenyl-1,10-phenanthroline ("DDPA"), 4,7-diphenyl-1,10-phenanthroline ("DPA"), or the like; azole compounds (e. g., 2-(4-biphenyl)-5-(4-t-butylphenyl)-1,3,4-oxadiazole ("PBD") or the like, 3-(4-biphenyl)-4-phenyl-5-(4-t-butylphenyl)-1,2,4-triazole ("TAZ") or the like; other similar compounds; or any one or more combinations thereof. Alternatively, optional layer (d) may be inorganic and comprise BaO, LiF, $Li_2O$, or the like.

The electron injection/transport layer (d) can be formed using any conventional means, including spin-coating, casting, and printing, such as gravure printing. The layer can also be applied by ink jet printing, thermal patterning, or chemical or physical vapor deposition.

The cathode layer (e) is an electrode that is particularly efficient for injecting electrons or negative charge carriers. The cathode layer (e) can be any metal or nonmetal having a lower work function than the first electrical contact layer (in this case, the anode layer (a)). Materials for the second electrical contact layer can be selected from alkali metals of Group 1 (e. g., Li, Na, K, Rb, Cs), the Group 2 (alkaline earth) metals, the Group 12 metals, the rare earths, the lanthanides (e. g., Ce, Sm, Eu, or the like), and the actinides. Materials, such as aluminum, indium, calcium, barium, yttrium, and magnesium, and combinations thereof, may also be used. Li-containing organometallic compounds, LiF, and $Li_2O$ can also be deposited between the organic layer and the cathode layer to lower the operating voltage. Specific non-limiting examples of materials for the cathode layer (e) include barium, lithium, cerium, cesium, europium, rubidium, yttrium, magnesium, or samarium.

The cathode layer (e) is usually formed by a chemical or physical vapor deposition process. In general, the cathode layer will be patterned, as discussed above in reference to the anode layer (a) and optional hole injecting layer (b). If the device lies within an array, the cathode layer (e) may be patterned into substantially parallel strips, where the lengths of the cathode layer strips extend in substantially the same direction and substantially perpendicular to the lengths of the anode layer strips.

Electronic elements called pixels are formed at the cross points (where an anode layer strip intersects a cathode layer strip when the array is seen from a plan or top view).

In other embodiments, additional layer(s) may be present within organic electronic devices. For example, a layer (not shown) between the hole injecting layer (b) and the active layer (c) may facilitate positive charge transport, band-gap matching of the layers, function as a protective layer, or the like. Similarly, additional layers (not shown) between the electron injecting layer (d) and the cathode layer (e) may facilitate negative charge transport, band-gap matching between the layers, function as a protective layer, or the like. Layers that are known in the art can be used. Some or all of the layers may be surface treated to increase charge carrier transport efficiency. The choice of materials for each of the component layers may be determined by balancing the goals of providing a device with high device efficiency with the cost of manufacturing, manufacturing complexities, or potentially other factors.

The charge transport layers (b) and (d) are generally of the same type as the active layer (c). More specifically, if the active layer (c) has a small molecule compound, then the charge transport layers (b) and (d), if either or both are present, can have a different small molecule compound. If the active layer (c) has a polymer, the charge transport layers (b) and (d), if either or both are present, can also have a different polymer. Still, the active layer (c) may be a small molecule compound, and any of its adjacent charge transport layers may be polymers.

Each functional layer may be made up of more than one layer. For example, the cathode layer may comprise a layer of a Group I metal and a layer of aluminum. The Group I metal may lie closer to the active layer (c), and the aluminum may help to protect the Group I metal from environmental contaminants, such as water.

Although not meant to limit, the different layers may have the following range of thicknesses: inorganic anode layer (a), usually no greater than approximately 500 nm, for example, approximately 50-200 nm; optional hole-injecting layer (b), usually no greater than approximately 100 nm, for example, approximately 50-200 nm; active layer (c), usually no greater than approximately 100 nm, for example, approximately 10-80 nm; optional electron-injecting layer (d), usually no greater than approximately 100 nm, for example, approximately 10-80 nm; and cathode layer (e), usually no greater than approximately 1000 nm, for example, approximately 30-500 nm. If the anode layer (a) or the cathode layer (e) needs to transmit at least some light, the thickness of such layer may not exceed approximately 100 nm.

The location of the electron-hole recombination zone in the device, and thus the emission spectrum of the device, can be affected by the relative thickness of each layer. For example, when a potential light-emitting compound, such as $Alq_3$ is used in the electron transport layer (d), the electron-hole recombination zone can lie within the $Alq_3$ layer.

The emission would then be that of $Alq_3$, and not a desired sharp emission. Thus, the thickness of the electron-transport layer should be chosen so that the electron-hole recombination zone lies within the light-emitting layer (i.e., active layer (c)). The desired ratio of layer thicknesses can depend on the exact nature of the materials used.

The efficiency of the devices made with metal complexes can be further improved by optimizing the other layers in the device. For example, more efficient cathodes such as Ca, Ba, Mg/Ag, or LiF/Al can be used. Shaped substrates and hole transport materials that result in a reduction in operating voltage or increase quantum efficiency are also applicable. Additional layers can also be added to tailor the energy levels of the various layers and facilitate electroluminescence.

Depending upon the application of the electronic device, the active layer (c) can be a light-emitting layer that is activated by a signal (such as in a light-emitting diode) or a layer of material that responds to radiant energy and generates a signal with or without an applied potential (such as detectors or voltaic cells). Examples of electronic devices that may respond to radiant energy are selected from photoconductive cells, photoresistors, photoswitches, phototransistors, and phototubes, and photovoltaic cells. After reading this specification, skilled artisans will be capable of selecting material(s) that for their particular applications.

The electroluminescent devices may be employed for full color display panels in, for example, mobile phones, televisions and personal computer screens. Accordingly the present invention relates also to a device selected from stationary and mobile displays, such as displays for computers, mobile phones, laptops, pdas, TV sets, displays in printers, kitchen equipment, billboards, lightings, information boards and destination boards in trains and buses, containing an organic light emitting diode according to the present invention.

In OLEDs, electrons and holes, injected from the cathode (e) and anode (a) layers, respectively, into the photoactive layer (c), form negative and positively charged polarons in the active layer (c). These polarons migrate under the influence of the applied electric field, forming a polaron exciton with an oppositely charged species and subsequently undergoing radiative recombination. A sufficient potential difference between the anode and cathode, usually less than approximately 20 volts, and in some instances no greater than approximately 5 volts, may be applied to the device. The actual potential difference may depend on the use of the device in a larger electronic component. In many embodiments, the anode layer (a) is biased to a positive voltage and the cathode layer (e) is at substantially ground potential or zero volts during the operation of the electronic device. A battery or other power source(s) may be electrically connected to the electronic device as part of a circuit.

In other embodiments, the metal complex compound can be used as a charge transport material in layer (b) or (d).

The compound does not need to be in a solid matrix diluent (e.g., host charge transport material) when used in layer (b) (c), or (d) in order to be effective. A layer greater than approximately 1% by weight of the metal complex compound, based on the total weight of the layer, and up to substantially 100% of the complex compound can be used as the active layer (c). Additional materials can be present in the active layer (c) with the complex compound. For example, a fluorescent dye may be present to alter the color of emission.

A diluent may also be added. The diluent can be a polymeric material, such as poly(N-vinyl carbazole) and polysilane. It can also be a small molecule, such as 4,4'-N,N'-dicarbazole biphenyl or tertiary aromatic amines. When a diluent is used, the complex compound is generally present in a small amount, usually less than 20% by weight, preferably less than 10% by weight, based on the total weight of the layer.

The metallic complexes may be used in applications other than electronic devices. For example, the complexes may be used as catalysts or indicators (e. g., oxygen-sensitive indicators, phosphorescent indicators in bioassays, or the like).

The following examples illustrate certain features and advantages of the present invention. They are intended to be illustrative of the invention, but not limiting. All percentages are by weight, unless otherwise indicated. Abbreviations, used in claims or elsewhere, are known in the art and include the following ones:

Ph phenyl
t- denotes a tertiary (alkyl) group, such as t-Bu standing for tertiary butyl
Bu butyl
LC liquid chromatography
MS mass spectrometry
CIE International Commission on Illumination

EXAMPLES

Example 1 a) Tetrakis(2-phenylpyridinato-$C^2$,N')(μ-dichloro)-diiridium(III)

In a 100 ml 3-necked-flask equipped with a reflux condenser iridum(III)chloride hydrate (201.2 mg, 0.67 mmol, 1 eq.) is partially solved in 25 ml of a 3:1 mixture of 2-ethoxyethanol and water (degassed with $N_2$) giving an olive-green solution and a brown-black insoluble solid. 2-Phenylpyridine (0.4 ml, 2.80 mmol, 4.2 eq.) is then added and the reaction mixture heated to 120° C.; the insoluble solid dissolves and an orange-yellow precipitate appears. After stirring over night at 120° C. and cooling at room temperature the yellow product is filtered off, washed with ethanol and acetone and dried in vacuo giving a yellow powder. Yield: 265.5 mg (0.25 mmol, 73%), yellow powder.

b) Synthesis of 1,2,4-Triazol-2-ium-5-ylidene Iridium (III) complex

In a dried Schlenck tube 85.5 mg (0.26 mmol, 2.4 eq.) of methoxy-1,3,4-triphenyl-1,2,4(5H)-triazoline are heated to 90° C. under vacuum over night. After cooling, 9 ml of toluene are added to the free carbene, followed by 115.6 mg (0.11 mmol, 1 eq.) of tetrakis(2-phenylpyridinato-$C^2$,N')(μ-dichloro)-diiridium(III). The yellow suspension is stirred for 4 h at 120° C. After cooling the reaction mixture is diluted with toluene and extracted with 10% $NaHCO_3$ (5×15 ml). The organic phase is dried over $NaSO_4$, the solvent is evaporated and the crude product is purified by column chromatography (dichloromethane, 7.5 g silica) giving a yellow solid (yield: 77.4 mg (47%)).

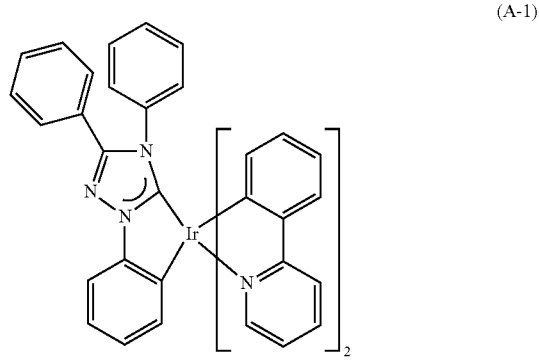

(A-1)

MS (+TOF MS): m/z 797.2157 ([M]$^+$), 643.1429 ([M-ppy]$^+$), 501.0947 ([M-PhTri]$^+$); $\lambda_{PL, sol}$ (toluene): 499 nm.

Example 2

According to the procedure described in Example 1 0.06 g (26% yield) of the compound below are obtained after chromatography.

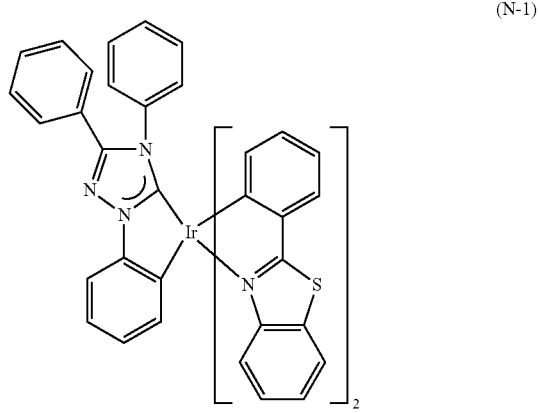

(N-1)

MS (LC-MS, ES+): m/z 909.5 ([M]$^+$); 699.5 ([M-$C_{13}H_8NS$]$^+$); $\lambda_{PL, sol}$ (toluene): 547 nm.

Example 3

According to the procedure described in Example 1 1.10 g (55% yield) of the compound below are obtained after precipitation.

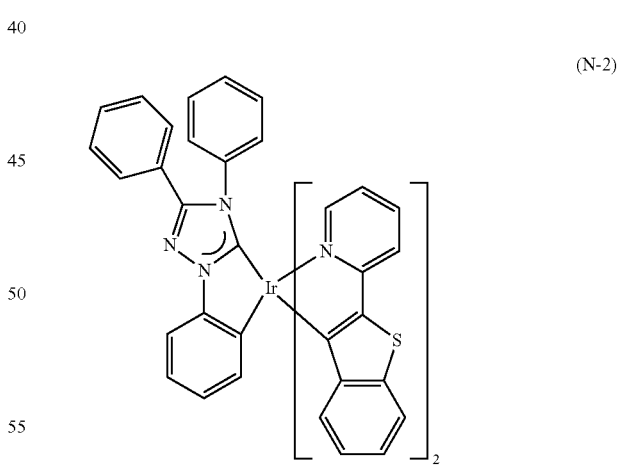

(N-2)

MS (LC-MS, ES+): m/z 909.3 ([M]$^+$); $\lambda_{PL, sol}$ (toluene): 590 nm.

Example 4

According to the procedure described in Example 1 0.1 g (70% yield) of the compound below are obtained after chromatography.

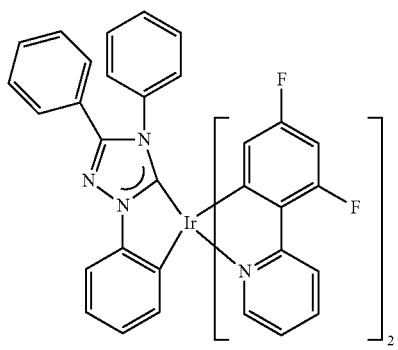

(A-252)

MS (LC-MS, ES+): m/z 869.7 ([M]$^+$); $\lambda_{PL, sol}$ (toluene): 485 nm.

Example 5

According to the procedure described in Example 1 0.073 g (24% yield) of the compound below are obtained after chromatography.

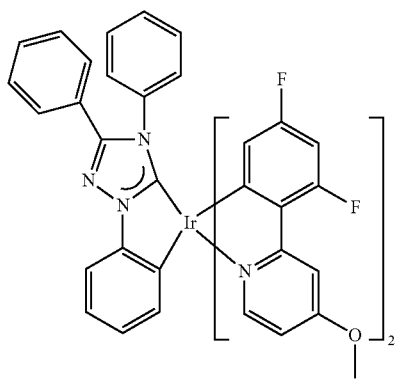

(A-80)

MS (LC-MS, ES+): m/z 929.6 ([M]$^+$); $\lambda_{PL, sol}$ (toluene): 471 nm.

Example 6

According to the procedure described in Example 1 0.50 g (45% yield) of the compound below are obtained after chromatography.

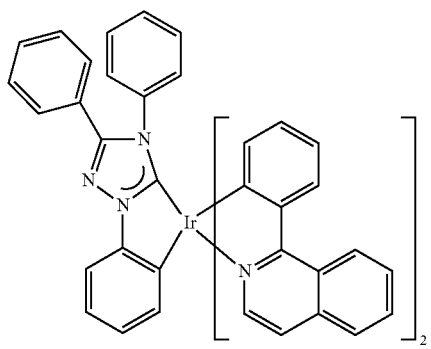

(A-82)

MS (LC-MS, ES+): m/z 897.4 ([M]$^+$); $\lambda_{PL, sol}$ (toluene): 608 nm.

Example 7

According to the procedure described in Example 1 0.50 g (45% yield) of the compound below are obtained after chromatography.

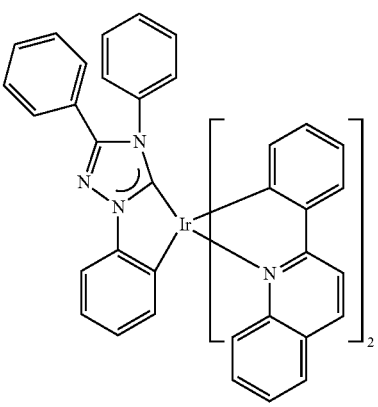

(A-253)

MS (LC-MS, ES+): m/z 897.4 ([M]$^+$); $\lambda_{PL, sol}$ (toluene): 612 nm.

Example 8

According to the procedure described in Example 1 0.16 g (58% yield) of the compound below are obtained after chromatography.

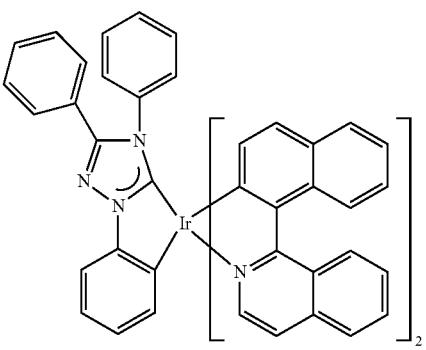

(A-254)

MS (APCI MS): m/z 998 ([M+1]$^+$), $\lambda_{PL, sol}$ (toluene): 648 nm

Example 9

According to the procedure described in Example 1 0.16 g (58% yield) of the compound below are obtained after chromatography.

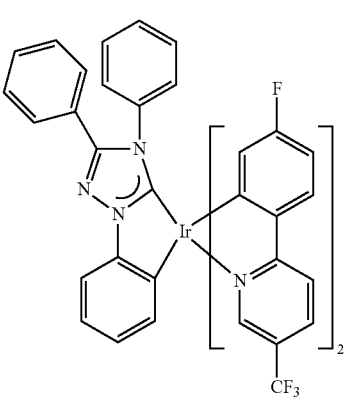

(A-81)

MS (+TOF MS): m/z 968.1 ([M]+); 729.1 ([M-$C_{12}H_6F_4N$]+), $\lambda_{PL,\,sol}$ (toluene): 511 nm.

Example 10

According to the procedure described in Example 1 0.09 g (41% yield) of the compound below are obtained after chromatography.

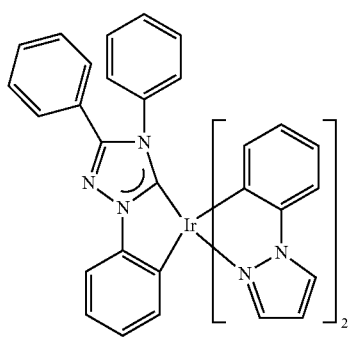

(N-3)

MS (LC-MS, ES+): m/z 775 ([M]+); 632 ([M-ppz]+); $\lambda_{PL,\,sol}$ (toluene): 469 nm/500 nm.

Example 11

According to the procedure described in Example 1 0.09 g (31% yield) of the compound below are obtained after chromatography.

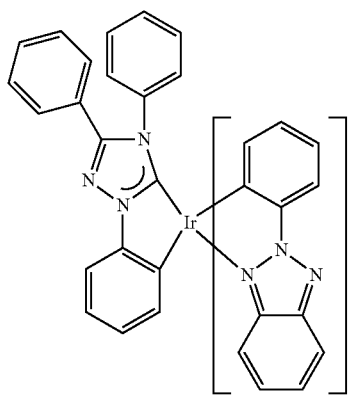

(N-4)

MS (EI-MS): m/z 877 ([M]+); $\lambda_{PL,\,sol}$ (toluene): 570 nm.

Example 12 a) In a dried Schlenk tube under nitrogen 9 ml of a 3:1 mixture of 1-propanol and water is added and degassed. 2-phenylpyridine (250 µl, 1.75 mmol, 2.5 eq.) and potassium tetrachloroplatinate(II) (0.29 g, 0.70 mmol, 1 eq.) is then added and the reaction mixture is heated to 120° C. After stirring over night at this temperature and cooling to room temperature the yellow product is filtered off and washed with ethanol. The product is purified by column chromatography (heptan:ethylacetate: 3:1) giving a yellow solid. Yield: 0.24 g (89%), yellow powder.

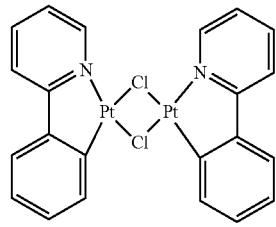

b) According to the procedure described in Example 1 0.16 g (47% yield) of the compound below are obtained.

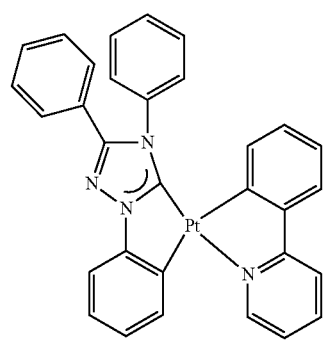

(H-1)

MS (+TOF MS): m/z 646 ([M]+); $\lambda_{PL,\,sol}$ (toluene): 484 nm/516 nm.

Example 13

1-Methyl-3-phenyl-imidazolium trifluoromethanesulfonic acid (0.09 g, 0.32 mmol) were placed in a dried Schlenk tube under nitrogen and stirred at room temperature for 45 minutes in 3.3 ml of THF. The yellow suspension was cooled down to −60° C. and lithiumdiisopropylamid (0.35 mmol, THF solution) was added. The reactions mixture was warmed up to room temperature, and then solvent was removed by evaporation. The residue was dissolved in 5.1ml toluene and tetrakis[2-(2-pyridinyl-N)phenyl-C]-di- -chlorodi-iridium(III) (0.20 g, 0.19 mmol) and triethylamine (43.8 µl, 0.32 mmol) were added. The reaction mixture was stirred for 18 hours at 100° C. After cooling, the reaction mixture was diluted with dichloromethane and extracted twice with water. The organic phase was dried over $NaSO_4$, the solvent evaporated and the crude product purified by column chromatography. After crystallization from dichloromrthane/hexane 0.05 g (22%) of product were obtained.

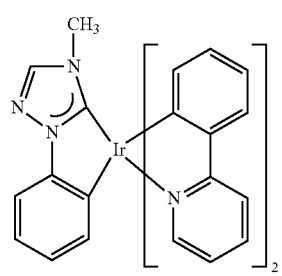

(B-14)

MS (+TOF MS): m/z 659 ([M]+)

Example 14

In a Schlenk tube 1,4-diphenyl-3-(trifluoromethyl)-4H-1,2,4-triazol-1-ium (0.47 g, 1.19 mmol), potassium tert.-butylate (0.13 g, 1.19 mmol) and o-xylene (16 ml) are stirred at 90° C. for 4 hours. Then tetrakis[3,5-difluoro-2-(4-methoxy-2-pyridinyl-N)phenyl-C]di- -chlorodi-iridium(III) (0.2 g, 0.15 mmol) is added and the reaction mixture is stirred at 135° C. for 20 hours. After cooling the solvent is removed by evaporation. The crude product is purified by column chromatography and crystallized from dichloromethane/hexane giving 0.08 g (29%) of the product.

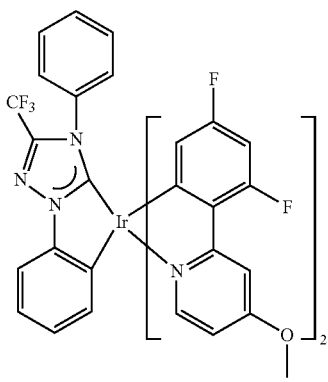

(A-164)

MS (+TOF MS): m/z 920 ([M]$^+$); $\lambda_{PL, sol}$ (toluene): 484 nm.

Example 15

The crude product is prepared according to the procedure described in Example 1, purified by column chromatography and crystallized from dichloromethane/hexane giving 0.09 g (27%) of the product.

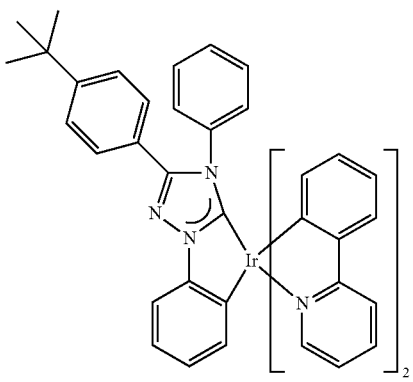

(A-165)

MS (+TOF MS): m/z 854 ([M]$^+$); $\lambda_{PL, sol}$ (toluene): 500 nm.

Application Examples

Device structure: On a glass substrate the following layer are superimposed: ITO (anode, 150 nm), PEDOT:PSS (100 nm), then the electro luminescent-polymer consisting of PVK, PBD, TPD, and 5% of the corresponding emitter (80 nm), finally barium (5 nm) and aluminum (cathode, 100 nm).

| Compound | Emission maximum (nm) | Efficiency (cd/A) | CIE Coordinates | Ex. Quantum Efficiency [%] |
|---|---|---|---|---|
| A-1 | 527 | 4.4 | 0.30/0.57 | 1.2 |
| A-80 | 487 | 0.31 | 0.26/0.33 | 0.16 |
| A-82 | 610 | 3.2 | 0.65/0.34 | 3.1 |
| A-81 | 487 | 0.28 | 0.31/0.36 | 0.15 |
| A-164 | 487 | 0.28 | 0.31/0.36 | 0.15 |

The invention claimed is:

1. A compound of formula (I)

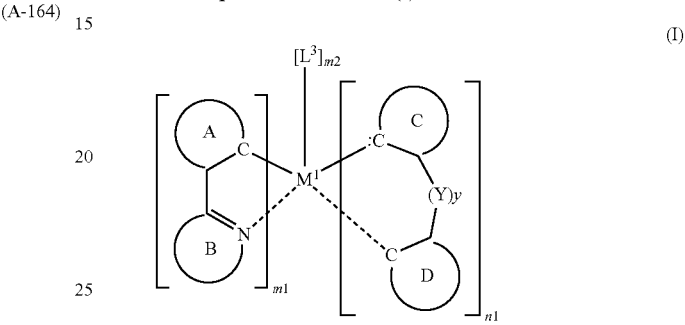

(I)

wherein
the ring A,

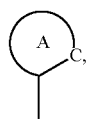

represents an optionally substituted aryl group which can optionally contain heteroatoms,
the ring B,

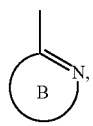

represents an optionally substituted nitrogen containing aryl group, which can optionally contain further heteroatoms, or the ring A may be taken with the ring B binding to the ring A to form a ring;
the group C,

represents an acyclic carbene or a cyclic carbene (ring C), which can optionally contain heteroatoms,
the ring D,

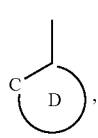

represents an optionally substituted aryl group which can optionally contain heteroatoms, n1 is an integer of 1 to 3,
m1 is an integer of 0, 1 or 2,
m2 is an integer 0 or 1,
$M^1$ is a metal with an atomic weight of greater than 40,
$L^3$ is a monodentate ligand or a bidentate ligand,
Y is —C(=O)— or —C($X^1$)$_2$—, wherein $X^1$ is hydrogen or $C_{1-4}$alkyl and
y is 0 or 1; with the proviso that the following compounds
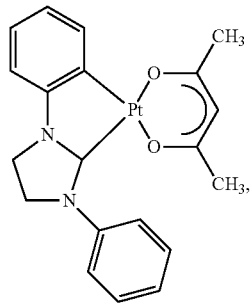
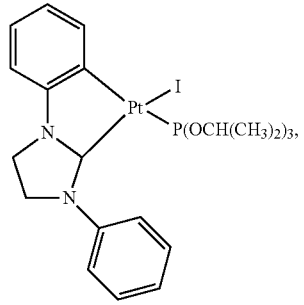
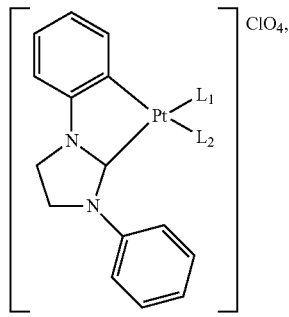
L$_1$ = MeCN
L$_2$ = 1/2 COD
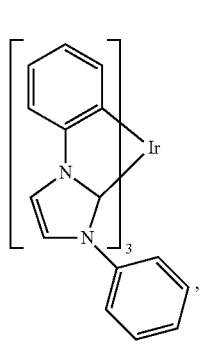
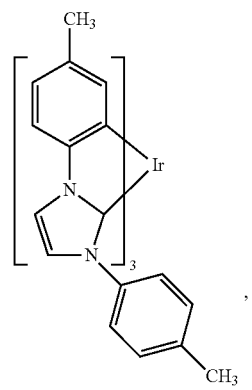
-continued
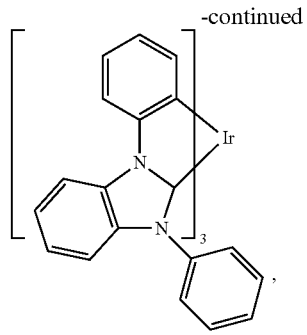
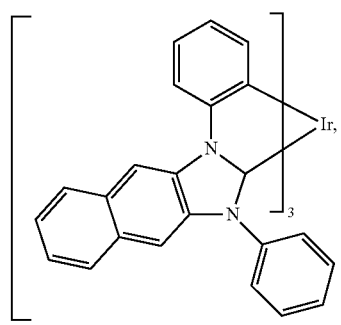
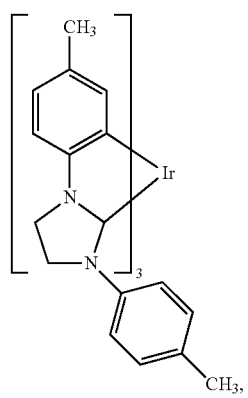
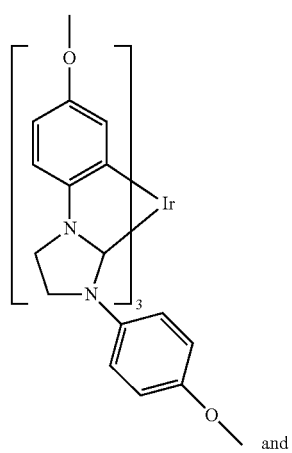
and -continued

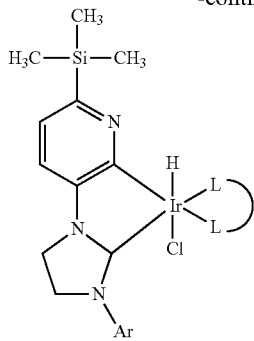

wherein L-L=η⁴–1,5-cyclooctadiene and Ar=2,6-diisopropylphenyl, are excluded.

2. The compound of claim 1, wherein the metal $M^1$ is selected from the group consisting of Tl, Pb, Bi, In, Sn, Sb, Te, Mo, Cr, Mn, Ta, V, Cu, Fe, Ru, Ni, Co, Ir, Pt, Pd, Rh, Re, Os, Ag and Au.

3. The compound of claim 2, wherein the metal $M^1$ is selected from the group consisting of Pt, Pd, Ag, Au, Ru and Ir.

4. The compound of claim 1, wherein

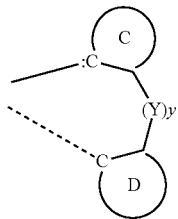 (L¹)

is a group of formula

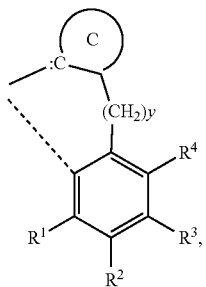

wherein
R¹ to R⁴ are substitutents and can be taken together to form a ring,
y is 0 or 1,
the group C,

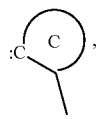, is a nucleophilic carbene of formula

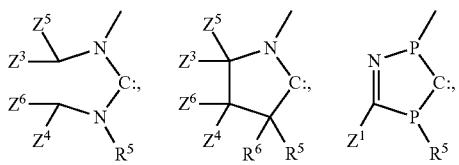

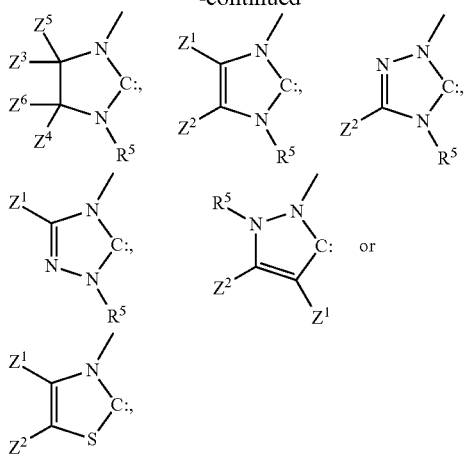

wherein
$R^5$ is hydrogen, $C_1$-$C_{24}$alkyl, $C_2$-$C_{24}$alkenyl, $C_2$-$C_{24}$alkynyl, $C_2$-$C_{24}$alkoxycarbonyl, $C_1$-$C_{24}$carboxylate, $C_1$-$C_{24}$alkoxy, $C_2$-$C_{24}$alkenyloxy, $C_2$-$C_{24}$alkynyloxy or aryloxy, which can optionally be substituted with $C_1$-$C_8$alkyl, halogen, $C_1$-$C_8$alkoxy or with a phenyl group which can be substituted with halogen, $C_1$-$C_8$alkyl, $C_1$-$C_8$alkoxy or aryl, which can optionally be substituted; and $R^6$, $Z^1$, $Z^2$, $Z^3$, $Z^4$, $Z^5$ and $Z^6$ are independently of each other selected from the group consisting of hydrogen, $C_1$-$C_{24}$alkyl, $C_1$-$C_{24}$halogenalkyl, $C_2$-$C_{24}$alkenyl, $C_2$-$C_{24}$alkynyl, $C_2$-$C_{24}$alkoxycarbonyl, aryl, $C_1$-$C_{24}$carboxylate, $C_1$-$C_{24}$alkoxy, $C_2$-$C_{24}$alkenyloxy, $C_2$-$C_{24}$alkynyloxy and aryloxy, with each of $Z^1$, $Z^2$, $Z^3$ and $Z^4$ optionally being substituted with $C_1$-$C_8$alkyl, halogen, $C_1$-$C_8$alkoxy or with a phenyl group, which can optionally be substituted with halogen, $C_1$-$C_8$alkyl or $C_1$-$C_8$alkoxy, or $Z^1$ and $Z^2$ form an aromatic or heteroaromatic ring, and/or $Z^3$, $Z^4$, $Z^5$ and $Z^6$ form an alkyl or heteroalkyl ring.

5. The compound of claim 4, wherein $R^1$, $R^2$, $R^3$ and $R^4$ are independently of each other hydrogen, halogen, nitro, cyano, $C_1$-$C_4$alkyl, $C_1$-$C_4$perfluoroalkyl, $C_1$-$C_4$alkoxy, —S—$C_1$-$C_4$alkyl, —O—$C_1$-$C_4$perfluoroalkyl, —$SO_2X^{22}$, —$CO_2H$, —$CO_2X^{22}$, wherein $X^{22}$ is $C_1$-$C_4$alkyl; $C_6H_4CF_3$, cyclohexyl, optionally substituted $C_6$-$C_{10}$aryl, optionally substituted —O—$CH_2$-$C_6$-$C_{10}$aryl or optionally substituted —O—$C_6$-$C_{10}$aryl.

6. The compound of claim 5, wherein $R^1$, $R^2$, $R^3$ and $R^4$ are independently of each other hydrogen, F, Cl, nitro, cyano, $C_1$-$C_4$alkyl, $C_1$-$C_4$perfluoroalkyl, $C_1$-$C_4$alkoxy, —S—$C_1$-$C_4$alkyl, —O—$C_1$-$C_4$perfluoroalkyl, —$SO_2X^{22}$, —$CO_2H$, —$CO_2X^{22}$, wherein $X^{22}$ is $C_1$-$C_4$alkyl; $C_6H_4CF_3$, cyclohexyl, optionally substituted phenyl, optionally substituted benzyloxy or optionally substituted phenoxy.

7. The compound of claim 1, wherein

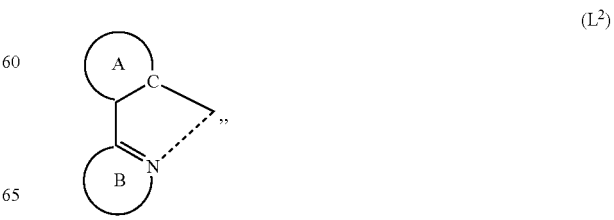 (L²)

is a group of formula

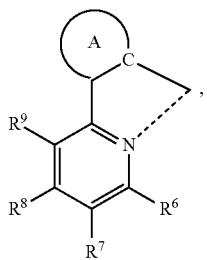

wherein $R^6$, $R^7$, $R^8$ and $R^9$ are independently of each other hydrogen, $C_1$-$C_{24}$alkyl, $C_2$-$C_{24}$alkenyl, $C_2$-$C_{24}$alkynyl, aryl, heteroaryl, $C_1$-$C_{24}$alkoxy, $C_1$-$C_{24}$alkylthio, cyano, $C_2$-$C_{24}$acyl, $C_1$-$C_{24}$alkyloxycarbonyl, a nitro group or a halogen atom; and the ring A represents an optionally substituted aryl or heteroaryl group; or the ring A may be taken with the pyridyl group binding to the ring A to form a ring; where the alkyl group, alkenyl group, alkynyl group, aryl group, heteroaryl group, alkoxy group, alkylthio group, acyl group and alkyloxycarbonyl group represented by $R^6$, $R^7$, $R^8$ and $R^9$ may be substituted.

8. The compound of claim 1, wherein $L^3$ is a bidentate ligand selected from the group consisting of

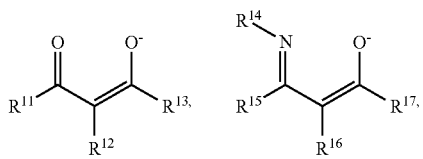

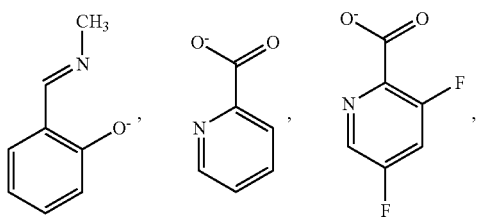

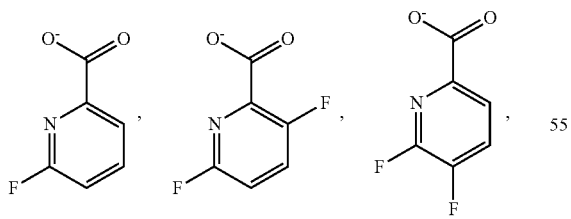

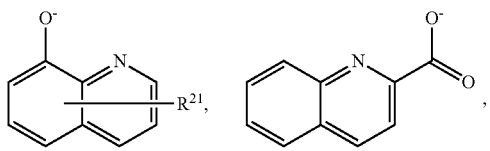

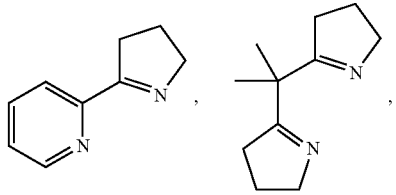

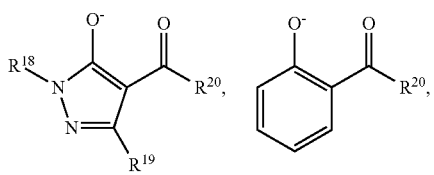

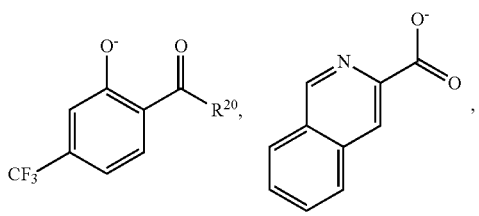

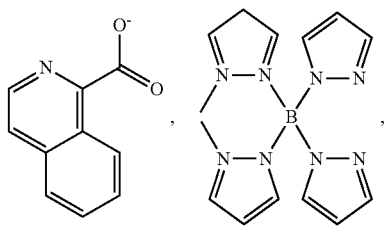

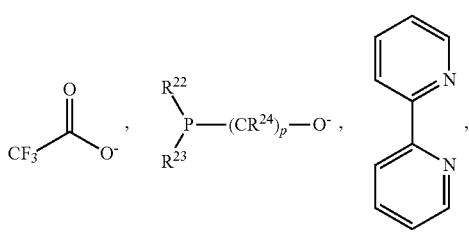

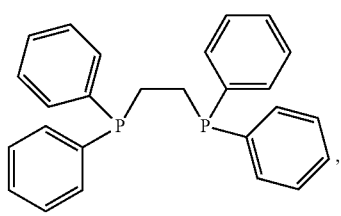

-continued

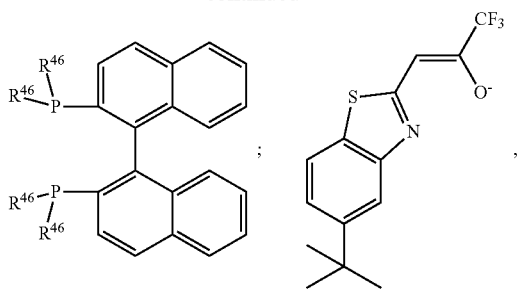

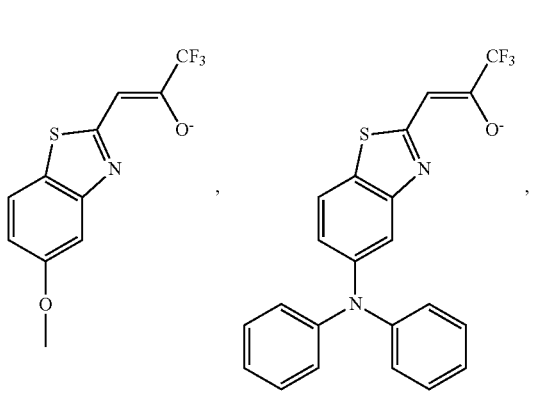

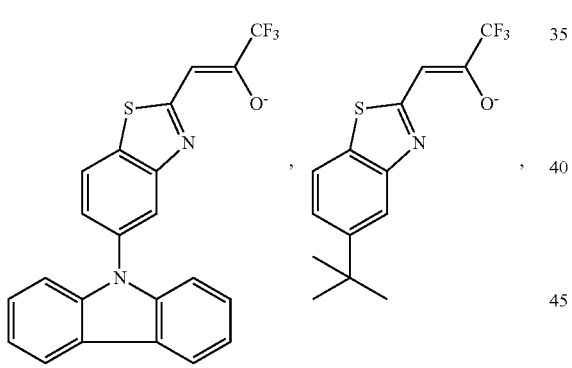

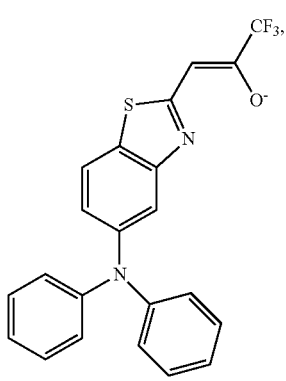

-continued

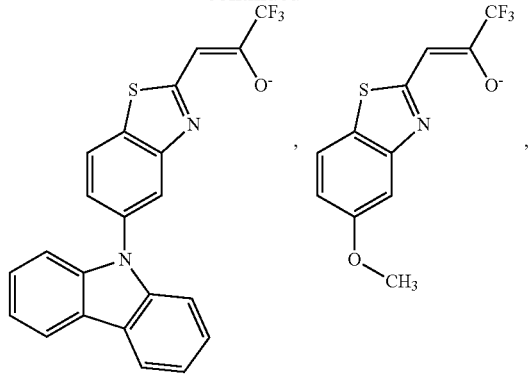

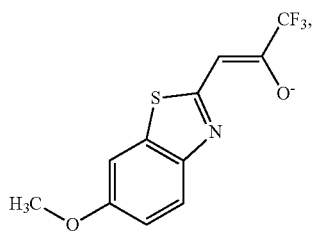

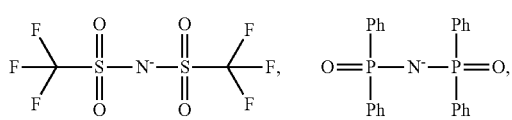

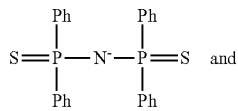

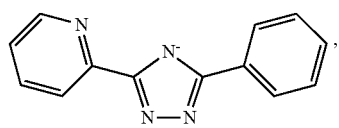

wherein
$R^{11}$ and $R^{15}$ are independently of each other hydrogen, $C_1$-$C_8$alkyl, $C_6$-$C_{18}$aryl, $C_2$-$C_{10}$heteroaryl or $C_1$-$C_8$perfluoroalkyl,
$R^{12}$ and $R^{16}$ are independently of each other hydrogen or $C_1$-$C_8$alkyl,
$R^{13}$ and $R^{17}$ are independently of each other hydrogen, $C_1$-$C_8$alkyl, $C_6$-$C_{18}$aryl, $C_2$-$C_{10}$heteroaryl, $C_1$-$C_8$perfluoroalkyl or $C_1$-$C_8$alkoxy,
$R^{14}$ is $C_1$-$C_8$alkyl, $C_6$-$C_{10}$aryl, $C_7$-$C_{11}$aralkyl or $C_1$-$C_8$alkoxy,
$R^{18}$ is $C_6$-$C_{10}$aryl,
$R^{19}$ is $C_1$-$C_8$alkyl,
$R^{20}$ is $C_1$-$C_8$alkyl or $C_6$-$C_{10}$aryl,
$R^{21}$ is hydrogen, $C_1$-$C_8$alkyl or $C_1$-$C_8$alkoxy, which may be partially or fully fluorinated,
$R^{22}$ and $R^{23}$ are independently of each other $C_n(H+F)_{2n+1}$ or $C_6(H+F)_5$,
$R^{24}$ can be the same or different at each occurrence and is selected from H and $C_n(H+F)_{2n+1}$,
p is 2 or 3 and
$R^{46}$ is $C_1$-$C_8$alkyl, $C_6$-$C_{18}$aryl, $C_1$-$C_8$alkoxy or $C_6$-$C_{18}$aryl, which is substituted by $C_1$-$C_8$alkyl.

9. The compound of claim 1 selected from the group consisting of

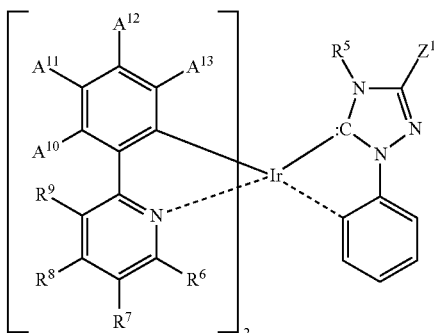

| Cpd. | R5 | R6 | R7 | R8 | R9 | A10 | A11 | A12 | A13 | Z1 |
|---|---|---|---|---|---|---|---|---|---|---|
| A-1 | Ph | H | H | H | H | H | H | H | H | Ph |
| A-2 | Ph | H | H | H | H | H | H | CH3 | H | Ph |
| A-3 | Ph | H | H | H | H | H | H | Ph | H | Ph |
| A-4 | Ph | H | H | H | H | H | H | t-Bu | H | Ph |
| A-5 | Ph | H | H | H | H | H | H | C6H11 | H | Ph |
| A-6 | Ph | H | H | H | H | H | H | F | H | Ph |
| A-7 | Ph | H | H | H | H | H | H | OCH3 | H | Ph |
| A-8 | Ph | H | H | H | H | H | H | OC6H5 | H | Ph |
| A-9 | Ph | H | H | H | H | H | H | OH | H | Ph |
| A-10 | Ph | H | H | H | H | H | H | OCF3 | H | Ph |
| A-11 | Ph | H | H | H | H | H | H | OSi(CH3)2C(CH3)3 | H | Ph |
| A-12 | Ph | H | H | H | H | H | H | CF3 | H | Ph |
| A-13 | Ph | H | H | H | H | H | H | SCH3 | H | Ph |
| A-14 | Ph | H | H | H | H | H | H | SO2CH3 | H | Ph |
| A-15 | Ph | H | H | H | H | H | H | SOCH3 | H | Ph |
| A-16 | Ph | H | H | H | H | H | H | SH | H | Ph |
| A-17 | Ph | H | H | H | H | H | H | NO2 | H | Ph |
| A-18 | Ph | H | H | H | H | H | H | N(CH3)2 | H | Ph |
| A-19 | Ph | H | H | H | H | H | H | NH2 | H | Ph |
| A-20 | Ph | H | H | H | H | H | H | NCOCH3 | H | Ph |
| A-21 | Ph | H | H | H | H | H | H | NSO2CH3 | H | Ph |
| A-22 | Ph | H | H | H | H | H | H | HNCH2CH3 | H | Ph |
| A-23 | Ph | H | H | H | H | H | H | CHO | H | Ph |
| A-24 | Ph | H | H | H | H | H | H | CH2OH | H | Ph |
| A-25 | Ph | H | H | H | H | H | H | CH2Br | H | Ph |
| A-26 | Ph | H | H | H | H | H | H | CH2CN | H | Ph |
| A-27 | Ph | H | H | H | H | H | H | CH2CO2H | H | Ph |
| A-28 | Ph | H | H | H | H | H | H | CH2OCH3 | H | Ph |
| A-29 | Ph | H | H | H | H | H | H | CH2N(CH2CH3)2 | H | Ph |
| A-30 | Ph | H | H | H | H | H | H | CHCHCO2CH3 | H | Ph |
| A-31 | Ph | H | H | H | H | H | H | CH2CH2CO2CH3 | H | Ph |
| A-32 | Ph | H | H | H | H | H | H | C6F5 | H | Ph |
| A-33 | Ph | H | H | H | H | H | H | H | CH3 | Ph |
| A-34 | Ph | H | H | H | H | CH3 | H | H | H | Ph |
| A-35 | Ph | H | H | H | H | H | H | H | CHCH2 | Ph |
| A-36 | Ph | H | H | H | H | CHCH2 | H | H | H | Ph |
| A-37 | Ph | H | H | H | H | H | H | Ph | Ph | Ph |
| A-38 | Ph | H | H | H | H | Ph | H | H | H | Ph |
| A-39 | Ph | H | H | H | H | C6F5 | H | H | H | Ph |
| A-40 | Ph | H | H | H | H | CF3 | H | CF3 | H | Ph |
| A-41 | Ph | H | H | H | H | H | H | CF3 | H | Ph |
| A-42 | Ph | H | H | H | H | CF3 | H | H | H | Ph |
| A-43 | Ph | H | H | H | H | F | H | H | H | Ph |
| A-44 | Ph | H | H | H | H | H | H | F | H | Ph |
| A-45 | Ph | H | H | H | H | F | H | F | H | Ph |
| A-46 | Ph | H | H | H | H | H | H | OCF3 | H | Ph |
| A-47 | Ph | H | H | H | H | OCF3 | H | H | H | Ph |
| A-48 | Ph | H | H | H | H | NO2 | H | CF3 | H | Ph |
| A-49 | Ph | H | H | H | H | CF3 | H | NO2 | H | Ph |
| A-50 | Ph | H | H | H | H | CN | H | H | H | Ph |
| A-51 | Ph | H | H | H | H | H | H | CN | H | Ph |
| A-52 | Ph | H | H | H | H | H | H | Si(CH3)3 | Ph |
| A-53 | Ph | H | H | H | H | Si(CH3)3 | H | H | H | Ph |
| A-54 | Ph | H | H | H | H | NO2 | H | CN | H | Ph |
| A-55 | Ph | H | H | H | H | CN | H | NO2 | H | Ph |
| A-56 | Ph | CF3 | H | H | H | H | H | H | H | Ph |
| A-57 | Ph | Cl | H | H | H | H | H | H | H | Ph |
| A-58 | Ph | NO2 | H | H | H | H | H | H | H | Ph |
| A-59 | Ph | CN | H | H | H | H | H | H | H | Ph |
| A-60 | Ph | CH3 | H | H | H | H | H | H | H | Ph |
| A-61 | Ph | OCH3 | H | H | H | H | H | H | H | Ph |

-continued

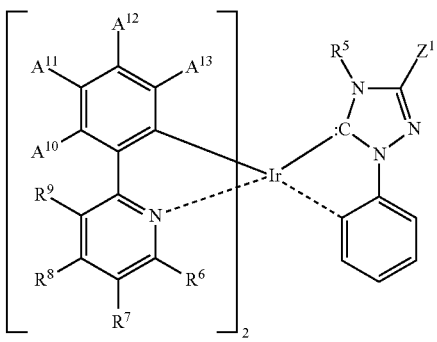

| Cpd. | R⁵ | R⁶ | R⁷ | R⁸ | R⁹ | A¹⁰ | A¹¹ | A¹² | A¹³ | Z¹ |
|---|---|---|---|---|---|---|---|---|---|---|
| A-62 | Ph | Ph | H | H | H | H | H | H | H | Ph |
| A-63 | Ph | F | H | H | H | H | H | H | H | Ph |
| A-64 | Ph | H | H | H | CF₃ | H | H | H | H | Ph |
| A-65 | Ph | H | H | H | CN | H | H | H | H | Ph |
| A-66 | Ph | H | H | H | NO₂ | H | H | H | H | Ph |
| A-67 | Ph | H | H | H | CH₃ | H | H | H | H | Ph |
| A-68 | Ph | H | H | H | Ph | H | H | H | H | Ph |
| A-69 | Ph | H | H | H | F | H | H | H | H | Ph |
| A-70 | Ph | H | H | H | OCH₃ | H | H | H | H | Ph |
| A-71 | Ph | H | H | CF₃ | H | H | H | H | H | Ph |
| A-72 | Ph | H | H | CH₃ | H | H | H | H | H | Ph |
| A-73 | Ph | H | CF₃ | H | H | H | H | H | H | Ph |
| A-74 | Ph | H | CH₃ | H | H | H | H | H | H | Ph |
| A-75 | Ph | H | F | H | H | H | H | H | H | Ph |
| A-76 | Ph | H | C₆F₅ | H | H | H | H | H | H | Ph |
| A-77 | Ph | H | H | C₆F₅ | H | H | H | H | H | Ph |
| A-78 | Ph | H | C₆H₅ | H | H | H | H | H | H | Ph |
| A-79 | Ph | H | H | C₆H₅ | H | H | H | H | H | Ph |
| A-80 | Ph | H | H | OCH₃ | H | F | H | F | H | Ph |
| A-81 | Ph | H | CF₃ | H | H | H | H | F | H | Ph |
| A-82 | Ph | H | H | 1) | 1) | H | H | H | H | Ph |
| A-83 | Ph | H | H | H | H | H | Si(CH₃)₂C₆F₁₃ | H | H | Ph |
| A-84 | Ph | H | H | OCH₃ | H | F | H | F | H | CF₃ |
| A-85 | Ph | H | C₆F₅ | H | H | H | H | F | H | Ph |
| A-86 | Ph | H | C₆F₅ | H | H | H | H | CF₃ | H | Ph |
| A-87 | Ph | H | C₆F₅ | H | H | H | C₆F₅ | H | H | Ph |
| A-88 | Ph | H | C₆F₅ | H | H | H | H | C₆F₅ | H | Ph |
| A-89 | Ph | H | H | C₆F₅ | H | H | C₆F₅ | H | H | Ph |
| A-90 | Ph | H | H | C₆F₅ | H | H | H | C₆F₅ | H | Ph |
| A-91 | Ph | H | H | OCH₃ | H | F | H | F | H | Ph |
| A-92 | Ph | H | H | OCH₃ | H | F | CN | F | H | Ph |
| A-93 | Ph | H | H | OCH₃ | H | CF₃ | H | CF₃ | H | Ph |
| A-94 | Ph | H | H | N(CH₃)₂ | H | F | H | F | H | PH |
| A-95 | Ph | H | H | N(CH₃)₂ | H | F | CN | F | H | Ph |
| A-96 | Ph | H | H | N(CH₃)₂ | H | CF₃ | H | CF₃ | H | Ph |
| A-97 | Ph | H | 1) | 1) | H | H | H | H | H | Ph |
| A-98 | Ph | H | 1) | 1) | H | H | H | CH₃ | H | Ph |
| A-99 | Ph | H | 1) | 1) | H | H | H | OCH₃ | H | Ph |
| A-100 | Ph | H | 1) | 1) | H | H | H | N(CH₃)₂ | H | Ph |
| A-101 | Ph | H | 1) | 1) | H | H | CH₃ | H | H | Ph |
| A-102 | Ph | H | 1) | 1) | H | H | OCH₃ | H | H | Ph |
| A-103 | Ph | H | 1) | 1) | H | H | N(CH₃)₂ | H | H | Ph |
| A-104 | Ph | H | H | 1) | 1) | H | H | H | H | Ph |
| A-105 | Ph | H | H | 1) | 1) | H | H | CH₃ | H | Ph |
| A-106 | Ph | H | H | 1) | 1) | H | H | OCH₃ | H | Ph |
| A-107 | Ph | H | H | 1) | 1) | H | H | N(CH₃)₂ | H | Ph |
| A-108 | Ph | H | H | 1) | 1) | H | CH₃ | H | H | Ph |
| A-109 | Ph | H | H | 1) | 1) | H | OCH₃ | H | H | Ph |
| A-110 | Ph | H | H | 1) | 1) | H | N(CH₃)₂ | H | H | Ph |
| A-111 | Ph | H | H | H | H | H | H | H | H | CF₃ |
| A-112 | Ph | H | H | H | H | H | H | CH₃ | H | CF₃ |
| A-113 | Ph | H | H | H | H | H | H | Ph | H | CF₃ |
| A-114 | Ph | H | H | H | H | H | H | t-Bu | H | CF₃ |
| A-115 | Ph | H | H | H | H | H | H | C₆H₁₁ | H | CF₃ |
| A-116 | Ph | H | H | H | H | H | H | F | H | CF₃ |
| A-117 | Ph | H | H | H | H | H | H | OCH₃ | H | CF₃ |
| A-118 | Ph | H | H | H | H | H | H | OC₆H₅ | H | CF₃ |
| A-119 | Ph | H | H | H | H | H | H | OH | H | CF₃ |
| A-120 | Ph | H | H | H | H | H | H | OCF₃ | H | CF₃ |
| A-121 | Ph | H | H | H | H | H | H | OSi(CH₃)₂C(CH₃)₃ | H | CF₃ |
| A-122 | Ph | H | H | H | H | H | H | CF₃ | H | CF₃ |

-continued

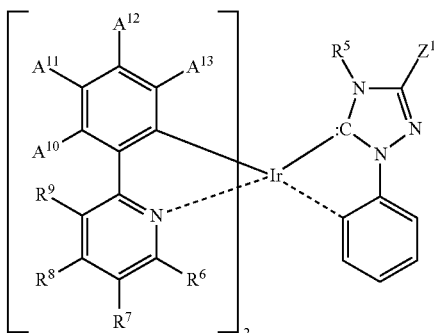

| Cpd. | R5 | R6 | R7 | R8 | R9 | A10 | A11 | A12 | A13 | Z1 |
|---|---|---|---|---|---|---|---|---|---|---|
| A-123 | Ph | H | H | H | H | H | H | SCH3 | H | CF3 |
| A-124 | Ph | H | H | H | H | H | H | SO2CH3 | H | CF3 |
| A-125 | Ph | H | H | H | H | H | H | SOCH3 | H | CF3 |
| A-126 | Ph | H | H | H | H | H | H | SH | H | CF3 |
| A-127 | Ph | H | H | H | H | H | H | NO2 | H | CF3 |
| A-128 | Ph | H | H | H | H | H | H | N(CH3)2 | H | CF3 |
| A-129 | Ph | H | H | H | H | H | H | NH2 | H | CF3 |
| A-130 | Ph | H | H | H | H | H | H | NCOCH3 | H | CF3 |
| A-131 | Ph | H | H | H | H | H | H | NSO2CH3 | H | CF3 |
| A-132 | Ph | H | H | H | H | H | H | HNCH2CH3 | H | CF3 |
| A-133 | Ph | H | H | H | H | H | H | CHO | H | CF3 |
| A-134 | Ph | H | H | H | H | H | H | CH2OH | H | CF3 |
| A-135 | Ph | H | H | H | H | H | H | CH2Br | H | CF3 |
| A-136 | Ph | H | H | H | H | H | H | CH2CN | H | CF3 |
| A-137 | Ph | H | H | H | H | H | H | CH2CO2H | H | CF3 |
| A-138 | Ph | H | H | H | H | H | H | CH2OCH3 | H | CF3 |
| A-139 | Ph | H | H | H | H | H | H | CH2N(CH2CH3)2 | H | CF3 |
| A-140 | Ph | H | H | H | H | H | H | CHCHCO2CH3 | H | CF3 |
| A-141 | Ph | H | H | H | H | H | H | CH2CH2CO2CH3 | H | CF3 |
| A-142 | Ph | H | H | H | H | H | H | C6F5 | H | CF3 |
| A-143 | Ph | H | H | H | H | H | H | H | CH3 | CF3 |
| A-144 | Ph | H | H | H | H | CH3 | H | H | H | CF3 |
| A-145 | Ph | H | H | H | H | H | H | H | CHCH2 | CF3 |
| A-146 | Ph | H | H | H | H | CHCH2 | H | H | H | CF3 |
| A-147 | Ph | H | H | H | H | H | H | Ph | H | CF3 |
| A-148 | Ph | H | H | H | H | Ph | H | H | H | CF3 |
| A-149 | Ph | H | H | H | H | C6F5 | H | H | H | CF3 |
| A-150 | Ph | H | H | H | H | CF3 | H | CF3 | H | CF3 |
| A-151 | Ph | H | H | H | H | H | H | CF3 | H | CF3 |
| A-152 | Ph | H | H | H | H | CF3 | H | H | H | CF3 |
| A-153 | Ph | H | H | H | H | F | H | H | H | CF3 |
| A-154 | Ph | H | H | H | H | H | H | F | H | CF3 |
| A-155 | Ph | H | H | H | H | F | H | F | H | CF3 |
| A-156 | Ph | H | H | H | H | H | H | OCF3 | H | CF3 |
| A-157 | Ph | H | H | H | H | OCF3 | H | H | H | CF3 |
| A-158 | Ph | H | H | H | H | NO2 | H | CF3 | H | CF3 |
| A-159 | Ph | H | H | H | H | CF3 | H | NO2 | H | CF3 |
| A-160 | Ph | H | H | H | H | CN | H | H | H | CF3 |
| A-161 | Ph | H | H | H | H | H | H | CN | H | CF3 |
| A-152 | Ph | H | H | H | H | H | H | Si(CH3)3 | H | CF3 |
| A-163 | Ph | H | H | H | H | Si(CH3)3 | H | H | H | CF3 |
| A-164 | Ph | H | H | H | H | NO2 | H | CN | H | CF3 |
| A-165 | Ph | H | H | H | H | CN | H | NO2 | H | CF3 |
| A-166 | Ph | CF3 | H | H | H | H | H | H | H | CF3 |
| A-167 | Ph | Cl | H | H | H | H | H | H | H | CF3 |
| A-168 | Ph | NO2 | H | H | H | H | H | H | H | CF3 |
| A-169 | Ph | CN | H | H | H | H | H | H | H | CF3 |
| A-170 | Ph | CH3 | H | H | H | H | H | H | H | CF3 |
| A-171 | Ph | OCH3 | H | H | H | H | H | H | H | CF3 |
| A-172 | Ph | Ph | H | H | H | H | H | H | H | CF3 |
| A-173 | Ph | F | H | H | H | H | H | H | H | CF3 |
| A-174 | Ph | H | H | H | CF3 | H | H | H | H | CF3 |
| A-175 | Ph | H | H | H | CN | H | H | H | H | CF3 |
| A-176 | Ph | H | H | H | NO2 | H | H | H | H | CF3 |
| A-177 | Ph | H | H | H | CH3 | H | H | H | H | CF3 |
| A-178 | Ph | H | H | H | Ph | H | H | H | H | CF3 |
| A-179 | Ph | H | H | H | F | H | H | H | H | CF3 |
| A-180 | Ph | H | H | H | OCH3 | H | H | H | H | CF3 |
| A-181 | Ph | H | H | CF3 | H | H | H | H | H | CF3 |
| A-182 | Ph | H | H | CH3 | H | H | H | H | H | CF3 |
| A-183 | Ph | H | CF3 | H | H | H | H | H | H | CF3 |

-continued

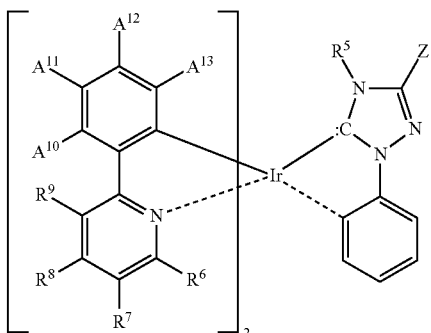

| Cpd. | R⁵ | R⁶ | R⁷ | R⁸ | R⁹ | A¹⁰ | A¹¹ | A¹² | A¹³ | Z¹ |
|---|---|---|---|---|---|---|---|---|---|---|
| A-184 | Ph | H | CH₃ | H | H | H | H | H | H | CF₃ |
| A-185 | Ph | H | F | H | H | H | H | H | H | CF₃ |
| A-186 | Ph | H | C₆F₅ | H | H | H | H | H | H | CF₃ |
| A-187 | Ph | H | H | C₆F₅ | H | H | H | H | H | CF₃ |
| A-188 | Ph | H | C₆H₅ | H | H | H | H | H | H | CF₃ |
| A-189 | Ph | H | H | C₆H₅ | H | H | H | H | H | CF₃ |
| A-190 | Ph | H | CF₃ | H | H | H | H | F | H | CF₃ |
| A-191 | Ph | H | F | H | H | H | H | CF₃ | H | CF₃ |
| A-192 | Ph | H | CN | H | H | H | H | F | H | CF₃ |
| A-193 | Ph | H | H | H | H | H | Si(CH₃)₂C₆F₁₃ | H | H | CF₃ |
| A-194 | Ph | H | F | H | H | H | F | CN | H | CF₃ |
| A-195 | Ph | H | C₆F₅ | H | H | H | H | F | H | CF₃ |
| A-196 | Ph | H | C₆F₅ | H | H | H | H | CF₃ | H | CF₃ |
| A-197 | Ph | H | C₆F₅ | H | H | C₆F₅ | H | H | H | CF₃ |
| A-198 | Ph | H | C₆F₅ | H | H | H | H | C₆F₅ | H | CF₃ |
| A-199 | Ph | H | H | C₆F₅ | H | C₆F₅ | H | H | H | CF₃ |
| A-200 | Ph | H | H | C₆F₅ | H | H | H | C₆F₅ | H | CF₃ |
| A-201 | Ph | H | H | OCH₃ | H | F | H | F | H | CF₃ |
| A-202 | Ph | H | H | OCH₃ | H | F | CN | F | H | CF₃ |
| A-203 | Ph | H | H | OCH₃ | H | CF₃ | H | CF₃ | H | CF₃ |
| A-204 | Ph | H | H | N(CH₃)₂ | H | F | H | F | H | CF₃ |
| A-205 | Ph | H | H | N(CH₃)₂ | H | F | CN | F | H | CF₃ |
| A-206 | Ph | H | H | N(CH₃)₂ | H | CF₃ | H | CF₃ | H | CF₃ |
| A-207 | Ph | 1) | 1) | H | H | H | H | H | H | CF₃ |
| A-208 | Ph | 1) | 1) | H | H | H | H | CH₃ | H | CF₃ |
| A-209 | Ph | 1) | 1) | H | H | H | H | OCH₃ | H | CF₃ |
| A-210 | Ph | 1) | 1) | H | H | H | H | N(CH₃)₂ | H | CF₃ |
| A-211 | Ph | 1) | 1) | H | H | H | CH₃ | H | H | CF₃ |
| A-212 | Ph | 1) | 1) | H | H | H | OCH₃ | H | H | CF₃ |
| A-213 | Ph | 1) | 1) | H | H | H | N(CH₃)₂ | H | H | CF₃ |
| A-214 | Ph | H | H | 1) | 1) | H | H | H | H | CF₃ |
| A-215 | Ph | H | H | 1) | 1) | H | H | CH₃ | H | CF₃ |
| A-216 | Ph | H | H | 1) | 1) | H | H | OCH₃ | H | CF₃ |
| A-217 | Ph | H | H | 1) | 1) | H | H | N(CH₃)₂ | H | CF₃ |
| A-218 | Ph | H | H | 1) | 1) | H | CH₃ | H | H | CF₃ |
| A-219 | Ph | H | H | 1) | 1) | H | OCH₃ | H | H | CF₃ |
| A-210 | Ph | H | H | 1) | 1) | H | N(CH₃)₂ | H | H | CF₃ |
| A-211 | Ph | H | H | H | H | H | H | H | H | 2) |
| A-212 | Ph | H | H | H | H | H | H | CH₃ | H | 2) |
| A-213 | Ph | H | H | H | H | H | H | Ph | H | 2) |
| A-214 | Ph | H | H | H | H | H | H | t-Bu | H | 2) |
| A-215 | Ph | H | H | H | H | H | H | C₆H₁₁ | H | 2) |
| A-216 | Ph | H | H | H | H | H | H | F | H | 2) |
| A-217 | Ph | H | H | H | H | H | H | OCH₃ | H | 2) |
| A-218 | Ph | H | H | H | H | H | H | OC₆H₅ | H | 2) |
| A-219 | Ph | H | H | H | H | H | H | OH | H | 2) |
| A-220 | Ph | H | H | H | H | H | H | OCF₃ | H | 2) |
| A-221 | Ph | H | H | H | H | H | H | OSi(CH₃)₂C(CH₃)₃ | H | 2) |
| A-222 | Ph | H | H | H | H | H | H | CF₃ | H | 2) |
| A-223 | Ph | H | H | H | H | H | H | SCH₃ | H | 2) |
| A-224 | Ph | H | H | H | H | H | H | SO₂CH₃ | H | 2) |
| A-225 | Ph | H | H | H | H | H | H | SOCH₃ | H | 2) |
| A-226 | Ph | H | H | H | H | H | H | SH | H | 2) |
| A-227 | Ph | H | H | H | H | H | H | NO₂ | H | 2) |
| A-228 | Ph | H | H | H | H | H | H | N(CH₃)₂ | H | 2) |
| A-229 | Ph | H | H | H | H | H | H | NH₂ | H | 2) |
| A-230 | Ph | H | H | H | H | H | H | NCOCH₃ | H | 2) |
| A-231 | Ph | H | H | H | H | H | H | NSO₂CH₃ | H | 2) |
| A-232 | Ph | H | H | H | H | H | H | HNCH₂CH₃ | H | 2) |
| A-233 | Ph | H | H | H | H | H | H | CHO | H | 2) |
| A-234 | Ph | H | H | H | H | H | H | CH₂OH | H | 2) |

-continued

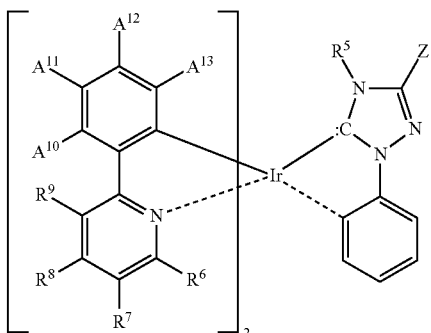

| Cpd. | R5 | R6 | R7 | R8 | R9 | A10 | A11 | A12 | A13 | Z1 |
|---|---|---|---|---|---|---|---|---|---|---|
| A-235 | Ph | H | H | H | H | H | H | $CH_2Br$ | H | 2) |
| A-236 | Ph | H | H | H | H | H | H | $CH_2CN$ | H | 2) |
| A-237 | Ph | H | H | H | H | H | H | $CH_2CO_2H$ | H | 2) |
| A-238 | Ph | H | H | H | H | H | H | $CH_2OCH_3$ | H | 2) |
| A-239 | Ph | H | H | H | H | H | H | $CH_2N(CH_2CH_3)_2$ | H | 2) |
| A-240 | Ph | H | H | H | H | H | H | $CHCHCO_2CH_3$ | H | 2) |
| A-241 | Ph | H | H | H | H | H | H | $CH_2CH_2CO_2CH_3$ | H | 2) |
| A-242 | Ph | H | H | H | H | H | H | $C_6F_5$ | H | 2) |
| A-243 | Ph | H | H | H | H | H | H | H | $CH_3$ | 2) |
| A-244 | Ph | H | H | H | H | H | $CH_3$ | H | H | 2) |
| A-245 | Ph | H | H | H | H | H | H | H | $CHCH_2$ | 2) |
| A-246 | Ph | H | H | H | H | H | $CHCH_2$ | H | H | 2) |
| A-247 | Ph | H | H | H | H | H | H | H | Ph | 2) |
| A-248 | Ph | H | H | H | H | H | Ph | H | H | 2) |
| A-249 | Ph | H | H | H | H | H | $C_6F_5$ | H | H | 2) |
| A-250 | Ph | H | H | H | H | H | $CF_3$ | H | $CF_3$ | 2) |
| A-251 | Ph | H | H | H | H | H | H | H | $CF_3$ | 2) |
| A-252 | Ph | H | H | H | H | H | $CF_3$ | H | H | 2) |
| A-253 | Ph | H | H | H | H | H | F | H | H | 2) |
| A-254 | Ph | H | H | H | H | H | H | H | F | 2) |
| A-255 | Ph | H | H | H | H | H | F | H | F | 2) |
| A-256 | Ph | H | H | H | H | H | H | H | $OCF_3$ | 2) |
| A-257 | Ph | H | H | H | H | H | $OCF_3$ | H | H | 2) |
| A-258 | Ph | H | H | H | H | H | $NO_2$ | H | $CF_3$ | 2) |
| A-259 | Ph | H | H | H | H | H | $CF_3$ | H | $NO_2$ | 2) |
| A-260 | Ph | H | H | H | H | H | CN | H | H | 2) |
| A-261 | Ph | H | H | H | H | H | H | H | CN | 2) |
| A-252 | Ph | H | H | H | H | H | H | H | $Si(CH_3)_3$ | 2) |
| A-263 | Ph | H | H | H | H | H | $Si(CH_3)_3$ | H | H | 2) |
| A-264 | Ph | H | H | H | H | H | $NO_2$ | H | CN | 2) |
| A-265 | Ph | H | H | H | H | H | CN | H | $NO_2$ | 2) |
| A-266 | Ph | $CF_3$ | H | H | H | H | H | H | H | 2) |
| A-267 | Ph | Cl | H | H | H | H | H | H | H | 2) |
| A-268 | Ph | $NO_2$ | H | H | H | H | H | H | H | 2) |
| A-269 | Ph | CN | H | H | H | H | H | H | H | 2) |
| A-270 | Ph | $CH_3$ | H | H | H | H | H | H | H | 2) |
| A-271 | Ph | $OCH_3$ | H | H | H | H | H | H | H | 2) |
| A-272 | Ph | Ph | H | H | H | H | H | H | H | 2) |
| A-273 | Ph | F | H | H | H | H | H | H | H | 2) |
| A-274 | Ph | H | H | H | $CF_3$ | H | H | H | H | 2) |
| A-275 | Ph | H | H | H | CN | H | H | H | H | 2) |
| A-276 | Ph | H | H | H | $NO_2$ | H | H | H | H | 2) |
| A-277 | Ph | H | H | H | $CH_3$ | H | H | H | H | 2) |
| A-278 | Ph | H | H | H | Ph | H | H | H | H | 2) |
| A-279 | Ph | H | H | H | F | H | H | H | H | 2) |
| A-280 | Ph | H | H | H | $OCH_3$ | H | H | H | H | 2) |
| A-281 | Ph | H | H | $CF_3$ | H | H | H | H | H | 2) |
| A-282 | Ph | H | H | $CH_3$ | H | H | H | H | H | 2) |
| A-283 | Ph | H | $CF_3$ | H | H | H | H | H | H | 2) |
| A-284 | Ph | H | $CH_3$ | H | H | H | H | H | H | 2) |
| A-285 | Ph | H | F | H | H | H | H | H | H | 2) |
| A-286 | Ph | H | $C_6F_5$ | H | H | H | H | H | H | 2) |
| A-287 | Ph | H | H | $C_6F_5$ | H | H | H | H | H | 2) |
| A-288 | Ph | H | $C_6H_5$ | H | H | H | H | H | H | 2) |
| A-289 | Ph | H | H | $C_6H_5$ | H | H | H | H | H | 2) |
| A-290 | Ph | H | $CF_3$ | H | H | H | H | F | H | 2) |
| A-291 | Ph | H | F | H | H | H | H | $CF_3$ | H | 2) |
| A-292 | Ph | H | CN | H | H | H | H | F | H | 2) |
| A-293 | Ph | H | H | H | H | H | $Si(CH_3)_2C_6F_5$ | H | H | 2) |
| A-294 | Ph | H | F | H | H | H | F | CN | H | 2) |
| A-295 | Ph | H | $C_6F_5$ | H | H | H | H | F | H | 2) |

-continued

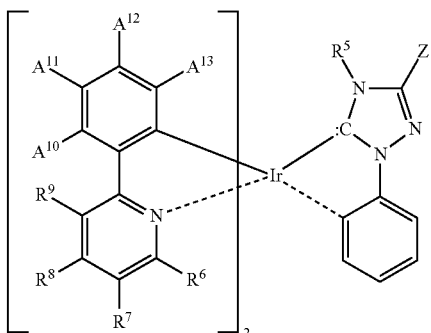

| Cpd. | R⁵ | R⁶ | R⁷ | R⁸ | R⁹ | A¹⁰ | A¹¹ | A¹² | A¹³ | Z¹ |
|---|---|---|---|---|---|---|---|---|---|---|
| A-296 | Ph | H | C₆F₅ | H | H | H | H | CF₃ | H | 2) |
| A-297 | Ph | H | C₆F₅ | H | H | H | C₆F₅ | H | H | 2) |
| A-298 | Ph | H | C₆F₅ | H | H | H | H | C₆F₅ | H | 2) |
| A-299 | Ph | H | H | C₆F₅ | H | H | C₆F₅ | H | H | 2) |
| A-300 | Ph | H | C₆F₅ | H | H | H | H | C₆F₅ | H | 2) |
| A-301 | Ph | H | H | OCH₃ | H | F | H | F | H | 2) |
| A-302 | Ph | H | H | OCH₃ | H | F | CN | F | H | 2) |
| A-303 | Ph | H | H | OCH₃ | H | CF₃ | H | CF₃ | H | 2) |
| A-304 | Ph | H | H | N(CH₃)₂ | H | F | H | F | H | 2) |
| A-305 | Ph | H | H | N(CH₃)₂ | H | F | CN | F | H | 2) |
| A-306 | Ph | H | H | N(CH₃)₂ | H | CF₃ | H | CF₃ | H | 2) |
| A-307 | Ph | 1) | 1) | H | H | H | H | H | H | 2) |
| A-308 | Ph | 1) | 1) | H | H | H | H | CH₃ | H | 2) |
| A-309 | Ph | 1) | 1) | H | H | H | H | OCH₃ | H | 2) |
| A-310 | Ph | 1) | 1) | H | H | H | H | N(CH₃)₂ | H | 2) |
| A-311 | Ph | 1) | 1) | H | H | H | CH₃ | H | H | 2) |
| A-312 | Ph | 1) | 1) | H | H | H | OCH₃ | H | H | 2) |
| A-313 | Ph | 1) | 1) | H | H | H | N(CH₃)₂ | H | H | 2) |
| A-314 | Ph | H | H | 1) | 1) | H | H | H | H | 2) |
| A-315 | Ph | H | H | 1) | 1) | H | H | CH₃ | H | 2) |
| A-316 | Ph | H | H | 1) | 1) | H | H | OCH₃ | H | 2) |
| A-317 | Ph | H | H | 1) | 1) | H | H | N(CH₃)₂ | H | 2) |
| A-318 | Ph | H | H | 1) | 1) | H | CH₃ | H | H | 2) |
| A-319 | Ph | H | H | 1) | 1) | H | OCH₃ | H | H | 2) |
| A-320 | Ph | H | H | 1) | 1) | H | N(CH₃)₂ | H | H | 2) |

1)R⁸ and R⁹ together form a group ⌬ , R⁵ and R⁶ together form a group ⌬ , 2)4-C₆H₄C(CH)₃.

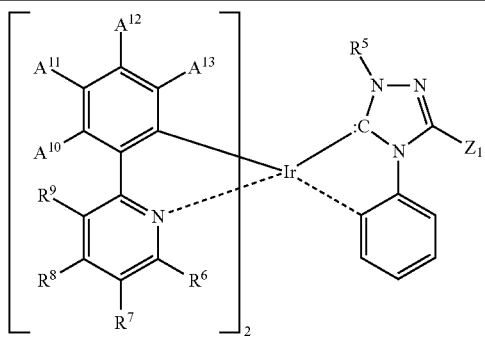

| Cpd. | R⁵ | R⁶ | R⁷ | R⁸ | R⁹ | A¹⁰ | A¹¹ | A¹² | A¹³ | Z¹ |
|---|---|---|---|---|---|---|---|---|---|---|
| A'-1 | Ph | H | H | H | H | H | H | H | H | Ph |
| A'-2 | Ph | H | H | H | H | H | H | CH₃ | H | Ph |
| A'-3 | Ph | H | H | H | H | H | H | Ph | H | Ph |
| A'-4 | Ph | H | H | H | H | H | H | t-Bu | H | Ph |
| A'-5 | Ph | H | H | H | H | H | H | C₆H₁₁ | H | Ph |
| A'-6 | Ph | H | H | H | H | H | H | F | H | Ph |

-continued

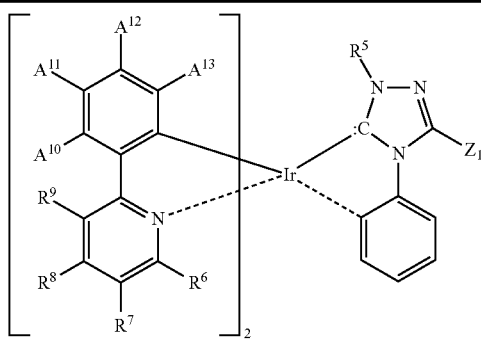

| Cpd. | R⁵ | R⁶ | R⁷ | R⁸ | R⁹ | A¹⁰ | A¹¹ | A¹² | A¹³ | Z¹ |
|---|---|---|---|---|---|---|---|---|---|---|
| A'-7 | Ph | H | H | H | H | H | H | OCH₃ | H | Ph |
| A'-8 | Ph | H | H | H | H | H | H | OC₆H₅ | H | Ph |
| A'-9 | Ph | H | H | H | H | H | H | OH | H | Ph |
| A'-10 | Ph | H | H | H | H | H | H | OCF₃ | H | Ph |
| A'-11 | Ph | H | H | H | H | H | H | OSi(CH₃)₂C(CH₃)₃ | H | Ph |
| A'-12 | Ph | H | H | H | H | H | H | CF₃ | H | Ph |
| A'-13 | Ph | H | H | H | H | H | H | SCH₃ | H | Ph |
| A'-14 | Ph | H | H | H | H | H | H | SO₂CH₃ | H | Ph |
| A'-15 | Ph | H | H | H | H | H | H | SOCH₃ | H | Ph |
| A'-16 | Ph | H | H | H | H | H | H | SH | H | Ph |
| A'-17 | Ph | H | H | H | H | H | H | NO₂ | H | Ph |
| A'-18 | Ph | H | H | H | H | H | H | N(CH₃)₂ | H | Ph |
| A'-19 | Ph | H | H | H | H | H | H | NH₂ | H | Ph |
| A'-20 | Ph | H | H | H | H | H | H | NCOCH₃ | H | Ph |
| A'-21 | Ph | H | H | H | H | H | H | NSO₂CH₃ | H | Ph |
| A'-22 | Ph | H | H | H | H | H | H | HNCH₂CH₃ | H | Ph |
| A'-23 | Ph | H | H | H | H | H | H | CHO | H | Ph |
| A'-24 | Ph | H | H | H | H | H | H | CH₂OH | H | Ph |
| A'-25 | Ph | H | H | H | H | H | H | CH₂Br | H | Ph |
| A'-26 | Ph | H | H | H | H | H | H | CH₂CN | H | Ph |
| A'-27 | Ph | H | H | H | H | H | H | CH₂CO₂H | H | Ph |
| A'-28 | Ph | H | H | H | H | H | H | CH₂OCH₃ | H | Ph |
| A'-29 | Ph | H | H | H | H | H | H | CH₂N(CH₂CH₃)₂ | H | Ph |
| A'-30 | Ph | H | H | H | H | H | H | CHCHCO₂CH₃ | H | Ph |
| A'-31 | Ph | H | H | H | H | H | H | CH₂CH₂CO₂CH₃ | H | Ph |
| A'-32 | Ph | H | H | H | H | H | H | C₆F₅ | H | Ph |
| A'-33 | Ph | H | H | H | H | H | H | H | CH₃ | Ph |
| A'-34 | Ph | H | H | H | H | H | CH₃ | H | H | Ph |
| A'-35 | Ph | H | H | H | H | H | H | H | CHCH₂ | Ph |
| A'-36 | Ph | H | H | H | H | H | CHCH₂ | H | H | Ph |
| A'-37 | Ph | H | H | H | H | H | H | H | Ph | Ph |
| A'-38 | Ph | H | H | H | H | H | Ph | H | H | Ph |
| A'-39 | Ph | H | H | H | H | H | C₆F₅ | H | H | Ph |
| A'-40 | Ph | H | H | H | H | H | CF₃ | H | CF₃ | Ph |
| A'-41 | Ph | H | H | H | H | H | H | H | CF₃ | Ph |
| A'-42 | Ph | H | H | H | H | H | CF₃ | H | H | Ph |
| A'-43 | Ph | H | H | H | H | H | F | H | H | Ph |
| A'-44 | Ph | H | H | H | H | H | H | H | F | Ph |
| A'-45 | Ph | H | H | H | H | H | F | H | F | Ph |
| A'-46 | Ph | H | H | H | H | H | H | H | OCF₃ | Ph |
| A'-47 | Ph | H | H | H | H | H | OCF₃ | H | H | Ph |
| A'-48 | Ph | H | H | H | H | H | NO₂ | H | CF₃ | Ph |
| A'-49 | Ph | H | H | H | H | H | CF₃ | H | NO₂ | Ph |
| A'-50 | Ph | H | H | H | H | H | CN | H | H | Ph |
| A'-51 | Ph | H | H | H | H | H | H | H | CN | Ph |
| A'-52 | Ph | H | H | H | H | H | H | H | Si(CH₃)₃ | Ph |
| A'-53 | Ph | H | H | H | H | H | Si(CH₃)₃ | H | H | Ph |
| A'-54 | Ph | H | H | H | H | H | NO₂ | H | CN | Ph |
| A'-55 | Ph | H | H | H | H | H | CN | H | NO₂ | Ph |
| A'-56 | Ph | CF₃ | H | H | H | H | H | H | H | Ph |
| A'-57 | Ph | Cl | H | H | H | H | H | H | H | Ph |
| A'-58 | Ph | NO₂ | H | H | H | H | H | H | H | Ph |
| A'-59 | Ph | CN | H | H | H | H | H | H | H | Ph |
| A'-60 | Ph | CH₃ | H | H | H | H | H | H | H | Ph |
| A'-61 | Ph | OCH₃ | H | H | H | H | H | H | H | Ph |
| A'-62 | Ph | Ph | H | H | H | H | H | H | H | Ph |
| A'-63 | Ph | F | H | H | H | H | H | H | H | Ph |
| A'-64 | Ph | H | H | H | CF₃ | H | H | H | H | Ph |
| A'-65 | Ph | H | H | H | CN | H | H | H | H | Ph |
| A'-66 | Ph | H | H | H | NO₂ | H | H | H | H | Ph |
| A'-67 | Ph | H | H | H | CH₃ | H | H | H | H | Ph |

-continued

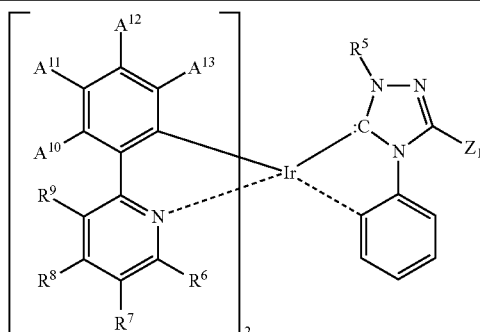

| Cpd. | R⁵ | R⁶ | R⁷ | R⁸ | R⁹ | A¹⁰ | A¹¹ | A¹² | A¹³ | Z¹ |
|---|---|---|---|---|---|---|---|---|---|---|
| A'-68 | Ph | H | H | H | Ph | H | H | H | H | Ph |
| A'-69 | Ph | H | H | H | F | H | H | H | H | Ph |
| A'-70 | Ph | H | H | H | OCH₃ | H | H | H | H | Ph |
| A'-71 | Ph | H | H | CF₃ | H | H | H | H | H | Ph |
| A'-72 | Ph | H | H | CH₃ | H | H | H | H | H | Ph |
| A'-73 | Ph | H | CF₃ | H | H | H | H | H | H | Ph |
| A'-74 | Ph | H | CH₃ | H | H | H | H | H | H | Ph |
| A'-75 | Ph | H | F | H | H | H | H | H | H | Ph |
| A'-76 | Ph | H | C₆F₅ | H | H | H | H | H | H | Ph |
| A'-77 | Ph | H | H | C₆F₅ | H | H | H | H | H | Ph |
| A'-78 | Ph | H | C₆H₅ | H | H | H | H | H | H | Ph |
| A'-79 | Ph | H | H | C₆H₅ | H | H | H | H | H | Ph |
| A'-80 | Ph | H | CF₃ | H | H | H | H | F | H | Ph |
| A'-81 | Ph | H | F | H | H | H | H | CF₃ | H | Ph |
| A'-82 | Ph | H | CN | H | H | H | H | F | H | Ph |
| A'-83 | Ph | H | H | H | H | H | Si(CH₃)₂C₆F₁₃ | H | H | Ph |
| A'-84 | Ph | H | F | H | H | H | F | CN | H | Ph |
| A'-85 | Ph | H | C₆F₅ | H | H | H | H | F | H | Ph |
| A'-86 | Ph | H | C₆F₅ | H | H | H | H | CF₃ | H | Ph |
| A'-87 | Ph | H | C₆F₅ | H | H | H | C₆F₅ | H | H | Ph |
| A'-88 | Ph | H | C₆F₅ | H | H | H | H | C₆F₅ | H | Ph |
| A'-89 | Ph | H | H | C₆F₅ | H | H | C₆F₅ | H | H | Ph |
| A'-90 | Ph | H | H | C₆F₅ | H | H | H | C₆F₅ | H | Ph |
| A'-91 | Ph | H | H | OCH₃ | H | F | H | F | H | Ph |
| A'-92 | Ph | H | H | OCH₃ | H | F | CN | F | H | Ph |
| A'-93 | Ph | H | H | OCH₃ | H | CF₃ | H | CF₃ | H | Ph |
| A'-94 | Ph | H | H | N(CH₃)₂ | H | F | H | F | H | PH |
| A'-95 | Ph | H | H | N(CH₃)₂ | H | F | CN | F | H | Ph |
| A'-96 | Ph | H | H | N(CH₃)₂ | H | CF₃ | H | CF₃ | H | Ph |
| A'-97 | Ph | 1) | 1) | H | H | H | H | H | H | Ph |
| A'-98 | Ph | 1) | 1) | H | H | H | H | CH₃ | H | Ph |
| A'-99 | Ph | 1) | 1) | H | H | H | H | OCH₃ | H | Ph |
| A'-100 | Ph | 1) | 1) | H | H | H | H | N(CH₃)₂ | H | Ph |
| A'-101 | Ph | 1) | 1) | H | H | H | CH₃ | H | H | Ph |
| A'-102 | Ph | 1) | 1) | H | H | H | OCH₃ | H | H | Ph |
| A'-103 | Ph | 1) | 1) | H | H | H | N(CH₃)₂ | H | H | Ph |
| A'-104 | Ph | H | H | 1) | 1) | H | H | H | H | Ph |
| A'-105 | Ph | H | H | 1) | 1) | H | H | CH₃ | H | Ph |
| A'-106 | Ph | H | H | 1) | 1) | H | H | OCH₃ | H | Ph |
| A'-107 | Ph | H | H | 1) | 1) | H | H | N(CH₃)₂ | H | Ph |
| A'-108 | Ph | H | H | 1) | 1) | H | CH₃ | H | H | Ph |
| A'-109 | Ph | H | H | 1) | 1) | H | OCH₃ | H | H | Ph |
| A'-110 | Ph | H | H | 1) | 1) | H | N(CH₃)₂ | H | H | Ph |
| A'-111 | Ph | H | H | H | H | H | H | H | H | CF₃ |
| A'-112 | Ph | H | H | H | H | H | H | CH₃ | H | CF₃ |
| A'-113 | Ph | H | H | H | H | H | H | Ph | H | CF₃ |
| A'-114 | Ph | H | H | H | H | H | H | t-Bu | H | CF₃ |
| A'-115 | Ph | H | H | H | H | H | H | C₆H₁₁ | H | CF₃ |
| A'-116 | Ph | H | H | H | H | H | H | F | H | CF₃ |
| A'-117 | Ph | H | H | H | H | H | H | OCH₃ | H | CF₃ |
| A'-118 | Ph | H | H | H | H | H | H | OC₆H₅ | H | CF₃ |
| A'-119 | Ph | H | H | H | H | H | H | OH | H | CF₃ |
| A'-120 | Ph | H | H | H | H | H | H | OCF₃ | H | CF₃ |
| A'-121 | Ph | H | H | H | H | H | H | OSi(CH₃)₂C(CH₃)₃ | H | CF₃ |
| A'-122 | Ph | H | H | H | H | H | H | CF₃ | H | CF₃ |
| A'-123 | Ph | H | H | H | H | H | H | SCH₃ | H | CF₃ |
| A'-124 | Ph | H | H | H | H | H | H | SO₂CH₃ | H | CF₃ |
| A'-125 | Ph | H | H | H | H | H | H | SOCH₃ | H | CF₃ |
| A'-126 | Ph | H | H | H | H | H | H | SH | H | CF₃ |
| A'-127 | Ph | H | H | H | H | H | H | NO₂ | H | CF₃ |
| A'-128 | Ph | H | H | H | H | H | H | N(CH₃)₂ | H | CF₃ |

-continued

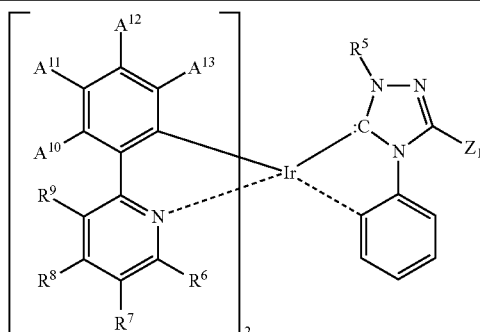

| Cpd. | R⁵ | R⁶ | R⁷ | R⁸ | R⁹ | A¹⁰ | A¹¹ | A¹² | A¹³ | Z¹ |
|---|---|---|---|---|---|---|---|---|---|---|
| A'-129 | Ph | H | H | H | H | H | H | NH₂ | H | CF₃ |
| A'-130 | Ph | H | H | H | H | H | H | NCOCH₃ | H | CF₃ |
| A'-131 | Ph | H | H | H | H | H | H | NSO₂CH₃ | H | CF₃ |
| A'-132 | Ph | H | H | H | H | H | H | HNCH₂CH₃ | H | CF₃ |
| A'-133 | Ph | H | H | H | H | H | H | CHO | H | CF₃ |
| A'-134 | Ph | H | H | H | H | H | H | CH₂OH | H | CF₃ |
| A'-135 | Ph | H | H | H | H | H | H | CH₂Br | H | CF₃ |
| A'-136 | Ph | H | H | H | H | H | H | CH₂CN | H | CF₃ |
| A'-137 | Ph | H | H | H | H | H | H | CH₂CO₂H | H | CF₃ |
| A'-138 | Ph | H | H | H | H | H | H | CH₂OCH₃ | H | CF₃ |
| A'-139 | Ph | H | H | H | H | H | H | CH₂N(CH₂CH₃)₂ | H | CF₃ |
| A'-140 | Ph | H | H | H | H | H | H | CHCHCO₂CH₃ | H | CF₃ |
| A'-141 | Ph | H | H | H | H | H | H | CH₂CH₂CO₂CH₃ | H | CF₃ |
| A'-142 | Ph | H | H | H | H | H | H | C₆F₅ | H | CF₃ |
| A'-143 | Ph | H | H | H | H | H | H | H | CH₃ | CF₃ |
| A'-144 | Ph | H | H | H | H | H | CH₃ | H | H | CF₃ |
| A'-145 | Ph | H | H | H | H | H | H | H | CHCH₂ | CF₃ |
| A'-146 | Ph | H | H | H | H | H | CHCH₂ | H | H | CF₃ |
| A'-147 | Ph | H | H | H | H | H | H | H | Ph | CF₃ |
| A'-148 | Ph | H | H | H | H | H | Ph | H | H | CF₃ |
| A'-149 | Ph | H | H | H | H | H | C₆F₅ | H | H | CF₃ |
| A'-150 | Ph | H | H | H | H | H | CF₃ | H | CF₃ | CF₃ |
| A'-151 | Ph | H | H | H | H | H | H | H | CF₃ | CF₃ |
| A'-152 | Ph | H | H | H | H | H | CF₃ | H | H | CF₃ |
| A'-153 | Ph | H | H | H | H | H | F | H | H | CF₃ |
| A'-154 | Ph | H | H | H | H | H | H | H | F | CF₃ |
| A'-155 | Ph | H | H | H | H | H | F | H | F | CF₃ |
| A'-156 | Ph | H | H | H | H | H | H | H | OCF₃ | CF₃ |
| A'-157 | Ph | H | H | H | H | H | OCF₃ | H | H | CF₃ |
| A'-158 | Ph | H | H | H | H | H | NO₂ | H | CF₃ | CF₃ |
| A'-159 | Ph | H | H | H | H | H | CF₃ | H | NO₂ | CF₃ |
| A'-160 | Ph | H | H | H | H | H | CN | H | H | CF₃ |
| A'-161 | Ph | H | H | H | H | H | H | H | CN | CF₃ |
| A'-162 | Ph | H | H | H | H | H | H | H | Si(CH₃)₃ | CF₃ |
| A'-163 | Ph | H | H | H | H | H | Si(CH₃)₃ | H | H | CF₃ |
| A'-164 | Ph | H | H | H | H | H | NO₂ | H | CN | CF₃ |
| A'-165 | Ph | H | H | H | H | H | CN | H | NO₂ | CF₃ |
| A'-166 | Ph | CF₃ | H | H | H | H | H | H | H | CF₃ |
| A'-167 | Ph | Cl | H | H | H | H | H | H | H | CF₃ |
| A'-168 | Ph | NO₂ | H | H | H | H | H | H | H | CF₃ |
| A'-169 | Ph | CN | H | H | H | H | H | H | H | CF₃ |
| A'-170 | Ph | CH₃ | H | H | H | H | H | H | H | CF₃ |
| A'-171 | Ph | OCH₃ | H | H | H | H | H | H | H | CF₃ |
| A'-172 | Ph | Ph | H | H | H | H | H | H | H | CF₃ |
| A'-173 | Ph | F | H | H | H | H | H | H | H | CF₃ |
| A'-174 | Ph | H | H | H | CF₃ | H | H | H | H | CF₃ |
| A'-175 | Ph | H | H | H | CN | H | H | H | H | CF₃ |
| A'-176 | Ph | H | H | H | NO₂ | H | H | H | H | CF₃ |
| A'-177 | Ph | H | H | H | CH₃ | H | H | H | H | CF₃ |
| A'-178 | Ph | H | H | H | Ph | H | H | H | H | CF₃ |
| A'-179 | Ph | H | H | H | F | H | H | H | H | CF₃ |
| A'-180 | Ph | H | H | H | OCH₃ | H | H | H | H | CF₃ |
| A'-181 | Ph | H | H | CF₃ | H | H | H | H | H | CF₃ |
| A'-182 | Ph | H | H | CH₃ | H | H | H | H | H | CF₃ |
| A'-183 | Ph | H | CF₃ | H | H | H | H | H | H | CF₃ |
| A'-184 | Ph | H | CH₃ | H | H | H | H | H | H | CF₃ |
| A'-185 | Ph | H | F | H | H | H | H | H | H | CF₃ |
| A'-186 | Ph | H | C₆F₅ | H | H | H | H | H | H | CF₃ |
| A'-187 | Ph | H | H | C₆F₅ | H | H | H | H | H | CF₃ |
| A'-188 | Ph | H | C₆H₅ | H | H | H | H | H | H | CF₃ |
| A'-189 | Ph | H | H | C₆H₅ | H | H | H | H | H | CF₃ |

-continued

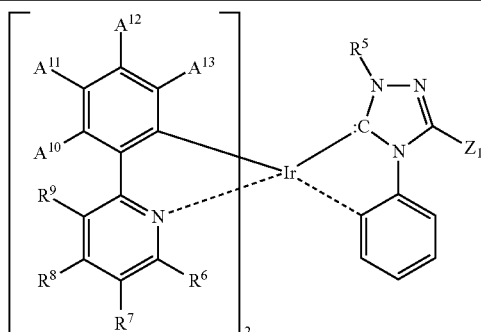

| Cpd. | R⁵ | R⁶ | R⁷ | R⁸ | R⁹ | A¹⁰ | A¹¹ | A¹² | A¹³ | Z¹ |
|---|---|---|---|---|---|---|---|---|---|---|
| A'-190 | Ph | H | CF₃ | H | H | H | H | F | H | CF₃ |
| A'-191 | Ph | H | F | H | H | H | H | CF₃ | H | CF₃ |
| A'-192 | Ph | H | CN | H | H | H | H | F | H | CF₃ |
| A'-193 | Ph | H | H | H | H | H | Si(CH₃)₂C₆F₁₃ | H | H | CF₃ |
| A'-194 | Ph | H | F | H | H | H | F | CN | H | CF₃ |
| A'-195 | Ph | H | C₆F₅ | H | H | H | H | F | H | CF₃ |
| A'-196 | Ph | H | C₆F₅ | H | H | H | H | CF₃ | H | CF₃ |
| A'-197 | Ph | H | C₆F₅ | H | H | H | C₆F₅ | H | H | CF₃ |
| A'-198 | Ph | H | C₆F₅ | H | H | H | H | C₆F₅ | H | CF₃ |
| A'-199 | Ph | H | H | C₆F₅ | H | H | C₆F₅ | H | H | CF₃ |
| A'-200 | Ph | H | H | C₆F₅ | H | H | H | C₆F₅ | H | CF₃ |
| A'-201 | Ph | H | H | OCH₃ | H | F | H | F | H | CF₃ |
| A'-202 | Ph | H | H | OCH₃ | H | F | CN | F | H | CF₃ |
| A'-203 | Ph | H | H | OCH₃ | H | CF₃ | H | CF₃ | H | CF₃ |
| A'-204 | Ph | H | H | N(CH₃)₂ | H | F | H | F | H | CF₃ |
| A'-205 | Ph | H | H | N(CH₃)₂ | H | F | CN | F | H | CF₃ |
| A'-206 | Ph | H | H | N(CH₃)₂ | H | CF₃ | H | CF₃ | H | CF₃ |
| A'-207 | Ph | 1) | 1) | H | H | H | H | H | H | CF₃ |
| A'-208 | Ph | 1) | 1) | H | H | H | H | CH₃ | H | CF₃ |
| A'-209 | Ph | 1) | 1) | H | H | H | H | OCH₃ | H | CF₃ |
| A'-210 | Ph | 1) | 1) | H | H | H | H | N(CH₃)₂ | H | CF₃ |
| A'-211 | Ph | 1) | 1) | H | H | H | CH₃ | H | H | CF₃ |
| A'-212 | Ph | 1) | 1) | H | H | H | OCH₃ | H | H | CF₃ |
| A'-213 | Ph | 1) | 1) | H | H | H | N(CH₃)₂ | H | H | CF₃ |
| A'-214 | Ph | H | H | 1) | 1) | H | H | H | H | CF₃ |
| A'-215 | Ph | H | H | 1) | 1) | H | H | CH₃ | H | CF₃ |
| A'-216 | Ph | H | H | 1) | 1) | H | H | OCH₃ | H | CF₃ |
| A'-217 | Ph | H | H | 1) | 1) | H | H | N(CH₃)₂ | H | CF₃ |
| A'-218 | Ph | H | H | 1) | 1) | H | CH₃ | H | H | CF₃ |
| A'-219 | Ph | H | H | 1) | 1) | H | OCH₃ | H | H | CF₃ |
| A'-210 | Ph | H | H | 1) | 1) | H | N(CH₃)₂ | H | H | CF₃ |
| A'-211 | Ph | H | H | H | H | H | H | H | H | 2) |
| A'-212 | Ph | H | H | H | H | H | H | CH₃ | H | 2) |
| A'-213 | Ph | H | H | H | H | H | H | Ph | H | 2) |
| A'-214 | Ph | H | H | H | H | H | H | t-Bu | H | 2) |
| A'-215 | Ph | H | H | H | H | H | H | C₆H₁₁ | H | 2) |
| A'-216 | Ph | H | H | H | H | H | H | F | H | 2) |
| A'-217 | Ph | H | H | H | H | H | H | OCH₃ | H | 2) |
| A'-218 | Ph | H | H | H | H | H | H | OC₆H₅ | H | 2) |
| A'-219 | Ph | H | H | H | H | H | H | OH | H | 2) |
| A'-220 | Ph | H | H | H | H | H | H | OCF₃ | H | 2) |
| A'-221 | Ph | H | H | H | H | H | H | OSi(CH₃)₂C(CH₃)₃ | H | 2) |
| A'-222 | Ph | H | H | H | H | H | H | CF₃ | H | 2) |
| A'-223 | Ph | H | H | H | H | H | H | SCH₃ | H | 2) |
| A'-224 | Ph | H | H | H | H | H | H | SO₂CH₃ | H | 2) |
| A'-225 | Ph | H | H | H | H | H | H | SOCH₃ | H | 2) |
| A'-226 | Ph | H | H | H | H | H | H | SH | H | 2) |
| A'-227 | Ph | H | H | H | H | H | H | NO₂ | H | 2) |
| A'-228 | Ph | H | H | H | H | H | H | N(CH₃)₂ | H | 2) |
| A'-229 | Ph | H | H | H | H | H | H | NH₂ | H | 2) |
| A'-230 | Ph | H | H | H | H | H | H | NCOCH₃ | H | 2) |
| A'-231 | Ph | H | H | H | H | H | H | NSO₂CH₃ | H | 2) |
| A'-232 | Ph | H | H | H | H | H | H | HNCH₂CH₃ | H | 2) |
| A'-233 | Ph | H | H | H | H | H | H | CHO | H | 2) |
| A'-234 | Ph | H | H | H | H | H | H | CH₂OH | H | 2) |
| A'-235 | Ph | H | H | H | H | H | H | CH₂Br | H | 2) |
| A'-236 | Ph | H | H | H | H | H | H | CH₂CN | H | 2) |
| A'-237 | Ph | H | H | H | H | H | H | CH₂CO₂H | H | 2) |
| A'-238 | Ph | H | H | H | H | H | H | CH₂OCH₃ | H | 2) |
| A'-239 | Ph | H | H | H | H | H | H | CH₂N(CH₂CH₃)₂ | H | 2) |
| A'-240 | Ph | H | H | H | H | H | H | CHCHCO₂CH₃ | H | 2) |

-continued

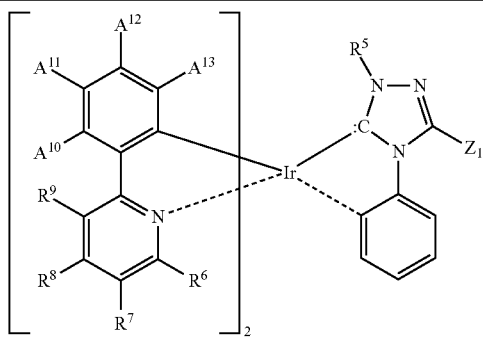

| Cpd. | R⁵ | R⁶ | R⁷ | R⁸ | R⁹ | A¹⁰ | A¹¹ | A¹² | A¹³ | Z¹ |
|---|---|---|---|---|---|---|---|---|---|---|
| A'-241 | Ph | H | H | H | H | H | H | CH₂CH₂CO₂CH₃ | H | 2) |
| A'-242 | Ph | H | H | H | H | H | H | C₆F₅ | H | 2) |
| A'-243 | Ph | H | H | H | H | H | H | H | CH₃ | 2) |
| A'-244 | Ph | H | H | H | H | H | CH₃ | H | H | 2) |
| A'-245 | Ph | H | H | H | H | H | H | H | CHCH₂ | 2) |
| A'-246 | Ph | H | H | H | H | H | CHCH₂ | H | H | 2) |
| A'-247 | Ph | H | H | H | H | H | H | H | Ph | 2) |
| A'-248 | Ph | H | H | H | H | H | Ph | H | H | 2) |
| A'-249 | Ph | H | H | H | H | H | C₆F₅ | H | H | 2) |
| A'-250 | Ph | H | H | H | H | H | CF₃ | H | CF₃ | 2) |
| A'-251 | Ph | H | H | H | H | H | H | H | CF₃ | 2) |
| A'-252 | Ph | H | H | H | H | H | CF₃ | H | H | 2) |
| A'-253 | Ph | H | H | H | H | H | F | H | H | 2) |
| A'-254 | Ph | H | H | H | H | H | H | H | F | 2) |
| A'-255 | Ph | H | H | H | H | H | F | H | F | 2) |
| A'-256 | Ph | H | H | H | H | H | H | H | OCF₃ | 2) |
| A'-257 | Ph | H | H | H | H | H | OCF₃ | H | H | 2) |
| A'-258 | Ph | H | H | H | H | H | NO₂ | H | CF₃ | 2) |
| A'-259 | Ph | H | H | H | H | H | CF₃ | H | NO₂ | 2) |
| A'-260 | Ph | H | H | H | H | H | CN | H | H | 2) |
| A'-261 | Ph | H | H | H | H | H | H | H | CN | 2) |
| A'-252 | Ph | H | H | H | H | H | H | H | Si(CH₃)₃ | 2) |
| A'-263 | Ph | H | H | H | H | H | Si(CH₃)₃ | H | H | 2) |
| A'-264 | Ph | H | H | H | H | H | NO₂ | H | CN | 2) |
| A'-265 | Ph | H | H | H | H | H | CN | H | NO₂ | 2) |
| A'-266 | Ph | CF₃ | H | H | H | H | H | H | H | 2) |
| A'-267 | Ph | Cl | H | H | H | H | H | H | H | 2) |
| A'-268 | Ph | NO₂ | H | H | H | H | H | H | H | 2) |
| A'-269 | Ph | CN | H | H | H | H | H | H | H | 2) |
| A'-270 | Ph | CH₃ | H | H | H | H | H | H | H | 2) |
| A'-271 | Ph | OCH₃ | H | H | H | H | H | H | H | 2) |
| A'-272 | Ph | Ph | H | H | H | H | H | H | H | 2) |
| A'-273 | Ph | F | H | H | H | H | H | H | H | 2) |
| A'-274 | Ph | H | H | H | CF₃ | H | H | H | H | 2) |
| A'-275 | Ph | H | H | H | CN | H | H | H | H | 2) |
| A'-276 | Ph | H | H | H | NO₂ | H | H | H | H | 2) |
| A'-277 | Ph | H | H | H | CH₃ | H | H | H | H | 2) |
| A'-278 | Ph | H | H | H | Ph | H | H | H | H | 2) |
| A'-279 | Ph | H | H | H | F | H | H | H | H | 2) |
| A'-280 | Ph | H | H | H | OCH₃ | H | H | H | H | 2) |
| A'-281 | Ph | H | H | CF₃ | H | H | H | H | H | 2) |
| A'-282 | Ph | H | H | CH₃ | H | H | H | H | H | 2) |
| A'-283 | Ph | H | CF₃ | H | H | H | H | H | H | 2) |
| A'-284 | Ph | H | CH₃ | H | H | H | H | H | H | 2) |
| A'-285 | Ph | H | F | H | H | H | H | H | H | 2) |
| A'-286 | Ph | H | C₆F₅ | H | H | H | H | H | H | 2) |
| A'-287 | Ph | H | H | C₆F₅ | H | H | H | H | H | 2) |
| A'-288 | Ph | H | C₆H₅ | H | H | H | H | H | H | 2) |
| A'-289 | Ph | H | H | C₆H₅ | H | H | H | H | H | 2) |
| A'-290 | Ph | H | CF₃ | H | H | H | H | F | H | 2) |
| A'-291 | Ph | H | F | H | H | H | H | CF₃ | H | 2) |
| A'-292 | Ph | H | CN | H | H | H | H | F | H | 2) |
| A'-293 | Ph | H | H | H | H | H | Si(CH₃)₂C₆F₅ | H | H | 2) |
| A'-294 | Ph | H | F | H | H | H | F | CN | H | 2) |
| A'-295 | Ph | H | C₆F₅ | H | H | H | H | F | H | 2) |
| A'-296 | Ph | H | C₆F₅ | H | H | H | H | CF₃ | H | 2) |
| A'-297 | Ph | H | C₆F₅ | H | H | H | C₆F₅ | H | H | 2) |
| A'-298 | Ph | H | C₆F₅ | H | H | H | H | C₆F₅ | H | 2) |
| A'-299 | Ph | H | H | C₆F₅ | H | H | C₆F₅ | H | H | 2) |
| A'-300 | Ph | H | H | C₆F₅ | H | H | H | C₆F₅ | H | 2) |
| A'-301 | Ph | H | H | OCH₃ | H | F | H | F | H | 2) |

-continued

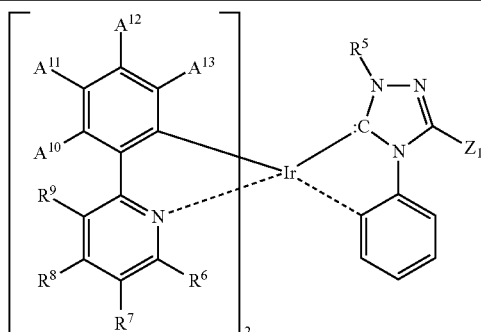

| Cpd. | R⁵ | R⁶ | R⁷ | R⁸ | R⁹ | A¹⁰ | A¹¹ | A¹² | A¹³ | Z¹ |
|---|---|---|---|---|---|---|---|---|---|---|
| A'-302 | Ph | H | H | OCH₃ | H | F | CN | F | H | 2) |
| A'-303 | Ph | H | H | OCH₃ | H | CF₃ | H | CF₃ | H | 2) |
| A'-304 | Ph | H | H | N(CH₃)₂ | H | F | H | F | H | 2) |
| A'-305 | Ph | H | H | N(CH₃)₂ | H | F | CN | F | H | 2) |
| A'-306 | Ph | H | H | N(CH₃)₂ | H | CF₃ | H | CF₃ | H | 2) |
| A'-307 | Ph | 1) | 1) | H | H | H | H | H | H | 2) |
| A'-308 | Ph | 1) | 1) | H | H | H | H | CH₃ | H | 2) |
| A'-309 | Ph | 1) | 1) | H | H | H | H | OCH₃ | H | 2) |
| A'-310 | Ph | 1) | 1) | H | H | H | H | N(CH₃)₂ | H | 2) |
| A'-311 | Ph | 1) | 1) | H | H | H | CH₃ | H | H | 2) |
| A'-312 | Ph | 1) | 1) | H | H | H | OCH₃ | H | H | 2) |
| A'-313 | Ph | 1) | 1) | H | H | H | N(CH₃)₂ | H | H | 2) |
| A'-314 | Ph | H | H | 1) | 1) | H | H | H | H | 2) |
| A'-315 | Ph | H | H | 1) | 1) | H | H | CH₃ | H | 2) |
| A'-316 | Ph | H | H | 1) | 1) | H | H | OCH₃ | H | 2) |
| A'-317 | Ph | H | H | 1) | 1) | H | H | N(CH₃)₂ | H | 2) |
| A'-318 | Ph | H | H | 1) | 1) | H | CH₃ | H | H | 2) |
| A'-319 | Ph | H | H | 1) | 1) | H | OCH₃ | H | H | 2) |
| A'-320 | Ph | H | H | 1) | 1) | H | N(CH₃)₂ | H | H | 2) |

1) R⁸ and R⁹ together form a group , R⁵ and R⁶ together form a group , 2) 4-C₆H₄C(CH)₃;

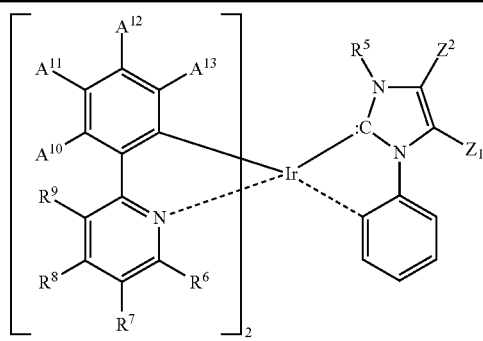

| Cpd. | R⁵ | R⁶ | R⁷ | R⁸ | R⁹ | A¹⁰ | A¹¹ | A¹² | A¹³ | Z¹ = Z² |
|---|---|---|---|---|---|---|---|---|---|---|
| B-1 | Ph | H | H | H | H | H | H | H | H | H |
| B-2 | Ph | H | H | H | H | H | H | CH₃ | H | H |
| B-3 | Ph | H | H | H | H | H | H | Ph | H | H |
| B-4 | Ph | H | H | H | H | H | H | t-Bu | H | H |
| B-5 | Ph | H | H | H | H | H | H | C₆H₁₁ | H | H |
| B-6 | Ph | H | H | H | H | H | H | F | H | H |
| B-7 | Ph | H | H | H | H | H | H | OCH₃ | H | H |
| B-8 | Ph | H | H | H | H | H | H | OC₆H₅ | H | H |
| B-9 | Ph | H | H | H | H | H | H | OH | H | H |
| B-10 | Ph | H | H | H | H | H | H | OCF₃ | H | H |
| B-11 | Ph | H | H | H | H | H | H | OSi(CH₃)₂C(CH₃)₃ | H | H |

-continued

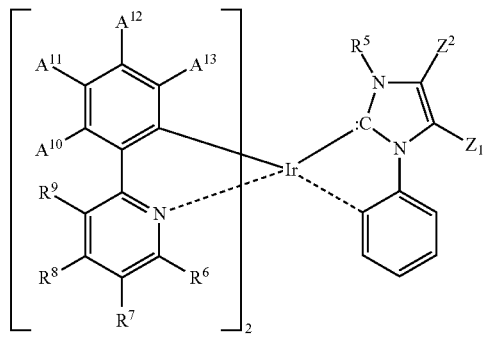

| Cpd. | R[5] | R[6] | R[7] | R[8] | R[9] | A[10] | A[11] | A[12] | A[13] | Z[1] = Z[2] |
|---|---|---|---|---|---|---|---|---|---|---|
| B-12 | Ph | H | H | H | H | H | H | CF$_3$ | H | H |
| B-13 | Ph | H | H | H | H | H | H | SCH$_3$ | H | H |
| B-14 | Ph | H | H | H | H | H | H | SO$_2$CH$_3$ | H | H |
| B-15 | Ph | H | H | H | H | H | H | SOCH$_3$ | H | H |
| B-16 | Ph | H | H | H | H | H | H | SH | H | H |
| B-17 | Ph | H | H | H | H | H | H | NO$_2$ | H | H |
| B-18 | Ph | H | H | H | H | H | H | N(CH$_3$)$_2$ | H | H |
| B-19 | Ph | H | H | H | H | H | H | NH$_2$ | H | H |
| B-20 | Ph | H | H | H | H | H | H | NCOCH$_3$ | H | H |
| B-21 | Ph | H | H | H | H | H | H | NSO$_2$CH$_3$ | H | H |
| B-22 | Ph | H | H | H | H | H | H | HNCH$_2$CH$_3$ | H | H |
| B-23 | Ph | H | H | H | H | H | H | CHO | H | H |
| B-24 | Ph | H | H | H | H | H | H | CH$_2$OH | H | H |
| B-25 | Ph | H | H | H | H | H | H | CH$_2$Br | H | H |
| B-26 | Ph | H | H | H | H | H | H | CH$_2$CN | H | H |
| B-27 | Ph | H | H | H | H | H | H | CH$_2$CO$_2$H | H | H |
| B-28 | Ph | H | H | H | H | H | H | CH$_2$OCH$_3$ | H | H |
| B-29 | Ph | H | H | H | H | H | H | CH$_2$N(CH$_2$CH$_3$)$_2$ | H | H |
| B-30 | Ph | H | H | H | H | H | H | CHCHCO$_2$CH$_3$ | H | H |
| B-31 | Ph | H | H | H | H | H | H | CH$_2$CH$_2$CO$_2$CH$_3$ | H | H |
| B-32 | Ph | H | H | H | H | H | H | C$_6$F$_5$ | H | H |
| B-33 | Ph | H | H | H | H | H | H | H | CH$_3$ | H |
| B-34 | Ph | H | H | H | H | H | CH$_3$ | H | H | H |
| B-35 | Ph | H | H | H | H | H | H | H | CHCH$_2$ | H |
| B-36 | Ph | H | H | H | H | H | CHCH$_2$ | H | H | H |
| B-37 | Ph | H | H | H | H | H | H | H | Ph | H |
| B-38 | Ph | H | H | H | H | H | Ph | H | H | H |
| B-39 | Ph | H | H | H | H | H | C$_6$F$_5$ | H | H | H |
| B-40 | Ph | H | H | H | H | H | CF$_3$ | H | CF$_3$ | H |
| B-41 | Ph | H | H | H | H | H | H | H | CF$_3$ | H |
| B-42 | Ph | H | H | H | H | H | CF$_3$ | H | H | H |
| B-43 | Ph | H | H | H | H | H | F | H | H | H |
| B-44 | Ph | H | H | H | H | H | H | H | F | H |
| B-45 | Ph | H | H | H | H | H | F | H | F | H |
| B-46 | Ph | H | H | H | H | H | H | H | OCF$_3$ | H |
| B-47 | Ph | H | H | H | H | H | OCF$_3$ | H | H | H |
| B-48 | Ph | H | H | H | H | H | NO$_2$ | H | CF$_3$ | H |
| B-49 | Ph | H | H | H | H | H | CF$_3$ | H | NO$_2$ | H |
| B-50 | Ph | H | H | H | H | H | CN | H | H | H |
| B-51 | Ph | H | H | H | H | H | H | H | CN | H |
| B-52 | Ph | H | H | H | H | H | H | H | Si(CH$_3$)$_3$ | H |
| B-53 | Ph | H | H | H | H | H | Si(CH$_3$)$_3$ | H | H | H |
| B-54 | Ph | H | H | H | H | H | NO$_2$ | H | CN | H |
| B-55 | Ph | H | H | H | H | H | CN | H | NO$_2$ | H |
| B-56 | Ph | CF$_3$ | H | H | H | H | H | H | H | H |
| B-57 | Ph | Cl | H | H | H | H | H | H | H | H |
| B-58 | Ph | NO$_2$ | H | H | H | H | H | H | H | H |
| B-59 | Ph | CN | H | H | H | H | H | H | H | H |
| B-60 | Ph | CH$_3$ | H | H | H | H | H | H | H | H |
| B-61 | Ph | OCH$_3$ | H | H | H | H | H | H | H | H |
| B-62 | Ph | Ph | H | H | H | H | H | H | H | H |
| B-63 | Ph | F | H | H | H | H | H | H | H | H |
| B-64 | Ph | H | H | H | CF$_3$ | H | H | H | H | H |
| B-65 | Ph | H | H | H | CN | H | H | H | H | H |
| B-66 | Ph | H | H | H | NO$_2$ | H | H | H | H | H |
| B-67 | Ph | H | H | H | CH$_3$ | H | H | H | H | H |
| B-68 | Ph | H | H | H | Ph | H | H | H | H | H |
| B-69 | Ph | H | H | H | F | H | H | H | H | H |
| B-70 | Ph | H | H | H | OCH$_3$ | H | H | H | H | H |
| B-71 | Ph | H | H | CF$_3$ | H | H | H | H | H | H |
| B-72 | Ph | H | H | CH$_3$ | H | H | H | H | H | H |

-continued

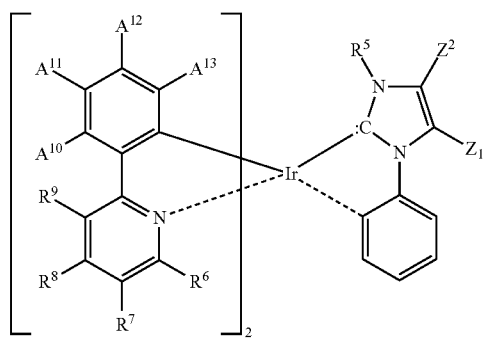

| Cpd. | R⁵ | R⁶ | R⁷ | R⁸ | R⁹ | A¹⁰ | A¹¹ | A¹² | A¹³ | Z¹ = Z² |
|---|---|---|---|---|---|---|---|---|---|---|
| B-73 | Ph | H | CF₃ | H | H | H | H | H | H | H |
| B-74 | Ph | H | CH₃ | H | H | H | H | H | H | H |
| B-75 | Ph | H | F | H | H | H | H | H | H | H |
| B-76 | Ph | H | C₆F₅ | H | H | H | H | H | H | H |
| B-77 | Ph | H | H | C₆F₅ | H | H | H | H | H | H |
| B-78 | Ph | H | C₆H₅ | H | H | H | H | H | H | H |
| B-79 | Ph | H | H | C₆H₅ | H | H | H | H | H | H |
| B-80 | Ph | H | H | OCH₃ | H | F | H | F | H | H |
| B-81 | Ph | H | CF₃ | H | H | H | H | F | H | H |
| B-82 | Ph | H | H | 1) | 1) | H | H | H | H | H |
| B-83 | Ph | H | H | H | H | H | Si(CH₃)₂C₆F₁₃ | H | H | H |
| B-84 | CH₃ | H | H | H | H | H | H | H | H | H |
| B-85 | Ph | H | C₆F₅ | H | H | H | H | F | H | H |
| B-86 | Ph | H | C₆F₅ | H | H | H | H | CF₃ | H | H |
| B-87 | Ph | H | C₆F₅ | H | H | H | C₆F₅ | H | H | H |
| B-88 | Ph | H | C₆F₅ | H | H | H | H | C₆F₅ | H | H |
| B-89 | Ph | H | H | C₆F₅ | H | H | C₆F₅ | H | H | H |
| B-90 | Ph | H | H | C₆F₅ | H | H | H | C₆F₅ | H | H |
| B-91 | Ph | H | H | OCH₃ | H | F | H | F | H | H |
| B-92 | Ph | H | H | OCH₃ | H | F | CN | F | H | H |
| B-93 | Ph | H | H | OCH₃ | H | CF₃ | H | CF₃ | H | H |
| B-94 | Ph | H | H | N(CH₃)₂ | H | F | H | F | H | H |
| B-95 | Ph | H | H | N(CH₃)₂ | H | F | CN | F | H | H |
| B-96 | Ph | H | H | N(CH₃)₂ | H | CF₃ | H | CF₃ | H | H |
| B-97 | Ph | 1) | 1) | H | H | H | H | H | H | H |
| B-98 | Ph | 1) | 1) | H | H | H | H | CH₃ | H | H |
| B-99 | Ph | 1) | 1) | H | H | H | H | OCH₃ | H | H |
| B-100 | Ph | 1) | 1) | H | H | H | H | N(CH₃)₂ | H | H |
| B-101 | Ph | 1) | 1) | H | H | H | CH₃ | H | H | H |
| B-102 | Ph | 1) | 1) | H | H | H | OCH₃ | H | H | H |
| B-103 | Ph | 1) | 1) | H | H | H | N(CH₃)₂ | H | H | H |
| B-104 | Ph | H | H | 1) | 1) | H | H | H | H | H |
| B-105 | Ph | H | H | 1) | 1) | H | H | CH₃ | H | H |
| B-106 | Ph | H | H | 1) | 1) | H | H | OCH₃ | H | H |
| B-107 | Ph | H | H | 1) | 1) | H | H | N(CH₃)₂ | H | H |
| B-108 | Ph | H | H | 1) | 1) | H | CH₃ | H | H | H |
| B-109 | Ph | H | H | 1) | 1) | H | OCH₃ | H | H | H |
| B-110 | Ph | H | H | 1) | 1) | H | N(CH₃)₂ | H | H | H |

1) R⁸ and R⁹ together form a group , R⁵ and R⁶ together form a group ;

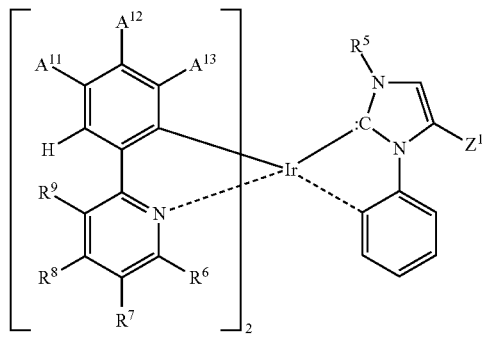

| Cpd. | R⁵ | R⁶ | R⁷ | R⁸ | R⁹ | A¹¹ | A¹² | A¹³ | Z¹ |
|---|---|---|---|---|---|---|---|---|---|
| B'-1 | Ph | H | H | H | H | H | H | H | Ph |
| B'-2 | Ph | H | H | H | H | H | CH₃ | H | Ph |
| B'-3 | Ph | H | H | H | H | H | Ph | H | Ph |
| B'-4 | Ph | H | H | H | H | H | t-Bu | H | Ph |
| B'-5 | Ph | H | H | H | H | H | C₆H₁₁ | H | Ph |
| B'-6 | Ph | H | H | H | H | H | F | H | Ph |
| B'-7 | Ph | H | H | H | H | H | OCH₃ | H | Ph |
| B'-8 | Ph | H | H | H | H | H | OC₆H₅ | H | Ph |
| B'-9 | Ph | H | H | H | H | H | OH | H | Ph |
| B'-10 | Ph | H | H | H | H | H | OCF₃ | H | Ph |
| B'-11 | Ph | H | H | H | H | H | OSi(CH₃)₂C(CH₃)₃ | H | Ph |
| B'-12 | Ph | H | H | H | H | H | CF₃ | H | Ph |
| B'-13 | Ph | H | H | H | H | H | SCH₃ | H | Ph |
| B'-14 | Ph | H | H | H | H | H | SO₂CH₃ | H | Ph |
| B'-15 | Ph | H | H | H | H | H | SOCH₃ | H | Ph |
| B'-16 | Ph | H | H | H | H | H | SH | H | Ph |
| B'-17 | Ph | H | H | H | H | H | NO₂ | H | Ph |
| B'-18 | Ph | H | H | H | H | H | N(CH₃)₂ | H | Ph |
| B'-19 | Ph | H | H | H | H | H | NH₂ | H | Ph |
| B'-20 | Ph | H | H | H | H | H | NCOCH₃ | H | Ph |
| B'-21 | Ph | H | H | H | H | H | NSO₂CH₃ | H | Ph |
| B'-22 | Ph | H | H | H | H | H | HNCH₂CH₃ | H | Ph |
| B'-23 | Ph | H | H | H | H | H | CHO | H | Ph |
| B'-24 | Ph | H | H | H | H | H | CH₂OH | H | Ph |
| B'-25 | Ph | H | H | H | H | H | CH₂Br | H | Ph |
| B'-26 | Ph | H | H | H | H | H | CH₂CN | H | Ph |
| B'-27 | Ph | H | H | H | H | H | CH₂CO₂H | H | Ph |
| B'-28 | Ph | H | H | H | H | H | CH₂OCH₃ | H | Ph |
| B'-29 | Ph | H | H | H | H | H | CH₂N(CH₂CH₃)₂ | H | Ph |
| B'-30 | Ph | H | H | H | H | H | CHCHCO₂CH₃ | H | Ph |
| B'-31 | Ph | H | H | H | H | H | CH₂CH₂CO₂CH₃ | H | Ph |
| B'-32 | Ph | H | H | H | H | H | C₆F₅ | H | Ph |
| B'-33 | Ph | H | H | H | H | H | H | CH₃ | Ph |
| B'-34 | Ph | H | H | H | H | CH₃ | H | H | Ph |
| B'-35 | Ph | H | H | H | H | H | H | CHCH₂ | Ph |
| B'-36 | Ph | H | H | H | H | CHCH₂ | H | H | Ph |
| B'-37 | Ph | H | H | H | H | H | H | Ph | Ph |
| B'-38 | Ph | H | H | H | H | Ph | H | H | Ph |
| B'-39 | Ph | H | H | H | H | C₆F₅ | H | H | Ph |
| B'-40 | Ph | H | H | H | H | CF₃ | H | CF₃ | Ph |
| B'-41 | Ph | H | H | H | H | H | H | CF₃ | Ph |
| B'-42 | Ph | H | H | H | H | CF₃ | H | H | Ph |
| B'-43 | Ph | H | H | H | H | F | H | H | Ph |
| B'-44 | Ph | H | H | H | H | H | H | F | Ph |
| B'-45 | Ph | H | H | H | H | F | H | F | Ph |
| B'-46 | Ph | H | H | H | H | H | H | OCF₃ | Ph |
| B'-47 | Ph | H | H | H | H | OCF₃ | H | H | Ph |
| B'-48 | Ph | H | H | H | H | NO₂ | H | CF₃ | Ph |
| B'-49 | Ph | H | H | H | H | CF₃ | H | NO₂ | Ph |
| B'-50 | Ph | H | H | H | H | CN | H | H | Ph |
| B'-51 | Ph | H | H | H | H | H | H | CN | Ph |
| B'-52 | Ph | H | H | H | H | H | H | Si(CH₃)₃ | Ph |
| B'-53 | Ph | H | H | H | H | Si(CH₃)₃ | H | H | Ph |
| B'-54 | Ph | H | H | H | H | NO₂ | H | CN | Ph |
| B'-55 | Ph | H | H | H | H | CN | H | NO₂ | Ph |
| B'-56 | Ph | CF₃ | H | H | H | H | H | H | Ph |
| B'-57 | Ph | Cl | H | H | H | H | H | H | Ph |
| B'-58 | Ph | NO₂ | H | H | H | H | H | H | Ph |
| B'-59 | Ph | NO₂ | H | H | H | H | H | H | Ph |
| B'-60 | Ph | CH₃ | H | H | H | H | H | H | Ph |
| B'-61 | Ph | OCH₃ | H | H | H | H | H | H | Ph |

-continued

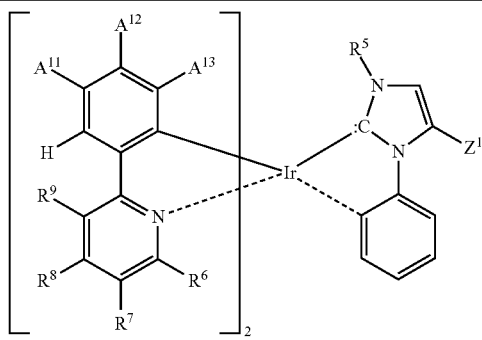

| Cpd. | R5 | R6 | R7 | R8 | R9 | A11 | A12 | A13 | Z1 |
|---|---|---|---|---|---|---|---|---|---|
| B'-62 | Ph | Ph | H | H | H | H | H | H | Ph |
| B'-63 | Ph | F | H | H | H | H | H | H | Ph |
| B'-64 | Ph | H | H | H | CF3 | H | H | H | Ph |
| B'-65 | Ph | H | H | H | CN | H | H | H | Ph |
| B'-66 | Ph | H | H | H | NO2 | H | H | H | Ph |
| B'-67 | Ph | H | H | H | CH3 | H | H | H | Ph |
| B'-68 | Ph | H | H | H | Ph | H | H | H | Ph |
| B'-69 | Ph | H | H | H | F | H | H | H | Ph |
| B'-70 | Ph | H | H | H | OCH3 | H | H | H | Ph |
| B'-71 | Ph | H | H | CF3 | H | H | H | H | Ph |
| B'-72 | Ph | H | H | CH3 | H | H | H | H | Ph |
| B'-73 | Ph | H | CF3 | H | H | H | H | H | Ph |
| B'-74 | Ph | H | CH3 | H | H | H | H | H | Ph |
| B'-75 | Ph | H | F | H | H | H | H | H | Ph |
| B'-76 | Ph | H | C6F5 | H | H | H | H | H | Ph |
| B'-77 | Ph | H | H | C6F5 | H | H | H | H | Ph |
| B'-78 | Ph | H | C6H5 | H | H | H | H | H | Ph |
| B'-79 | Ph | H | H | C6H5 | H | H | H | H | Ph |

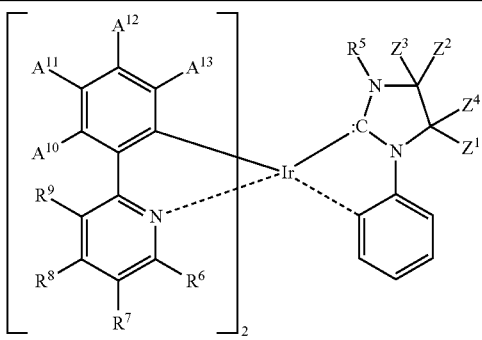

| Cpd. | R5 | R6 | R7 | R8 | R9 | A10 | A11 | A12 | A13 | 1) |
|---|---|---|---|---|---|---|---|---|---|---|
| C-1 | Ph | H | H | H | H | H | H | H | H | H |
| C-2 | Ph | H | H | H | H | H | H | CH3 | H | H |
| C-3 | Ph | H | H | H | H | H | H | Ph | H | H |
| C-4 | Ph | H | H | H | H | H | H | t-Bu | H | H |
| C-5 | Ph | H | H | H | H | H | H | C6H11 | H | H |
| C-6 | Ph | H | H | H | H | H | H | F | H | H |
| C-7 | Ph | H | H | H | H | H | H | OCH3 | H | H |
| C-8 | Ph | H | H | H | H | H | H | OC6H5 | H | H |
| C-9 | Ph | H | H | H | H | H | H | OH | H | H |
| C-10 | Ph | H | H | H | H | H | H | OCF3 | H | H |
| C-11 | Ph | H | H | H | H | H | H | OSi(CH3)2C(CH3)3 | H | H |
| C-12 | Ph | H | H | H | H | H | H | CF3 | H | H |
| C-13 | Ph | H | H | H | H | H | H | SCH3 | H | H |
| C-14 | Ph | H | H | H | H | H | H | SO2CH3 | H | H |
| C-15 | Ph | H | H | H | H | H | H | SOCH3 | H | H |
| C-16 | Ph | H | H | H | H | H | H | SH | H | H |
| C-17 | Ph | H | H | H | H | H | H | NO2 | H | H |
| C-18 | Ph | H | H | H | H | H | H | N(CH3)2 | H | H |
| C-19 | Ph | H | H | H | H | H | H | NH2 | H | H |

-continued

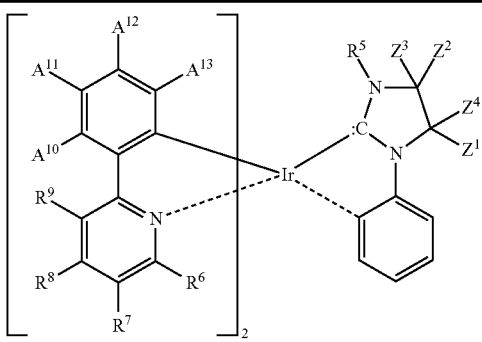

| Cpd. | R⁵ | R⁶ | R⁷ | R⁸ | R⁹ | A¹⁰ | A¹¹ | A¹² | A¹³ | 1) |
|---|---|---|---|---|---|---|---|---|---|---|
| C-20 | Ph | H | H | H | H | H | H | NCOCH₃ | H | H |
| C-21 | Ph | H | H | H | H | H | H | NSO₂CH₃ | H | H |
| C-22 | Ph | H | H | H | H | H | H | HNCH₂CH₃ | H | H |
| C-23 | Ph | H | H | H | H | H | H | CHO | H | H |
| C-24 | Ph | H | H | H | H | H | H | CH₂OH | H | H |
| C-25 | Ph | H | H | H | H | H | H | CH₂Br | H | H |
| C-26 | Ph | H | H | H | H | H | H | CH₂CN | H | H |
| C-27 | Ph | H | H | H | H | H | H | CH₂CO₂H | H | H |
| C-28 | Ph | H | H | H | H | H | H | CH₂OCH₃ | H | H |
| C-29 | Ph | H | H | H | H | H | H | CH₂N(CH₂CH₃)₂ | H | H |
| C-30 | Ph | H | H | H | H | H | H | CHCHCO₂CH₃ | H | H |
| C-31 | Ph | H | H | H | H | H | H | CH₂CH₂CO₂CH₃ | H | H |
| C-32 | Ph | H | H | H | H | H | H | C₆F₅ | H | H |
| C-33 | Ph | H | H | H | H | H | H | H | CH₃ | H |
| C-34 | Ph | H | H | H | H | H | CH₃ | H | H | H |
| C-35 | Ph | H | H | H | H | H | H | H | CHCH₂ | H |
| C-36 | Ph | H | H | H | H | H | CHCH₂ | H | H | H |
| C-37 | Ph | H | H | H | H | H | H | H | Ph | H |
| C-38 | Ph | H | H | H | H | H | Ph | H | H | H |
| C-39 | Ph | H | H | H | H | H | C₆F₅ | H | H | H |
| C-40 | Ph | H | H | H | H | H | CF₃ | H | CF₃ | H |
| C-41 | Ph | H | H | H | H | H | H | H | CF₃ | H |
| C-42 | Ph | H | H | H | H | H | CF₃ | H | H | H |
| C-43 | Ph | H | H | H | H | H | F | H | H | H |
| C-44 | Ph | H | H | H | H | H | H | H | F | H |
| C-45 | Ph | H | H | H | H | H | F | H | F | H |
| C-46 | Ph | H | H | H | H | H | H | H | OCF₃ | H |
| C-47 | Ph | H | H | H | H | H | OCF₃ | H | H | H |
| C-48 | Ph | H | H | H | H | H | NO₂ | H | CF₃ | H |
| C-49 | Ph | H | H | H | H | H | CF₃ | H | NO₂ | H |
| C-50 | Ph | H | H | H | H | H | CN | H | H | H |
| C-51 | Ph | H | H | H | H | H | H | H | CN | H |
| C-52 | Ph | H | H | H | H | H | H | H | Si(CH₃)₃ | H |
| C-53 | Ph | H | H | H | H | H | Si(CH₃)₃ | H | H | H |
| C-54 | Ph | H | H | H | H | H | NO₂ | H | CN | H |
| C-55 | Ph | H | H | H | H | H | CN | H | NO₂ | H |
| C-56 | Ph | CF₃ | H | H | H | H | H | H | H | H |
| C-57 | Ph | Cl | H | H | H | H | H | H | H | H |
| C-58 | Ph | NO₂ | H | H | H | H | H | H | H | H |
| C-59 | Ph | CN | H | H | H | H | H | H | H | H |
| C-60 | Ph | CH₃ | H | H | H | H | H | H | H | H |
| C-61 | Ph | OCH₃ | H | H | H | H | H | H | H | H |
| C-62 | Ph | Ph | H | H | H | H | H | H | H | H |
| C-63 | Ph | F | H | H | H | H | H | H | H | H |
| C-64 | Ph | H | H | H | CF₃ | H | H | H | H | H |
| C-65 | Ph | H | H | H | CN | H | H | H | H | H |
| C-66 | Ph | H | H | H | NO₂ | H | H | H | H | H |
| C-67 | Ph | H | H | H | CH₃ | H | H | H | H | H |
| C-68 | Ph | H | H | H | Ph | H | H | H | H | H |
| C-69 | Ph | H | H | H | F | H | H | H | H | H |
| C-70 | Ph | H | H | H | OCH₃ | H | H | H | H | H |
| C-71 | Ph | H | H | CF₃ | H | H | H | H | H | H |
| C-72 | Ph | H | H | CH₃ | H | H | H | H | H | H |
| C-73 | Ph | H | CF₃ | H | H | H | H | H | H | H |
| C-74 | Ph | H | CH₃ | H | H | H | H | H | H | H |
| C-75 | Ph | H | F | H | H | H | H | H | H | H |
| C-76 | Ph | H | C₆F₅ | H | H | H | H | H | H | H |
| C-77 | Ph | H | H | C₆F₅ | H | H | H | H | H | H |
| C-78 | Ph | H | C₆H₅ | H | H | H | H | H | H | H |
| C-79 | Ph | H | H | C₆H₅ | H | H | H | H | H | H |
| C-80 | Ph | H | H | OCH₃ | H | F | H | F | H | H |

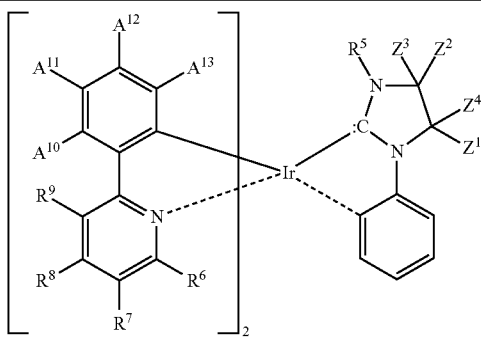

| Cpd. | R⁵ | R⁶ | R⁷ | R⁸ | R⁹ | A¹⁰ | A¹¹ | A¹² | A¹³ | 1) |
|---|---|---|---|---|---|---|---|---|---|---|
| C-81 | Ph | H | CF₃ | H | H | H | H | F | H | H |
| C-82 | Ph | H | H | 1) | 1) | H | H | H | H | H |
| C-83 | Ph | H | H | H | H | H | Si(CH₃)₂C₆F₁₃ | H | H | H |
| C-84 | CH₃ | H | H | H | H | H | H | H | H | H |
| C-85 | Ph | H | C₆F₅ | H | H | H | H | F | H | H |
| C-86 | Ph | H | C₆F₅ | H | H | H | H | CF₃ | H | H |
| C-87 | Ph | H | C₆F₅ | H | H | C₆F₅ | H | H | H | H |
| C-88 | Ph | H | C₆F₅ | H | H | H | H | C₆F₅ | H | H |
| C-89 | Ph | H | H | C₆F₅ | H | C₆F₅ | H | H | H | H |
| C-90 | Ph | H | H | C₆F₅ | H | H | H | C₆F₅ | H | H |
| C-91 | Ph | H | H | OCH₃ | H | F | H | F | H | H |
| C-92 | Ph | H | H | OCH₃ | H | F | CN | F | H | H |
| C-93 | Ph | H | H | OCH₃ | H | CF₃ | H | CF₃ | H | H |
| C-94 | Ph | H | H | N(CH₃)₂ | H | F | H | F | H | H |
| C-95 | Ph | H | H | N(CH₃)₂ | H | F | CN | F | H | H |
| C-96 | Ph | H | H | N(CH₃)₂ | H | CF₃ | H | CF₃ | H | H |
| C-97 | Ph | 1) | 1) | H | H | H | H | H | H | H |
| C-98 | Ph | 1) | 1) | H | H | H | H | CH₃ | H | H |
| C-99 | Ph | 1) | 1) | H | H | H | H | OCH₃ | H | H |
| C-100 | Ph | 1) | 1) | H | H | H | H | N(CH₃)₂ | H | H |
| C-101 | Ph | 1) | 1) | H | H | H | CH₃ | H | H | H |
| C-102 | Ph | 1) | 1) | H | H | H | OCH₃ | H | H | H |
| C-103 | Ph | 1) | 1) | H | H | H | N(CH₃)₂ | H | H | H |
| C-104 | Ph | H | H | 1) | 1) | H | H | H | H | H |
| C-105 | Ph | H | H | 1) | 1) | H | H | CH₃ | H | H |
| C-106 | Ph | H | H | 1) | 1) | H | H | OCH₃ | H | H |
| C-107 | Ph | H | H | 1) | 1) | H | H | N(CH₃)₂ | H | H |
| C-108 | Ph | H | H | 1) | 1) | H | CH₃ | H | H | H |
| C-109 | Ph | H | H | 1) | 1) | H | OCH₃ | H | H | H |
| C-110 | Ph | H | H | 1) | 1) | H | N(CH₃)₂ | H | H | H |

1) $Z^1 = Z^2 = Z^3 = Z^4$;

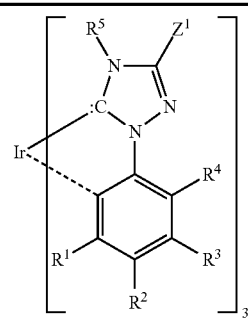

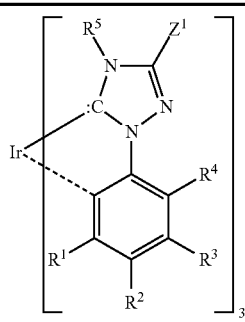

| Cpd. | R¹ | R² | R³ | R⁴ | R⁵ | Z¹ | Cpd. | R¹ | R² | R³ | R⁴ | R⁵ | Z¹ |
|---|---|---|---|---|---|---|---|---|---|---|---|---|---|
| D-1 | H | H | H | H | Ph | Ph | D-8 | H | F | H | H | Ph | Ph |
| D-2 | H | NO₂ | H | H | Ph | Ph | D-9 | H | OCH₃ | H | H | Ph | Ph |
| D-3 | H | CH₃ | H | H | Ph | Ph | D-10 | H | OPh | H | H | Ph | Ph |
| D-4 | H | C(CH₃)₃ | H | H | Ph | Ph | D-11 | H | CN | H | H | Ph | Ph |
| D-5 | H | CH(CH₃)₂ | H | H | Ph | Ph | D-12 | H | SCH₃ | H | H | Ph | Ph |
| D-6 | H | CF₃ | H | H | Ph | Ph | D-13 | H | CO₂CH₃ | H | H | Ph | Ph |
| D-7 | H | OCF₃ | H | H | Ph | Ph | D-14 | H | SO₂CH₃ | H | H | Ph | Ph |

-continued

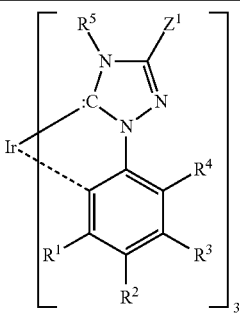

| Cpd. | R¹ | R² | R³ | R⁴ | R⁵ | Z¹ |
|---|---|---|---|---|---|---|
| D-15 | CH₃ | H | H | H | Ph | Ph |
| D-16 | F | H | H | H | Ph | Ph |
| D-17 | CF₃ | H | H | H | Ph | Ph |
| D-18 | C(CH₃)₃ | H | H | H | Ph | Ph |
| D-19 | CN | H | H | H | Ph | Ph |
| D-20 | NO₂ | H | H | H | Ph | Ph |
| D-21 | OCH₃ | H | H | H | Ph | Ph |
| D-22 | H | H | CH₃ | H | Ph | Ph |
| D-23 | H | H | F | H | Ph | Ph |
| D-24 | H | H | CF₃ | H | Ph | Ph |
| D-25 | H | H | OCF₃ | H | Ph | Ph |
| D-26 | H | H | CN | H | Ph | Ph |
| D-27 | H | H | NO₂ | H | Ph | Ph |
| D-28 | H | H | OCH₃ | H | Ph | Ph |
| D-29 | H | H | SCH₃ | H | Ph | Ph |
| D-30 | H | C₆H₄CF₃ | H | H | Ph | Ph |
| D-31 | H | H | H | H | Ph | CF₃ |
| D-32 | H | NO₂ | H | H | Ph | CF₃ |
| D-33 | H | CH₃ | H | H | Ph | CF₃ |
| D-34 | H | C(CH₃)₃ | H | H | Ph | CF₃ |
| D-35 | H | CH(CH₃)₂ | H | H | Ph | CF₃ |
| D-36 | H | CF₃ | H | H | Ph | CF₃ |
| D-37 | H | OCF₃ | H | H | Ph | CF₃ |
| D-38 | H | F | H | H | Ph | CF₃ |
| D-39 | H | OCH₃ | H | H | Ph | CF₃ |
| D-40 | H | OPh | H | H | Ph | CF₃ |
| D-41 | H | CN | H | H | Ph | CF₃ |
| D-42 | H | SCH₃ | H | H | Ph | CF₃ |
| D-43 | H | CO₂CH₃ | H | H | Ph | CF₃ |
| D-44 | H | SO₂CH₃ | H | H | Ph | CF₃ |
| D-45 | CH3 | H | H | H | Ph | CF₃ |
| D-46 | F | H | H | H | Ph | CF₃ |
| D-47 | CF3 | H | H | H | Ph | CF₃ |
| D-48 | C(CH3)3 | H | H | H | Ph | CF₃ |
| D-49 | CN | H | H | H | Ph | CF₃ |
| D-50 | NO2 | H | H | H | Ph | CF₃ |
| D-51 | OCH3 | H | H | H | Ph | CF₃ |
| D-52 | H | H | CH₃ | H | Ph | CF₃ |
| D-53 | H | H | F | H | Ph | CF₃ |
| D-54 | H | H | CF₃ | H | Ph | CF₃ |
| D-55 | H | H | OCF₃ | H | Ph | CF₃ |
| D-56 | H | H | CN | H | Ph | CF₃ |
| D-57 | H | H | NO₂ | H | Ph | CF₃ |
| D-58 | H | H | OCH₃ | H | Ph | CF₃ |
| D-59 | H | H | SCH₃ | H | Ph | CF₃ |
| D-60 | H | C₆H₄CF₃ | H | H | Ph | CF₃ |
| D-61 | H | H | H | H | Ph | 1) |
| D-62 | H | NO₂ | H | H | Ph | 1) |
| D-63 | H | CH₃ | H | H | Ph | 1) |
| D-64 | H | C(CH₃)₃ | H | H | Ph | 1) |
| D-65 | H | CH(CH₃)₂ | H | H | Ph | 1) |
| D-66 | H | CF₃ | H | H | Ph | 1) |
| D-67 | H | OCF₃ | H | H | Ph | 1) |
| D-68 | H | F | H | H | Ph | 1) |
| D-69 | H | OCH₃ | H | H | Ph | 1) |
| D-70 | H | OPh | H | H | Ph | 1) |
| D-71 | H | CN | H | H | Ph | 1) |
| D-72 | H | SCH₃ | H | H | Ph | 1) |
| D-73 | H | CO₂CH₃ | H | H | Ph | 1) |
| D-74 | H | SO₂CH₃ | H | H | Ph | 1) |
| D-75 | CH3 | H | H | H | Ph | 1) |
| D-76 | F | H | H | H | Ph | 1) |

-continued

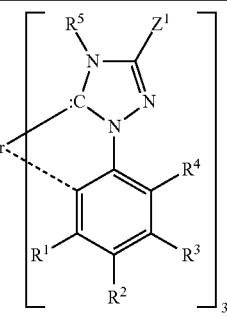

| Cpd. | R¹ | R² | R³ | R⁴ | R⁵ | Z¹ |
|---|---|---|---|---|---|---|
| D-77 | CF3 | H | H | H | Ph | 1) |
| D-78 | C(CH3)3 | H | H | H | Ph | 1) |
| D-79 | CN | H | H | H | Ph | 1) |
| D-80 | NO2 | H | H | H | Ph | 1) |
| D-81 | OCH3 | H | H | H | Ph | 1) |
| D-82 | H | H | CH₃ | H | Ph | 1) |
| D-83 | H | H | F | H | Ph | 1) |
| D-84 | H | H | CF₃ | H | Ph | 1) |
| D-85 | H | H | OCF₃ | H | Ph | 1) |
| D-86 | H | H | CN | H | Ph | 1) |
| D-87 | H | H | NO₂ | H | Ph | 1) |
| D-88 | H | H | OCH₃ | H | Ph | 1) |
| D-89 | H | H | SCH₃ | H | Ph | 1) |
| D-90 | H | C₆H₄CF₃ | H | H | Ph | 1) |

1) 4-C₆H₄C(CH)₃;

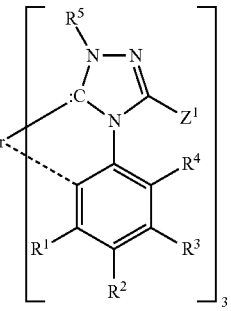

| Cpd. | R¹ | R² | R³ | R⁴ | R⁵ | Z¹ |
|---|---|---|---|---|---|---|
| E-1 | H | H | H | H | Ph | Ph |
| E-2 | H | NO₂ | H | H | Ph | Ph |
| E-3 | H | CH₃ | H | H | Ph | Ph |
| E-4 | H | C(CH₃)₃ | H | H | Ph | Ph |
| E-5 | H | CH(CH₃)₂ | H | H | Ph | Ph |
| E-6 | H | CF₃ | H | H | Ph | Ph |
| E-7 | H | OCF₃ | H | H | Ph | Ph |
| E-8 | H | F | H | H | Ph | Ph |
| E-9 | H | OCH₃ | H | H | Ph | Ph |
| E-10 | H | OPh | H | H | Ph | Ph |
| E-11 | H | CN | H | H | Ph | Ph |
| E-12 | H | SCH₃ | H | H | Ph | Ph |
| E-13 | H | CO₂CH₃ | H | H | Ph | Ph |
| E-14 | H | SO₂CH₃ | H | H | Ph | Ph |
| E-15 | H | C₆H₄CF₃ | H | H | Ph | Ph |
| E-16 | CH₃ | H | H | H | Ph | Ph |
| E-17 | F | H | H | H | Ph | Ph |
| E-18 | CF₃ | H | H | H | Ph | Ph |
| E-19 | C(CH₃)₃ | H | H | H | Ph | Ph |
| E-20 | CN | H | H | H | Ph | Ph |
| E-21 | NO₂ | H | H | H | Ph | Ph |
| E-22 | OCH₃ | H | H | H | Ph | Ph |
| E-23 | H | H | CH₃ | H | Ph | Ph |
| E-24 | H | H | F | H | Ph | Ph |

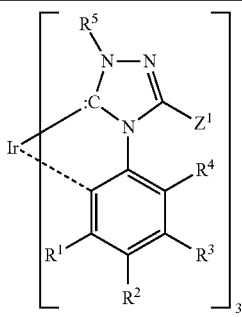

| Cpd. | R¹ | R² | R³ | R⁴ | R⁵ | Z¹ |
|---|---|---|---|---|---|---|
| E-25 | H | H | CF₃ | H | Ph | Ph |
| E-26 | H | H | OCF₃ | H | Ph | Ph |
| E-27 | H | H | CN | H | Ph | Ph |
| E-28 | H | H | NO₂ | H | Ph | Ph |
| E-29 | H | H | OCH₃ | H | Ph | Ph |
| E-30 | H | H | SCH₃ | H | Ph | Ph |
| E-31 | H | H | H | H | Ph | CF₃ |
| E-32 | H | NO₂ | H | H | Ph | CF₃ |
| E-33 | H | CH₃ | H | H | Ph | CF₃ |
| E-34 | H | C(CH₃)₃ | H | H | Ph | CF₃ |
| E-35 | H | CH(CH₃)₂ | H | H | Ph | CF₃ |
| E-36 | H | CF₃ | H | H | Ph | CF₃ |
| E-37 | H | OCF₃ | H | H | Ph | CF₃ |
| E-38 | H | F | H | H | Ph | CF₃ |
| E-39 | H | OCH₃ | H | H | Ph | CF₃ |
| E-40 | H | OPh | H | H | Ph | CF₃ |
| E-41 | H | CN | H | H | Ph | CF₃ |
| E-42 | H | SCH₃ | H | H | Ph | CF₃ |
| E-43 | H | CO₂CH₃ | H | H | Ph | CF₃ |
| E-44 | H | SO₂CH₃ | H | H | Ph | CF₃ |
| E-45 | CH₃ | H | H | H | Ph | CF₃ |
| E-46 | F | H | H | H | Ph | CF₃ |
| E-47 | CF₃ | H | H | H | Ph | CF₃ |
| E-48 | C(CH₃)₃ | H | H | H | Ph | CF₃ |
| E-49 | CN | H | H | H | Ph | CF₃ |
| E-50 | NO₂ | H | H | H | Ph | CF₃ |
| E-51 | OCH₃ | H | H | H | Ph | CF₃ |
| E-52 | H | H | CH₃ | H | Ph | CF₃ |
| E-53 | H | H | F | H | Ph | CF₃ |
| E-54 | H | H | CF₃ | H | Ph | CF₃ |
| E-55 | H | H | OCF₃ | H | Ph | CF₃ |
| E-56 | H | H | CN | H | Ph | CF₃ |
| E-57 | H | H | NO₂ | H | Ph | CF₃ |
| E-58 | H | H | OCH₃ | H | Ph | CF₃ |
| E-59 | H | H | SCH₃ | H | Ph | CF₃ |
| E-60 | H | C₆H₄CF₃ | H | H | Ph | CF₃ |
| E-61 | H | H | H | H | Ph | 1) |
| E-62 | H | NO₂ | H | H | Ph | 1) |
| E-63 | H | CH₃ | H | H | Ph | 1) |
| E-64 | H | C(CH₃)₃ | H | H | Ph | 1) |
| E-65 | H | CH(CH₃)₂ | H | H | Ph | 1) |
| E-66 | H | CF₃ | H | H | Ph | 1) |
| E-67 | H | OCF₃ | H | H | Ph | 1) |
| E-68 | H | F | H | H | Ph | 1) |
| E-69 | H | OCH₃ | H | H | Ph | 1) |
| E-70 | H | OPh | H | H | Ph | 1) |
| E-71 | H | CN | H | H | Ph | 1) |
| E-72 | H | SCH₃ | H | H | Ph | 1) |
| E-73 | H | CO₂CH₃ | H | H | Ph | 1) |
| E-74 | H | SO₂CH₃ | H | H | Ph | 1) |
| E-75 | CH₃ | H | H | H | Ph | 1) |
| E-76 | F | H | H | H | Ph | 1) |
| E-77 | CF₃ | H | H | H | Ph | 1) |
| E-78 | C(CH₃)₃ | H | H | H | Ph | 1) |
| E-79 | CN | H | H | H | Ph | 1) |
| E-80 | NO₂ | H | H | H | Ph | 1) |
| E-81 | OCH₃ | H | H | H | Ph | 1) |
| E-82 | H | H | CH₃ | H | Ph | 1) |
| E-83 | H | H | F | H | Ph | 1) |
| E-84 | H | H | CF₃ | H | Ph | 1) |
| E-85 | H | H | OCF₃ | H | Ph | 1) |
| E-86 | H | H | CN | H | Ph | 1) |

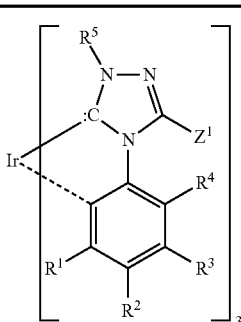

| Cpd. | R¹ | R² | R³ | R⁴ | R⁵ | Z¹ |
|---|---|---|---|---|---|---|
| E-87 | H | H | NO₂ | H | Ph | 1) |
| E-88 | H | H | OCH₃ | H | Ph | 1) |
| E-89 | H | H | SCH₃ | H | Ph | 1) |
| E-90 | H | C₆H₄CF₃ | H | H | Ph | 1) |

1) 4-C₆H₄C(CH)₃;

| Cpd. | R¹ | R² | R³ | R⁴ | R⁵ | Z¹ = Z² |
|---|---|---|---|---|---|---|
| F-1 | H | H | H | H | Ph | H |
| F-2 | H | NO₂ | H | H | Ph | H |
| F-3 | H | CH₃ | H | H | Ph | H |
| F-4 | H | C(CH₃)₃ | H | H | Ph | H |
| F-5 | H | CH(CH₃)₂ | H | H | Ph | H |
| F-6 | H | CF₃ | H | H | Ph | H |
| F-7 | H | OCF₃ | H | H | Ph | H |
| F-8 | H | F | H | H | Ph | H |
| F-9 | H | OCH₃ | H | H | Ph | H |
| F-10 | H | OPh | H | H | Ph | H |
| F-11 | H | CN | H | H | Ph | H |
| F-12 | H | SCH₃ | H | H | Ph | H |
| F-13 | H | CO₂CH₃ | H | H | Ph | H |
| F-14 | H | SO₂CH₃ | H | H | Ph | H |
| F-15 | CH₃ | H | H | H | Ph | H |
| F-16 | F | H | H | H | Ph | H |
| F-17 | CF₃ | H | H | H | Ph | H |
| F-18 | C(CH₃)₃ | H | H | H | Ph | H |
| F-19 | CN | H | H | H | Ph | H |
| F-20 | NO₂ | H | H | H | Ph | H |
| F-21 | OCH₃ | H | H | H | Ph | H |
| F-22 | H | H | CH₃ | H | Ph | H |
| F-23 | H | H | F | H | Ph | H |
| F-24 | H | H | CF₃ | H | Ph | H |
| F-25 | H | H | OCF₃ | H | Ph | H |
| F-26 | H | H | CN | H | Ph | H |
| F-27 | H | H | NO₂ | H | Ph | H |
| F-28 | H | H | OCH₃ | H | Ph | H |
| F-29 | H | H | SCH₃ | H | Ph | H |
| F-30 | H | C₆H₄CF₃ | H | H | Ph | H |

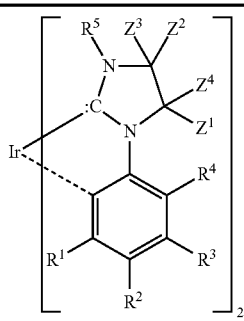
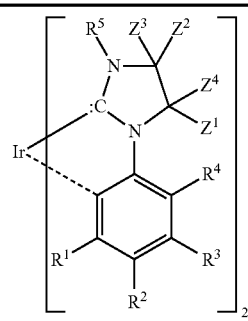

| Cpd. | R¹ | R² | R³ | R⁴ | R⁵ | 1) |
|---|---|---|---|---|---|---|
| G-1 | H | H | H | H | Ph | H |
| G-2 | H | NO₂ | H | H | Ph | H |
| G-3 | H | CH₃ | H | H | Ph | H |
| G-4 | H | C(CH₃)₃ | H | H | Ph | H |
| G-5 | H | CH(CH₃)₂ | H | H | Ph | H |
| G-6 | H | CF₃ | H | H | Ph | H |
| G-7 | H | OCF₃ | H | H | Ph | H |
| G-8 | H | F | H | H | Ph | H |
| G-9 | H | OCH₃ | H | H | Ph | H |
| G-10 | H | OPh | H | H | Ph | H |
| G-11 | H | CN | H | H | Ph | H |
| G-12 | H | SCH₃ | H | H | Ph | H |
| G-13 | H | CO₂CH₃ | H | H | Ph | H |
| G-14 | H | SO₂CH₃ | H | H | Ph | H |
| G-15 | CH₃ | H | H | H | Ph | H |
| G-16 | F | H | H | H | Ph | H |
| G-17 | CF₃ | H | H | H | Ph | H |
| G-18 | C(CH₃)₃ | H | H | H | Ph | H |
| G-19 | CN | H | H | H | Ph | H |
| G-20 | NO₂ | H | H | H | Ph | H |
| G-21 | OCH₃ | H | H | H | Ph | H |
| G-22 | H | H | CH₃ | H | Ph | H |
| G-23 | H | H | F | H | Ph | H |
| G-24 | H | H | CF₃ | H | Ph | H |
| G-25 | H | H | OCF₃ | H | Ph | H |
| G-26 | H | H | CN | H | Ph | H |
| G-27 | H | H | NO₂ | H | Ph | H |
| G-28 | H | H | OCH₃ | H | Ph | H |
| G-29 | H | H | SCH₃ | H | Ph | H |
| G-30 | H | C₆H₄CF₃ | H | H | Ph | H |

1) $Z^1 = Z^2 = Z^3 = Z^4$.

| Cpd. | R⁵ | R⁶ | R⁷ | R⁸ | R⁹ | A¹⁰ | A¹¹ | A¹² | A¹³ | Z¹ |
|---|---|---|---|---|---|---|---|---|---|---|
| H-1 | Ph | H | H | H | H | H | H | H | H | Ph |
| H-2 | Ph | H | H | H | H | H | H | CH₃ | H | Ph |
| H-3 | Ph | H | H | H | H | H | H | Ph | H | Ph |
| H-4 | Ph | H | H | H | H | H | H | t-Bu | H | Ph |
| H-5 | Ph | H | H | H | H | H | H | C₆H₁₁ | H | Ph |
| H-6 | Ph | H | H | H | H | H | H | F | H | Ph |
| H-7 | Ph | H | H | H | H | H | H | OCH₃ | H | Ph |
| H-8 | Ph | H | H | H | H | H | H | OC₆H₅ | H | Ph |
| H-9 | Ph | H | H | H | H | H | H | OH | H | Ph |
| H-10 | Ph | H | H | H | H | H | H | OCF₃ | H | Ph |
| H-11 | Ph | H | H | H | H | H | H | OSi(CH₃)₂C(CH₃)₃ | H | Ph |
| H-12 | Ph | H | H | H | H | H | H | CF₃ | H | Ph |
| H-13 | Ph | H | H | H | H | H | H | SCH₃ | H | Ph |
| H-14 | Ph | H | H | H | H | H | H | SO₂CH₃ | H | Ph |
| H-15 | Ph | H | H | H | H | H | H | SOCH₃ | H | Ph |
| H-16 | Ph | H | H | H | H | H | H | SH | H | Ph |
| H-17 | Ph | H | H | H | H | H | H | NO₂ | H | Ph |
| H-18 | Ph | H | H | H | H | H | H | N(CH₃)₂ | H | Ph |
| H-19 | Ph | H | H | H | H | H | H | NH₂ | H | Ph |
| H-20 | Ph | H | H | H | H | H | H | NCOCH₃ | H | Ph |
| H-21 | Ph | H | H | H | H | H | H | NSO₂CH₃ | H | Ph |
| H-22 | Ph | H | H | H | H | H | H | HNCH₂CH₃ | H | Ph |
| H-23 | Ph | H | H | H | H | H | H | CHO | H | Ph |
| H-24 | Ph | H | H | H | H | H | H | CH₂OH | H | Ph |

-continued

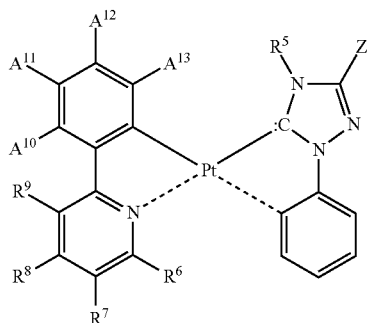

| Cpd. | R$^5$ | R$^6$ | R$^7$ | R$^8$ | R$^9$ | A$^{10}$ | A$^{11}$ | A$^{12}$ | A$^{13}$ | Z$^1$ |
|---|---|---|---|---|---|---|---|---|---|---|
| H-25 | Ph | H | H | H | H | H | H | CH$_2$Br | H | Ph |
| H-26 | Ph | H | H | H | H | H | H | CH$_2$CN | H | Ph |
| H-27 | Ph | H | H | H | H | H | H | CH$_2$CO$_2$H | H | Ph |
| H-28 | Ph | H | H | H | H | H | H | CH$_2$OCH$_3$ | H | Ph |
| H-29 | Ph | H | H | H | H | H | H | CH$_2$N(CH$_2$CH$_3$)$_2$ | H | Ph |
| H-30 | Ph | H | H | H | H | H | H | CHCHCO$_2$CH$_3$ | H | Ph |
| H-31 | Ph | H | H | H | H | H | H | CH$_2$CH$_2$CO$_2$CH$_3$ | H | Ph |
| H-32 | Ph | H | H | H | H | H | H | C$_6$F$_5$ | H | Ph |
| H-33 | Ph | H | H | H | H | H | H | H | CH$_3$ | Ph |
| H-34 | Ph | H | H | H | H | H | CH$_3$ | H | H | Ph |
| H-35 | Ph | H | H | H | H | H | H | H | CHCH$_2$ | Ph |
| H-36 | Ph | H | H | H | H | H | CHCH$_2$ | H | H | Ph |
| H-37 | Ph | H | H | H | H | H | H | H | Ph | Ph |
| H-38 | Ph | H | H | H | H | H | Ph | H | H | Ph |
| H-39 | Ph | H | H | H | H | H | C$_6$F$_5$ | H | H | Ph |
| H-40 | Ph | H | H | H | H | H | CF$_3$ | H | CF$_3$ | Ph |
| H-41 | Ph | H | H | H | H | H | H | H | CF$_3$ | Ph |
| H-42 | Ph | H | H | H | H | H | CF$_3$ | H | H | Ph |
| H-43 | Ph | H | H | H | H | H | F | H | H | Ph |
| H-44 | Ph | H | H | H | H | H | H | H | F | Ph |
| H-45 | Ph | H | H | H | H | H | F | H | F | Ph |
| H-46 | Ph | H | H | H | H | H | H | H | OCF$_3$ | Ph |
| H-47 | Ph | H | H | H | H | H | OCF$_3$ | H | H | Ph |
| H-48 | Ph | H | H | H | H | H | NO$_2$ | H | CF$_3$ | Ph |
| H-49 | Ph | H | H | H | H | H | CF$_3$ | H | NO$_2$ | Ph |
| H-50 | Ph | H | H | H | H | H | CN | H | H | Ph |
| H-51 | Ph | H | H | H | H | H | H | H | CN | Ph |
| H-52 | Ph | H | H | H | H | H | H | H | Si(CH$_3$)$_3$ | Ph |
| H-53 | Ph | H | H | H | H | H | Si(CH$_3$)$_3$ | H | H | Ph |
| H-54 | Ph | H | H | H | H | H | NO$_2$ | H | CN | Ph |
| H-55 | Ph | H | H | H | H | H | CN | H | NO$_2$ | Ph |
| H-56 | Ph | CF$_3$ | H | H | H | H | H | H | H | Ph |
| H-57 | Ph | Cl | H | H | H | H | H | H | H | Ph |
| H-58 | Ph | NO$_2$ | H | H | H | H | H | H | H | Ph |
| H-59 | Ph | CN | H | H | H | H | H | H | H | Ph |
| H-60 | Ph | CH$_3$ | H | H | H | H | H | H | H | Ph |
| H-61 | Ph | OCH$_3$ | H | H | H | H | H | H | H | Ph |
| H-62 | Ph | Ph | H | H | H | H | H | H | H | Ph |
| H-63 | Ph | F | H | H | H | H | H | H | H | Ph |
| H-64 | Ph | H | H | H | CF$_3$ | H | H | H | H | Ph |
| H-65 | Ph | H | H | H | CN | H | H | H | H | Ph |
| H-66 | Ph | H | H | H | NO$_2$ | H | H | H | H | Ph |
| H-67 | Ph | H | H | H | CH$_3$ | H | H | H | H | Ph |
| H-68 | Ph | H | H | H | Ph | H | H | H | H | Ph |
| H-69 | Ph | H | H | H | F | H | H | H | H | Ph |
| H-70 | Ph | H | H | H | OCH$_3$ | H | H | H | H | Ph |
| H-71 | Ph | H | H | CF$_3$ | H | H | H | H | H | Ph |
| H-72 | Ph | H | H | CH$_3$ | H | H | H | H | H | Ph |
| H-73 | Ph | H | CF$_3$ | H | H | H | H | H | H | Ph |
| H-74 | Ph | H | CH$_3$ | H | H | H | H | H | H | Ph |
| H-75 | Ph | H | F | H | H | H | H | H | H | Ph |
| H-76 | Ph | H | C$_6$F$_5$ | H | H | H | H | H | H | Ph |
| H-77 | Ph | H | H | C$_6$F$_5$ | H | H | H | H | H | Ph |
| H-78 | Ph | H | C$_6$H$_5$ | H | H | H | H | H | H | Ph |
| H-79 | Ph | H | H | C$_6$H$_5$ | H | H | H | H | H | Ph |
| H-80 | Ph | H | CF$_3$ | H | H | H | H | F | H | Ph |
| H-81 | Ph | H | F | H | H | H | H | CF$_3$ | H | Ph |
| H-82 | Ph | H | CN | H | H | H | H | F | H | Ph |
| H-83 | Ph | H | H | H | H | H | Si(CH$_3$)$_2$C$_6$F$_{13}$ | H | H | Ph |
| H-84 | Ph | H | F | H | H | H | F | CN | H | Ph |
| H-85 | Ph | H | C$_6$F$_5$ | H | H | H | H | F | H | Ph |
| H-86 | Ph | H | C$_6$F$_5$ | H | H | H | H | CF$_3$ | H | Ph |

-continued

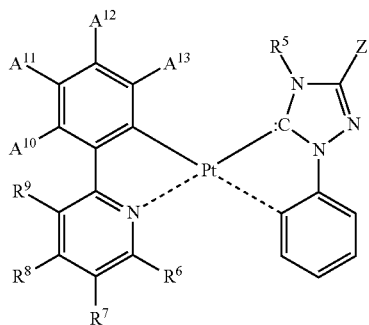

| Cpd. | R⁵ | R⁶ | R⁷ | R⁸ | R⁹ | A¹⁰ | A¹¹ | A¹² | A¹³ | Z¹ |
|---|---|---|---|---|---|---|---|---|---|---|
| H-87 | Ph | H | C₆F₅ | H | H | H | C₆F₅ | H | H | Ph |
| H-88 | Ph | H | C₆F₅ | H | H | H | H | C₆F₅ | H | Ph |
| H-89 | Ph | H | H | C₆F₅ | H | H | C₆F₅ | H | H | Ph |
| H-90 | Ph | H | H | C₆F₅ | H | H | H | C₆F₅ | H | Ph |
| H-91 | Ph | H | H | OCH₃ | H | F | H | F | H | Ph |
| H-92 | Ph | H | H | OCH₃ | H | F | CN | F | H | Ph |
| H-93 | Ph | H | H | OCH₃ | H | CF₃ | H | CF₃ | H | Ph |
| H-94 | Ph | H | H | N(CH₃)₂ | H | F | H | F | H | PH |
| H-95 | Ph | H | H | N(CH₃)₂ | H | F | CN | F | H | Ph |
| H-96 | Ph | H | H | N(CH₃)₂ | H | CF₃ | H | CF₃ | H | Ph |
| H-97 | Ph | 1) | 1) | H | H | H | H | H | H | Ph |
| H-98 | Ph | 1) | 1) | H | H | H | H | CH₃ | H | Ph |
| H-99 | Ph | 1) | 1) | H | H | H | H | OCH₃ | H | Ph |
| H-100 | Ph | 1) | 1) | H | H | H | H | N(CH₃)₂ | H | Ph |
| H-101 | Ph | 1) | 1) | H | H | H | CH₃ | H | H | Ph |
| H-102 | Ph | 1) | 1) | H | H | H | OCH₃ | H | H | Ph |
| H-103 | Ph | 1) | 1) | H | H | H | N(CH₃)₂ | H | H | Ph |
| H-104 | Ph | H | H | 1) | 1) | H | H | H | H | Ph |
| H-105 | Ph | H | H | 1) | 1) | H | H | CH₃ | H | Ph |
| H-106 | Ph | H | H | 1) | 1) | H | H | OCH₃ | H | Ph |
| H-107 | Ph | H | H | 1) | 1) | H | H | N(CH₃)₂ | H | Ph |
| H-108 | Ph | H | H | 1) | 1) | H | CH₃ | H | H | Ph |
| H-109 | Ph | H | H | 1) | 1) | H | OCH₃ | H | H | Ph |
| H-110 | Ph | H | H | 1) | 1) | H | N(CH₃)₂ | H | H | Ph |
| H-111 | Ph | H | H | H | H | H | H | H | H | CF₃ |
| H-112 | Ph | H | H | H | H | H | H | CH₃ | H | CF₃ |
| H-113 | Ph | H | H | H | H | H | H | Ph | H | CF₃ |
| H-114 | Ph | H | H | H | H | H | H | t-Bu | H | CF₃ |
| H-115 | Ph | H | H | H | H | H | H | C₆H₁₁ | H | CF₃ |
| H-116 | Ph | H | H | H | H | H | H | F | H | CF₃ |
| H-117 | Ph | H | H | H | H | H | H | OCH₃ | H | CF₃ |
| H-118 | Ph | H | H | H | H | H | H | OC₆H₅ | H | CF₃ |
| H-119 | Ph | H | H | H | H | H | H | OH | H | CF₃ |
| H-120 | Ph | H | H | H | H | H | H | OCF₃ | H | CF₃ |
| H-121 | Ph | H | H | H | H | H | H | OSi(CH₃)₂C(CH₃)₃ | H | CF₃ |
| H-122 | Ph | H | H | H | H | H | H | CF₃ | H | CF₃ |
| H-123 | Ph | H | H | H | H | H | H | SCH₃ | H | CF₃ |
| H-124 | Ph | H | H | H | H | H | H | SO₂CH₃ | H | CF₃ |
| H-125 | Ph | H | H | H | H | H | H | SOCH₃ | H | CF₃ |
| H-126 | Ph | H | H | H | H | H | H | SH | H | CF₃ |
| H-127 | Ph | H | H | H | H | H | H | NO₂ | H | CF₃ |
| H-128 | Ph | H | H | H | H | H | H | N(CH₃)₂ | H | CF₃ |
| H-129 | Ph | H | H | H | H | H | H | NH₂ | H | CF₃ |
| H-130 | Ph | H | H | H | H | H | H | NCOCH₃ | H | CF₃ |
| H-131 | Ph | H | H | H | H | H | H | NSO₂CH₃ | H | CF₃ |
| H-132 | Ph | H | H | H | H | H | H | HNCH₂CH₃ | H | CF₃ |
| H-133 | Ph | H | H | H | H | H | H | CHO | H | CF₃ |
| H-134 | Ph | H | H | H | H | H | H | CH₂OH | H | CF₃ |
| H-135 | Ph | H | H | H | H | H | H | CH₂Br | H | CF₃ |
| H-136 | Ph | H | H | H | H | H | H | CH₂CN | H | CF₃ |
| H-137 | Ph | H | H | H | H | H | H | CH₂CO₂H | H | CF₃ |
| H-138 | Ph | H | H | H | H | H | H | CH₂OCH₃ | H | CF₃ |
| H-139 | Ph | H | H | H | H | H | H | CH₂N(CH₂CH₃)₂ | H | CF₃ |
| H-140 | Ph | H | H | H | H | H | H | CHCHCO₂CH₃ | H | CF₃ |
| H-141 | Ph | H | H | H | H | H | H | CH₂CH₂CO₂CH₃ | H | CF₃ |
| H-142 | Ph | H | H | H | H | H | H | C₆F₅ | H | CF₃ |
| H-143 | Ph | H | H | H | H | H | H | H | CH₃ | CF₃ |
| H-144 | Ph | H | H | H | H | H | CH₃ | H | H | CF₃ |
| H-145 | Ph | H | H | H | H | H | H | H | CHCH₂ | CF₃ |
| H-146 | Ph | H | H | H | H | H | CHCH₂ | H | H | CF₃ |
| H-147 | Ph | H | H | H | H | H | H | H | Ph | CF₃ |
| H-148 | Ph | H | H | H | H | H | Ph | H | H | CF₃ |

-continued

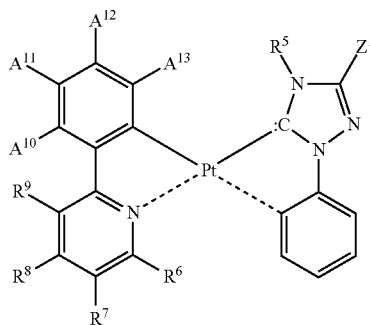

| Cpd. | R⁵ | R⁶ | R⁷ | R⁸ | R⁹ | A¹⁰ | A¹¹ | A¹² | A¹³ | Z¹ |
|---|---|---|---|---|---|---|---|---|---|---|
| H-149 | Ph | H | H | H | H | H | C₆F₅ | H | H | CF₃ |
| H-150 | Ph | H | H | H | H | H | CF₃ | H | CF₃ | CF₃ |
| H-151 | Ph | H | H | H | H | H | H | H | CF₃ | CF₃ |
| H-152 | Ph | H | H | H | H | H | CF₃ | H | H | CF₃ |
| H-153 | Ph | H | H | H | H | H | F | H | H | CF₃ |
| H-154 | Ph | H | H | H | H | H | H | H | F | CF₃ |
| H-155 | Ph | H | H | H | H | H | F | H | F | CF₃ |
| H-156 | Ph | H | H | H | H | H | H | H | OCF₃ | CF₃ |
| H-157 | Ph | H | H | H | H | H | OCF₃ | H | H | CF₃ |
| H-158 | Ph | H | H | H | H | H | NO₂ | H | CF₃ | CF₃ |
| H-159 | Ph | H | H | H | H | H | CF₃ | H | NO₂ | CF₃ |
| H-160 | Ph | H | H | H | H | H | CN | H | H | CF₃ |
| H-161 | Ph | H | H | H | H | H | H | H | CN | CF₃ |
| H-152 | Ph | H | H | H | H | H | H | H | Si(CH₃)₃ | CF₃ |
| H-163 | Ph | H | H | H | H | H | Si(CH₃)₃ | H | H | CF₃ |
| H-164 | Ph | H | H | H | H | H | NO₂ | H | CN | CF₃ |
| H-165 | Ph | H | H | H | H | H | CN | H | NO₂ | CF₃ |
| H-166 | Ph | CF₃ | H | H | H | H | H | H | H | CF₃ |
| H-167 | Ph | Cl | H | H | H | H | H | H | H | CF₃ |
| H-168 | Ph | NO₂ | H | H | H | H | H | H | H | CF₃ |
| H-169 | Ph | CN | H | H | H | H | H | H | H | CF₃ |
| H-170 | Ph | CH₃ | H | H | H | H | H | H | H | CF₃ |
| H-171 | Ph | OCH₃ | H | H | H | H | H | H | H | CF₃ |
| H-172 | Ph | Ph | H | H | H | H | H | H | H | CF₃ |
| H-173 | Ph | F | H | H | H | H | H | H | H | CF₃ |
| H-174 | Ph | H | H | H | CF₃ | H | H | H | H | CF₃ |
| H-175 | Ph | H | H | H | CN | H | H | H | H | CF₃ |
| H-176 | Ph | H | H | H | NO₂ | H | H | H | H | CF₃ |
| H-177 | Ph | H | H | H | CH₃ | H | H | H | H | CF₃ |
| H-178 | Ph | H | H | H | Ph | H | H | H | H | CF₃ |
| H-179 | Ph | H | H | H | F | H | H | H | H | CF₃ |
| H-180 | Ph | H | H | H | OCH₃ | H | H | H | H | CF₃ |
| H-181 | Ph | H | H | CF₃ | H | H | H | H | H | CF₃ |
| H-182 | Ph | H | H | CH₃ | H | H | H | H | H | CF₃ |
| H-183 | Ph | H | CF₃ | H | H | H | H | H | H | CF₃ |
| H-184 | Ph | H | CH₃ | H | H | H | H | H | H | CF₃ |
| H-185 | Ph | H | F | H | H | H | H | H | H | CF₃ |
| H-186 | Ph | H | C₆F₅ | H | H | H | H | H | H | CF₃ |
| H-187 | Ph | H | H | C₆F₅ | H | H | H | H | H | CF₃ |
| H-188 | Ph | H | C₆H₅ | H | H | H | H | H | H | CF₃ |
| H-189 | Ph | H | H | C₆H₅ | H | H | H | H | H | CF₃ |
| H-190 | Ph | H | CF₃ | H | H | H | H | F | H | CF₃ |
| H-191 | Ph | H | F | H | H | H | H | CF₃ | H | CF₃ |
| H-192 | Ph | H | CN | H | H | H | H | F | H | CF₃ |
| H-193 | Ph | H | H | H | H | H | Si(CH₃)₂C₆F₁₃ | H | H | CF₃ |
| H-194 | Ph | H | F | H | H | H | F | CN | H | CF₃ |
| H-195 | Ph | H | C₆F₅ | H | H | H | H | F | H | CF₃ |
| H-196 | Ph | H | C₆F₅ | H | H | H | H | CF₃ | H | CF₃ |
| H-197 | Ph | H | C₆F₅ | H | H | H | C₆F₅ | H | H | CF₃ |
| H-198 | Ph | H | C₆F₅ | H | H | H | H | C₆F₅ | H | CF₃ |
| H-199 | Ph | H | H | C₆F₅ | H | H | C₆F₅ | H | H | CF₃ |
| H-200 | Ph | H | H | C₆F₅ | H | H | H | C₆F₅ | H | CF₃ |
| H-201 | Ph | H | H | OCH₃ | H | F | H | F | H | CF₃ |
| H-202 | Ph | H | H | OCH₃ | H | F | CN | F | H | CF₃ |
| H-203 | Ph | H | H | OCH₃ | H | CF₃ | H | CF₃ | H | CF₃ |
| H-204 | Ph | H | H | N(CH₃)₂ | H | F | H | F | H | CF₃ |
| H-205 | Ph | H | H | N(CH₃)₂ | H | F | CN | F | H | CF₃ |
| H-206 | Ph | H | H | N(CH₃)₂ | H | CF₃ | H | CF₃ | H | CF₃ |
| H-207 | Ph | 1) | 1) | H | H | H | H | H | H | CF₃ |
| H-208 | Ph | 1) | 1) | H | H | H | H | CH₃ | H | CF₃ |
| H-209 | Ph | 1) | 1) | H | H | H | H | OCH₃ | H | CF₃ |
| H-210 | Ph | 1) | 1) | H | H | H | H | N(CH₃)₂ | H | CF₃ |

-continued

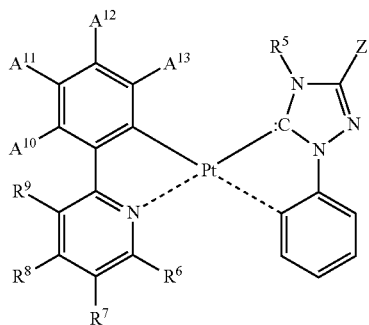

| Cpd. | R⁵ | R⁶ | R⁷ | R⁸ | R⁹ | A¹⁰ | A¹¹ | A¹² | A¹³ | Z¹ |
|---|---|---|---|---|---|---|---|---|---|---|
| H-211 | Ph | 1) | 1) | H | H | H | CH₃ | H | H | CF₃ |
| H-212 | Ph | 1) | 1) | H | H | H | OCH₃ | H | H | CF₃ |
| H-213 | Ph | 1) | 1) | H | H | H | N(CH₃)₂ | H | H | CF₃ |
| H-214 | Ph | H | H | 1) | 1) | H | H | H | H | CF₃ |
| H-215 | Ph | H | H | 1) | 1) | H | H | CH₃ | H | CF₃ |
| H-216 | Ph | H | H | 1) | 1) | H | H | OCH₃ | H | CF₃ |
| H-217 | Ph | H | H | 1) | 1) | H | H | N(CH₃)₂ | H | CF₃ |
| H-218 | Ph | H | H | 1) | 1) | H | CH₃ | H | H | CF₃ |
| H-219 | Ph | H | H | 1) | 1) | H | OCH₃ | H | H | CF₃ |
| H-210 | Ph | H | H | 1) | 1) | H | N(CH₃)₂ | H | H | CF₃ |
| H-211 | Ph | H | H | H | H | H | H | H | H | 2) |
| H-212 | Ph | H | H | H | H | H | H | CH₃ | H | 2) |
| H-213 | Ph | H | H | H | H | H | H | Ph | H | 2) |
| H-214 | Ph | H | H | H | H | H | H | t-Bu | H | 2) |
| H-215 | Ph | H | H | H | H | H | H | C₆H₁₁ | H | 2) |
| H-216 | Ph | H | H | H | H | H | H | F | H | 2) |
| H-217 | Ph | H | H | H | H | H | H | OCH₃ | H | 2) |
| H-218 | Ph | H | H | H | H | H | H | OC₆H₅ | H | 2) |
| H-219 | Ph | H | H | H | H | H | H | OH | H | 2) |
| H-220 | Ph | H | H | H | H | H | H | OCF₃ | H | 2) |
| H-221 | Ph | H | H | H | H | H | H | OSi(CH₃)₂C(CH₃)₃ | H | 2) |
| H-222 | Ph | H | H | H | H | H | H | CF₃ | H | 2) |
| H-223 | Ph | H | H | H | H | H | H | SCH₃ | H | 2) |
| H-224 | Ph | H | H | H | H | H | H | SO₂CH₃ | H | 2) |
| H-225 | Ph | H | H | H | H | H | H | SOCH₃ | H | 2) |
| H-226 | Ph | H | H | H | H | H | H | SH | H | 2) |
| H-227 | Ph | H | H | H | H | H | H | NO₂ | H | 2) |
| H-228 | Ph | H | H | H | H | H | H | N(CH₃)₂ | H | 2) |
| H-229 | Ph | H | H | H | H | H | H | NH₂ | H | 2) |
| H-230 | Ph | H | H | H | H | H | H | NCOCH₃ | H | 2) |
| H-231 | Ph | H | H | H | H | H | H | NSO₂CH₃ | H | 2) |
| H-232 | Ph | H | H | H | H | H | H | HNCH₂CH₃ | H | 2) |
| H-233 | Ph | H | H | H | H | H | H | CHO | H | 2) |
| H-234 | Ph | H | H | H | H | H | H | CH₂OH | H | 2) |
| H-235 | Ph | H | H | H | H | H | H | CH₂Br | H | 2) |
| H-236 | Ph | H | H | H | H | H | H | CH₂CN | H | 2) |
| H-237 | Ph | H | H | H | H | H | H | CH₂CO₂H | H | 2) |
| H-238 | Ph | H | H | H | H | H | H | CH₂OCH₃ | H | 2) |
| H-239 | Ph | H | H | H | H | H | H | CH₂N(CH₂CH₃)₂ | H | 2) |
| H-240 | Ph | H | H | H | H | H | H | CHCHCO₂CH₃ | H | 2) |
| H-241 | Ph | H | H | H | H | H | H | CH₂CH₂CO₂CH₃ | H | 2) |
| H-242 | Ph | H | H | H | H | H | H | C₆F₅ | H | 2) |
| H-243 | Ph | H | H | H | H | H | H | H | CH₃ | 2) |
| H-244 | Ph | H | H | H | H | H | CH₃ | H | H | 2) |
| H-245 | Ph | H | H | H | H | H | H | H | CHCH₂ | 2) |
| H-246 | Ph | H | H | H | H | H | CHCH₂ | H | H | 2) |
| H-247 | Ph | H | H | H | H | H | H | H | Ph | 2) |
| H-248 | Ph | H | H | H | H | H | Ph | H | H | 2) |
| H-249 | Ph | H | H | H | H | H | C₆F₅ | H | H | 2) |
| H-250 | Ph | H | H | H | H | H | CF₃ | H | CF₃ | 2) |
| H-251 | Ph | H | H | H | H | H | H | H | CF₃ | 2) |
| H-252 | Ph | H | H | H | H | H | CF₃ | H | H | 2) |
| H-253 | Ph | H | H | H | H | H | F | H | H | 2) |
| H-254 | Ph | H | H | H | H | H | H | H | F | 2) |
| H-255 | Ph | H | H | H | H | H | F | H | F | 2) |
| H-256 | Ph | H | H | H | H | H | H | H | OCF₃ | 2) |
| H-257 | Ph | H | H | H | H | H | OCF₃ | H | H | 2) |
| H-258 | Ph | H | H | H | H | H | NO₂ | H | CF₃ | 2) |
| H-259 | Ph | H | H | H | H | H | CF₃ | H | NO₂ | 2) |
| H-260 | Ph | H | H | H | H | H | CN | H | H | 2) |
| H-261 | Ph | H | H | H | H | H | H | H | CN | 2) |
| H-252 | Ph | H | H | H | H | H | H | H | Si(CH₃)₃ | 2) |

-continued

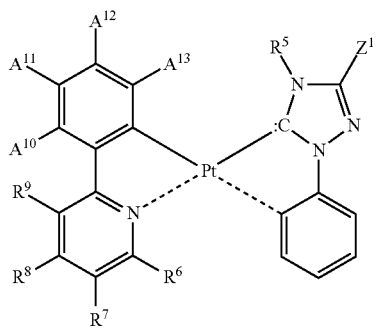

| Cpd. | R5 | R6 | R7 | R8 | R9 | A10 | A11 | A12 | A13 | Z1 |
|---|---|---|---|---|---|---|---|---|---|---|
| H-263 | Ph | H | H | H | H | H | Si(CH3)3 | H | H | 2) |
| H-264 | Ph | H | H | H | H | H | NO2 | H | CN | 2) |
| H-265 | Ph | H | H | H | H | H | CN | H | NO2 | 2) |
| H-266 | Ph | CF3 | H | H | H | H | H | H | H | 2) |
| H-267 | Ph | Cl | H | H | H | H | H | H | H | 2) |
| H-268 | Ph | NO2 | H | H | H | H | H | H | H | 2) |
| H-269 | Ph | CN | H | H | H | H | H | H | H | 2) |
| H-270 | Ph | CH3 | H | H | H | H | H | H | H | 2) |
| H-271 | Ph | OCH3 | H | H | H | H | H | H | H | 2) |
| H-272 | Ph | Ph | H | H | H | H | H | H | H | 2) |
| H-273 | Ph | F | H | H | H | H | H | H | H | 2) |
| H-274 | Ph | H | H | H | CF3 | H | H | H | H | 2) |
| H-275 | Ph | H | H | H | CN | H | H | H | H | 2) |
| H-276 | Ph | H | H | H | NO2 | H | H | H | H | 2) |
| H-277 | Ph | H | H | H | CH3 | H | H | H | H | 2) |
| H-278 | Ph | H | H | H | Ph | H | H | H | H | 2) |
| H-279 | Ph | H | H | H | F | H | H | H | H | 2) |
| H-280 | Ph | H | H | H | OCH3 | H | H | H | H | 2) |
| H-281 | Ph | H | H | CF3 | H | H | H | H | H | 2) |
| H-282 | Ph | H | H | CH3 | H | H | H | H | H | 2) |
| H-283 | Ph | H | CF3 | H | H | H | H | H | H | 2) |
| H-284 | Ph | H | CH3 | H | H | H | H | H | H | 2) |
| H-285 | Ph | H | F | H | H | H | H | H | H | 2) |
| H-286 | Ph | H | C6F5 | H | H | H | H | H | H | 2) |
| H-287 | Ph | H | H | C6F5 | H | H | H | H | H | 2) |
| H-288 | Ph | H | C6H5 | H | H | H | H | H | H | 2) |
| H-289 | Ph | H | H | C6H5 | H | H | H | H | H | 2) |
| H-290 | Ph | H | CF3 | H | H | H | H | F | H | 2) |
| H-291 | Ph | H | F | H | H | H | H | CF3 | H | 2) |
| H-292 | Ph | H | CN | H | H | H | H | F | H | 2) |
| H-293 | Ph | H | H | H | H | H | Si(CH3)2C6F5 | H | H | 2) |
| H-294 | Ph | H | F | H | H | H | F | CN | H | 2) |
| H-295 | Ph | H | C6F5 | H | H | H | H | F | H | 2) |
| H-296 | Ph | H | C6F5 | H | H | H | H | CF3 | H | 2) |
| H-297 | Ph | H | C6F5 | H | H | H | C6F5 | H | H | 2) |
| H-298 | Ph | H | C6F5 | H | H | H | H | C6F5 | H | 2) |
| H-299 | Ph | H | H | C6F5 | H | H | C6F5 | H | H | 2) |
| H-300 | Ph | H | H | C6F5 | H | H | H | C6F5 | H | 2) |
| H-301 | Ph | H | H | OCH3 | H | F | H | F | H | 2) |
| H-302 | Ph | H | H | OCH3 | H | F | CN | F | H | 2) |
| H-303 | Ph | H | H | OCH3 | H | CF3 | H | CF3 | H | 2) |
| H-304 | Ph | H | H | N(CH3)2 | H | F | H | F | H | 2) |
| H-305 | Ph | H | H- | N(CH3)2 | H | F | CN | F | H | 2) |
| H-306 | Ph | H | H | N(CH3)2 | H | CF3 | H | CF3 | H | 2) |
| H-307 | Ph | 1) | 1) | H | H | H | H | H | H | 2) |
| H-308 | Ph | 1) | 1) | H | H | H | H | CH3 | H | 2) |
| H-309 | Ph | 1) | 1) | H | H | H | H | OCH3 | H | 2) |
| H-310 | Ph | 1) | 1) | H | H | H | H | N(CH3)2 | H | 2) |
| H-311 | Ph | 1) | 1) | H | H | H | CH3 | H | H | 2) |
| H-312 | Ph | 1) | 1) | H | H | H | OCH3 | H | H | 2) |
| H-313 | Ph | 1) | 1) | H | H | H | N(CH3)2 | H | H | 2) |
| H-314 | Ph | H | H | 1) | 1) | H | H | H | H | 2) |
| H-315 | Ph | H | H | 1) | 1) | H | H | CH3 | H | 2) |
| H-316 | Ph | H | H | 1) | 1) | H | H | OCH3 | H | 2) |
| H-317 | Ph | H | H | 1) | 1) | H | H | N(CH3)2 | H | 2) |
| H-318 | Ph | H | H | 1) | 1) | H | CH3 | H | H | 2) |

-continued

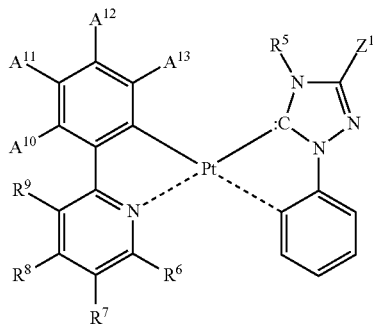

| Cpd. | R⁵ | R⁶ | R⁷ | R⁸ | R⁹ | A¹⁰ | A¹¹ | A¹² | A¹³ | Z¹ |
|---|---|---|---|---|---|---|---|---|---|---|
| H-319 | Ph | H | H | 1) | 1) | H | OCH₃ | H | H | 2) |
| H-320 | Ph | H | H | 1) | 1) | H | N(CH₃)₂ | H | H | 2) |

1) R⁸ and R⁹ together form a group ⟨⟩, R⁵ and R⁶ together form a group ⟨⟩, 2) 4-C₆H₄C(CH)₃.

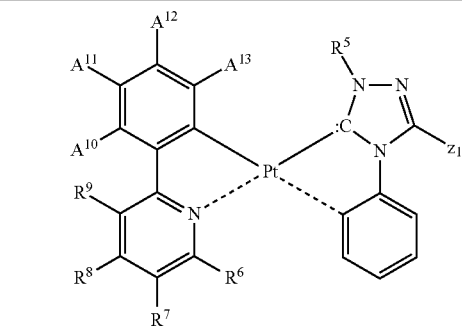

| Cpd. | R⁵ | R⁶ | R⁷ | R⁸ | R⁹ | A¹⁰ | A¹¹ | A¹² | A¹³ | Z¹ |
|---|---|---|---|---|---|---|---|---|---|---|
| H'-1 | Ph | H | H | H | H | H | H | H | H | Ph |
| H'-2 | Ph | H | H | H | H | H | H | CH₃ | H | Ph |
| H'-3 | Ph | H | H | H | H | H | H | Ph | H | Ph |
| H'-4 | Ph | H | H | H | H | H | H | t-Bu | H | Ph |
| H'-5 | Ph | H | H | H | H | H | H | C₆H₁₁ | H | Ph |
| H'-6 | Ph | H | H | H | H | H | H | F | H | Ph |
| H'-7 | Ph | H | H | H | H | H | H | OCH₃ | H | Ph |
| H'-8 | Ph | H | H | H | H | H | H | OC₆H₅ | H | Ph |
| H'-9 | Ph | H | H | H | H | H | H | OH | H | Ph |
| H'-10 | Ph | H | H | H | H | H | H | OCF₃ | H | Ph |
| H'-11 | Ph | H | H | H | H | H | H | OSi(CH₃)₂C(CH₃)₃ | H | Ph |
| H'-12 | Ph | H | H | H | H | H | H | CF₃ | H | Ph |
| H'-13 | Ph | H | H | H | H | H | H | SCH₃ | H | Ph |
| H'-14 | Ph | H | H | H | H | H | H | SO₂CH₃ | H | Ph |
| H'-15 | Ph | H | H | H | H | H | H | SOCH₃ | H | Ph |
| H'-16 | Ph | H | H | H | H | H | H | SH | H | Ph |
| H'-17 | Ph | H | H | H | H | H | H | NO₂ | H | Ph |
| H'-18 | Ph | H | H | H | H | H | H | N(CH₃)₂ | H | Ph |
| H'-19 | Ph | H | H | H | H | H | H | NH₂ | H | Ph |
| H'-20 | Ph | H | H | H | H | H | H | NCOCH₃ | H | Ph |
| H'-21 | Ph | H | H | H | H | H | H | NSO₂CH₃ | H | Ph |
| H'-22 | Ph | H | H | H | H | H | H | HNCH₂CH₃ | H | Ph |
| H'-23 | Ph | H | H | H | H | H | H | CHO | H | Ph |
| H'-24 | Ph | H | H | H | H | H | H | CH₂OH | H | Ph |
| H'-25 | Ph | H | H | H | H | H | H | CH₂Br | H | Ph |
| H'-26 | Ph | H | H | H | H | H | H | CH₂CN | H | Ph |
| H'-27 | Ph | H | H | H | H | H | H | CH₂CO₂H | H | Ph |
| H'-28 | Ph | H | H | H | H | H | H | CH₂OCH₃ | H | Ph |
| H'-29 | Ph | H | H | H | H | H | H | CH₂N(CH₂CH₃)₂ | H | Ph |
| H'-30 | Ph | H | H | H | H | H | H | CHCHCO₂CH₃ | H | Ph |
| H'-31 | Ph | H | H | H | H | H | H | CH₂CH₂CO₂CH₃ | H | Ph |

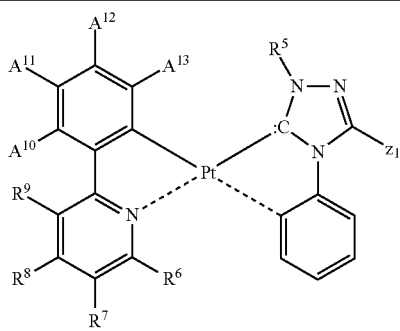

| Cpd. | $R^5$ | $R^6$ | $R^7$ | $R^8$ | $R^9$ | $A^{10}$ | $A^{11}$ | $A^{12}$ | $A^{13}$ | $Z^1$ |
|---|---|---|---|---|---|---|---|---|---|---|
| H'-32 | Ph | H | H | H | H | H | H | $C_6F_5$ | H | Ph |
| H'-33 | Ph | H | H | H | H | H | H | H | $CH_3$ | Ph |
| H'-34 | Ph | H | H | H | H | H | $CH_3$ | H | H | Ph |
| H'-35 | Ph | H | H | H | H | H | H | H | $CHCH_2$ | Ph |
| H'-36 | Ph | H | H | H | H | H | $CHCH_2$ | H | H | Ph |
| H'-37 | Ph | H | H | H | H | H | H | H | Ph | Ph |
| H'-38 | Ph | H | H | H | H | H | Ph | H | H | Ph |
| H'-39 | Ph | H | H | H | H | H | $C_6F_5$ | H | H | Ph |
| H'-40 | Ph | H | H | H | H | H | $CF_3$ | H | $CF_3$ | Ph |
| H'-41 | Ph | H | H | H | H | H | H | H | $CF_3$ | Ph |
| H'-42 | Ph | H | H | H | H | H | $CF_3$ | H | H | Ph |
| H'-43 | Ph | H | H | H | H | H | F | H | H | Ph |
| H'-44 | Ph | H | H | H | H | H | H | H | F | Ph |
| H'-45 | Ph | H | H | H | H | H | F | H | F | Ph |
| H'-46 | Ph | H | H | H | H | H | H | H | $OCF_3$ | Ph |
| H'-47 | Ph | H | H | H | H | H | $OCF_3$ | H | H | Ph |
| H'-48 | Ph | H | H | H | H | H | $NO_2$ | H | $CF_3$ | Ph |
| H'-49 | Ph | H | H | H | H | H | $CF_3$ | H | $NO_2$ | Ph |
| H'-50 | Ph | H | H | H | H | H | CN | H | H | Ph |
| H'-51 | Ph | H | H | H | H | H | H | H | CN | Ph |
| H'-52 | Ph | H | H | H | H | H | H | H | $Si(CH_3)_3$ | Ph |
| H'-53 | Ph | H | H | H | H | H | $Si(CH_3)_3$ | H | H | Ph |
| H'-54 | Ph | H | H | H | H | H | $NO_2$ | H | CN | Ph |
| H'-55 | Ph | H | H | H | H | H | CN | H | $NO_2$ | Ph |
| H'-56 | Ph | $CF_3$ | H | H | H | H | H | H | H | Ph |
| H'-57 | Ph | Cl | H | H | H | H | H | H | H | Ph |
| H'-58 | Ph | $NO_2$ | H | H | H | H | H | H | H | Ph |
| H'-59 | Ph | CN | H | H | H | H | H | H | H | Ph |
| H'-60 | Ph | $CH_3$ | H | H | H | H | H | H | H | Ph |
| H'-61 | Ph | $OCH_3$ | H | H | H | H | H | H | H | Ph |
| H'-62 | Ph | Ph | H | H | H | H | H | H | H | Ph |
| H'-63 | Ph | F | H | H | H | H | H | H | H | Ph |
| H'-64 | Ph | H | H | H | $CF_3$ | H | H | H | H | Ph |
| H'-65 | Ph | H | H | H | CN | H | H | H | H | Ph |
| H'-66 | Ph | H | H | H | $NO_2$ | H | H | H | H | Ph |
| H'-67 | Ph | H | H | H | $CH_3$ | H | H | H | H | Ph |
| H'-68 | Ph | H | H | H | Ph | H | H | H | H | Ph |
| H'-69 | Ph | H | H | H | F | H | H | H | H | Ph |
| H'-70 | Ph | H | H | H | $OCH_3$ | H | H | H | H | Ph |
| H'-71 | Ph | H | H | $CF_3$ | H | H | H | H | H | Ph |
| H'-72 | Ph | H | H | $CH_3$ | H | H | H | H | H | Ph |
| H'-73 | Ph | H | $CF_3$ | H | H | H | H | H | H | Ph |
| H'-74 | Ph | H | $CH_3$ | H | H | H | H | H | H | Ph |
| H'-75 | Ph | H | F | H | H | H | H | H | H | Ph |
| H'-76 | Ph | H | $C_6F_5$ | H | H | H | H | H | H | Ph |
| H'-77 | Ph | H | H | $C_6F_5$ | H | H | H | H | H | Ph |
| H'-78 | Ph | H | $C_6H_5$ | H | H | H | H | H | H | Ph |
| H'-79 | Ph | H | H | $C_6H_5$ | H | H | H | H | H | Ph |
| H'-80 | Ph | H | $CF_3$ | H | H | H | H | F | H | Ph |
| H'-81 | Ph | H | F | H | H | H | H | $CF_3$ | H | Ph |
| H'-82 | Ph | H | CN | H | H | H | H | F | H | Ph |
| H'-83 | Ph | H | H | H | H | H | $Si(CH_3)_2C_6F_{13}$ | H | H | Ph |
| H'-84 | Ph | H | F | H | H | H | F | CN | H | Ph |
| H'-85 | Ph | H | $C_6F_5$ | H | H | H | H | F | H | Ph |
| H'-86 | Ph | H | $C_6F_5$ | H | H | H | H | $CF_3$ | H | Ph |
| H'-87 | Ph | H | $C_6F_5$ | H | H | H | $C_6F_5$ | H | H | Ph |
| H'-88 | Ph | H | $C_6F_5$ | H | H | H | H | $C_6F_5$ | H | Ph |
| H'-89 | Ph | H | H | $C_6F_5$ | H | H | $C_6F_5$ | H | H | Ph |
| H'-90 | Ph | H | H | $C_6F_5$ | H | H | H | $C_6F_5$ | H | Ph |
| H'-91 | Ph | H | H | $OCH_3$ | H | F | H | F | H | Ph |
| H'-92 | Ph | H | H | $OCH_3$ | H | F | CN | F | H | Ph |
| H'-93 | Ph | H | H | $OCH_3$ | H | $CF_3$ | H | $CF_3$ | H | Ph |

-continued

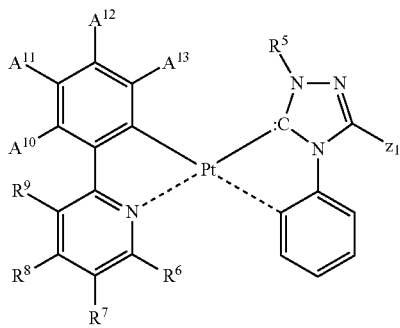

| Cpd. | R⁵ | R⁶ | R⁷ | R⁸ | R⁹ | A¹⁰ | A¹¹ | A¹² | A¹³ | Z¹ |
|---|---|---|---|---|---|---|---|---|---|---|
| H'-94 | Ph | H | H | N(CH₃)₂ | H | F | H | F | H | PH |
| H'-95 | Ph | H | H | N(CH₃)₂ | H | F | CN | F | H | Ph |
| H'-96 | Ph | H | H | N(CH₃)₂ | H | CF₃ | H | CF₃ | H | Ph |
| H'-97 | Ph | 1) | 1) | H | H | H | H | H | H | Ph |
| H'-98 | Ph | 1) | 1) | H | H | H | H | CH₃ | H | Ph |
| H'-99 | Ph | 1) | 1) | H | H | H | H | OCH₃ | H | Ph |
| H'-100 | Ph | 1) | 1) | H | H | H | H | N(CH₃)₂ | H | Ph |
| H'-101 | Ph | 1) | 1) | H | H | H | CH₃ | H | H | Ph |
| H'-102 | Ph | 1) | 1) | H | H | H | OCH₃ | H | H | Ph |
| H'-103 | Ph | 1) | 1) | H | H | H | N(CH₃)₂ | H | H | Ph |
| H'-104 | Ph | H | H | 1) | 1) | H | H | H | H | Ph |
| H'-105 | Ph | H | H | 1) | 1) | H | H | CH₃ | H | Ph |
| H'-106 | Ph | H | H | 1) | 1) | H | H | OCH₃ | H | Ph |
| H'-107 | Ph | H | H | 1) | 1) | H | H | N(CH₃)₂ | H | Ph |
| H'-108 | Ph | H | H | 1) | 1) | H | CH₃ | H | H | Ph |
| H'-109 | Ph | H | H | 1) | 1) | H | OCH₃ | H | H | Ph |
| H'-110 | Ph | H | H | 1) | 1) | H | N(CH₃)₂ | H | H | Ph |
| H'-111 | Ph | H | H | H | H | H | H | H | H | CF₃ |
| H'-112 | Ph | H | H | H | H | H | H | CH₃ | H | CF₃ |
| H'-113 | Ph | H | H | H | H | H | H | Ph | H | CF₃ |
| H'-114 | Ph | H | H | H | H | H | H | t-Bu | H | CF₃ |
| H'-115 | Ph | H | H | H | H | H | H | C₆H₁₁ | H | CF₃ |
| H'-116 | Ph | H | H | H | H | H | H | F | H | CF₃ |
| H'-117 | Ph | H | H | H | H | H | H | OCH₃ | H | CF₃ |
| H'-118 | Ph | H | H | H | H | H | H | OC₆H₅ | H | CF₃ |
| H'-119 | Ph | H | H | H | H | H | H | OH | H | CF₃ |
| H'-120 | Ph | H | H | H | H | H | H | OCF₃ | H | CF₃ |
| H'-121 | Ph | H | H | H | H | H | H | OSi(CH₃)₂C(CH₃)₃ | H | CF₃ |
| H'-122 | Ph | H | H | H | H | H | H | CF₃ | H | CF₃ |
| H'-123 | Ph | H | H | H | H | H | H | SCH₃ | H | CF₃ |
| H'-124 | Ph | H | H | H | H | H | H | SO₂CH₃ | H | CF₃ |
| H'-125 | Ph | H | H | H | H | H | H | SOCH₃ | H | CF₃ |
| H'-126 | Ph | H | H | H | H | H | H | SH | H | CF₃ |
| H'-127 | Ph | H | H | H | H | H | H | NO₂ | H | CF₃ |
| H'-128 | Ph | H | H | H | H | H | H | N(CH₃)₂ | H | CF₃ |
| H'-129 | Ph | H | H | H | H | H | H | NH₂ | H | CF₃ |
| H'-130 | Ph | H | H | H | H | H | H | NCOCH₃ | H | CF₃ |
| H'-131 | Ph | H | H | H | H | H | H | NSO₂CH₃ | H | CF₃ |
| H'-132 | Ph | H | H | H | H | H | H | HNCH₂CH₃ | H | CF₃ |
| H'-133 | Ph | H | H | H | H | H | H | CHO | H | CF₃ |
| H'-134 | Ph | H | H | H | H | H | H | CH₂OH | H | CF₃ |
| H'-135 | Ph | H | H | H | H | H | H | CH₂Br | H | CF₃ |
| H'-136 | Ph | H | H | H | H | H | H | CH₂CN | H | CF₃ |
| H'-137 | Ph | H | H | H | H | H | H | CH₂CO₂H | H | CF₃ |
| H'-138 | Ph | H | H | H | H | H | H | CH₂OCH₃ | H | CF₃ |
| H'-139 | Ph | H | H | H | H | H | H | CH₂N(CH₂CH₃)₂ | H | CF₃ |
| H'-140 | Ph | H | H | H | H | H | H | CHCHCO₂CH₃ | H | CF₃ |
| H'-141 | Ph | H | H | H | H | H | H | CH₂CH₂CO₂CH₃ | H | CF₃ |
| H'-142 | Ph | H | H | H | H | H | H | C₆F₅ | H | CF₃ |
| H'-143 | Ph | H | H | H | H | H | H | H | CH₃ | CF₃ |
| H'-144 | Ph | H | H | H | H | H | CH₃ | H | H | CF₃ |
| H'-145 | Ph | H | H | H | H | H | H | H | CHCH₂ | CF₃ |
| H'-146 | Ph | H | H | H | H | H | CHCH₂ | H | H | CF₃ |
| H'-147 | Ph | H | H | H | H | H | H | H | Ph | CF₃ |
| H'-148 | Ph | H | H | H | H | H | Ph | H | H | CF₃ |
| H'-149 | Ph | H | H | H | H | H | C₆F₅ | H | H | CF₃ |
| H'-150 | Ph | H | H | H | H | H | CF₃ | H | CF₃ | CF₃ |
| H'-151 | Ph | H | H | H | H | H | H | H | CF₃ | CF₃ |
| H'-152 | Ph | H | H | H | H | H | CF₃ | H | H | CF₃ |
| H'-153 | Ph | H | H | H | H | H | F | H | H | CF₃ |
| H'-154 | Ph | H | H | H | H | H | H | H | F | CF₃ |
| H'-155 | Ph | H | H | H | H | H | F | H | F | CF₃ |

-continued

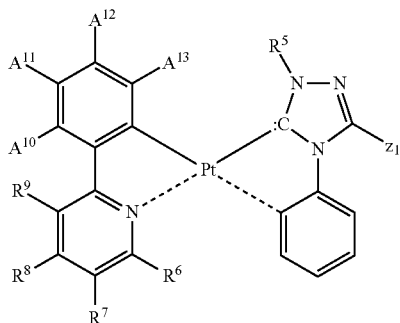

| Cpd. | R⁵ | R⁶ | R⁷ | R⁸ | R⁹ | A¹⁰ | A¹¹ | A¹² | A¹³ | Z¹ |
|---|---|---|---|---|---|---|---|---|---|---|
| H'-156 | Ph | H | H | H | H | H | H | H | OCF₃ | CF₃ |
| H'-157 | Ph | H | H | H | H | H | OCF₃ | H | H | CF₃ |
| H'-158 | Ph | H | H | H | H | H | NO₂ | H | CF₃ | CF₃ |
| H'-159 | Ph | H | H | H | H | H | CF₃ | H | NO₂ | CF₃ |
| H'-160 | Ph | H | H | H | H | H | CN | H | H | CF₃ |
| H'-161 | Ph | H | H | H | H | H | H | H | CN | CF₃ |
| H'-162 | Ph | H | H | H | H | H | H | H | Si(CH₃)₃ | CF₃ |
| H'-163 | Ph | H | H | H | H | H | Si(CH₃)₃ | H | H | CF₃ |
| H'-164 | Ph | H | H | H | H | H | NO₂ | H | CN | CF₃ |
| H'-165 | Ph | H | H | H | H | H | CN | H | NO₂ | CF₃ |
| H'-166 | Ph | CF₃ | H | H | H | H | H | H | H | CF₃ |
| H'-167 | Ph | Cl | H | H | H | H | H | H | H | CF₃ |
| H'-168 | Ph | NO₂ | H | H | H | H | H | H | H | CF₃ |
| H'-169 | Ph | CN | H | H | H | H | H | H | H | CF₃ |
| H'-170 | Ph | CH₃ | H | H | H | H | H | H | H | CF₃ |
| H'-171 | Ph | OCH₃ | H | H | H | H | H | H | H | CF₃ |
| H'-172 | Ph | Ph | H | H | H | H | H | H | H | CF₃ |
| H'-173 | Ph | F | H | H | H | H | H | H | H | CF₃ |
| H'-174 | Ph | H | H | H | CF₃ | H | H | H | H | CF₃ |
| H'-175 | Ph | H | H | H | CN | H | H | H | H | CF₃ |
| H'-176 | Ph | H | H | H | NO₂ | H | H | H | H | CF₃ |
| H'-177 | Ph | H | H | H | CH₃ | H | H | H | H | CF₃ |
| H'-178 | Ph | H | H | H | Ph | H | H | H | H | CF₃ |
| H'-179 | Ph | H | H | H | F | H | H | H | H | CF₃ |
| H'-180 | Ph | H | H | H | OCH₃ | H | H | H | H | CF₃ |
| H'-181 | Ph | H | H | CF₃ | H | H | H | H | H | CF₃ |
| H'-182 | Ph | H | H | CH₃ | H | H | H | H | H | CF₃ |
| H'-183 | Ph | H | CF₃ | H | H | H | H | H | H | CF₃ |
| H'-184 | Ph | H | CH₃ | H | H | H | H | H | H | CF₃ |
| H'-185 | Ph | H | F | H | H | H | H | H | H | CF₃ |
| H'-186 | Ph | H | C₆F₅ | H | H | H | H | H | H | CF₃ |
| H'-187 | Ph | H | H | C₆F₅ | H | H | H | H | H | CF₃ |
| H'-188 | Ph | H | C₆H₅ | H | H | H | H | H | H | CF₃ |
| H'-189 | Ph | H | H | C₆H₅ | H | H | H | H | H | CF₃ |
| H'-190 | Ph | H | CF₃ | H | H | H | H | F | H | CF₃ |
| H'-191 | Ph | H | F | H | H | H | H | CF₃ | H | CF₃ |
| H'-192 | Ph | H | CN | H | H | H | H | F | H | CF₃ |
| H'-193 | Ph | H | H | H | H | H | Si(CH₃)₂C₆F₁₃ | H | H | CF₃ |
| H'-194 | Ph | H | F | H | H | H | F | CN | H | CF₃ |
| H'-195 | Ph | H | C₆F₅ | H | H | H | H | F | H | CF₃ |
| H'-196 | Ph | H | C₆F₅ | H | H | H | H | CF₃ | H | CF₃ |
| H'-197 | Ph | H | C₆F₅ | H | H | H | C₆F₅ | H | H | CF₃ |
| H'-198 | Ph | H | C₆F₅ | H | H | H | H | C₆F₅ | H | CF₃ |
| H'-199 | Ph | H | H | C₆F₅ | H | H | C₆F₅ | H | H | CF₃ |
| H'-200 | Ph | H | H | C₆F₅ | H | H | H | C₆F₅ | H | CF₃ |
| H'-201 | Ph | H | H | OCH₃ | H | F | H | F | H | CF₃ |
| H'-202 | Ph | H | H | OCH₃ | H | F | CN | F | H | CF₃ |
| H'-203 | Ph | H | H | OCH₃ | H | CF₃ | H | CF₃ | H | CF₃ |
| H'-204 | Ph | H | H | N(CH₃)₂ | H | F | H | F | H | CF₃ |
| H'-205 | Ph | H | H | N(CH₃)₂ | H | F | CN | F | H | CF₃ |
| H'-206 | Ph | H | H | N(CH₃)₂ | H | CF₃ | H | CF₃ | H | CF₃ |
| H'-207 | Ph | 1) | 1) | H | H | H | H | H | H | CF₃ |
| H'-208 | Ph | 1) | 1) | H | H | H | H | CH₃ | H | CF₃ |
| H'-209 | Ph | 1) | 1) | H | H | H | H | OCH₃ | H | CF₃ |
| H'-210 | Ph | 1) | 1) | H | H | H | H | N(CH₃)₂ | H | CF₃ |
| H'-211 | Ph | 1) | 1) | H | H | H | CH₃ | H | H | CF₃ |
| H'-212 | Ph | 1) | 1) | H | H | H | OCH₃ | H | H | CF₃ |
| H'-213 | Ph | 1) | 1) | H | H | H | N(CH₃)₂ | H | H | CF₃ |
| H'-214 | Ph | H | H | 1) | 1) | H | H | H | H | CF₃ |
| H'-215 | Ph | H | H | 1) | 1) | H | H | CH₃ | H | CF₃ |
| H'-216 | Ph | H | H | 1) | 1) | H | H | OCH₃ | H | CF₃ |
| H'-217 | Ph | H | H | 1) | 1) | H | H | N(CH₃)₂ | H | CF₃ |

-continued

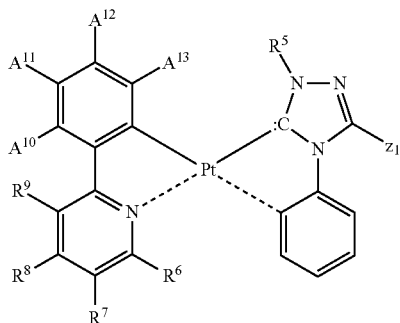

| Cpd. | $R^5$ | $R^6$ | $R^7$ | $R^8$ | $R^9$ | $A^{10}$ | $A^{11}$ | $A^{12}$ | $A^{13}$ | $Z^1$ |
|---|---|---|---|---|---|---|---|---|---|---|
| H'-218 | Ph | H | H | 1) | 1) | H | $CH_3$ | H | H | $CF_3$ |
| H'-219 | Ph | H | H | 1) | 1) | H | $OCH_3$ | H | H | $CF_3$ |
| H'-220 | Ph | H | H | 1) | 1) | H | $N(CH_3)_2$ | H | H | $CF_3$ |
| H'-221 | Ph | H | H | H | H | H | H | H | H | 2) |
| H'-222 | Ph | H | H | H | H | H | H | $CH_3$ | H | 2) |
| H'-223 | Ph | H | H | H | H | H | H | Ph | H | 2) |
| H'-224 | Ph | H | H | H | H | H | H | t-Bu | H | 2) |
| H'-225 | Ph | H | H | H | H | H | H | $C_6H_{11}$ | H | 2) |
| H'-226 | Ph | H | H | H | H | H | H | F | H | 2) |
| H'-227 | Ph | H | H | H | H | H | H | $OCH_3$ | H | 2) |
| H'-228 | Ph | H | H | H | H | H | H | $OC_6H_5$ | H | 2) |
| H'-229 | Ph | H | H | H | H | H | H | OH | H | 2) |
| H'-230 | Ph | H | H | H | H | H | H | $OCF_3$ | H | 2) |
| H'-231 | Ph | H | H | H | H | H | H | $OSi(CH_3)_2C(CH_3)_3$ | H | 2) |
| H'-232 | Ph | H | H | H | H | H | H | $CF_3$ | H | 2) |
| H'-233 | Ph | H | H | H | H | H | H | $SCH_3$ | H | 2) |
| H'-234 | Ph | H | H | H | H | H | H | $SO_2CH_3$ | H | 2) |
| H'-235 | Ph | H | H | H | H | H | H | $SOCH_3$ | H | 2) |
| H'-236 | Ph | H | H | H | H | H | H | SH | H | 2) |
| H'-237 | Ph | H | H | H | H | H | H | $NO_2$ | H | 2) |
| H'-238 | Ph | H | H | H | H | H | H | $N(CH_3)_2$ | H | 2) |
| H'-239 | Ph | H | H | H | H | H | H | $NH_2$ | H | 2) |
| H'-240 | Ph | H | H | H | H | H | H | $NCOCH_3$ | H | 2) |
| H'-241 | Ph | H | H | H | H | H | H | $NSO_2CH_3$ | H | 2) |
| H'-242 | Ph | H | H | H | H | H | H | $HNCH_2CH_3$ | H | 2) |
| H'-243 | Ph | H | H | H | H | H | H | CHO | H | 2) |
| H'-244 | Ph | H | H | H | H | H | H | $CH_2OH$ | H | 2) |
| H'-245 | Ph | H | H | H | H | H | H | $CH_2Br$ | H | 2) |
| H'-246 | Ph | H | H | H | H | H | H | $CH_2CN$ | H | 2) |
| H'-247 | Ph | H | H | H | H | H | H | $CH_2CO_2H$ | H | 2) |
| H'-248 | Ph | H | H | H | H | H | H | $CH_2OCH_3$ | H | 2) |
| H'-249 | Ph | H | H | H | H | H | H | $CH_2N(CH_2CH_3)_2$ | H | 2) |
| H'-250 | Ph | H | H | H | H | H | H | $CHCHCO_2CH_3$ | H | 2) |
| H'-251 | Ph | H | H | H | H | H | H | $CH_2CH_2CO_2CH_3$ | H | 2) |
| H'-252 | Ph | H | H | H | H | H | H | $C_6F_5$ | H | 2) |
| H'-253 | Ph | H | H | H | H | H | H | H | $CH_3$ | 2) |
| H'-254 | Ph | H | H | H | H | H | $CH_3$ | H | H | 2) |
| H'-255 | Ph | H | H | H | H | H | H | H | $CHCH_2$ | 2) |
| H'-256 | Ph | H | H | H | H | H | $CHCH_2$ | H | H | 2) |
| H'-257 | Ph | H | H | H | H | H | H | H | Ph | 2) |
| H'-258 | Ph | H | H | H | H | H | Ph | H | H | 2) |
| H'-259 | Ph | H | H | H | H | H | $C_6F_5$ | H | H | 2) |
| H'-260 | Ph | H | H | H | H | H | $CF_3$ | H | $CF_3$ | 2) |
| H'-261 | Ph | H | H | H | H | H | H | H | $CF_3$ | 2) |
| H'-262 | Ph | H | H | H | H | H | $CF_3$ | H | H | 2) |
| H'-263 | Ph | H | H | H | H | H | F | H | H | 2) |
| H'-264 | Ph | H | H | H | H | H | H | H | F | 2) |
| H'-265 | Ph | H | H | H | H | H | F | H | F | 2) |
| H'-266 | Ph | H | H | H | H | H | H | H | $OCF_3$ | 2) |
| H'-267 | Ph | H | H | H | H | H | $OCF_3$ | H | H | 2) |
| H'-268 | Ph | H | H | H | H | H | $NO_2$ | H | $CF_3$ | 2) |
| H'-269 | Ph | H | H | H | H | H | $CF_3$ | H | $NO_2$ | 2) |
| H'-270 | Ph | H | H | H | H | H | CN | H | H | 2) |
| H'-271 | Ph | H | H | H | H | H | H | H | CN | 2) |
| H'-272 | Ph | H | H | H | H | H | H | H | $Si(CH_3)_3$ | 2) |
| H'-273 | Ph | H | H | H | H | H | $Si(CH_3)_3$ | H | H | 2) |
| H'-274 | Ph | H | H | H | H | H | $NO_2$ | H | CN | 2) |
| H'-275 | Ph | H | H | H | H | H | CN | H | $NO_2$ | 2) |
| H'-276 | Ph | $CF_3$ | H | H | H | H | H | H | H | 2) |
| H'-277 | Ph | Cl | H | H | H | H | H | H | H | 2) |
| H'-278 | Ph | $NO_2$ | H | H | H | H | H | H | H | 2) |
| H'-279 | Ph | CN | H | H | H | H | H | H | H | 2) |

-continued

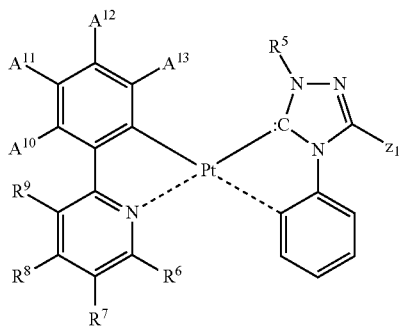

| Cpd. | R⁵ | R⁶ | R⁷ | R⁸ | R⁹ | A¹⁰ | A¹¹ | A¹² | A¹³ | Z¹ |
|---|---|---|---|---|---|---|---|---|---|---|
| H'-280 | Ph | CH₃ | H | H | H | H | H | H | H | 2) |
| H'-281 | Ph | OCH₃ | H | H | H | H | H | H | H | 2) |
| H'-282 | Ph | Ph | H | H | H | H | H | H | H | 2) |
| H'-283 | Ph | F | H | H | H | H | H | H | H | 2) |
| H'-284 | Ph | H | H | H | CF₃ | H | H | H | H | 2) |
| H'-285 | Ph | H | H | H | CN | H | H | H | H | 2) |
| H'-286 | Ph | H | H | H | NO₂ | H | H | H | H | 2) |
| H'-287 | Ph | H | H | H | CH₃ | H | H | H | H | 2) |
| H'-288 | Ph | H | H | H | Ph | H | H | H | H | 2) |
| H'-289 | Ph | H | H | H | F | H | H | H | H | 2) |
| H'-290 | Ph | H | H | H | OCH₃ | H | H | H | H | 2) |
| H'-291 | Ph | H | H | CF₃ | H | H | H | H | H | 2) |
| H'-292 | Ph | H | H | CH₃ | H | H | H | H | H | 2) |
| H'-293 | Ph | H | CF₃ | H | H | H | H | H | H | 2) |
| H'-294 | Ph | H | CH₃ | H | H | H | H | H | H | 2) |
| H'-295 | Ph | H | F | H | H | H | H | H | H | 2) |
| H'-296 | Ph | H | C₆F₅ | H | H | H | H | H | H | 2) |
| H'-297 | Ph | H | H | C₆F₅ | H | H | H | H | H | 2) |
| H'-298 | Ph | H | C₆H₅ | H | H | H | H | H | H | 2) |
| H'-299 | Ph | H | H | C₆H₅ | H | H | H | H | H | 2) |
| H'-300 | Ph | H | CF₃ | H | H | H | H | F | H | 2) |
| H'-301 | Ph | H | F | H | H | H | H | CF₃ | H | 2) |
| H'-302 | Ph | H | CN | H | H | H | H | F | H | 2) |
| H'-303 | Ph | H | H | H | H | H | Si(CH₃)₂C₆F₅ | H | H | 2) |
| H'-304 | Ph | H | F | H | H | H | F | CN | H | 2) |
| H'-305 | Ph | H | C₆F₅ | H | H | H | H | F | H | 2) |
| H'-306 | Ph | H | C₆F₅ | H | H | H | H | CF₃ | H | 2) |
| H'-307 | Ph | H | C₆F₅ | H | H | H | C₆F₅ | H | H | 2) |
| H'-308 | Ph | H | C₆F₅ | H | H | H | H | C₆F₅ | H | 2) |
| H'-309 | Ph | H | H | C₆F₅ | H | H | C₆F₅ | H | H | 2) |
| H'-310 | Ph | H | H | C₆F₅ | H | H | H | C₆F₅ | H | 2) |
| H'-311 | Ph | H | H | OCH₃ | H | F | H | F | H | 2) |
| H'-312 | Ph | H | H | OCH₃ | H | F | CN | F | H | 2) |
| H'-313 | Ph | H | H | OCH₃ | H | CF₃ | H | CF₃ | H | 2) |
| H'-314 | Ph | H | H | N(CH₃)₂ | H | F | H | F | H | 2) |
| H'-315 | Ph | H | H | N(CH₃)₂ | H | F | CN | F | H | 2) |
| H'-316 | Ph | H | H | N(CH₃)₂ | H | CF₃ | H | CF₃ | H | 2) |
| H'-317 | Ph | 1) | 1) | H | H | H | H | H | H | 2) |
| H'-318 | Ph | 1) | 1) | H | H | H | H | CH₃ | H | 2) |
| H'-319 | Ph | 1) | 1) | H | H | H | H | OCH₃ | H | 2) |
| H'-320 | Ph | 1) | 1) | H | H | H | H | N(CH₃)₂ | H | 2) |
| H'-321 | Ph | 1) | 1) | H | H | H | CH₃ | H | H | 2) |
| H'-322 | Ph | 1) | 1) | H | H | H | OCH₃ | H | H | 2) |
| H'-323 | Ph | 1) | 1) | H | H | H | N(CH₃)₂ | H | H | 2) |
| H'-324 | Ph | H | H | 1) | 1) | H | H | H | H | 2) |
| H'-325 | Ph | H | H | 1) | 1) | H | H | CH₃ | H | 2) |
| H'-326 | Ph | H | H | 1) | 1) | H | H | OCH₃ | H | 2) |
| H'-327 | Ph | H | H | 1) | 1) | H | H | N(CH₃)₂ | H | 2) |
| H'-328 | Ph | H | H | 1) | 1) | H | CH₃ | H | H | 2) |
| H'-329 | Ph | H | H | 1) | 1) | H | OCH₃ | H | H | 2) |
| H'-330 | Ph | H | H | 1) | 1) | H | N(CH₃)₂ | H | H | 2) |

1) R⁸ and R⁹ together form a group ⟨⟩, R⁵ and R⁶ together form a group ⟨⟩, 2) 4-C₆H₄C(CH)₃;

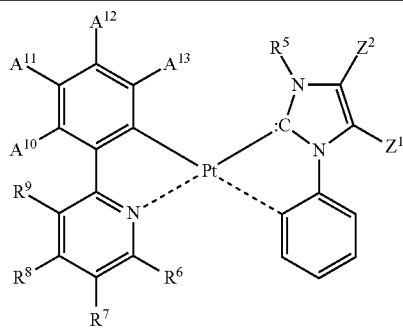

| Cpd. | R$^5$ | R$^6$ | R$^7$ | R$^8$ | R$^9$ | A$^{10}$ | A$^{11}$ | A$^{12}$ | A$^{13}$ | Z$^1$ = Z$^2$ |
|---|---|---|---|---|---|---|---|---|---|---|
| I-1 | Ph | H | H | H | H | H | H | H | H | H |
| I-2 | Ph | H | H | H | H | H | H | CH$_3$ | H | H |
| I-3 | Ph | H | H | H | H | H | H | Ph | H | H |
| I-4 | Ph | H | H | H | H | H | H | t-Bu | H | H |
| I-5 | Ph | H | H | H | H | H | H | C$_6$H$_{11}$ | H | H |
| I-6 | Ph | H | H | H | H | H | H | F | H | H |
| I-7 | Ph | H | H | H | H | H | H | OCH$_3$ | H | H |
| I-8 | Ph | H | H | H | H | H | H | OC$_6$H$_5$ | H | H |
| I-9 | Ph | H | H | H | H | H | H | OH | H | H |
| I-10 | Ph | H | H | H | H | H | H | OCF$_3$ | H | H |
| I-11 | Ph | H | H | H | H | H | H | OSi(CH$_3$)$_2$C(CH$_3$)$_3$ | H | H |
| I-12 | Ph | H | H | H | H | H | H | CF$_3$ | H | H |
| I-13 | Ph | H | H | H | H | H | H | SCH$_3$ | H | H |
| I-14 | Ph | H | H | H | H | H | H | SO$_2$CH$_3$ | H | H |
| I-15 | Ph | H | H | H | H | H | H | SOCH$_3$ | H | H |
| I-16 | Ph | H | H | H | H | H | H | SH | H | H |
| I-17 | Ph | H | H | H | H | H | H | NO$_2$ | H | H |
| I-18 | Ph | H | H | H | H | H | H | N(CH$_3$)$_2$ | H | H |
| I-19 | Ph | H | H | H | H | H | H | NH$_2$ | H | H |
| I-20 | Ph | H | H | H | H | H | H | NCOCH$_3$ | H | H |
| I-21 | Ph | H | H | H | H | H | H | NSO$_2$CH$_3$ | H | H |
| I-22 | Ph | H | H | H | H | H | H | HNCH$_2$CH$_3$ | H | H |
| I-23 | Ph | H | H | H | H | H | H | CHO | H | H |
| I-24 | Ph | H | H | H | H | H | H | CH$_2$OH | H | H |
| I-25 | Ph | H | H | H | H | H | H | CH$_2$Br | H | H |
| I-26 | Ph | H | H | H | H | H | H | CH$_2$CN | H | H |
| I-27 | Ph | H | H | H | H | H | H | CH$_2$CO$_2$H | H | H |
| I-28 | Ph | H | H | H | H | H | H | CH$_2$OCH$_3$ | H | H |
| I-29 | Ph | H | H | H | H | H | H | CH$_2$N(CH$_2$CH$_3$)$_2$ | H | H |
| I-30 | Ph | H | H | H | H | H | H | CHCHCO$_2$CH$_3$ | H | H |
| I-31 | Ph | H | H | H | H | H | H | CH$_2$CH$_2$CO$_2$CH$_3$ | H | H |
| I-32 | Ph | H | H | H | H | H | H | C$_6$F$_5$ | H | H |
| I-33 | Ph | H | H | H | H | H | H | H | CH$_3$ | H |
| I-34 | Ph | H | H | H | H | H | CH$_3$ | H | H | H |
| I-35 | Ph | H | H | H | H | H | H | H | CHCH$_2$ | H |
| I-36 | Ph | H | H | H | H | H | CHCH$_2$ | H | H | H |
| I-37 | Ph | H | H | H | H | H | H | H | Ph | H |
| I-38 | Ph | H | H | H | H | H | Ph | H | H | H |
| I-39 | Ph | H | H | H | H | H | C$_6$F$_5$ | H | H | H |
| I-40 | Ph | H | H | H | H | H | CF$_3$ | H | CF$_3$ | H |
| I-41 | Ph | H | H | H | H | H | H | H | CF$_3$ | H |
| I-42 | Ph | H | H | H | H | H | CF$_3$ | H | H | H |
| I-43 | Ph | H | H | H | H | H | F | H | H | H |
| I-44 | Ph | H | H | H | H | H | H | H | F | H |
| I-45 | Ph | H | H | H | H | H | F | H | F | H |
| I-46 | Ph | H | H | H | H | H | H | H | OCF$_3$ | H |
| I-47 | Ph | H | H | H | H | H | OCF$_3$ | H | H | H |
| I-48 | Ph | H | H | H | H | H | NO$_2$ | H | CF$_3$ | H |
| I-49 | Ph | H | H | H | H | H | CF$_3$ | H | NO$_2$ | H |
| I-50 | Ph | H | H | H | H | H | CN | H | H | H |
| I-51 | Ph | H | H | H | H | H | H | H | CN | H |
| I-52 | Ph | H | H | H | H | H | H | H | Si(CH$_3$)$_3$ | H |
| I-53 | Ph | H | H | H | H | H | Si(CH$_3$)$_3$ | H | H | H |
| I-54 | Ph | H | H | H | H | H | NO$_2$ | H | CN | H |
| I-55 | Ph | H | H | H | H | H | CN | H | NO$_2$ | H |
| I-56 | Ph | CF$_3$ | H | H | H | H | H | H | H | H |
| I-57 | Ph | Cl | H | H | H | H | H | H | H | H |
| I-58 | Ph | NO$_2$ | H | H | H | H | H | H | H | H |
| I-59 | Ph | CN | H | H | H | H | H | H | H | H |
| I-60 | Ph | CH$_3$ | H | H | H | H | H | H | H | H |
| I-61 | Ph | OCH$_3$ | H | H | H | H | H | H | H | H |
| I-62 | Ph | Ph | H | H | H | H | H | H | H | H |

-continued

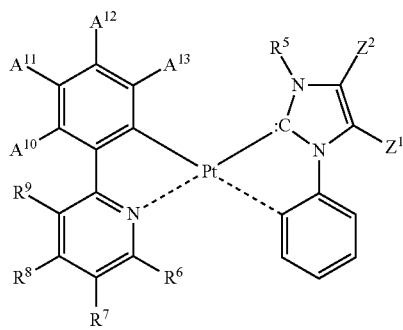

| Cpd. | R⁵ | R⁶ | R⁷ | R⁸ | R⁹ | A¹⁰ | A¹¹ | A¹² | A¹³ | Z¹ = Z² |
|---|---|---|---|---|---|---|---|---|---|---|
| I-63 | Ph | F | H | H | H | H | H | H | H | H |
| I-64 | Ph | H | H | H | CF₃ | H | H | H | H | H |
| I-65 | Ph | H | H | H | CN | H | H | H | H | H |
| I-66 | Ph | H | H | H | NO₂ | H | H | H | H | H |
| I-67 | Ph | H | H | H | CH₃ | H | H | H | H | H |
| I-68 | Ph | H | H | H | Ph | H | H | H | H | H |
| I-69 | Ph | H | H | H | F | H | H | H | H | H |
| I-70 | Ph | H | H | H | OCH₃ | H | H | H | H | H |
| I-71 | Ph | H | H | CF₃ | H | H | H | H | H | H |
| I-72 | Ph | H | H | CH₃ | H | H | H | H | H | H |
| I-73 | Ph | H | CF₃ | H | H | H | H | H | H | H |
| I-74 | Ph | H | CH₃ | H | H | H | H | H | H | H |
| I-75 | Ph | H | F | H | H | H | H | H | H | H |
| I-76 | Ph | H | C₆F₅ | H | H | H | H | H | H | H |
| I-77 | Ph | H | H | C₆F₅ | H | H | H | H | H | H |
| I-78 | Ph | H | C₆H₅ | H | H | H | H | H | H | H |
| I-79 | Ph | H | H | C₆H₅ | H | H | H | H | H | H |
| I-80 | Ph | H | H | OCH₃ | H | F | H | F | H | H |
| I-81 | Ph | H | CF₃ | H | H | H | H | F | H | H |
| I-82 | Ph | H | H | ¹⁾ | ¹⁾ | H | H | H | H | H |
| I-83 | Ph | H | H | H | H | H | Si(CH₃)₂C₆F₁₃ | H | H | H |
| I-84 | CH₃ | H | H | H | H | H | H | H | H | H |
| I-85 | Ph | H | C₆F₅ | H | H | H | H | F | H | H |
| I-86 | Ph | H | C₆F₅ | H | H | H | H | CF₃ | H | H |
| I-87 | Ph | H | C₆F₅ | H | H | H | C₆F₅ | H | H | H |
| I-88 | Ph | H | C₆F₅ | H | H | H | H | C₆F₅ | H | H |
| I-89 | Ph | H | H | C₆F₅ | H | H | C₆F₅ | H | H | H |
| I-90 | Ph | H | H | C₆F₅ | H | H | H | C₆F₅ | H | H |
| I-91 | Ph | H | H | OCH₃ | H | F | H | F | H | H |
| I-92 | Ph | H | H | OCH₃ | H | F | CN | F | H | H |
| I-93 | Ph | H | H | OCH₃ | H | CF₃ | H | CF₃ | H | H |
| I-94 | Ph | H | H. | N(CH₃)₂ | H | F | H | F | H | H |
| I-95 | Ph | H | H | N(CH₃)₂ | H | F | CN | F | H | H |
| I-96 | Ph | H | H | N(CH₃)₂ | H | CF₃ | H | CF₃ | H | H |
| I-97 | Ph | ¹⁾ | ¹⁾ | H | H | H | H | H | H | H |
| I-98 | Ph | ¹⁾ | ¹⁾ | H | H | H | H | CH₃ | H | H |
| I-99 | Ph | ¹⁾ | ¹⁾ | H | H | H | H | OCH₃ | H | H |
| I-100 | Ph | ¹⁾ | ¹⁾ | H | H | H | H | N(CH₃)₂ | H | H |
| I-101 | Ph | ¹⁾ | ¹⁾ | H | H | H | CH₃ | H | H | H |
| I-102 | Ph | ¹⁾ | ¹⁾ | H | H | H | OCH₃ | H | H | H |
| I-103 | Ph | ¹⁾ | ¹⁾ | H | H | H | N(CH₃)₂ | H | H | H |
| I-104 | Ph | H | H | ¹⁾ | ¹⁾ | H | H | H | H | H |
| I-105 | Ph | H | H | ¹⁾ | ¹⁾ | H | H | CH₃ | H | H |
| I-106 | Ph | H | H | ¹⁾ | ¹⁾ | H | H | OCH₃ | H | H |
| I-107 | Ph | H | H | ¹⁾ | ¹⁾ | H | H | N(CH₃)₂ | H | H |
| I-108 | Ph | H | H | ¹⁾ | ¹⁾ | H | CH₃ | H | H | H |
| I-109 | Ph | H | H | ¹⁾ | ¹⁾ | H | OCH₃ | H | H | H |
| I-110 | Ph | H | H | ¹⁾ | ¹⁾ | H | N(CH₃)₂ | H | H | H |

¹⁾ R⁸ and R⁹ together form a group 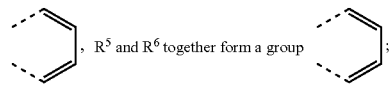, R⁵ and R⁶ together form a group ;

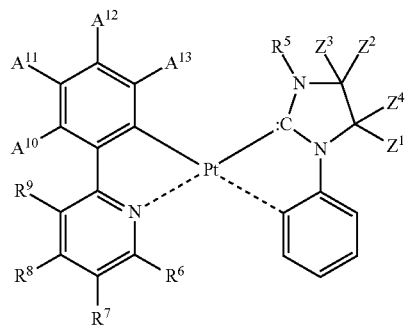

| Cpd. | R⁵ | R⁶ | R⁷ | R⁸ | R⁹ | A¹⁰ | A¹¹ | A¹² | A¹³ | 2) |
|---|---|---|---|---|---|---|---|---|---|---|
| J-1 | Ph | H | H | H | H | H | H | H | H | H |
| J-2 | Ph | H | H | H | H | H | H | CH₃ | H | H |
| J-3 | Ph | H | H | H | H | H | H | Ph | H | H |
| J-4 | Ph | H | H | H | H | H | H | t-Bu | H | H |
| J-5 | Ph | H | H | H | H | H | H | C₆H₁₁ | H | H |
| J-6 | Ph | H | H | H | H | H | H | F | H | H |
| J-7 | Ph | H | H | H | H | H | H | OCH₃ | H | H |
| J-8 | Ph | H | H | H | H | H | H | OC₆H₅ | H | H |
| J-9 | Ph | H | H | H | H | H | H | OH | H | H |
| J-10 | Ph | H | H | H | H | H | H | OCF₃ | H | H |
| J-11 | Ph | H | H | H | H | H | H | OSi(CH₃)₂C(CH₃)₃ | H | H |
| J-12 | Ph | H | H | H | H | H | H | CF₃ | H | H |
| J-13 | Ph | H | H | H | H | H | H | SCH₃ | H | H |
| J-14 | Ph | H | H | H | H | H | H | SO₂CH₃ | H | H |
| J-15 | Ph | H | H | H | H | H | H | SOCH₃ | H | H |
| J-16 | Ph | H | H | H | H | H | H | SH | H | H |
| J-17 | Ph | H | H | H | H | H | H | NO₂ | H | H |
| J-18 | Ph | H | H | H | H | H | H | N(CH₃)₂ | H | H |
| J-19 | Ph | H | H | H | H | H | H | NH₂ | H | H |
| J-20 | Ph | H | H | H | H | H | H | NCOCH₃ | H | H |
| J-21 | Ph | H | H | H | H | H | H | NSO₂CH₃ | H | H |
| J-22 | Ph | H | H | H | H | H | H | HNCH₂CH₃ | H | H |
| J-23 | Ph | H | H | H | H | H | H | CHO | H | H |
| J-24 | Ph | H | H | H | H | H | H | CH₂OH | H | H |
| J-25 | Ph | H | H | H | H | H | H | CH₂Br | H | H |
| J-26 | Ph | H | H | H | H | H | H | CH₂CN | H | H |
| J-27 | Ph | H | H | H | H | H | H | CH₂CO₂H | H | H |
| J-28 | Ph | H | H | H | H | H | H | CH₂OCH₃ | H | H |
| J-29 | Ph | H | H | H | H | H | H | CH₂N(CH₂CH₃)₂ | H | H |
| J-30 | Ph | H | H | H | H | H | H | CHCHCO₂CH₃ | H | H |
| J-31 | Ph | H | H | H | H | H | H | CH₂CH₂CO₂CH₃ | H | H |
| J-32 | Ph | H | H | H | H | H | H | C₆F₅ | H | H |
| J-33 | Ph | H | H | H | H | H | H | H | CH₃ | H |
| J-34 | Ph | H | H | H | H | H | CH₃ | H | H | H |
| J-35 | Ph | H | H | H | H | H | H | H | CHCH₂ | H |
| J-36 | Ph | H | H | H | H | H | CHCH₂ | H | H | H |
| J-37 | Ph | H | H | H | H | H | H | H | Ph | H |
| J-38 | Ph | H | H | H | H | H | Ph | H | H | H |
| J-39 | Ph | H | H | H | H | H | C₆F₅ | H | H | H |
| J-40 | Ph | H | H | H | H | H | CF₃ | H | CF₃ | H |
| J-41 | Ph | H | H | H | H | H | H | H | CF₃ | H |
| J-42 | Ph | H | H | H | H | H | CF₃ | H | H | H |
| J-43 | Ph | H | H | H | H | H | F | H | H | H |
| J-44 | Ph | H | H | H | H | H | H | H | F | H |
| J-45 | Ph | H | H | H | H | H | F | H | F | H |
| J-46 | Ph | H | H | H | H | H | H | H | OCF₃ | H |
| J-47 | Ph | H | H | H | H | H | OCF₃ | H | H | H |
| J-48 | Ph | H | H | H | H | H | NO₂ | H | CF₃ | H |
| J-49 | Ph | H | H | H | H | H | CF₃ | H | NO₂ | H |
| J-50 | Ph | H | H | H | H | H | CN | H | H | H |
| J-51 | Ph | H | H | H | H | H | H | H | CN | H |
| J-52 | Ph | H | H | H | H | H | H | H | Si(CH₃)₃ | H |
| J-53 | Ph | H | H | H | H | H | Si(CH₃)₃ | H | H | H |
| J-54 | Ph | H | H | H | H | H | NO₂ | H | CN | H |
| J-55 | Ph | H | H | H | H | H | CN | H | NO₂ | H |
| J-56 | Ph | CF₃ | H | H | H | H | H | H | H | H |
| J-57 | Ph | Cl | H | H | H | H | H | H | H | H |
| J-58 | Ph | NO₂ | H | H | H | H | H | H | H | H |
| J-59 | Ph | CN | H | H | H | H | H | H | H | H |
| J-60 | Ph | CH₃ | H | H | H | H | H | H | H | H |
| J-61 | Ph | OCH₃ | H | H | H | H | H | H | H | H |
| J-62 | Ph | Ph | H | H | H | H | H | H | H | H |

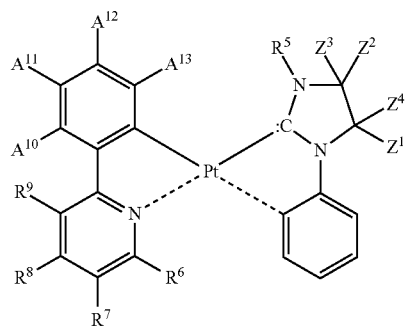

| Cpd. | R⁵ | R⁶ | R⁷ | R⁸ | R⁹ | A¹⁰ | A¹¹ | A¹² | A¹³ | 2) |
|---|---|---|---|---|---|---|---|---|---|---|
| J-63 | Ph | F | H | H | H | H | H | H | H | H |
| J-64 | Ph | H | H | H | CF₃ | H | H | H | H | H |
| J-65 | Ph | H | H | H | CN | H | H | H | H | H |
| J-66 | Ph | H | H | H | NO₂ | H | H | H | H | H |
| J-67 | Ph | H | H | H | CH₃ | H | H | H | H | H |
| J-68 | Ph | H | H | H | Ph | H | H | H | H | H |
| J-69 | Ph | H | H | H | F | H | H | H | H | H |
| J-70 | Ph | H | H | H | OCH₃ | H | H | H | H | H |
| J-71 | Ph | H | H | CF₃ | H | H | H | H | H | H |
| J-72 | Ph | H | H | CH₃ | H | H | H | H | H | H |
| J-73 | Ph | H | CF₃ | H | H | H | H | H | H | H |
| J-74 | Ph | H | CH₃ | H | H | H | H | H | H | H |
| J-75 | Ph | H | F | H | H | H | H | H | H | H |
| J-76 | Ph | H | C₆F₅ | H | H | H | H | H | H | H |
| J-77 | Ph | H | H | C₆F₅ | H | H | H | H | H | H |
| J-78 | Ph | H | C₆H₅ | H | H | H | H | H | H | H |
| J-79 | Ph | H | H | C₆H₅ | H | H | H | H | H | H |
| J-80 | Ph | H | H | OCH₃ | H | F | H | F | H | H |
| J-81 | Ph | H | CF₃ | H | H | H | H | F | H | H |
| J-82 | Ph | H | H | 1) | 1) | H | H | H | H | H |
| J-83 | Ph | H | H | H | H | H | Si(CH₃)₂C₆F₁₃ | H | H | H |
| J-84 | CH₃ | H | H | H | H | H | H | H | H | H |
| J-85 | Ph | H | C₆F₅ | H | H | H | H | F | H | H |
| J-86 | Ph | H | C₆F₅ | H | H | H | H | CF₃ | H | H |
| J-87 | Ph | H | C₆F₅ | H | H | H | C₆F₅ | H | H | H |
| J-88 | Ph | H | C₆F₅ | H | H | H | H | C₆F₅ | H | H |
| J-89 | Ph | H | H | C₆F₅ | H | H | C₆F₅ | H | H | H |
| J-90 | Ph | H | H | C₆F₅ | H | H | H | C₆F₅ | H | H |
| J-91 | Ph | H | H | OCH₃ | H | F | H | F | H | H |
| J-92 | Ph | H | H | OCH₃ | H | F | CN | F | H | H |
| J-93 | Ph | H | H | OCH₃ | H | CF₃ | H | CF₃ | H | H |
| J-94 | Ph | H | H | N(CH₃)₂ | H | F | H | F | H | H |
| J-95 | Ph | H | H | N(CH₃)₂ | H | F | CN | F | H | H |
| J-96 | Ph | H | H | N(CH₃)₂ | H | CF₃ | H | CF₃ | H | H |
| J-97 | Ph | 1) | 1) | H | H | H | H | H | H | H |
| J-98 | Ph | 1) | 1) | H | H | H | H | CH₃ | H | H |
| J-99 | Ph | 1) | 1) | H | H | H | H | OCH₃ | H | H |
| J-100 | Ph | 1) | 1) | H | H | H | H | N(CH₃)₂ | H | H |
| J-101 | Ph | 1) | 1) | H | H | H | CH₃ | H | H | H |
| J-102 | Ph | 1) | 1) | H | H | H | OCH₃ | H | H | H |
| J-103 | Ph | 1) | 1) | H | H | H | N(CH₃)₂ | H | H | H |
| J-104 | Ph | H | H | 1) | 1) | H | H | H | H | H |
| J-105 | Ph | H | H | 1) | 1) | H | H | CH₃ | H | H |
| J-106 | Ph | H | H | 1) | 1) | H | H | OCH₃ | H | H |
| J-107 | Ph | H | H | 1) | 1) | H | H | N(CH₃)₂ | H | H |
| J-108 | Ph | H | H | 1) | 1) | H | CH₃ | H | H | H |
| J-109 | Ph | H | H | 1) | 1) | H | OCH₃ | H | H | H |
| J-110 | Ph | H | H | 1) | 1) | H | N(CH₃)₂ | H | H | H |

1) R⁸ and R⁹ together form a group

2) $Z^1 = Z^2 = Z^3 = Z^4$;

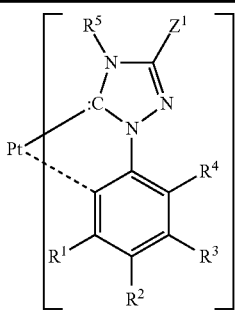

| Cpd. | R¹ | R² | R³ | R⁴ | R⁵ | Z¹ |
|---|---|---|---|---|---|---|
| K-1 | H | H | H | H | Ph | Ph |
| K-2 | H | NO₂ | H | H | Ph | Ph |
| K-3 | H | CH₃ | H | H | Ph | Ph |
| K-4 | H | C(CH₃)₃ | H | H | Ph | Ph |
| K-5 | H | CH(CH₃)₂ | H | H | Ph | Ph |
| K-6 | H | CF₃ | H | H | Ph | Ph |
| K-7 | H | OCF₃ | H | H | Ph | Ph |
| K-8 | H | F | H | H | Ph | Ph |
| K-9 | H | OCH₃ | H | H | Ph | Ph |
| K-10 | H | OPh | H | H | Ph | Ph |
| K-11 | H | CN | H | H | Ph | Ph |
| K-12 | H | SCH₃ | H | H | Ph | Ph |
| K-13 | H | CO₂CH₃ | H | H | Ph | Ph |
| K-14 | H | SO₂CH₃ | H | H | Ph | Ph |
| K-15 | H | C₆H₄CF₃ | H | H | Ph | Ph |
| K-16 | CH₃ | H | H | H | Ph | Ph |
| K-17 | F | H | H | H | Ph | Ph |
| K-18 | CF₃ | H | H | H | Ph | Ph |
| K-19 | C(CH₃)₃ | H | H | H | Ph | Ph |
| K-20 | CN | H | H | H | Ph | Ph |
| K-21 | NO₂ | H | H | H | Ph | Ph |
| K-22 | OCH₃ | H | H | H | Ph | Ph |
| K-23 | H | H | CH₃ | H | Ph | Ph |
| K-24 | H | H | F | H | Ph | Ph |
| K-25 | H | H | CF₃ | H | Ph | Ph |
| K-26 | H | H | OCF₃ | H | Ph | Ph |
| K-27 | H | H | CN | H | Ph | Ph |
| K-28 | H | H | NO₂ | H | Ph | Ph |
| K-29 | H | H | OCH₃ | H | Ph | Ph |
| K-30 | H | H | SCH₃ | H | Ph | Ph |
| K-31 | H | H | H | H | Ph | CF₃ |
| K-32 | H | NO₂ | H | H | Ph | CF₃ |
| K-33 | H | CH₃ | H | H | Ph | CF₃ |
| K-34 | H | C(CH₃)₃ | H | H | Ph | CF₃ |
| K-35 | H | CH(CH₃)₂ | H | H | Ph | CF₃ |
| K-36 | H | CF₃ | H | H | Ph | CF₃ |
| K-37 | H | OCF₃ | H | H | Ph | CF₃ |
| K-38 | H | F | H | H | Ph | CF₃ |
| K-39 | H | OCH₃ | H | H | Ph | CF₃ |
| K-40 | H | OPh | H | H | Ph | CF₃ |
| K-41 | H | CN | H | H | Ph | CF₃ |
| K-42 | H | SCH₃ | H | H | Ph | CF₃ |
| K-43 | H | CO₂CH₃ | H | H | Ph | CF₃ |
| K-44 | H | SO₂CH₃ | H | H | Ph | CF₃ |
| K-45 | CH₃ | H | H | H | Ph | CF₃ |
| K-46 | F | H | H | H | Ph | CF₃ |
| K-47 | CF₃ | H | H | H | Ph | CF₃ |
| K-48 | C(CH₃)₃ | H | H | H | Ph | CF₃ |
| K-49 | CN | H | H | H | Ph | CF₃ |
| K-50 | NO₂ | H | H | H | Ph | CF₃ |
| K-51 | OCH₃ | H | H | H | Ph | CF₃ |
| K-52 | H | H | CH₃ | H | Ph | CF₃ |
| K-53 | H | H | F | H | Ph | CF₃ |
| K-54 | H | H | CF₃ | H | Ph | CF₃ |
| K-55 | H | H | OCF₃ | H | Ph | CF₃ |
| K-56 | H | H | CN | H | Ph | CF₃ |
| K-57 | H | H | NO₂ | H | Ph | CF₃ |
| K-58 | H | H | OCH₃ | H | Ph | CF₃ |
| K-59 | H | H | SCH₃ | H | Ph | CF₃ |
| K-60 | H | C₆H₄CF₃ | H | H | Ph | CF₃ |
| K-61 | H | H | H | H | Ph | 1) |
| K-62 | H | NO₂ | H | H | Ph | 1) |

-continued

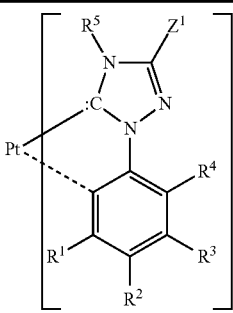

| Cpd. | R¹ | R² | R³ | R⁴ | R⁵ | Z¹ |
|---|---|---|---|---|---|---|
| K-63 | H | CH₃ | H | H | Ph | 1) |
| K-64 | H | C(CH₃)₃ | H | H | Ph | 1) |
| K-65 | H | CH(CH₃)₂ | H | H | Ph | 1) |
| K-66 | H | CF₃ | H | H | Ph | 1) |
| K-67 | H | OCF₃ | H | H | Ph | 1) |
| K-68 | H | F | H | H | Ph | 1) |
| K-69 | H | OCH₃ | H | H | Ph | 1) |
| K-70 | H | OPh | H | H | Ph | 1) |
| K-71 | H | CN | H | H | Ph | 1) |
| K-72 | H | SCH₃ | H | H | Ph | 1) |
| K-73 | H | CO₂CH₃ | H | H | Ph | 1) |
| K-74 | H | SO₂CH₃ | H | H | Ph | 1) |
| K-75 | CH₃ | H | H | H | Ph | 1) |
| K-76 | F | H | H | H | Ph | 1) |
| K-77 | CF₃ | H | H | H | Ph | 1) |
| K-78 | C(CH₃)₃ | H | H | H | Ph | 1) |
| K-79 | CN | H | H | H | Ph | 1) |
| K-80 | NO₂ | H | H | H | Ph | 1) |
| K-81 | OCH₃ | H | H | H | Ph | 1) |
| K-82 | H | H | CH₃ | H | Ph | 1) |
| K-83 | H | H | F | H | Ph | 1) |
| K-84 | H | H | CF₃ | H | Ph | 1) |
| K-85 | H | H | OCF₃ | H | Ph | 1) |
| K-86 | H | H | CN | H | Ph | 1) |
| K-87 | H | H | NO₂ | H | Ph | 1) |
| K-88 | H | H | OCH₃ | H | Ph | 1) |
| K-89 | H | H | SCH₃ | H | Ph | 1) |
| K-90 | H | C₆H₄CF₃ | H | H | Ph | 1) |

1) 4-C₆H₄C(CH)₃;

| Cpd. | R¹ | R² | R³ | R⁴ | R⁵ | Z¹ |
|---|---|---|---|---|---|---|
| K'-1 | H | H | H | H | Ph | Ph |
| K'-2 | H | NO₂ | H | H | Ph | Ph |
| K'-3 | H | CH₃ | H | H | Ph | Ph |
| K'-4 | H | C(CH₃)₃ | H | H | Ph | Ph |
| K'-5 | H | CH(CH₃)₂ | H | H | Ph | Ph |
| K'-6 | H | CF₃ | H | H | Ph | Ph |
| K'-7 | H | OCF₃ | H | H | Ph | Ph |
| K'-8 | H | F | H | H | Ph | Ph |
| K'-9 | H | OCH₃ | H | H | Ph | Ph |
| K'-10 | H | OPh | H | H | Ph | Ph |

-continued

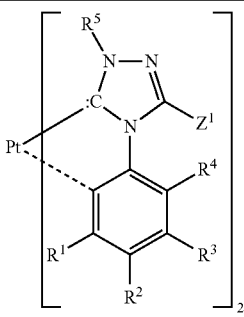

| Cpd. | R¹ | R² | R³ | R⁴ | R⁵ | Z¹ |
|---|---|---|---|---|---|---|
| K'-11 | H | CN | H | H | Ph | Ph |
| K'-12 | H | SCH₃ | H | H | Ph | Ph |
| K'-13 | H | CO₂CH₃ | H | H | Ph | Ph |
| K'-14 | H | SO₂CH₃ | H | H | Ph | Ph |
| K'-15 | H | C₆H₄CF₃ | H | H | Ph | Ph |
| K'-16 | CH₃ | H | H | H | Ph | Ph |
| K'-17 | F | H | H | H | Ph | Ph |
| K'-18 | CF₃ | H | H | H | Ph | Ph |
| K'-19 | C(CH₃)₃ | H | H | H | Ph | Ph |
| K'-20 | CN | H | H | H | Ph | Ph |
| K'-21 | NO₂ | H | H | H | Ph | Ph |
| K'-22 | OCH₃ | H | H | H | Ph | Ph |
| K'-23 | H | H | CH₃ | H | Ph | Ph |
| K'-24 | H | H | F | H | Ph | Ph |
| K'-25 | H | H | CF₃ | H | Ph | Ph |
| K'-26 | H | H | OCF₃ | H | Ph | Ph |
| K'-27 | H | H | CN | H | Ph | Ph |
| K'-28 | H | H | NO₂ | H | Ph | Ph |
| K'-29 | H | H | OCH₃ | H | Ph | Ph |
| K'-30 | H | H | SCH₃ | H | Ph | Ph |
| K'-31 | H | H | H | H | Ph | CF₃ |
| K'-32 | H | NO₂ | H | H | Ph | CF₃ |
| K'-33 | H | CH₃ | H | H | Ph | CF₃ |
| K'-34 | H | C(CH₃)₃ | H | H | Ph | CF₃ |
| K'-35 | H | CH(CH₃)₂ | H | H | Ph | CF₃ |
| K'-36 | H | CF₃ | H | H | Ph | CF₃ |
| K'-37 | H | OCF₃ | H | H | Ph | CF₃ |
| K'-38 | H | F | H | H | Ph | CF₃ |
| K'-39 | H | OCH₃ | H | H | Ph | CF₃ |
| K'-40 | H | OPh | H | H | Ph | CF₃ |
| K'-41 | H | CN | H | H | Ph | CF₃ |
| K'-42 | H | SCH₃ | H | H | Ph | CF₃ |
| K'-43 | H | CO₂CH₃ | H | H | Ph | CF₃ |
| K'-44 | H | SO₂CH₃ | H | H | Ph | CF₃ |
| K'-45 | CH₃ | H | H | H | Ph | CF₃ |
| K'-46 | F | H | H | H | Ph | CF₃ |
| K'-47 | CF₃ | H | H | H | Ph | CF₃ |
| K'-48 | C(CH₃)₃ | H | H | H | Ph | CF₃ |
| K'-49 | CN | H | H | H | Ph | CF₃ |
| K'-50 | NO₂ | H | H | H | Ph | CF₃ |
| K'-51 | OCH₃ | H | H | H | Ph | CF₃ |
| K'-52 | H | H | CH₃ | H | Ph | CF₃ |
| K'-53 | H | H | F | H | Ph | CF₃ |
| K'-54 | H | H | CF₃ | H | Ph | CF₃ |
| K'-55 | H | H | OCF₃ | H | Ph | CF₃ |
| K'-56 | H | H | CN | H | Ph | CF₃ |
| K'-57 | H | H | NO₂ | H | Ph | CF₃ |
| K'-58 | H | H | OCH₃ | H | Ph | CF₃ |
| K'-59 | H | H | SCH₃ | H | Ph | CF₃ |
| K'-60 | H | C₆H₄CF₃ | H | H | Ph | CF₃ |
| K'-61 | H | H | H | H | Ph | 1) |
| K'-62 | H | NO₂ | H | H | Ph | 1) |
| K'-63 | H | CH₃ | H | H | Ph | 1) |
| K'-64 | H | C(CH₃)₃ | H | H | Ph | 1) |
| K'-65 | H | CH(CH₃)₂ | H | H | Ph | 1) |
| K'-66 | H | CF₃ | H | H | Ph | 1) |
| K'-67 | H | OCF₃ | H | H | Ph | 1) |
| K'-68 | H | F | H | H | Ph | 1) |
| K'-69 | H | OCH₃ | H | H | Ph | 1) |
| K'-70 | H | OPh | H | H | Ph | 1) |
| K'-71 | H | CN | H | H | Ph | 1) |
| K'-72 | H | SCH₃ | H | H | Ph | 1) |

-continued

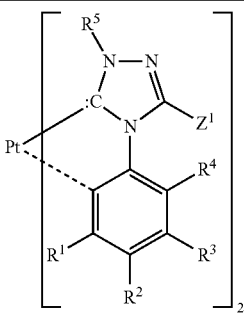

| Cpd. | R¹ | R² | R³ | R⁴ | R⁵ | Z¹ |
|---|---|---|---|---|---|---|
| K'-73 | H | CO₂CH₃ | H | H | Ph | 1) |
| K'-74 | H | SO₂CH₃ | H | H | Ph | 1) |
| K'-75 | CH3 | H | H | H | Ph | 1) |
| K'-76 | F | H | H | H | Ph | 1) |
| K'-77 | CF3 | H | H | H | Ph | 1) |
| K'-78 | C(CH3)3 | H | H | H | Ph | 1) |
| K'-79 | CN | H | H | H | Ph | 1) |
| K'-80 | NO2 | H | H | H | Ph | 1) |
| K'-81 | OCH3 | H | H | H | Ph | 1) |
| K'-82 | H | H | CH₃ | H | Ph | 1) |
| K'-83 | H | H | F | H | Ph | 1) |
| K'-84 | H | H | CF₃ | H | Ph | 1) |
| K'-85 | H | H | OCF₃ | H | Ph | 1) |
| K'-86 | H | H | CN | H | Ph | 1) |
| K'-87 | H | H | NO₂ | H | Ph | 1) |
| K'-88 | H | H | OCH₃ | H | Ph | 1) |
| K'-89 | H | H | SCH₃ | H | Ph | 1) |
| K'-90 | H | C₆H₄CF₃ | H | H | Ph | 1) |

1) 4-C₆H₄C(CH)₃;

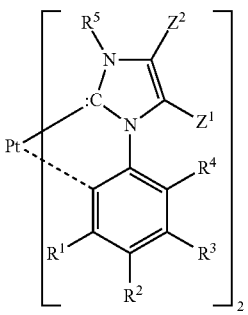

| Cpd. | R¹ | R² | R³ | R⁴ | R⁵ | Z¹ = Z² |
|---|---|---|---|---|---|---|
| L-1 | H | H | H | H | Ph | H |
| L-2 | H | NO₂ | H | H | Ph | H |
| L-3 | H | CH₃ | H | H | Ph | H |
| L-4 | H | C(CH₃)₃ | H | H | Ph | H |
| L-5 | H | CH(CH₃)₂ | H | H | Ph | H |
| L-6 | H | CF₃ | H | H | Ph | H |
| L-7 | H | OCF₃ | H | H | Ph | H |
| L-8 | H | F | H | H | Ph | H |
| L-9 | H | OCH₃ | H | H | Ph | H |
| L-10 | H | OPh | H | H | Ph | H |
| L-11 | H | CN | H | H | Ph | H |
| L-12 | H | SCH₃ | H | H | Ph | H |
| L-13 | H | CO₂CH₃ | H | H | Ph | H |
| L-14 | H | SO₂CH₃ | H | H | Ph | H |
| L-15 | CH₃ | H | H | H | Ph | H |
| L-16 | F | H | H | H | Ph | H |
| L-17 | CF₃ | H | H | H | Ph | H |
| L-18 | C(CH₃)₃ | H | H | H | Ph | H |
| L-19 | CN | H | H | H | Ph | H |
| L-20 | NO₂ | H | H | H | Ph | H |

-continued

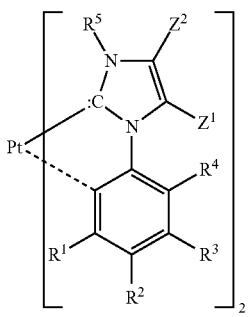

| Cpd. | R¹ | R² | R³ | R⁴ | R⁵ | Z¹ = Z² |
|---|---|---|---|---|---|---|
| L-21 | OCH₃ | H | H | H | Ph | H |
| L-22 | H | H | CH₃ | H | Ph | H |
| L-23 | H | H | F | H | Ph | H |
| L-24 | H | H | CF₃ | H | Ph | H |
| L-25 | H | H | OCF₃ | H | Ph | H |
| L-26 | H | H | CN | H | Ph | H |
| L-27 | H | H | NO₂ | H | Ph | H |
| L-28 | H | H | OCH₃ | H | Ph | H |
| L-29 | H | H | SCH₃ | H | Ph | H |
| L-30 | H | C₆H₄CF₃ | H | H | Ph | H |

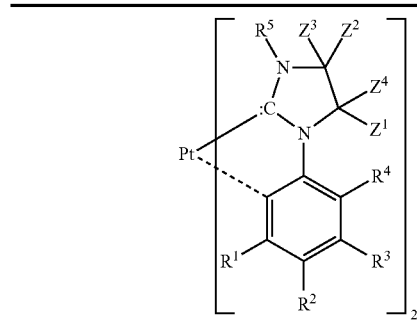

| Cpd. | R¹ | R² | R³ | R⁴ | R⁵ | 1) |
|---|---|---|---|---|---|---|
| M-1 | H | H | H | H | Ph | H |
| M-2 | H | NO₂ | H | H | Ph | H |
| M-3 | H | CH₃ | H | H | Ph | H |
| M-4 | H | C(CH₃)₃ | H | H | Ph | H |
| M-5 | H | CH(CH₃)₂ | H | H | Ph | H |
| M-6 | H | CF₃ | H | H | Ph | H |
| M-7 | H | OCF₃ | H | H | Ph | H |
| M-8 | H | F | H | H | Ph | H |
| M-9 | H | OCH₃ | H | H | Ph | H |
| M-10 | H | OPh | H | H | Ph | H |
| M-11 | H | CN | H | H | Ph | H |
| M-12 | H | SCH₃ | H | H | Ph | H |
| M-13 | H | CO₂CH₃ | H | H | Ph | H |
| M-14 | H | SO₂CH₃ | H | H | Ph | H |
| M-15 | CH₃ | H | H | H | Ph | H |
| M-16 | F | H | H | H | Ph | H |
| M-17 | CF₃ | H | H | H | Ph | H |
| M-18 | C(CH₃)₃ | H | H | H | Ph | H |
| M-19 | CN | H | H | H | Ph | H |
| M-20 | NO₂ | H | H | H | Ph | H |
| M-21 | OCH₃ | H | H | H | Ph | H |
| M-22 | H | H | CH₃ | H | Ph | H |
| M-23 | H | H | F | H | Ph | H |
| M-24 | H | H | CF₃ | H | Ph | H |
| M-25 | H | H | OCF₃ | H | Ph | H |
| M-26 | H | H | CN | H | Ph | H |
| M-27 | H | H | NO₂ | H | Ph | H |
| M-28 | H | H | OCH₃ | H | Ph | H |

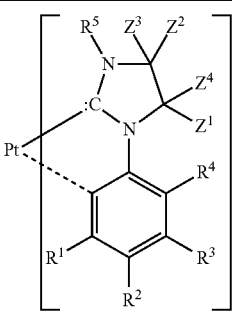

| Cpd. | R¹ | R² | R³ | R⁴ | R⁵ | 1) |
|---|---|---|---|---|---|---|
| M-29 | H | H | SCH₃ | H | Ph | H |
| M-30 | H | C₆H₄CF₃ | H | H | Ph | H |

1) $Z^1 = Z^2 = Z^3 = Z^4$;

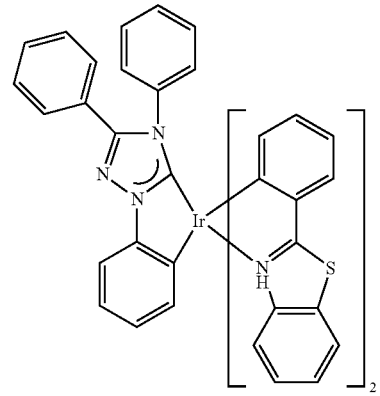

(N-1)

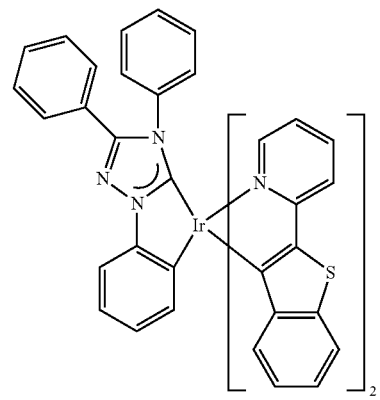

(N-2)

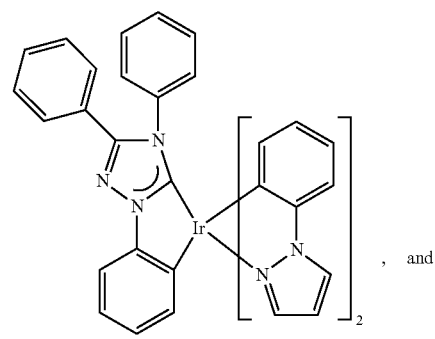

(N-3)

, and

-continued

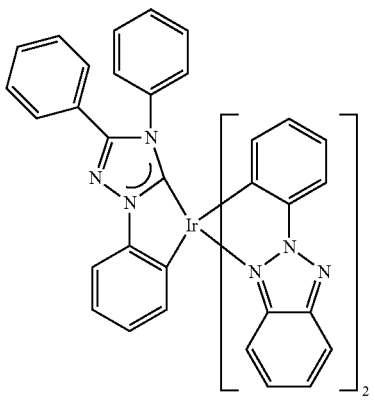

(N-4)

10. An organic electronic device, comprising an emitting layer wherein the emitting layer comprises a compound according to claim 9.

11. An organic electronic device according to claim 10 which is an organic light emitting diode.

12. A device selected from the group consisting of stationary or mobile displays, mobile phones, laptops, pdas, TV sets, displays in printers, kitchen equipment, billboards, lightings and information or destination boards in trains or buses, containing an organic light emitting diode according to claims 11.

13. The device of claim 10, further comprising a hole transport layer selected from the group consisting of polyvinyl-carbazol, N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehydediphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis (4-methylphenyl)-(1,1'-biphenyl)-4,4'-diamine (TTB), 4,4'-N,N-dicarbazole-biphenyl (CBP), N,N-dicarbazoyl-1,4-dimethene-benzene (DCB), porphyrinic compounds and combinations thereof.

14. An organic electronic device, comprising an emitting layer wherein the emitting layer comprises a compound according to claim 1.

15. The device of claim 14, further comprising a hole transport layer selected from the group consisting of polyvinyl-carbazol, N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl)biphenyl]4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino)benzaldehydediphenylhydrazone (DEH), triphenylamine (TPA), bis[4-(N,N-diethylamino)-2-methylphenyl](4-methylphenyl)methane (MPMP), 1-phenyl-3-[p-(diethylamino)styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), 4,4'-N,N-dicarbazole-biphenyl (CBP), N,N-dicarbazoyl-1,4-dimethene-benzene (DCB), porphyrinic compounds and combinations thereof.

16. A device selected from the group consisting of stationary or mobile displays, mobile phones, laptops, pdas, TV sets, displays in printers, kitchen equipment, billboards, lightings and information or destination boards in trains or buses, containing as an organic electronic device an organic light emitting diode according to claim 15.

17. A device selected from the group consisting of stationary or mobile displays, mobile phones, laptops, pdas, TV sets, displays in printers, kitchen equipment, billboards, lightings and information or destination boards in trains or buses, containing as an organic electronic device an organic light emitting diode according to claim 14.

18. An organic electronic device according to claim 14 which is a organic light emitting diode.

* * * * *